(12) United States Patent
Kim

(10) Patent No.: US 11,920,151 B2
(45) Date of Patent: Mar. 5, 2024

(54) METHOD FOR IDENTIFYING DNA BASE EDITING BY MEANS OF CYTOSINE DEAMINASE

(71) Applicants: TOOLGEN INCORPORATED, Seoul (KR); Seoul National University R&DB Foundation, Seoul (KR); INSTITUTE FOR BASIC SCIENCE, Daejeon (KR)

(72) Inventor: Daesik Kim, Seoul (KR)

(73) Assignees: TOOLGEN INCORPORATED, Seoul (KR); SEOUL NATIONAL UNIVERSITY R&Db FOUNDATION, Seoul (KR); INSTITUTE FOR BASIC SCIENCE, Daejeon (KR)

( * ) Notice: Subject to any disclaimer, the term of this patent is extended or adjusted under 35 U.S.C. 154(b) by 1277 days.

(21) Appl. No.: 16/332,036

(22) PCT Filed: Sep. 13, 2017

(86) PCT No.: PCT/KR2017/010056
§ 371 (c)(1),
(2) Date: Oct. 25, 2019

(87) PCT Pub. No.: WO2018/052247
PCT Pub. Date: Mar. 22, 2018

(65) Prior Publication Data
US 2020/0131536 A1    Apr. 30, 2020

Related U.S. Application Data

(60) Provisional application No. 62/445,310, filed on Jan. 12, 2017, provisional application No. 62/393,682, filed on Sep. 13, 2016.

(51) Int. Cl.
| | |
|---|---|
| C12N 15/90 | (2006.01) |
| C12N 9/22 | (2006.01) |
| C12N 9/78 | (2006.01) |
| C12N 15/113 | (2010.01) |
| C12Q 1/6806 | (2018.01) |
| C12Q 1/6869 | (2018.01) |
| G16B 30/00 | (2019.01) |

(52) U.S. Cl.
CPC .............. *C12N 15/90* (2013.01); *C12N 9/22* (2013.01); *C12N 9/78* (2013.01); *C12N 15/113* (2013.01); *C12Q 1/6806* (2013.01); *C12Q 1/6869* (2013.01); *G16B 30/00* (2019.02); *C12Y 305/04004* (2013.01)

(58) Field of Classification Search
None
See application file for complete search history.

(56) References Cited

U.S. PATENT DOCUMENTS

| | | | |
|---|---|---|---|
| 2015/0166980 A1 | 6/2015 | Liu et al. | |
| 2015/0226671 A1* | 8/2015 | Huang | ............. C12Q 1/34 435/6.1 |
| 2016/0304846 A1* | 10/2016 | Liu | .............. C12Y 301/00 |
| 2017/0121693 A1* | 5/2017 | Liu | .............. A61P 13/02 |

FOREIGN PATENT DOCUMENTS

| | | |
|---|---|---|
| WO | 2015-105928 | 7/2015 |
| WO | 2015-138620 | 9/2015 |
| WO | 2016-022363 | 2/2016 |

OTHER PUBLICATIONS

Kim et al., Digenome-seq: genome-wide profiling of CRISPR-Cas9 off-target effects in human cells. Nature Methods (2015) 12(3): 237-243 and Supplemental material (Year: 2015).*
Mung Bean Nuclease, NEB, www.neb.com/products/m0250-mung-bean-nuclease (archived from Sep. 18, 2015) [retrieved Sep. 16, 2022] (Year: 2015).*
Chaudhry and Weinfeld, Induction of double-strand breaks by S1 nuclease, mung bean nuclease and nuclease P1 in DNA containing abasic sites and nicks. Nucleic Acids Research (1995), 23(19): 3805-3809 (Year: 1995).*
Krokan et al., Base Excision Repair. Cold Spring Harbor Perspectives in Biology (2013), 5: a012583 (Year: 2013).*
Albert's Molecular Biology of the Cell, 5th Ed. (2008), Chapter 4: DNA, Chromosomes and Genomes (Year: 2008).*
Briggs et al., Removal of deaminated cytosines and detection of in vivo methylation in ancient DNA. Nucleic Acids Research (2010), 38: e87, 1-12 (Year: 2010).*
Daesik Kim et al, "Genome-wide target specificities of CRISPR RNA-guided programmable deaminases", Nature Biotechnology, vol. 35, No. 5, Apr. 10, 2017, pp. 475-480, XP055383071, ISSN 1087-0156. doi:10.1038/nbt.3852.
EPO, Supplementary European Search Report of EP 17851121.8 dated Mar. 30, 2020.
"User Enzyme", New England BioLabs, Inc., https://www.neb.com/products/m5505-user-enzyme.
"The new editor-targeted genome engineering in the absence of homology-directed repair", Cell Death Discovery, vol. 2, pp. 1-2, Jun. 13, 2016.
Alexis C. Komor et al., "Programmable editing of a target base in genomic DNA without double-stranded DNA cleavage", Nature, vol. 533, pp. 420-424 and Methods, May 19, 2016.

(Continued)

*Primary Examiner* — Samuel C Woolwine
*Assistant Examiner* — Catherine Konopka
(74) *Attorney, Agent, or Firm* — LEX IP MEISTER, PLLC

(57) ABSTRACT

Provided are: a composition for DNA double-strand breaks (DSBs), comprising (1) a cytosine deaminase and an inactivated target-specific endonuclease, (2) a guide RNA, and (3) a uracil-specific excision reagent (USER); a method for producing DNA double-strand breaks by means of a cytosine deaminase using the composition; a method for analyzing a DNA nucleic acid sequence to which base editing has been introduced by means of a cytosine deaminase; and a method for identifying (or measuring or detecting) base editing, base editing efficiency at an on-target site, an off-target site, and/or target specificity by means of a cytosine deaminase.

10 Claims, 47 Drawing Sheets

Specification includes a Sequence Listing.

(56) References Cited

OTHER PUBLICATIONS

Keiji Nishida et al., "Targeted nucleotide editing using hybrid prokaryotic and vertebrate adaptive immune systems", Science, vol. 353, Issue 6305, Sep. 16, 2016.

Yunqing Ma et al., "Targeted AIDID-mediated mutagenesis (TAM) enables efficient genomic diversification in mammalian cells", Nature Methods, vol. 13, No. 12, Dec. 2016.

Gaelen T Hess et al., "Directed evolution using dCas9-targeted somatic hypermutation in mammalian cells", Nature Methods, vol. 13, No. 12, pp. 1036-10742, Dec. 2016.

Luhan Yang et al., "Engineering and optimising deaminase fusions for genome editing", Nature communications, vol. 7, 2016.

Hyongbum Kim et al., "A guide to genome engineering with programmable nucleases", Nature Reviews, vol. 15, pp. 321-334, May 2014.

Shengdar Q Tsai et al., "GUIDE-seq enables genome-wide profiling of off-target cleavage by CRISPR-Cas nucleases", Nature biotechnology, vol. 33, No. 2, pp. 189-197, Feb. 2015.

Richard L Frock et al., "Genome-wide detection of DNA double-stranded breaks induced by engineered nucleases", Nature biotechnology, vol. 33, No. 2, Feb. 2015.

F. Ann Ran et al., "In vivo genome editing using *Staphylococcus aureus* Cas9", Nature, vol. 520, pp. 186-191, Apr. 2015.

Xiaoling Wang et al., "Unbiased detection of off-target cleavage by CRISPR-Cas9 and TALENs using integrase-defective lentiviral vectors", Nature biotechnology, vol. 33, No. 2, Feb. 2015.

Daesik Kim et al., "Genome-wide target specificities of CRISPR-Cas9 nucleases revealed by multiplex Digenome-seq", Genome research, vol. 26, pp. 406-415, 2016.

Daesik Kim et al., "Genome-wide analysis reveals specificities of Cpf1 endonucleases in human cells", Nature biotechnology, vol. 34, pp. 863-868, 2016.

Daesik Kim et al., "Digenome-seq: genome-wide profiling of CRISPR-Cas9 off-target effects in human cells", Nature methods, vol. 12, No. 3, pp. 237-243, 231 p following 243, Mar. 2015.

Sangsu Bae et al., "Cas-OFFinder: A fast and versatile algorithm that searches for potential off-target sites of Cas9 RNA-guided endonucleases", Bioinformatics, vol. 30, No. 10, 2014.

Luhan Yang et al., "Genome Editing With Targeted Deaminases", bioRxiv, 2016.

Stefanie V Lensing et al., "DSBCapture: in situ capture and sequencing of DNA breaks", Nature methods, vol. 13, No. 10, Oct. 2016.

\* cited by examiner

[FIG. 1a]
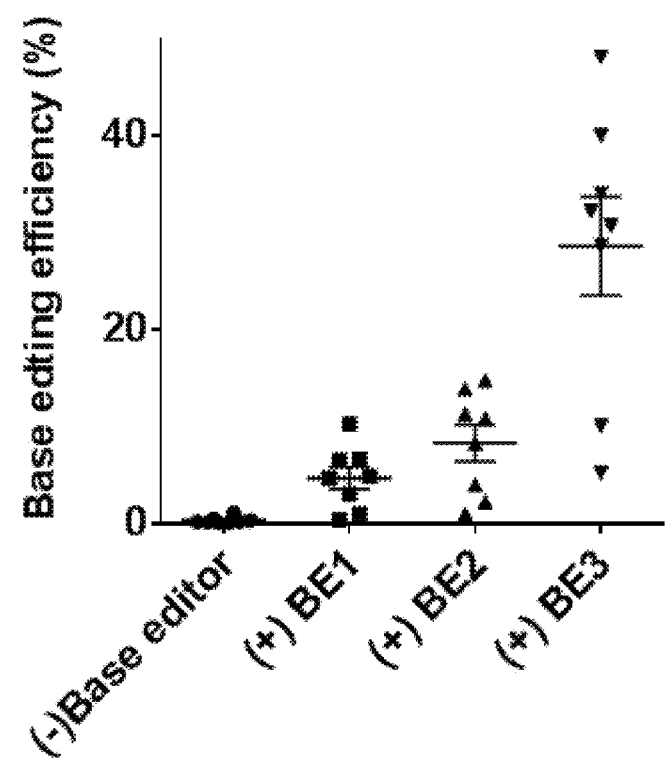

[FIG. 1b]
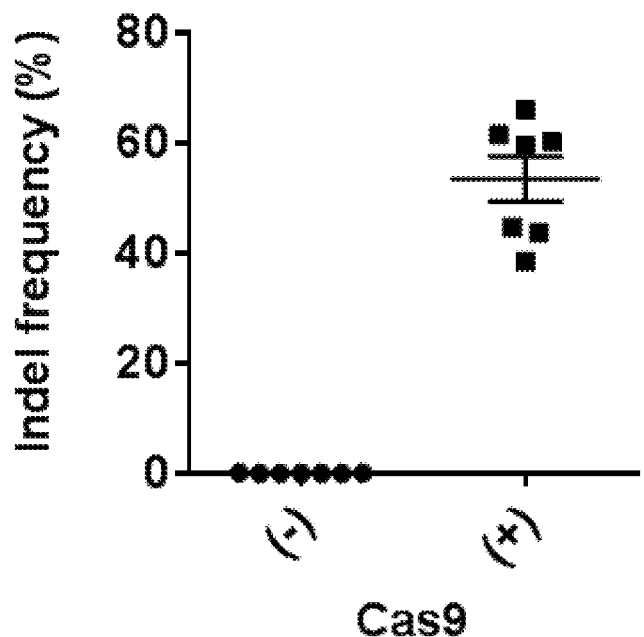
[FIG. 1c]
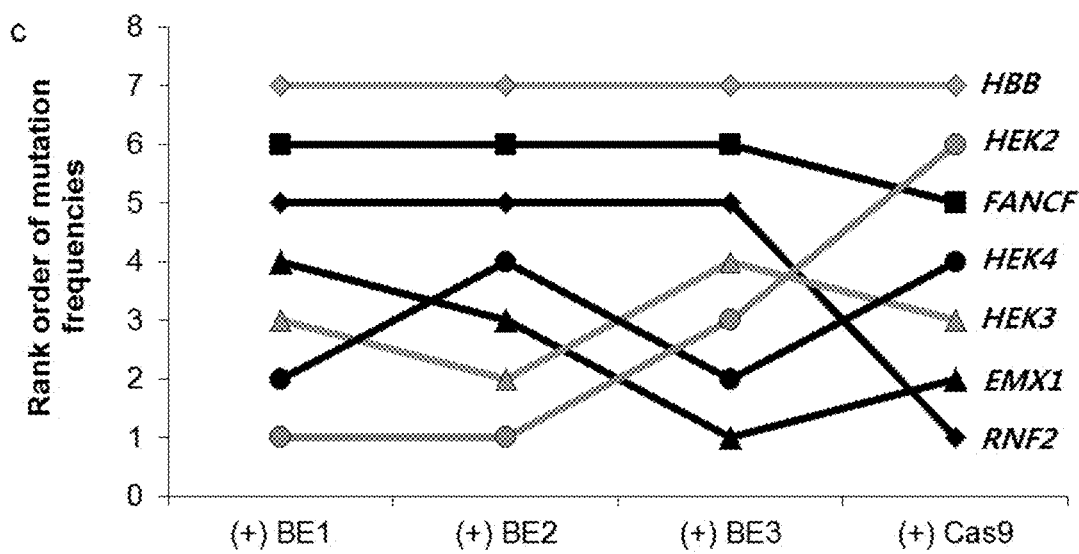

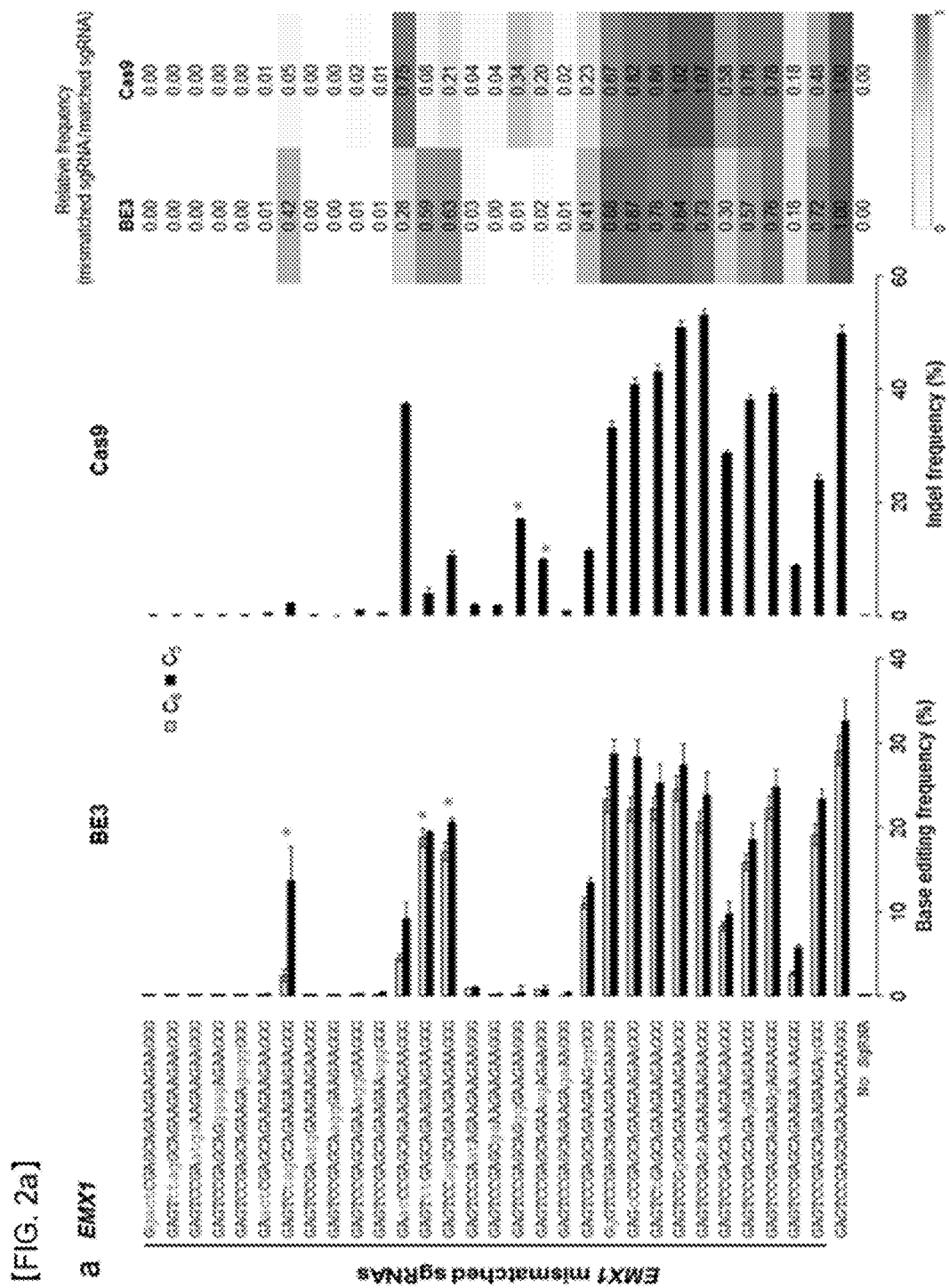
[FIG. 2a]

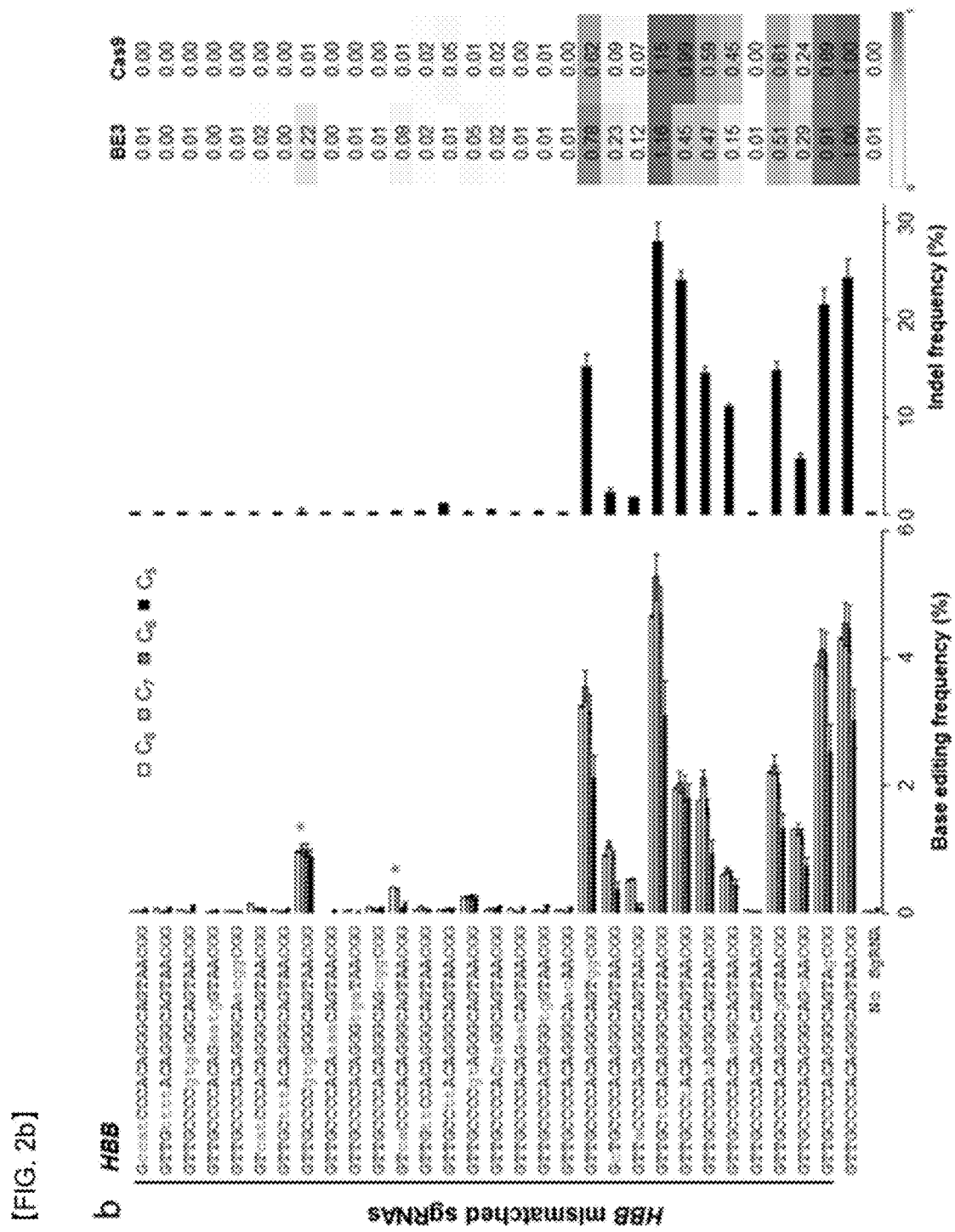
[FIG. 2b]

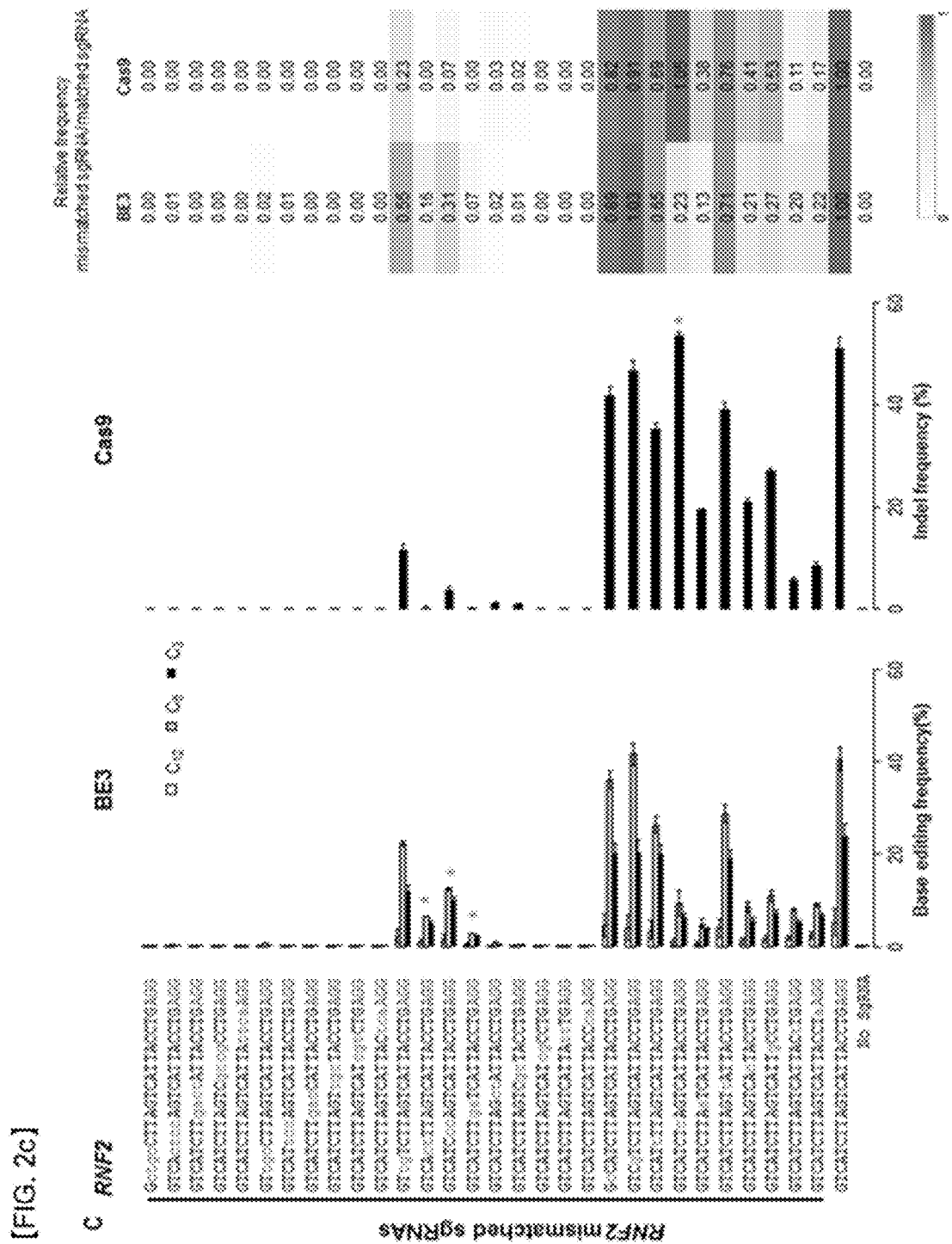

[FIG. 3a]
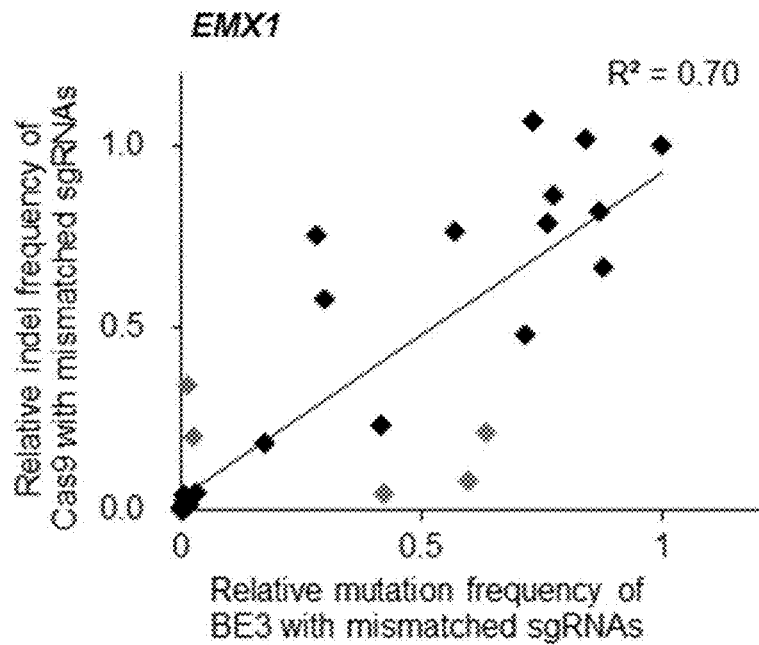
[FIG. 3b]
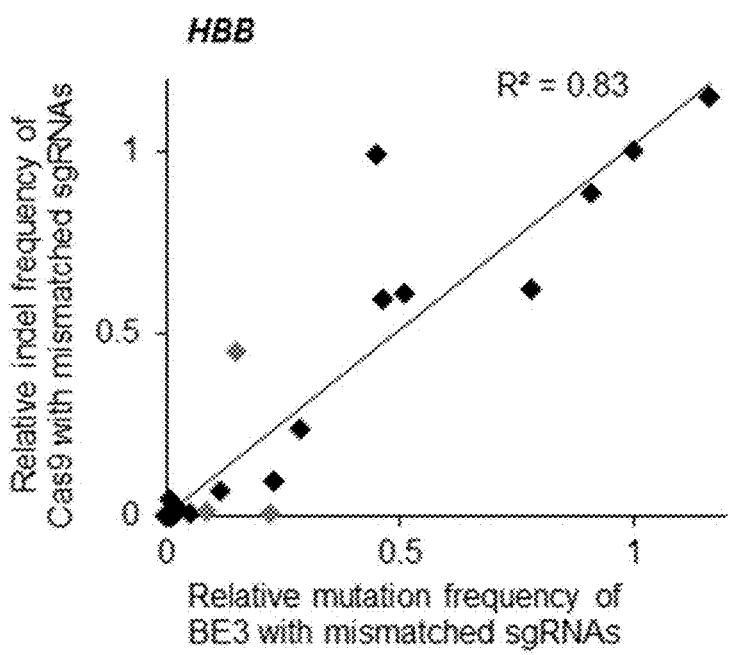

[FIG. 3c]
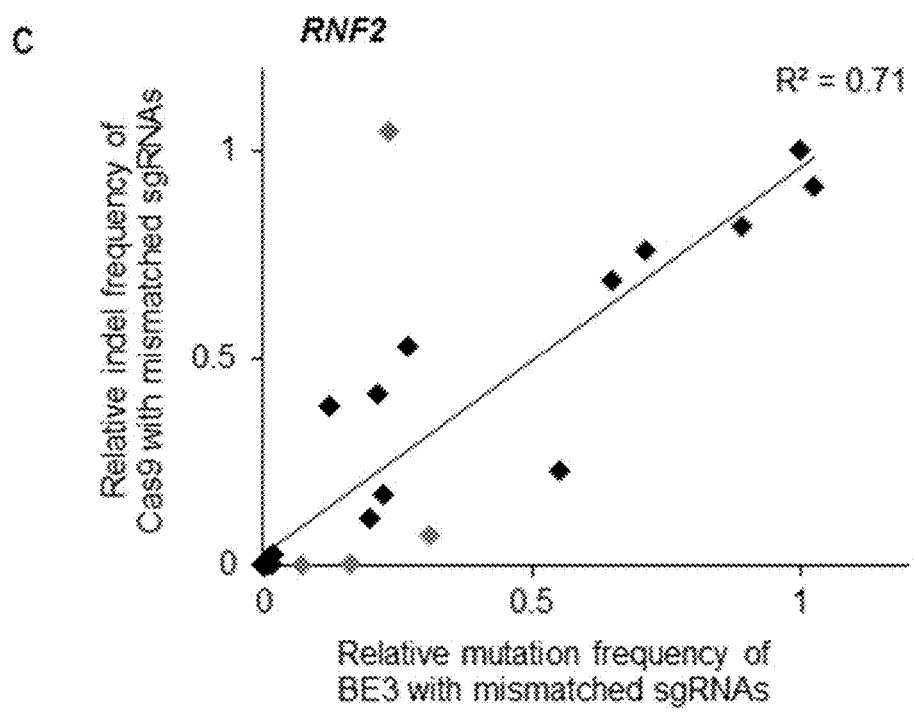

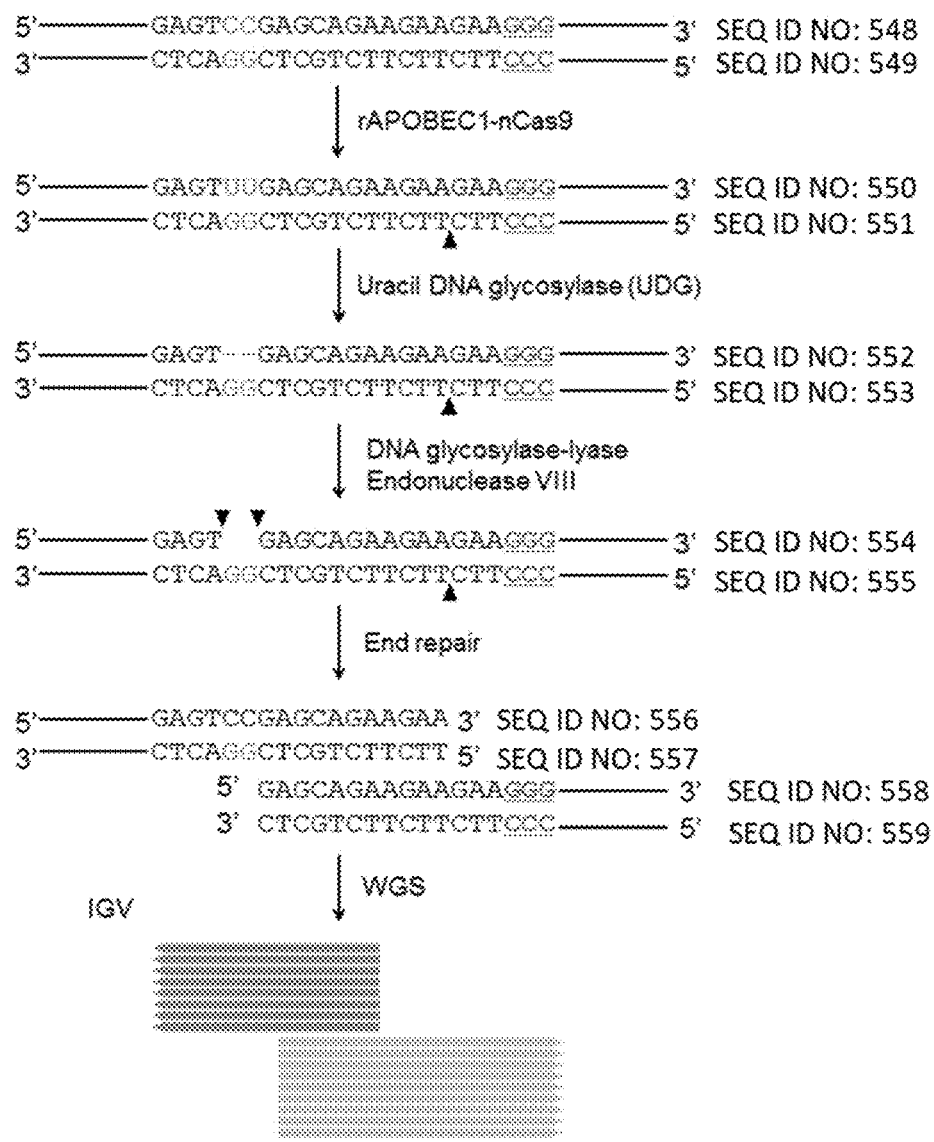
[FIG. 4a]

[FIG. 4b]
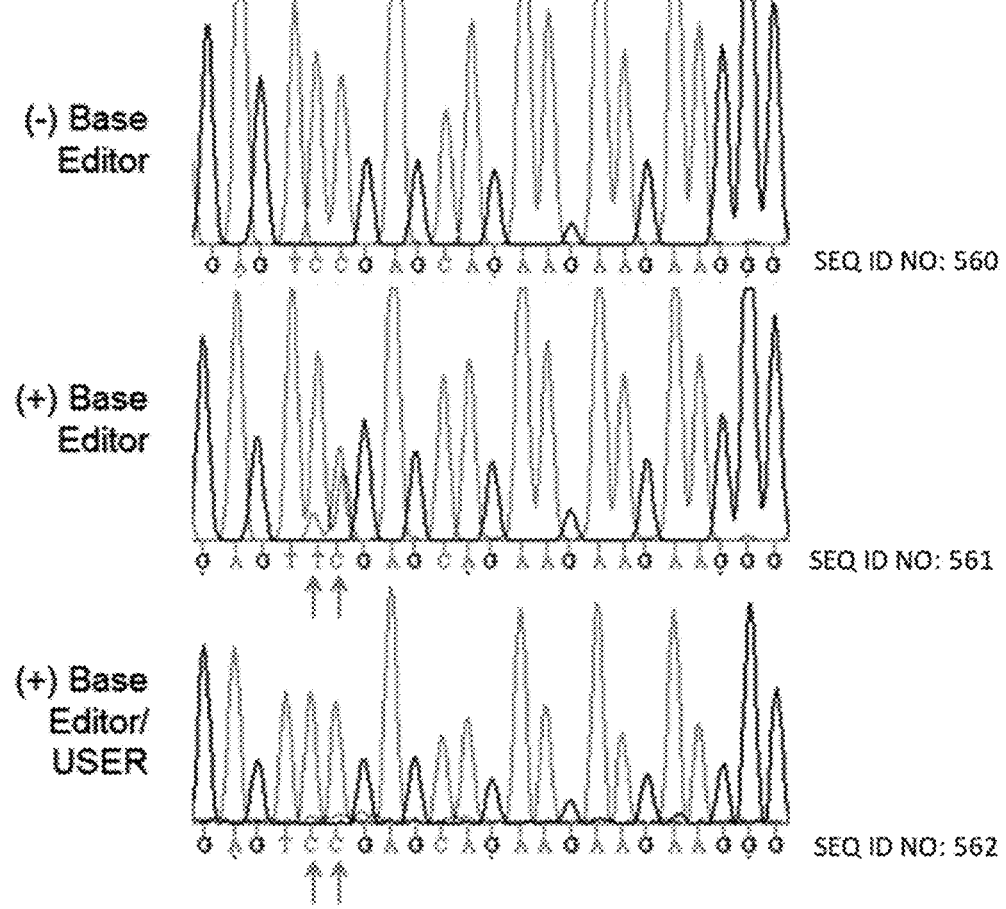
[FIG. 4c]

[FIG. 4d]
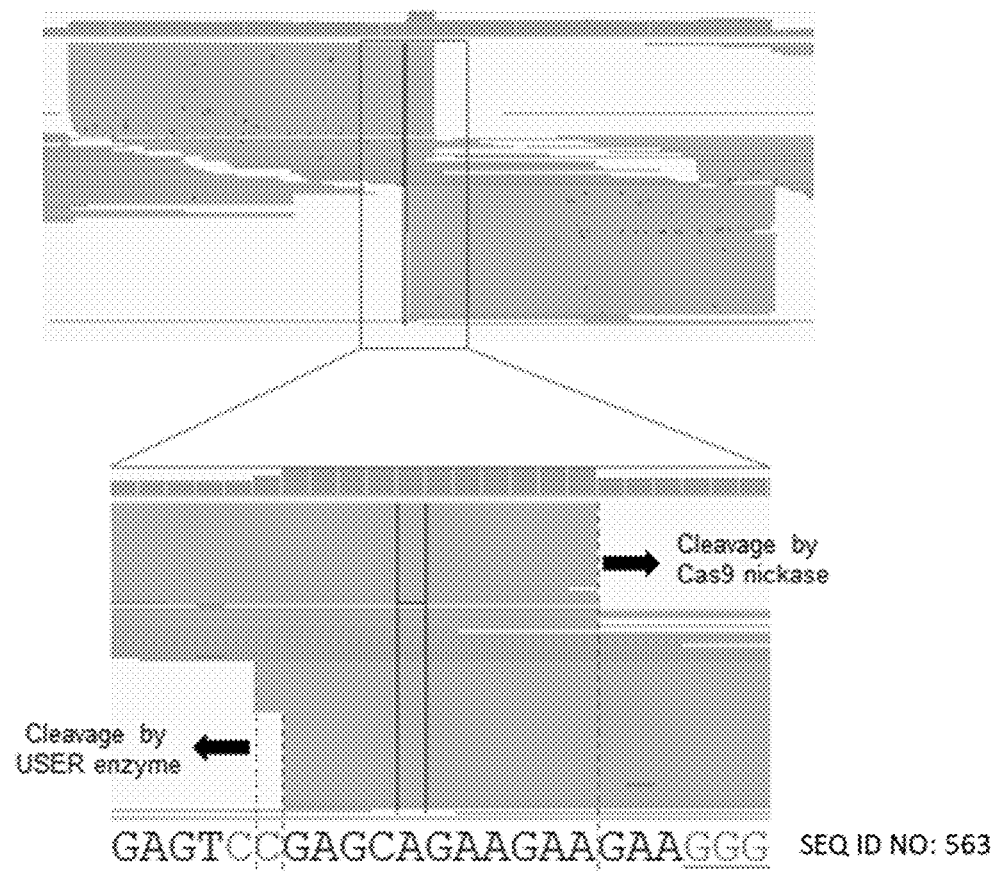

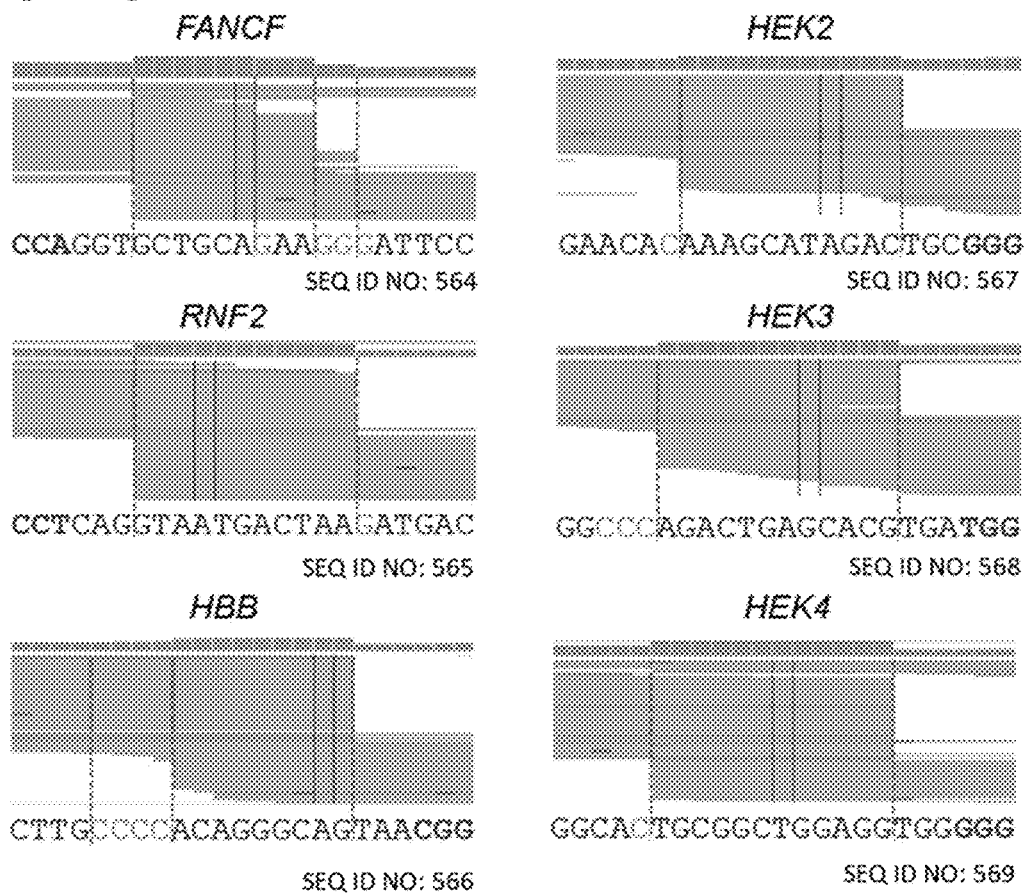
[FIG. 5]

[FIG. 6a]
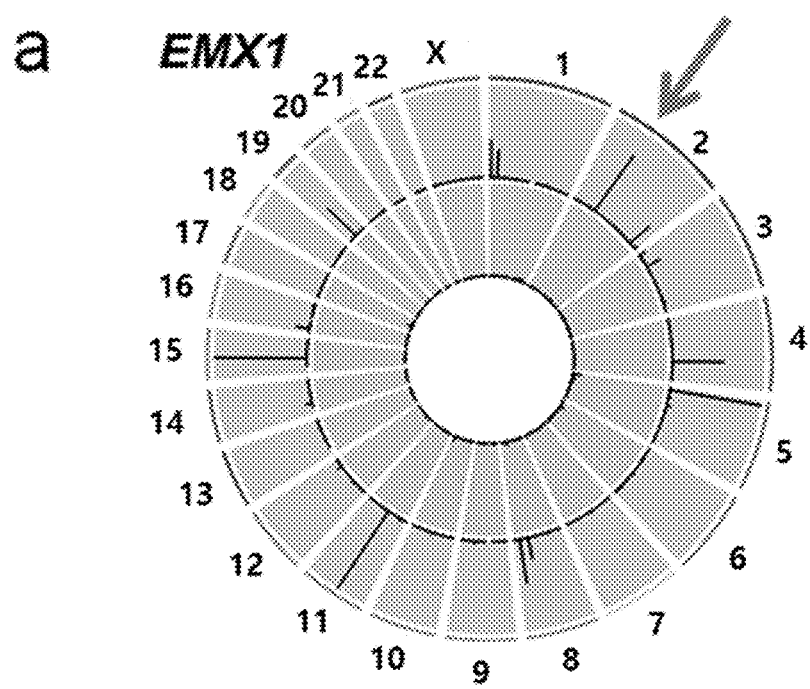
Untreated (+) Base Editor

[FIG. 6b]
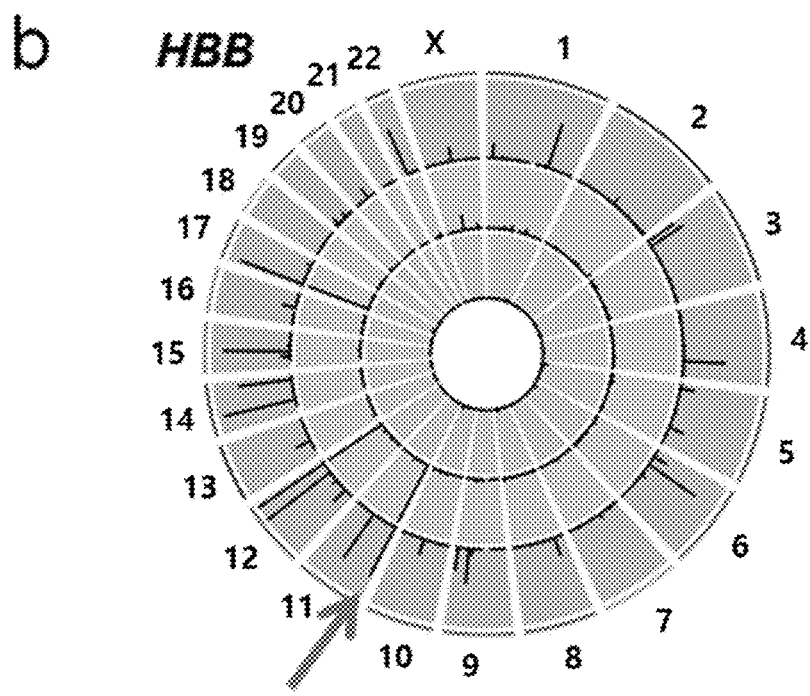

[FIG. 6c]
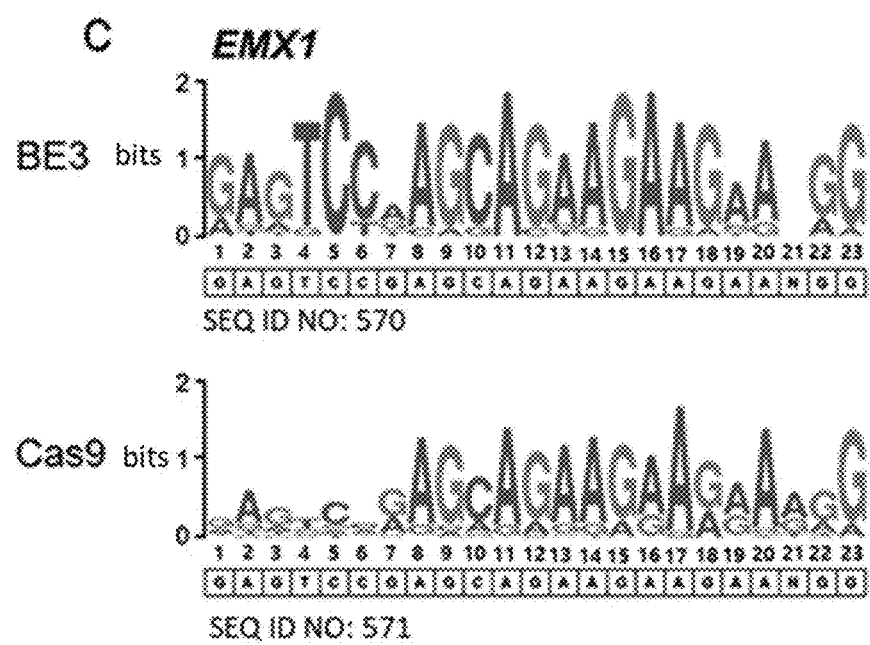

[FIG. 6d]
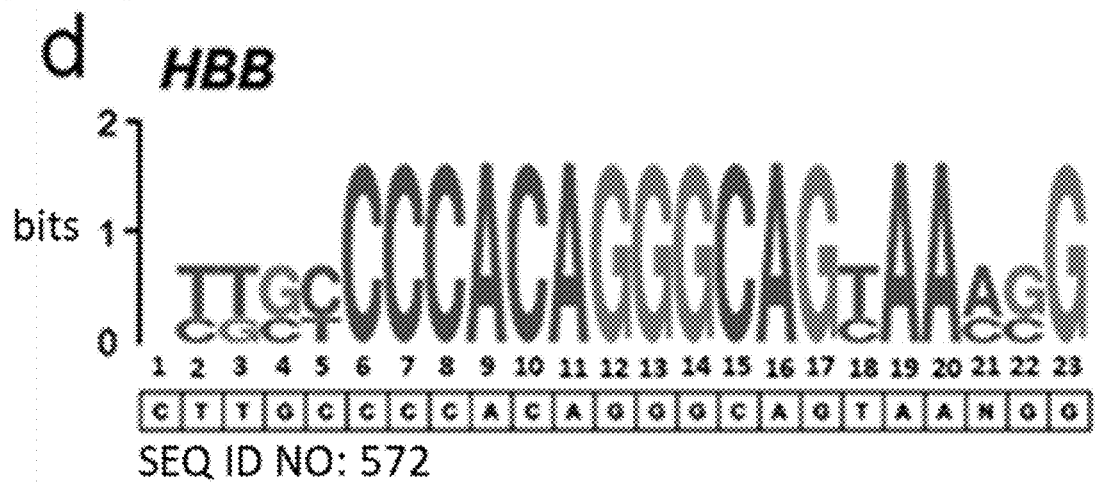
SEQ ID NO: 572
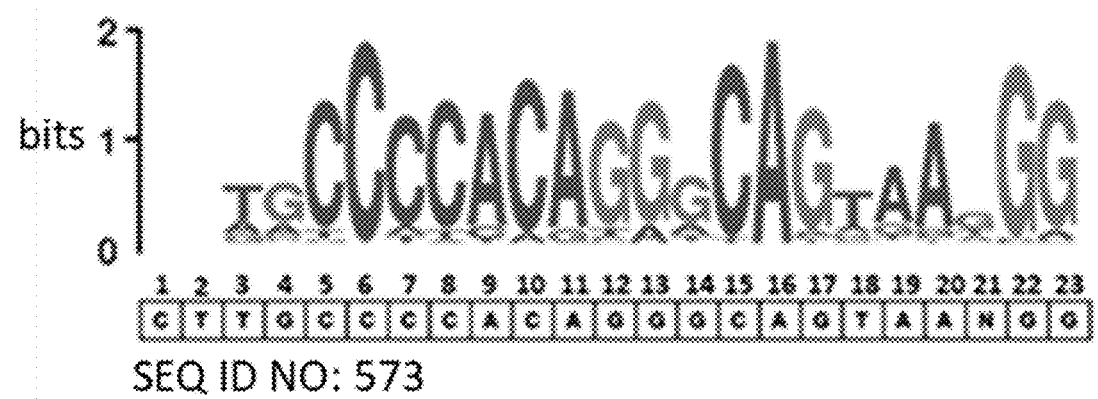
SEQ ID NO: 573

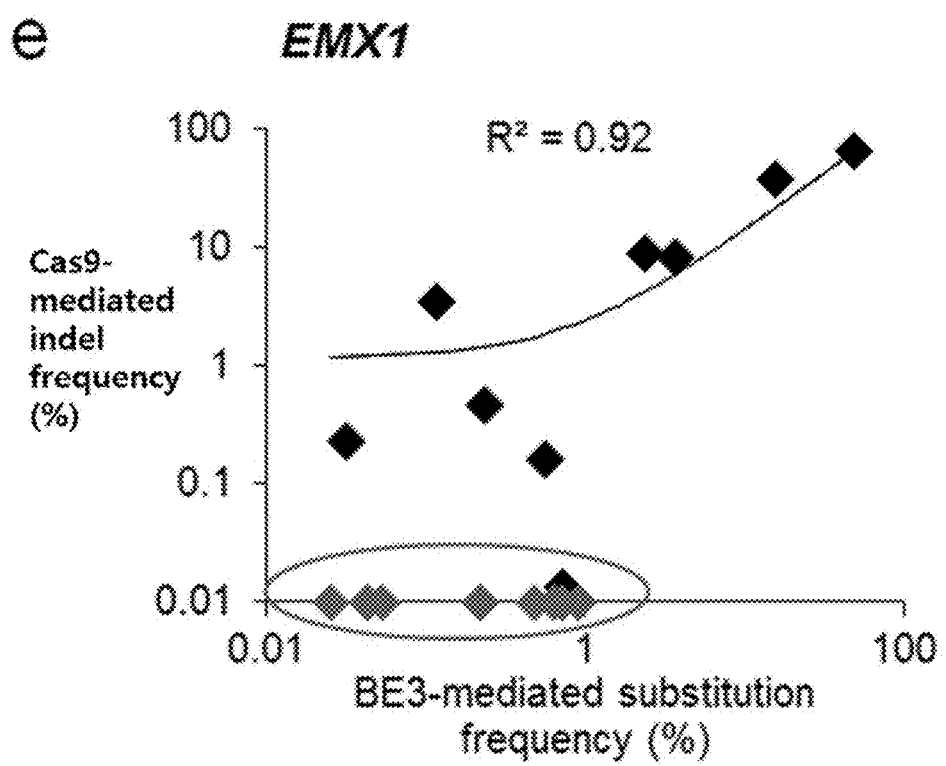
[FIG. 6e]

[FIG. 6f]
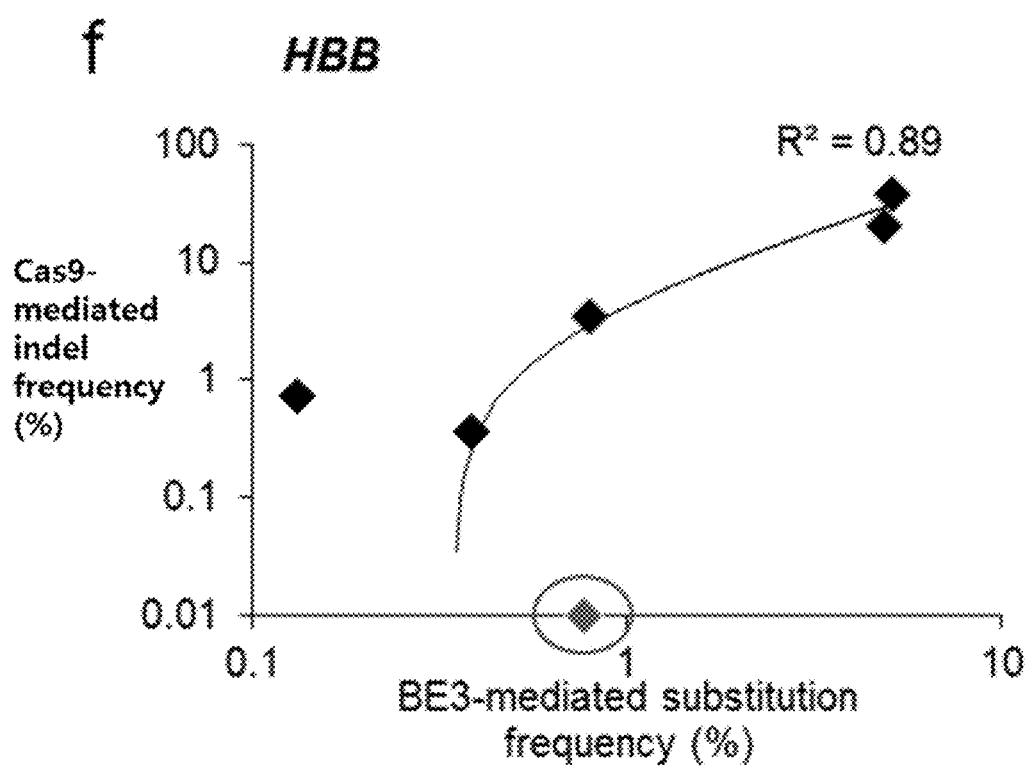

[FIG. 6g]
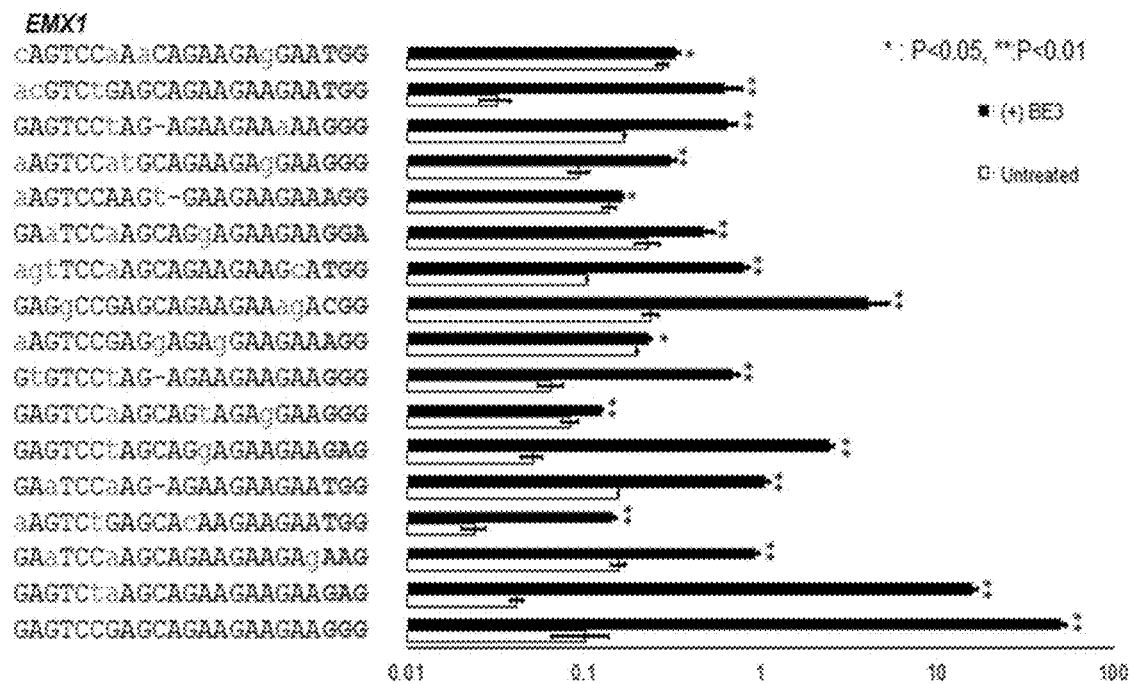

[FIG. 6h]
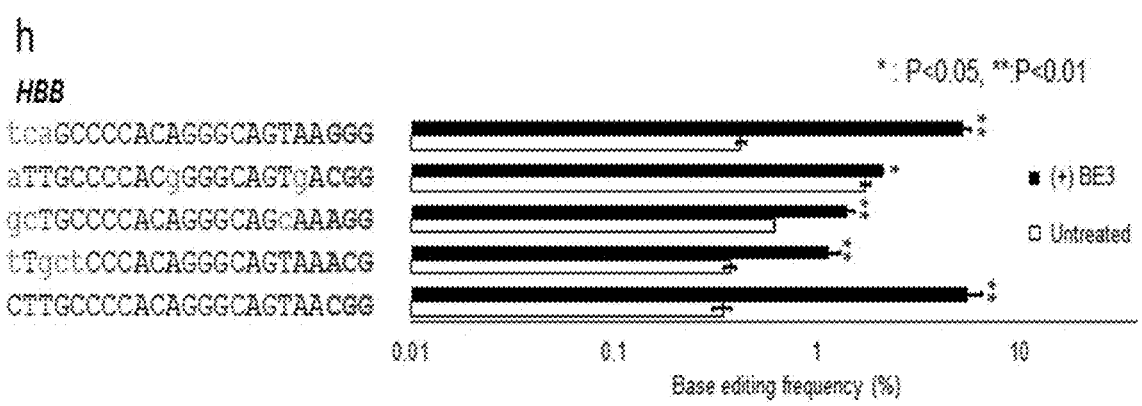

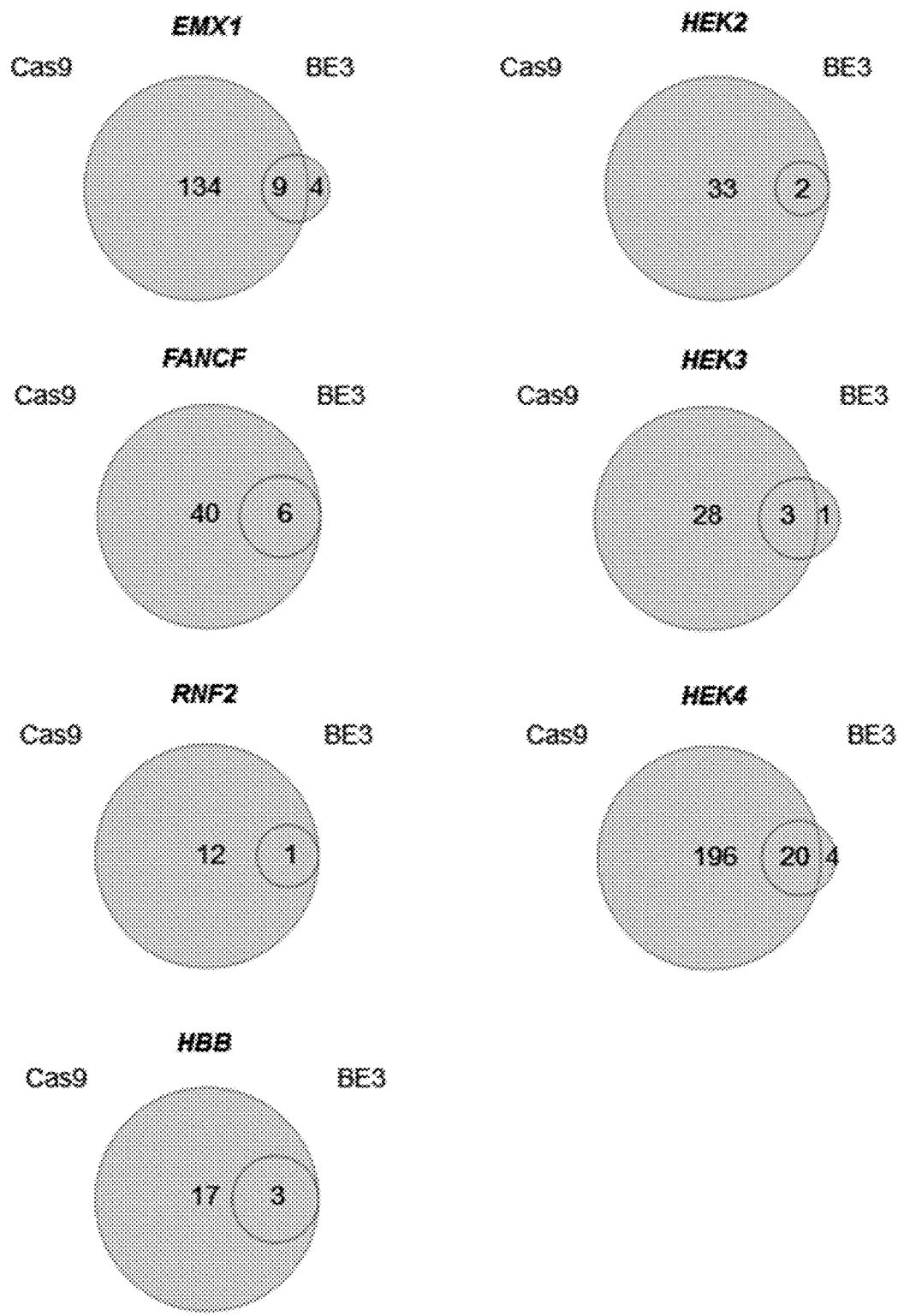
[FIG. 7]

[FIG. 8]
*FANCF*
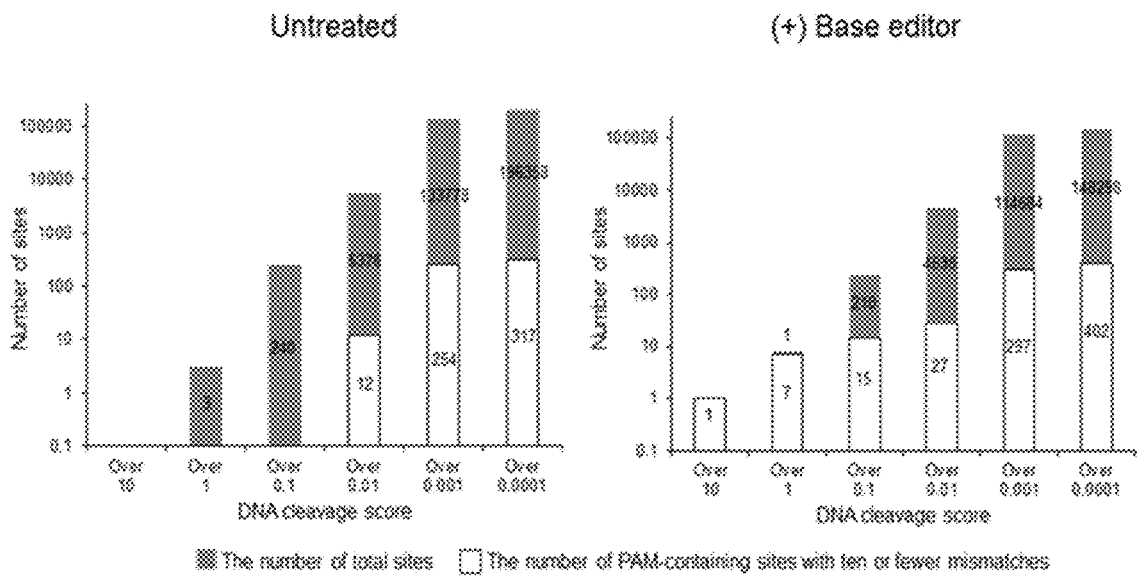

[FIG. 9]
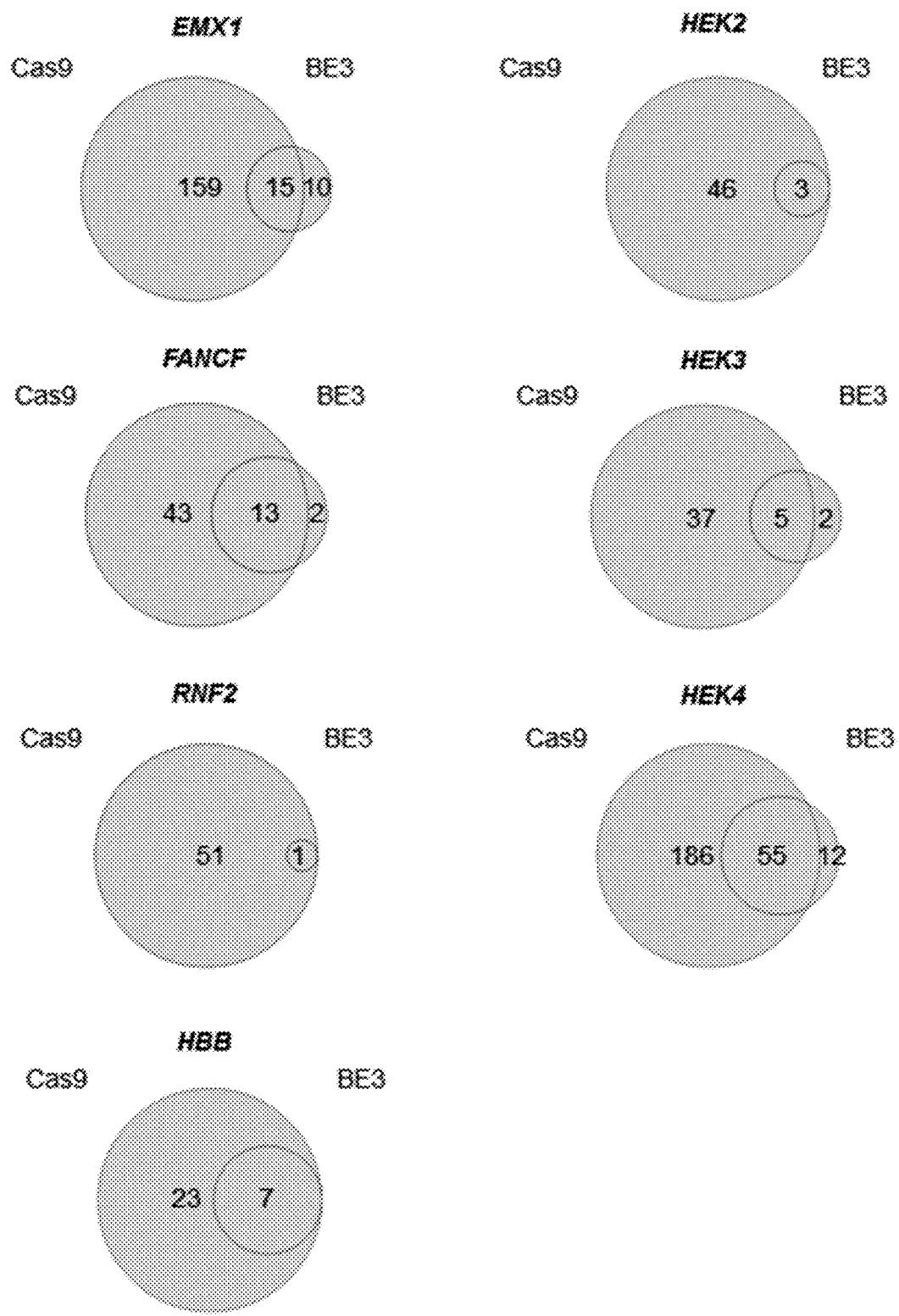

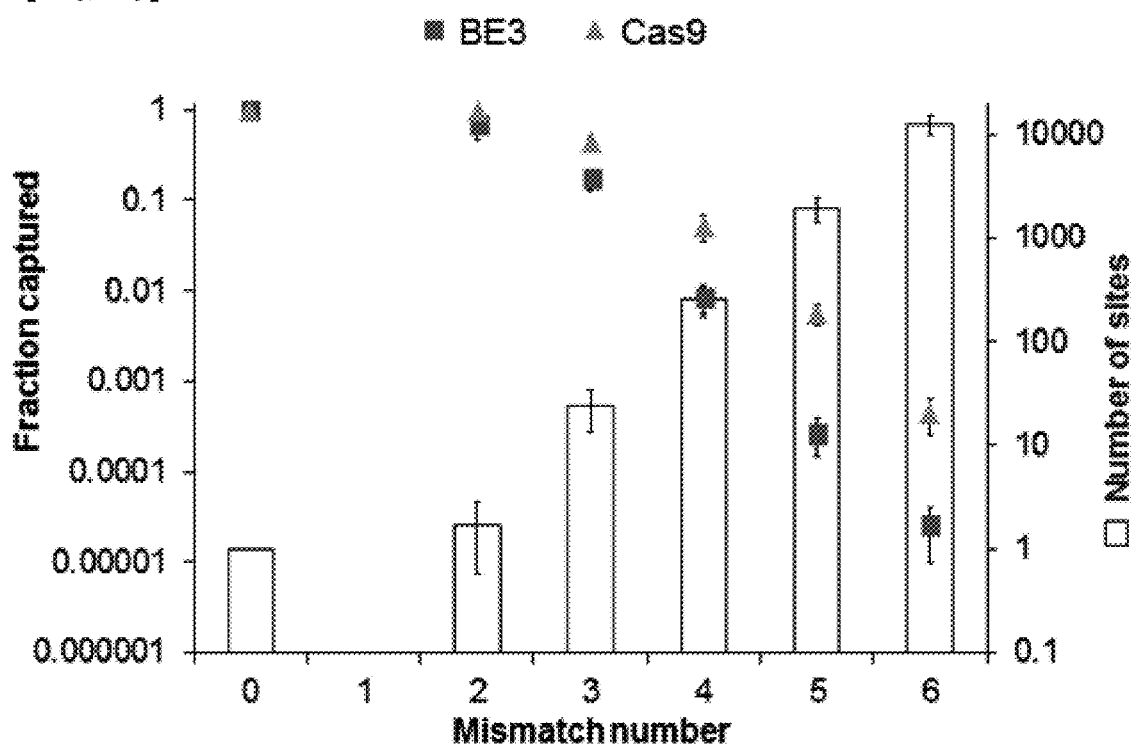
[FIG. 10]

[FIG. 11a]
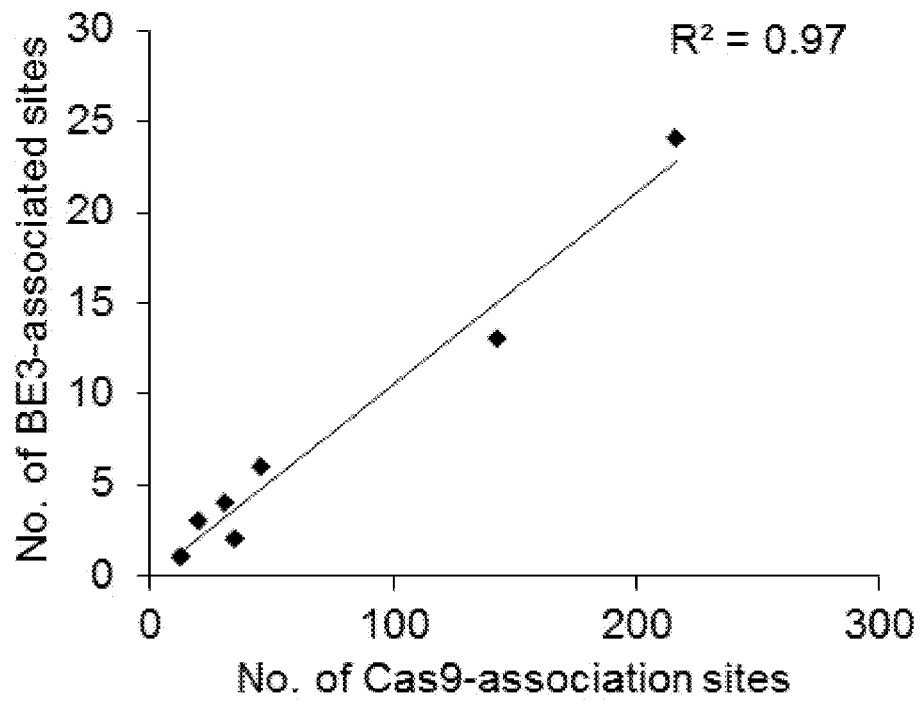

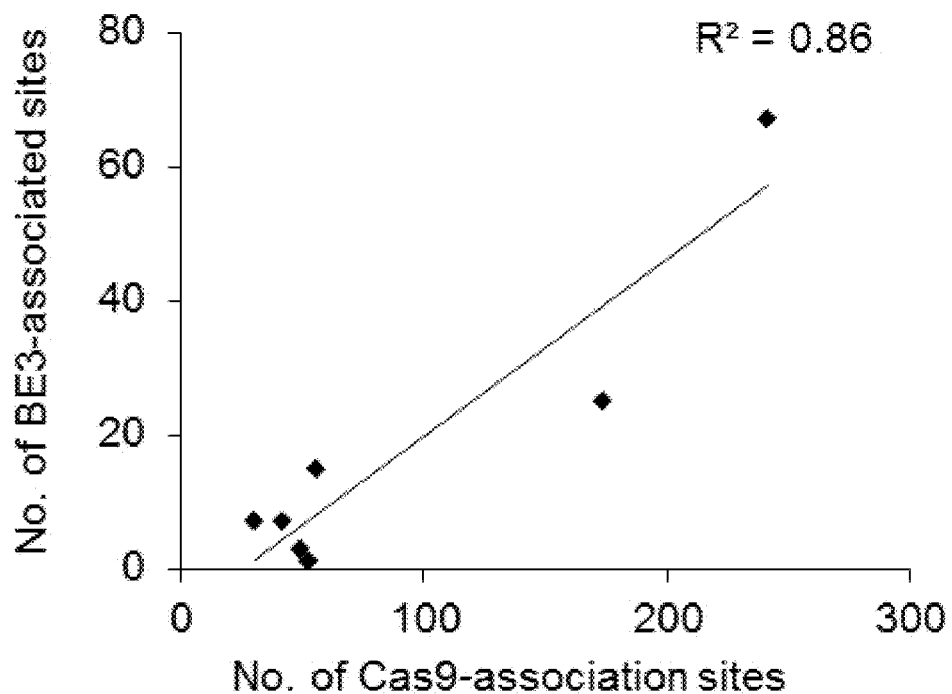
[FIG. 11b]

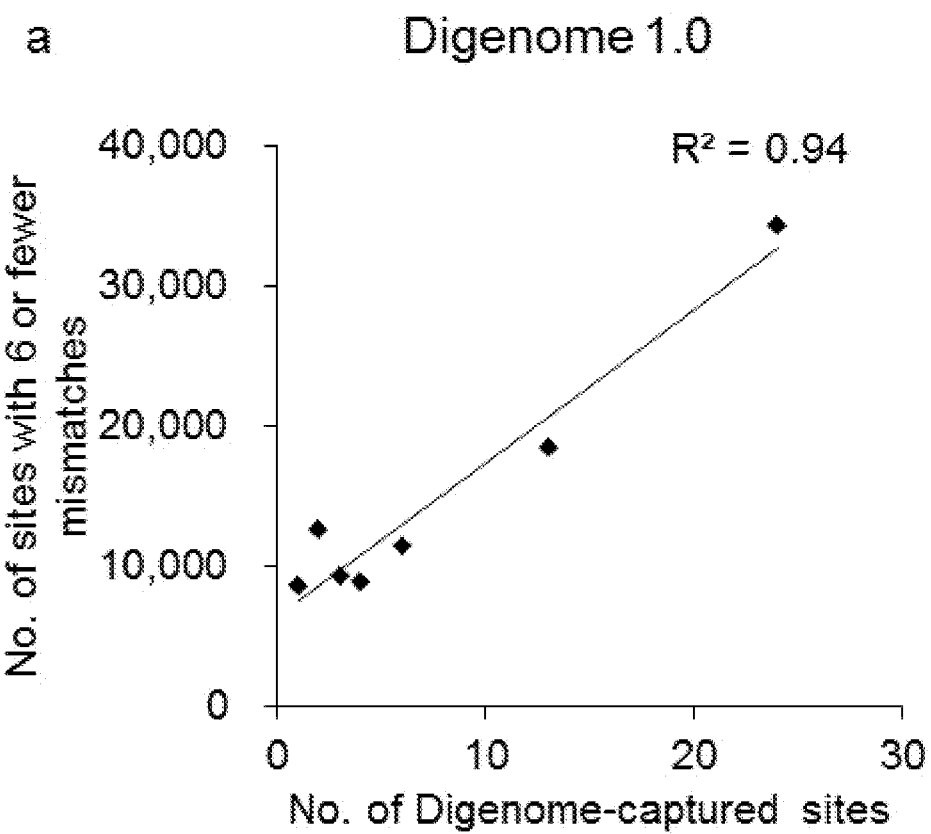
[FIG. 12a]

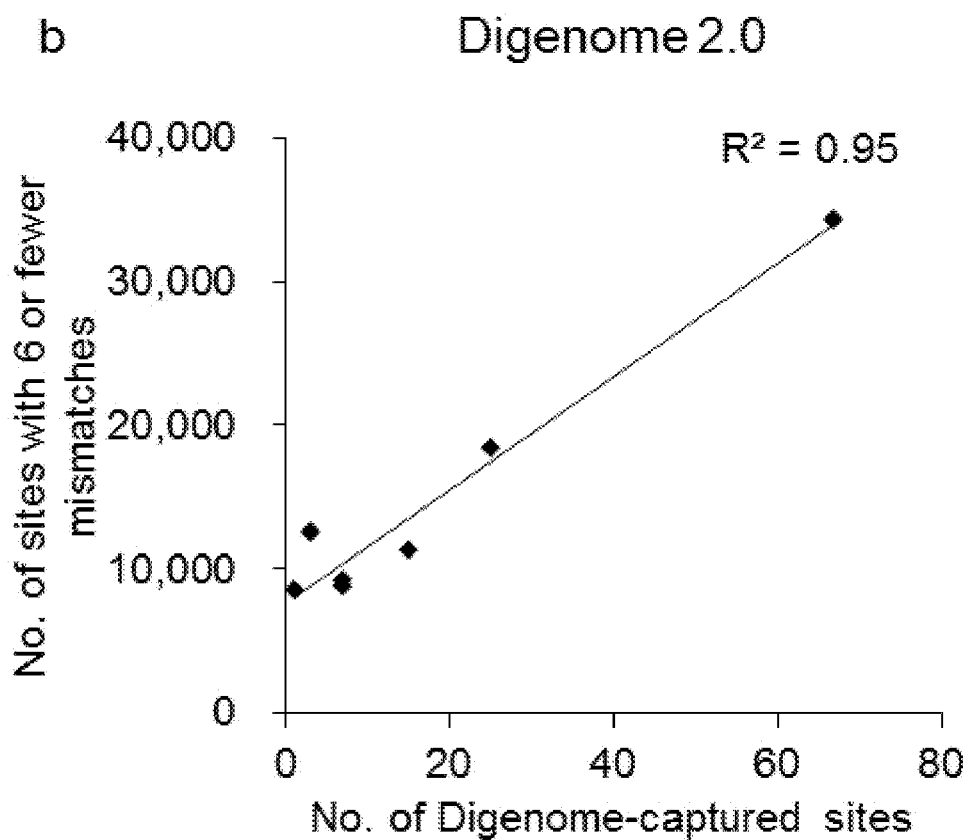
[FIG. 12b]

[FIG. 13]

EMX1

| | | |
|---|---|---|
| 5'- GAGTCCGAGCAGAAGAAGAAGGG -3' | On-target sequence | SEQ ID NO: 31 |
| 5'- GAGTtaGAGCAGAAGAAGAAAGG -3' | Off-target sequence | SEQ ID NO: 574 |

HEK2

| | | |
|---|---|---|
| 5'- GAACACAAAGCATAGACTGCGGG -3' | On-target sequence | SEQ ID NO: 153 |
| 5'- attaAgAtAGCATAGACTGCAGG -3' | Off-target sequence | SEQ ID NO: 575 |

HEK4

| | | |
|---|---|---|
| 5'- GGCACTGCGGCTGGAGGTGGGGG -3' | On-target sequence | SEQ ID NO: 162 |
| 5'- GGCAaTGtGGCTGaAGGTGGGG -3' | Off-target sequence | SEQ ID NO: 576 |

RNF2

| | | |
|---|---|---|
| 5'- GTCATCTTAGTCATTACCTGAGG -3' | On-target sequence | SEQ ID NO: 93 |
| 5'- aTtATtTTAGTCATTACCTtTGG -3' | Off-target sequence | SEQ ID NO: 577 |

HEK3

| | | |
|---|---|---|
| 5'- GGCCCAGACTGAGCACGTGATGG -3' | On-target sequence | SEQ ID NO: 156 |
| 5'- aaataAGACTGAGCACGTGgTGG -3' | Off-target sequence | SEQ ID NO: 578 |

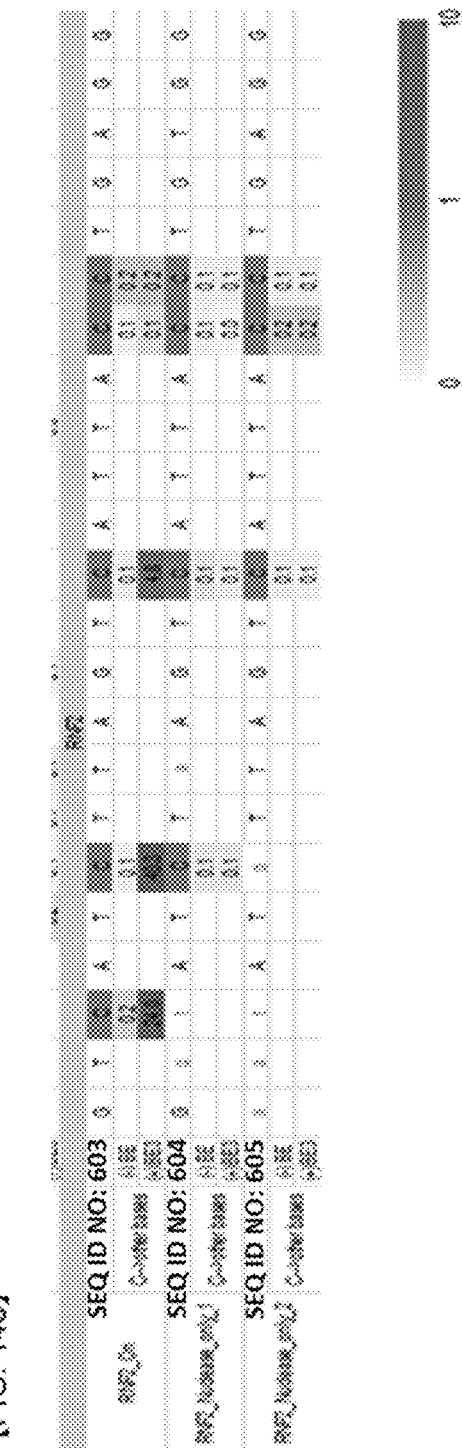
[FIG. 14c]

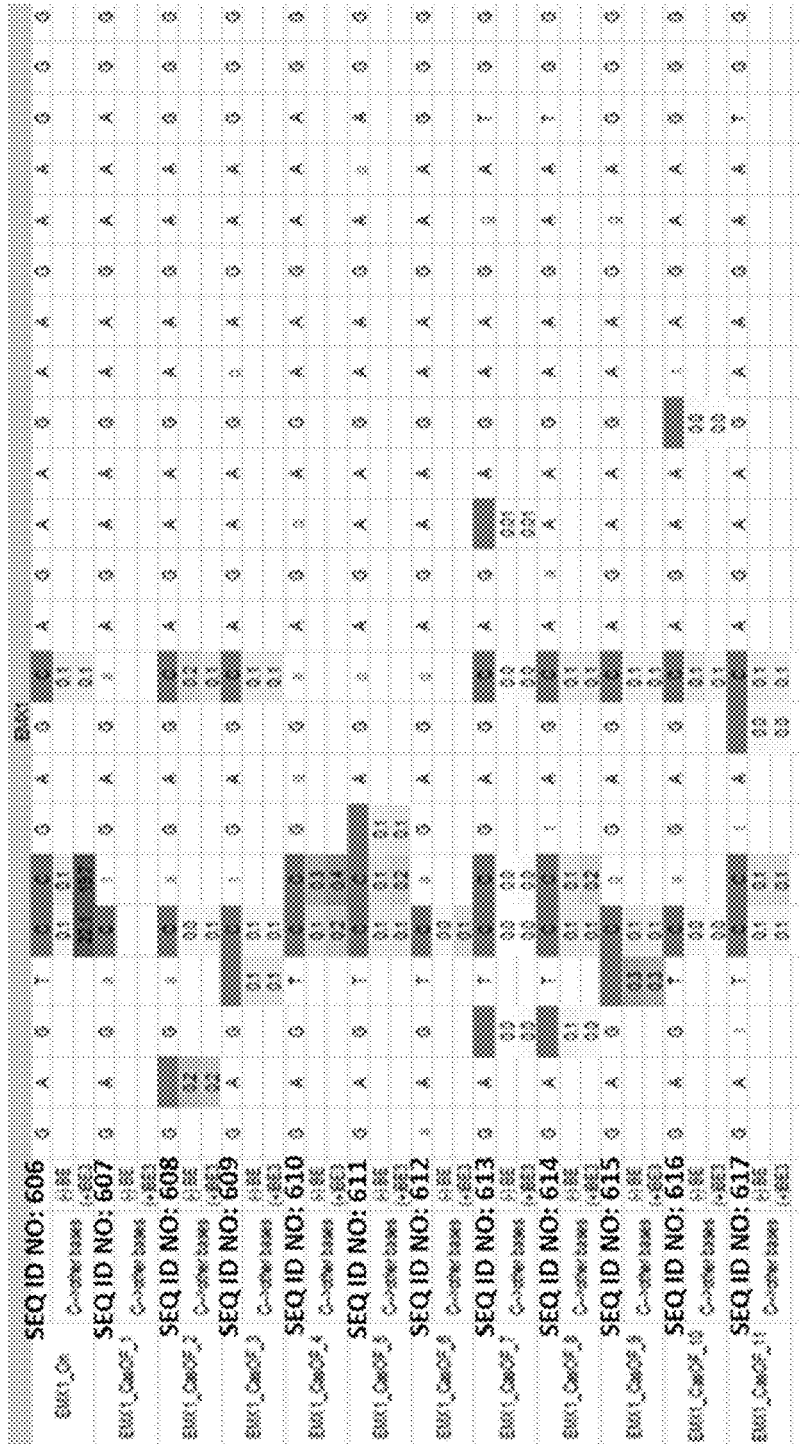
[FIG. 15a]

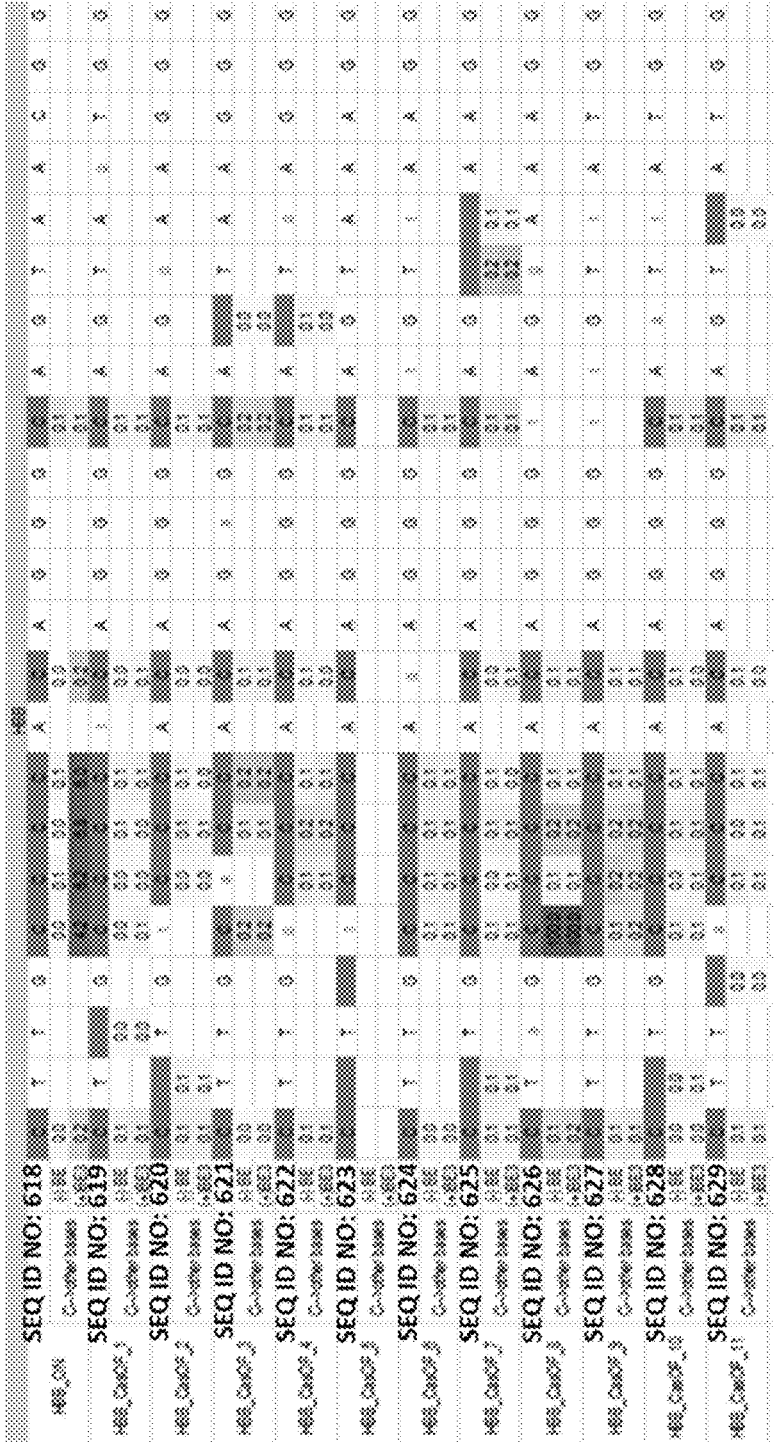
[FIG. 15b]

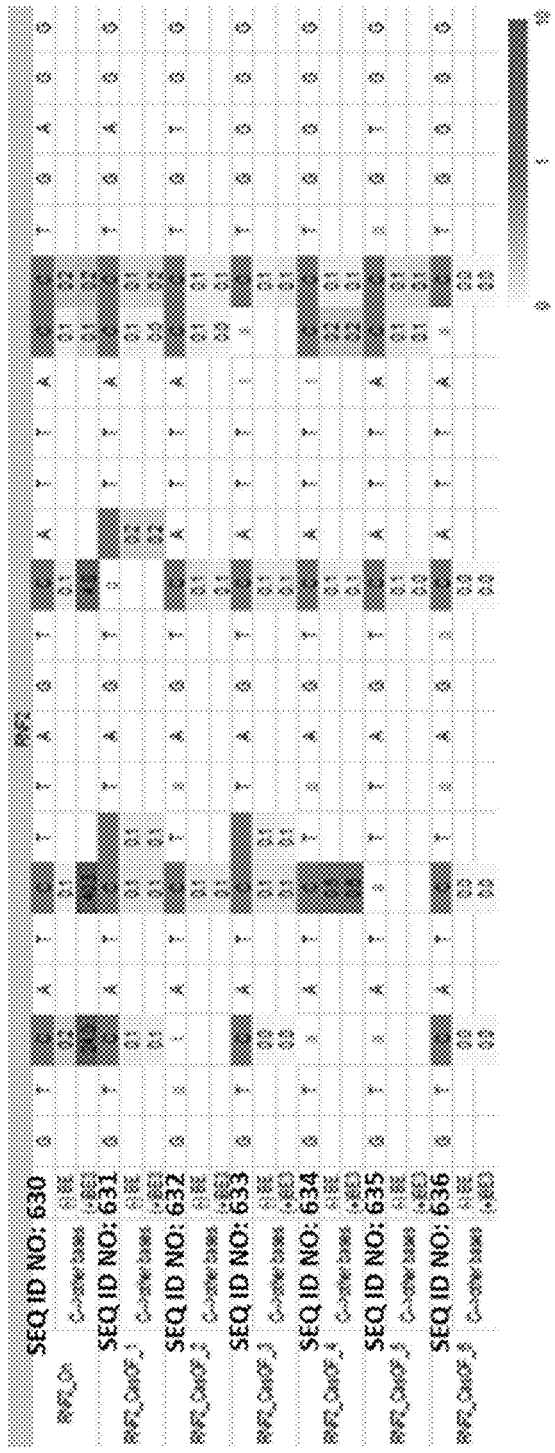
[FIG. 15c]

| | | |
|---|---|---|
| 5'-CTTGCCCCACAGGGCAGTAANGG-3' | *HBB* target sequence | SEQ ID NO: 637 |
| 5'-ggCCCCACAGGGCAGUAA-3' | gX$_{17}$ sgRNA | SEQ ID NO: 638 |
| 5'-gUGCCCCACAGGGCAGUAA-3' | gX$_{18}$ sgRNA | SEQ ID NO: 639 |
| 5'-gUUGCCCCACAGGGCAGUAA-3' | gX$_{19}$ sgRNA | SEQ ID NO: 640 |
| 5'-gCUUGCCCCACAGGGCAGUAA-3' | gX$_{20}$ sgRNA | SEQ ID NO: 641 |
| 5'-ggCUUGCCCCACAGGGCAGUAA-3' | ggX$_{20}$ sgRNA | SEQ ID NO: 642 |

[FIG. 16b]
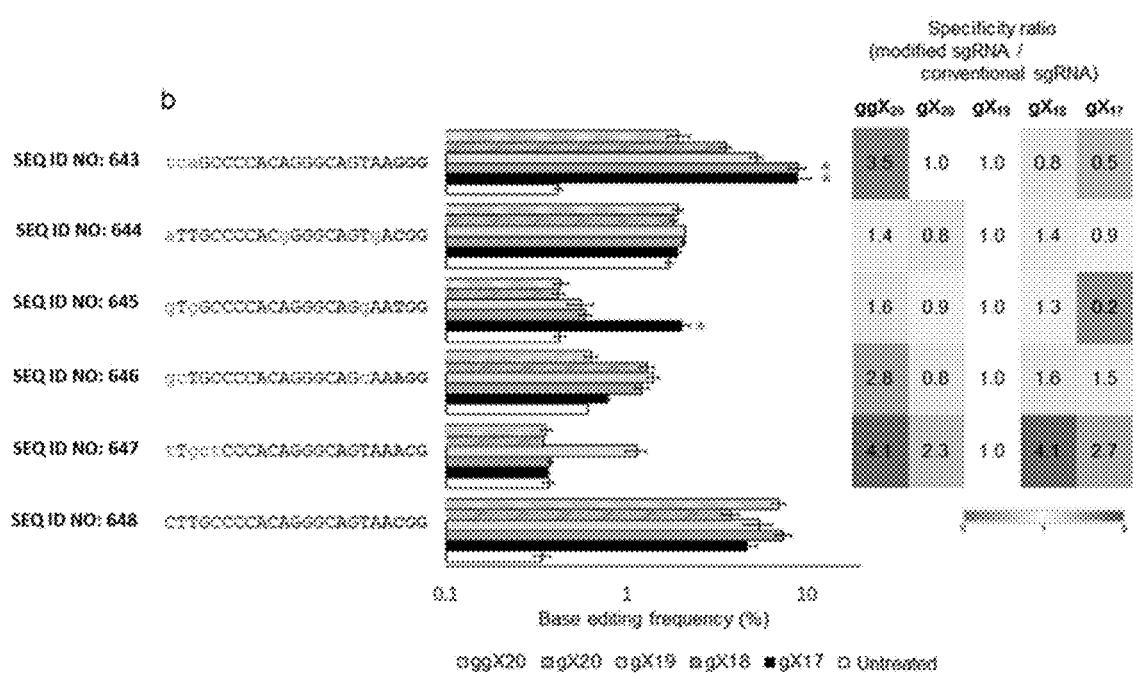

| | | |
|---|---|---|
| 5'-GAGTCCGAGCAGAAGAAGAANGG-3' | EMX1 Target sequence | SEQ ID NO: 649 |
| 5'-GTCCGAGCAGAAGAAGAA-3' | GX₁₇ sgRNA | SEQ ID NO: 650 |
| 5'-gGTCCGAGCAGAAGAAGAA-3' | gX₁₈ sgRNA | SEQ ID NO: 651 |
| 5'-GAGTCCGAGCAGAAGAAGAA-3' | GX₁₉ sgRNA | SEQ ID NO: 652 |
| 5'-gGAGTCCGAGCAGAAGAAGAA-3' | gX₂₀ sgRNA | SEQ ID NO: 653 |
| 5'-ggGAGTCCGAGCAGAAGAAGAA-3' | ggX₂₀ sgRNA | SEQ ID NO: 654 |

[FIG. 17b]
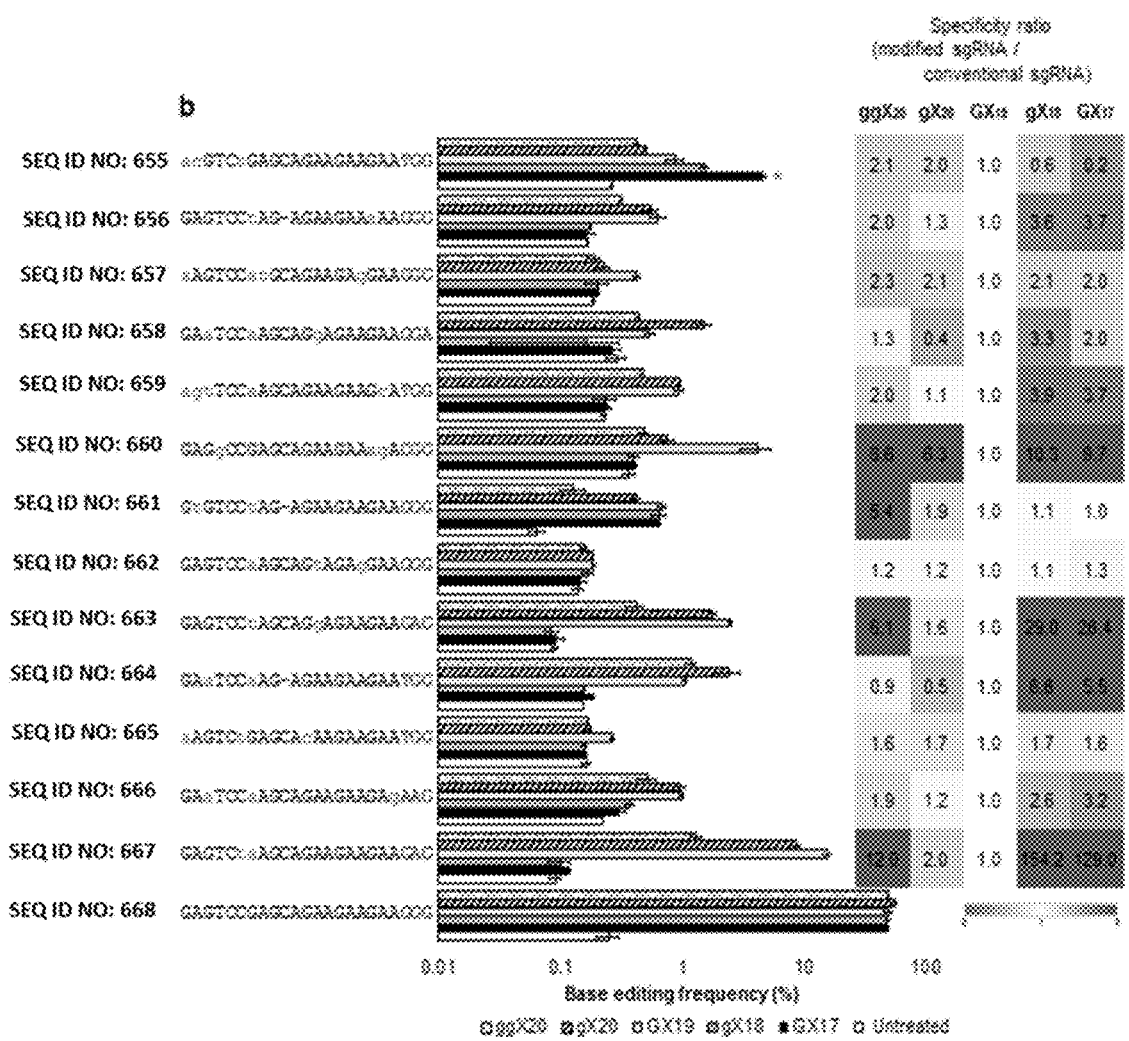

[FIG. 18a]
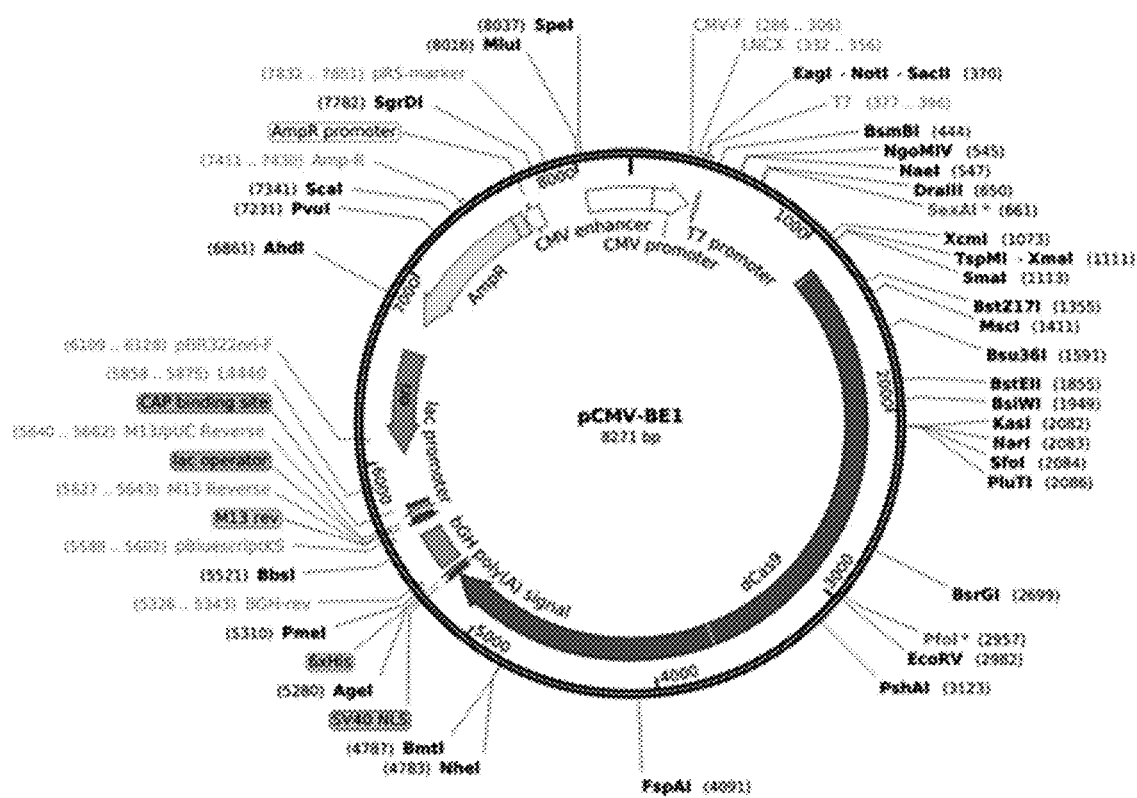

[FIG. 18b]
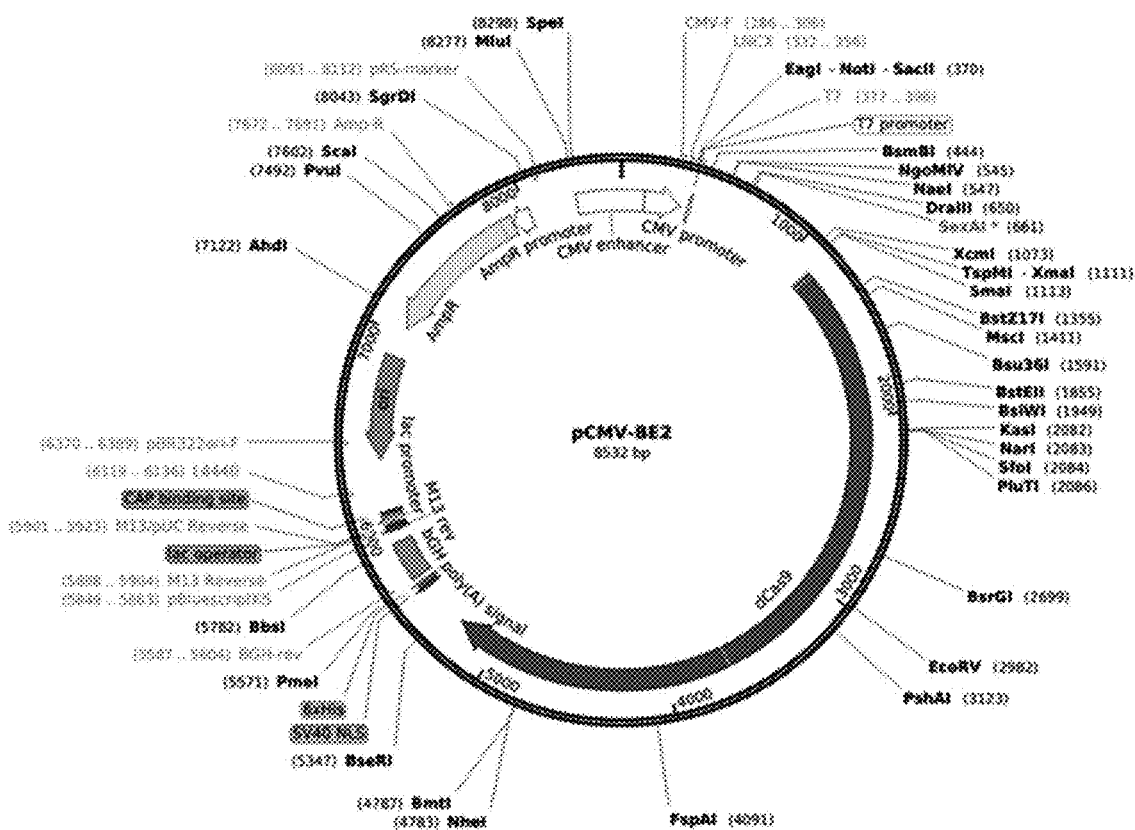

[FIG. 18c]
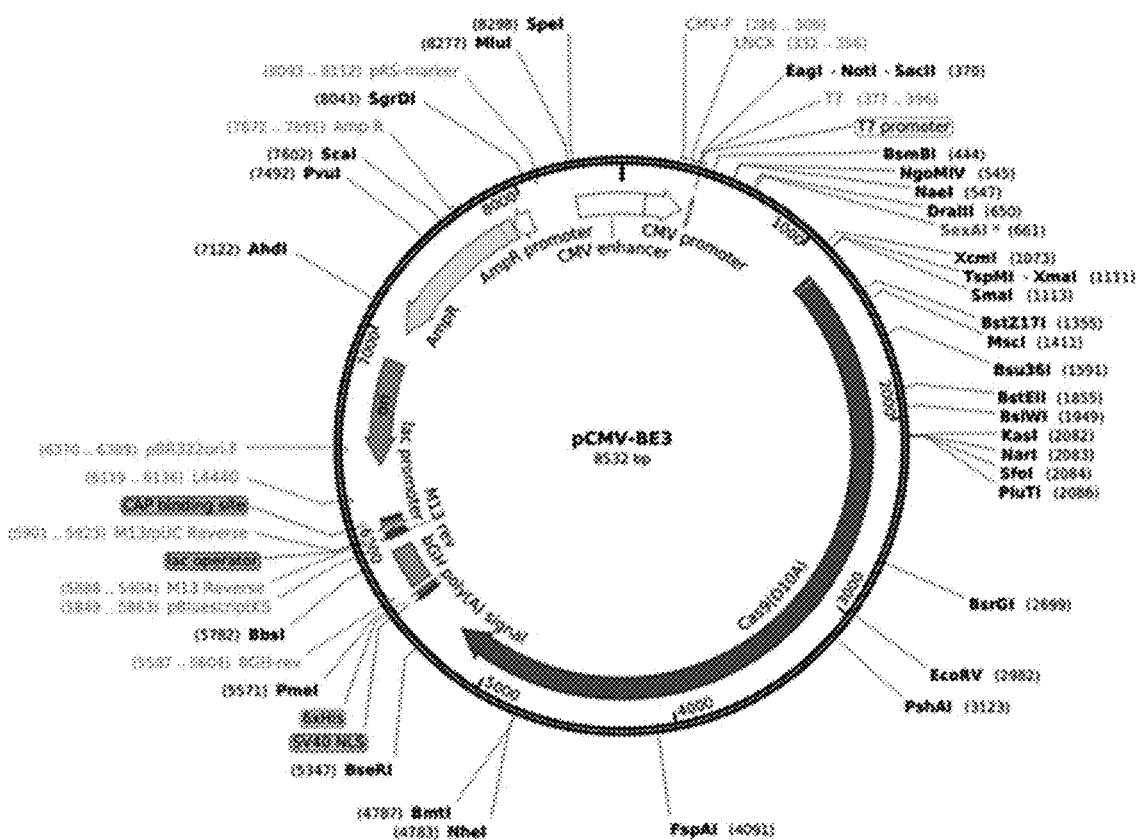

[FIG. 19]
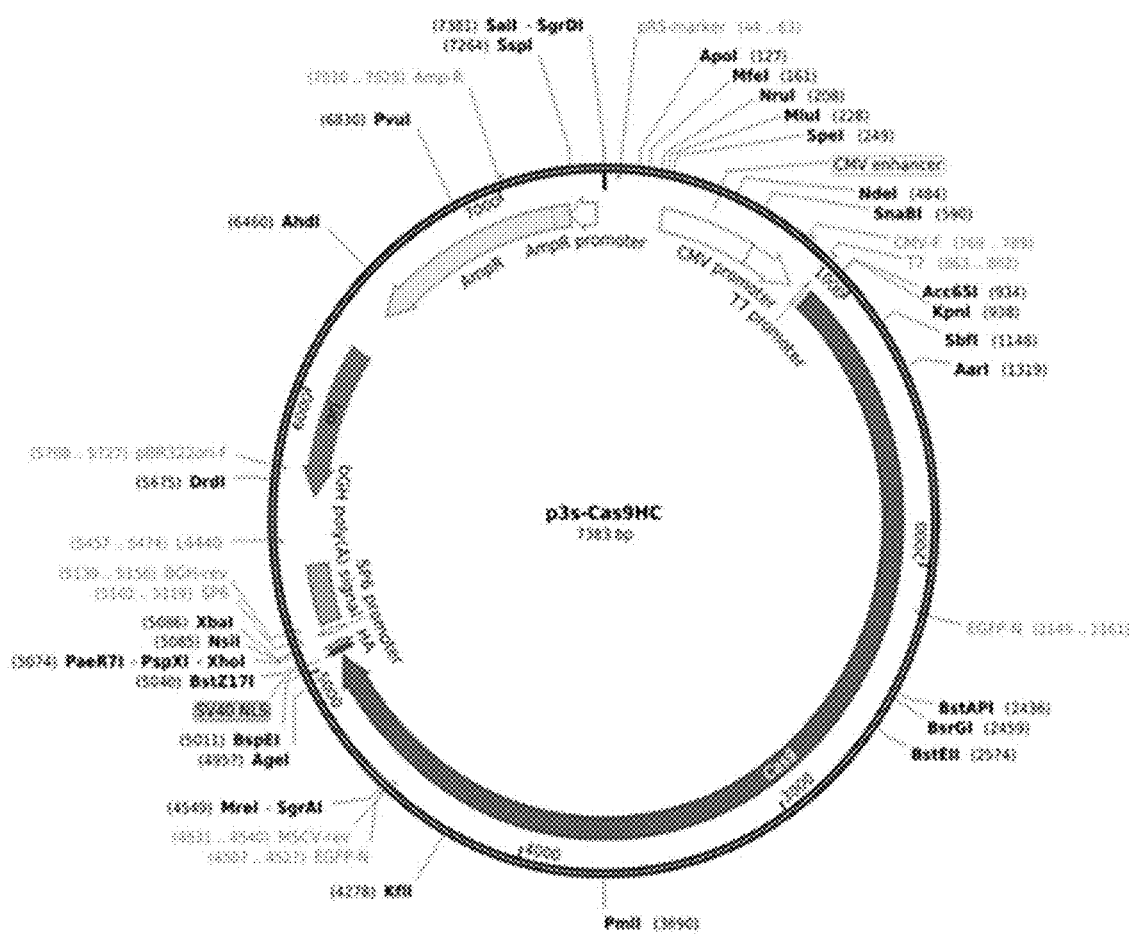

[FIG. 20]
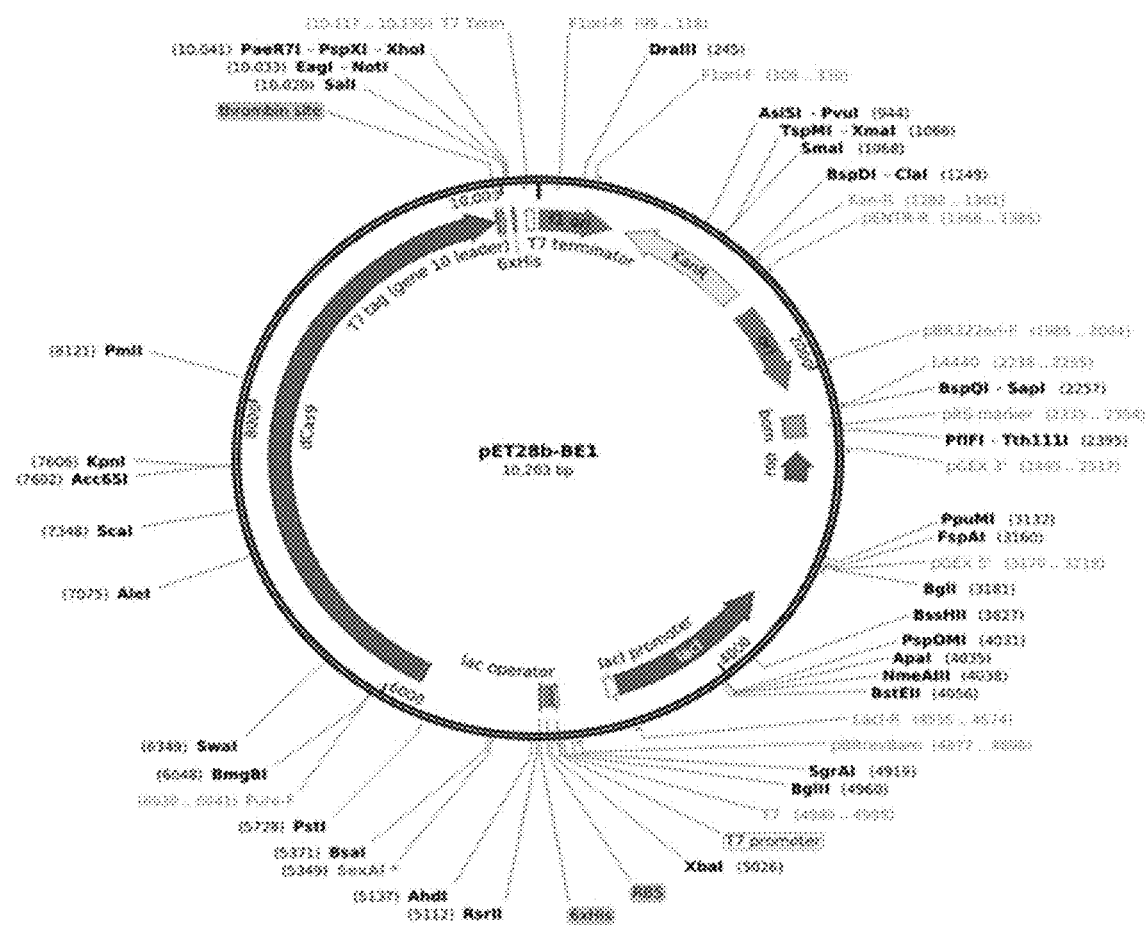

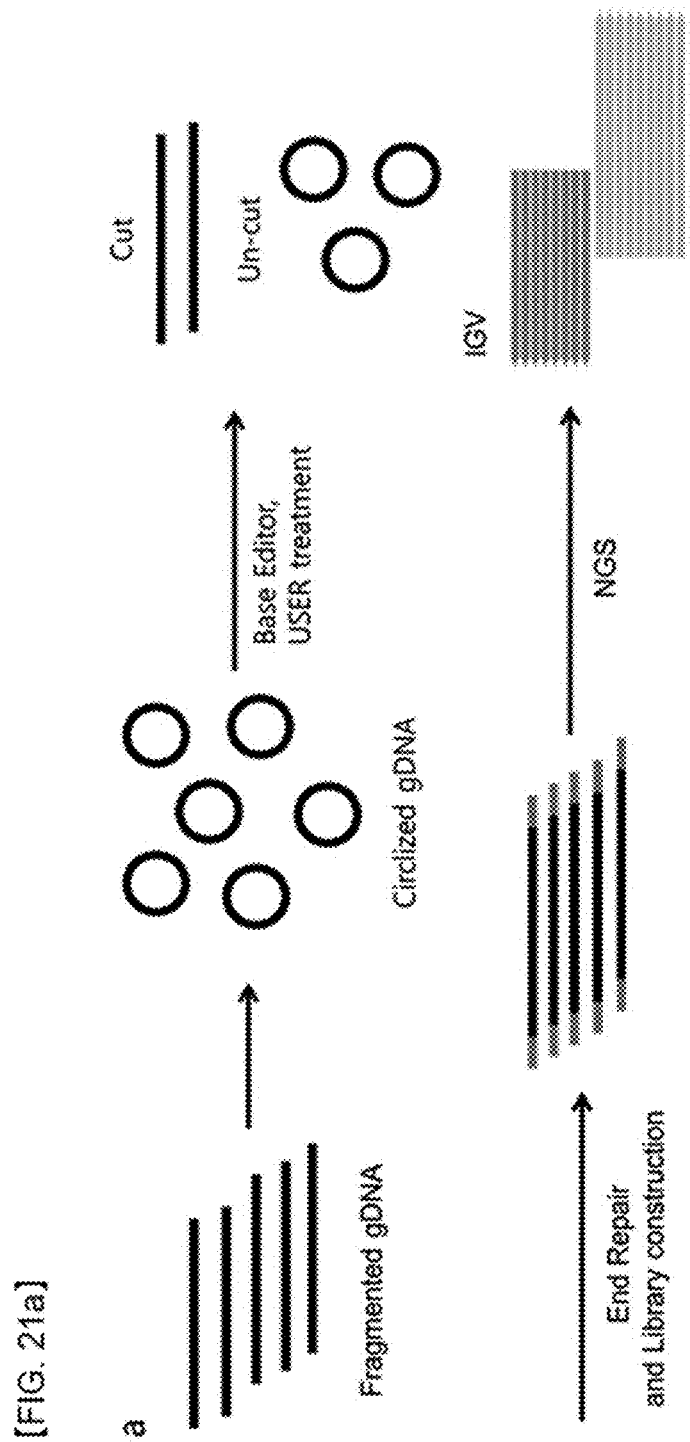
[FIG. 21a]

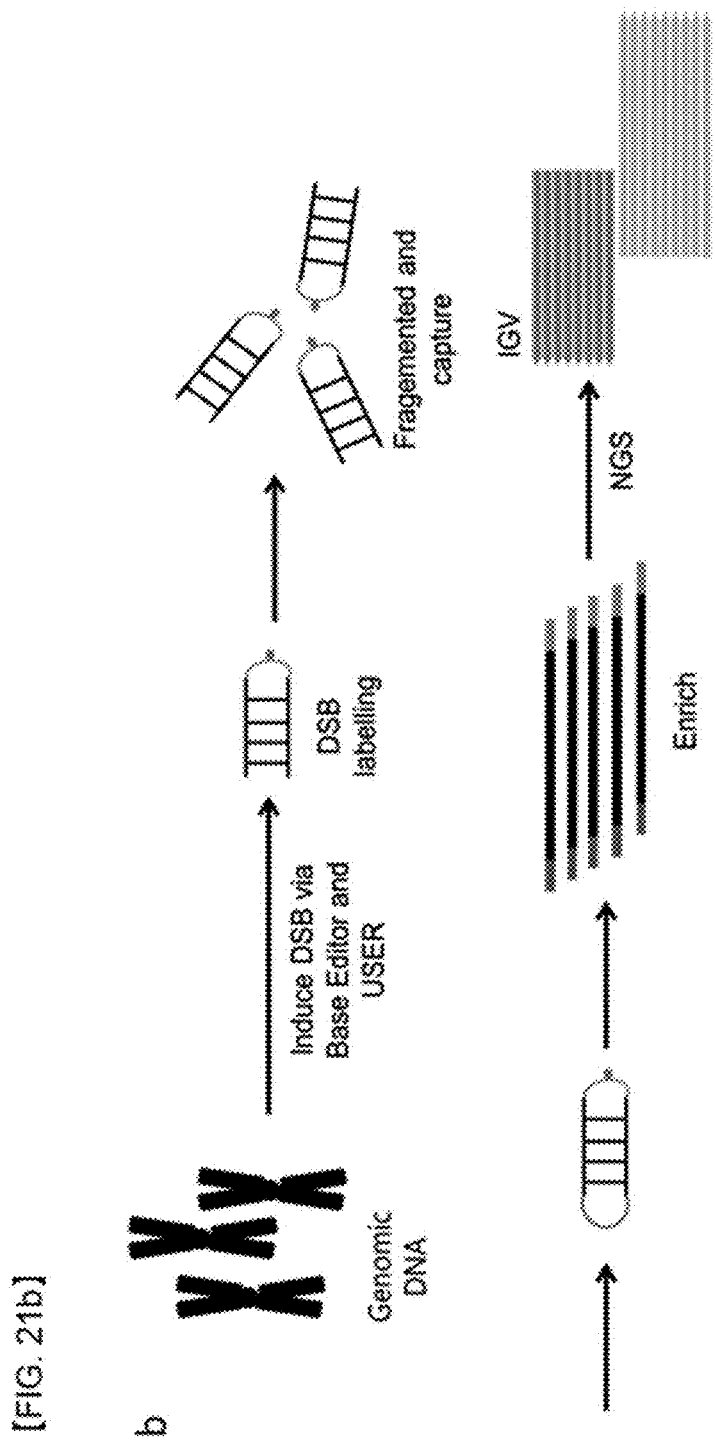
[FIG. 21b]

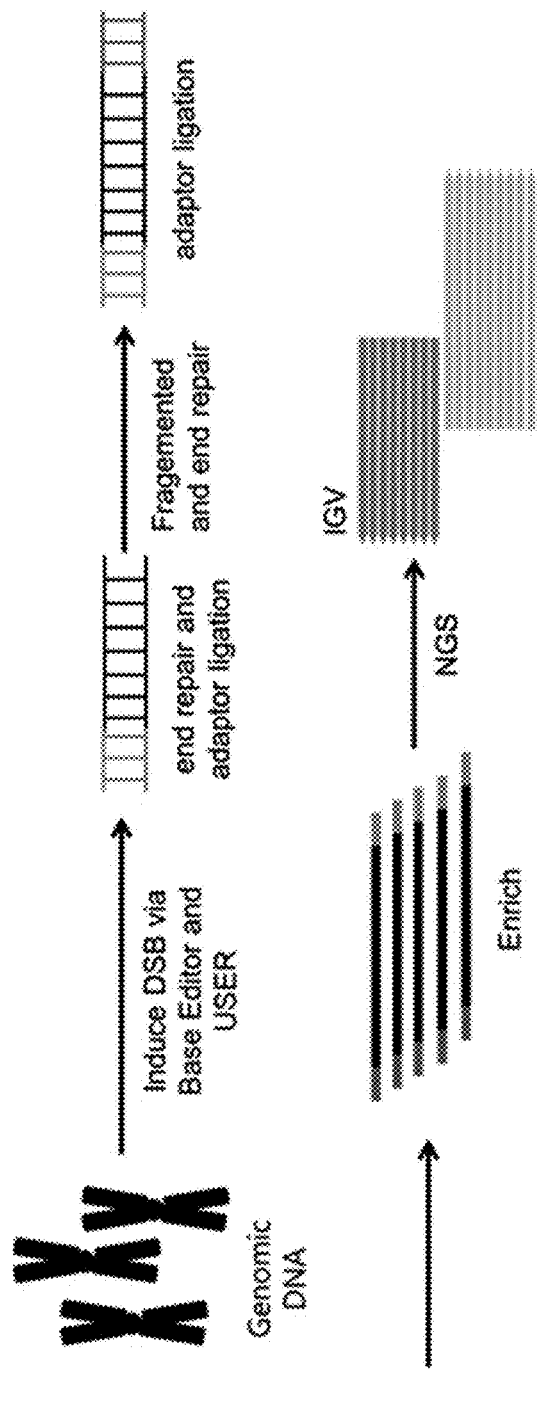

[FIG. 22]
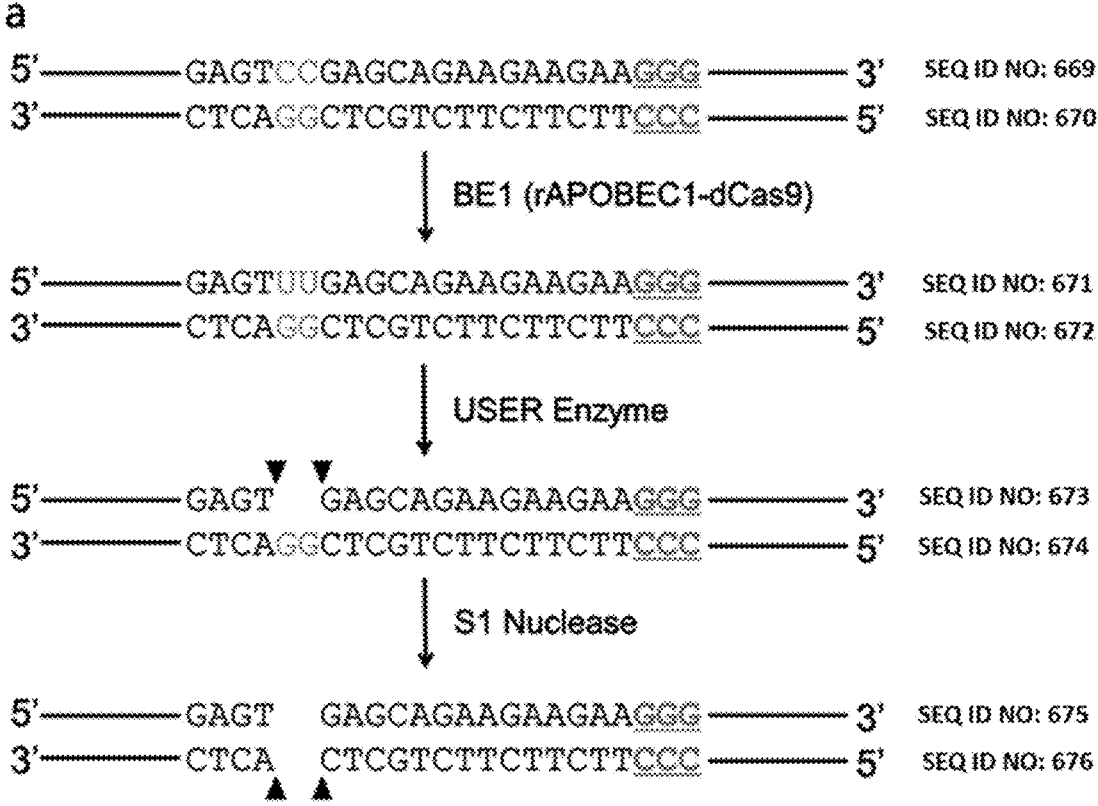

METHOD FOR IDENTIFYING DNA BASE EDITING BY MEANS OF CYTOSINE DEAMINASE

TECHNICAL FIELD

Provided are: a composition for DNA double-strand breaks (DSBs), comprising (1) a cytosine deaminase and an inactivated target-specific endonuclease, (2) a guide RNA, and (3) a uracil-specific excision reagent (USER); a method of generating DNA double-strand breaks by means of a cytosine deaminase using the composition; a method for analyzing a DNA nucleic acid sequence to which base editing has been introduced by means of a cytosine deaminase; and a method for identifying (or measuring or detecting) base editing site, base editing efficiency at on-target site, an off-target site, and/or target-specificity, by means of a cytosine deaminase.

BACKGROUND ART

Cas9-linked deaminases enable single-nucleotide conversions in a targeted manner to correct point mutations causing genetic disorders or introduce single-nucleotide variations of interest in human and other eukaryotic cells. Genome-wide target-specificities of these RNA-programmable deaminases, however, remain largely unknown.

Four different classes of programmable deaminases have been reported to date: 1) base editors (BEs) comprising catalytically-deficient Cas9 (dCas9) derived from *S. pyogenes* or D10A Cas9 nickase (nCas9) and rAPOBEC1, a cytidine deaminase from rat, 2) target-AID (activation-induced cytidine deaminase) comprising dCas9 or nCas9 and PmCDA1, an AID ortholog from sea lamprey, or human AID, 3) CRISPR-X composed of dCas9 and sgRNAs linked to MS2 RNA hairpins to recruit a hyperactive AID variant fused to MS2-binding protein, and 4) zinc-finger proteins or transcription activator-like effectors (TALEs) fused to a cytidine deaminase.

A programmable deaminase, consisting of a DNA binding module and cytidine deaminase, enables targeted nucleotide substitution or base editing in the genome without generating DNA double strand breaks (DSBs). Unlike programmable nucleas such as CRISPR-Cas9 and ZFNs, which induce small insertions or indels in the target site, programmable deaminases are able to convert C to T(U) (or to a lower frequency, C to G or A) within window of several nucleotides at a target site. Programmable deaminases can correct point mutations that cause genetic disorders in human cells, animals and plants, or can generate single nucleotide polymorphisms (SNPs).

Despite broad interest in base editing by programmable deaminase, there has not been developed any means for analyzing target-specificity of programmable deaminase to whole genome. Therefore, it is required to develop technologies to analyze target-specificity of programmable diaminnase to whole genome, thereby analyzing base editing efficiency, off-target site, and off-target effect of programmable diaminnase.

DISCLOSURE

Technical Problem

In this description, provided are technologies for analyzing target-specificity of a programmable deaminase to whole genome, and for analyzing base editing efficiency, off-target site, off-target effect, and the like of a programmable deaminase.

An embodiment provides a composition for DNA double strand breaks (DSBs) comprising (1) a cytosine deaminase and an inactivated target-specific endonuclease, or a cytosine deaminase coding gene and an inactivated target-specific endonuclease coding gene, or a plasmid comprising a cytosine deaminase coding gene and an inactivated target-specific endonuclease coding gene; (2) a guide RNA; and (3) a uracil-specific excision reagent (USER).

Another embodiment provides a method of generating DNA double strand break, the method comprising:
  (i) introducing or contacting (a) a cytosine deaminase and an inactivated target-specific endonuclease, or (b) a cytosine deaminase coding gene and an inactivated target-specific endonuclease coding gene, or (c) a plasmid comprising a cytosine deaminase coding gene and an inactivated target-specific endonuclease coding gene, into a cell or with DNA isolated from a cell, together with a guide RNA; and
  (ii) treating a uracil-specific excision reagent (USER).

Another embodiment provides a method of analyzing nucleic acid sequence of DNA in which a base editing is introduced by cytosine deaminase, comprising:
  (i) introducing or contacting (a) a cytosine deaminase and an inactivated target-specific endonuclease, or (b) a cytosine deaminase coding gene and an inactivated target-specific endonuclease coding gene, or (c) a plasmid comprising a cytosine deaminase coding gene and an inactivated target-specific endonuclease coding gene, into a cell or with DNA isolated from a cell, together with a guide RNA;
  (ii) treating a uracil-specific excision reagent (USER), to generate double strand break in the DNA; and
  (iii) analyzing nucleic acid sequence of the cleaved DNA fragment.

Another embodiment provides a method of identifying (or measuring or detecting) a base editing site, a base editing efficiency at on-target site, an off-target site, and/or a target-specificity, of cytosine deaminase, comprising:
  (i) introducing or contacting (a) a cytosine deaminase and an inactivated target-specific endonuclease, or (b) a cytosine deaminase coding gene and an inactivated target-specific endonuclease coding gene, or (c) a plasmid comprising a cytosine deaminase coding gene and an inactivated target-specific endonuclease coding gene, into a cell or with DNA isolated from a cell, together with a guide RNA;
  (ii) treating a uracil-specific excision reagent (USER), to generate double strand break in the DNA;
  (iii) analyzing nucleic acid sequence of the cleaved DNA fragment; and
  (iv) identifying the double strand break site in the nucleic acid sequence read obtained by said analysis.

Technical Solution

In this description, a modified Digenome-seq is used to assess specificities of a base editor (e.g., Base Editor 3 (BE3), composed of a Cas9 nickase and a deaminase, in the human genome. Genomic DNA is treated with BE3 and a mixture of DNA-modifying enzymes in vitro to produce DNA double-strand breaks (DSBs) at uracil-containing sites. BE3 off-target sites are computationally identified using whole genome sequencing data. BE3 is highly specific, inducing cytosine-to-uracil conversions at just 18±9 sites in the human genome. Digenome-seq is sensitive enough to capture BE3 off-target sites with a substitution frequency of 0.1%. Interestingly, BE3 and Cas9 off-target sites are often different, calling for independent assessments of genome-wide specificities.

First, a technique for generating double strand breaks in DNA using cytosine deaminase that does not induce double strand breakage in DNA, is provided.

An embodiment provides a composition for double strand breaks (DSBs) comprising (1) a cytosine deaminase and an inactivated target-specific endonuclease, or a cytosine deaminase coding gene and an inactivated target-specific endonuclease coding gene, or a plasmid comprising a cytosine deaminase coding gene and an inactivated target-specific endonuclease coding gene; (2) a guide RNA; and (3) a uracil-specific excision reagent (USER). The composition may be used in inducing DNA double-strand breaks using cytosine deaminase.

The cytosine deaminase refers to any enzyme having activity to convert a cytosine, which is found in nucleotide (e.g., cytosine present in double stranded DNA or RNA), to uracil (C-to-U conversion activity or C-to-U editing activity). The cytosine deaminase converts cytosine positioned on a strand where a PAM sequence linked to target sequence is present, to uracil. In an embodiment, the cytosine deaminase may be originated from mammals including primates such as humans and monkeys, rodents such as rats and mice, and the like, but not be limited thereto. For example, the cytosine deaminase may be at least one selected from the group consisting of enzymes belonging to APOBEC (apolipoprotein B mRNA editing enzyme, catalytic polypeptide-like) family, and for example, may be at least one selected from the following group, but not be limited to:

APOBEC1: *Homo sapiens* APOBEC1 (Protein: GenBank Accession Nos. NP_001291495.1, NP_001635.2, NP_005880.2, etc.; gene (mRNA or cDNA; described in the order of the above listed corresponding proteins): GenBank Accession Nos. NM_001304566.1, NM_001644.4, NM_005889.3, etc.), *Mus musculus* APOBEC1 (protein: GenBank Accession Nos. NP_001127863.1, NP_112436.1, etc.; gene: GenBank Accession Nos. NM_001134391.1, NM_031159.3, etc.);

APOBEC2: *Homo sapiens* APOBEC2 (protein: GenBank Accession No. NP_006780.1, etc.; gene: GenBank Accession No. NM_006789.3 etc.), mouse APOBEC2 (protein: GenBank Accession No. NP_033824.1, etc.; gene: GenBank Accession No. NM_009694. 3, etc.);

APOBEC3B: *Homo sapiens* APOBEC3B (protein: GenBank Accession Nos. NP_001257340.1, NP_004891.4, etc.; gene: GenBank Accession Nos. NM_001270411.1, NM_004900.4, etc.), *Mus musculus* APOBEC3B (proteins: GenBank Accession Nos. NP_001153887.1, NP_001333970.1, NP_084531.1, etc.; gene: GenBank Accession Nos. NM_001160415.1, NM_001347041.1, NM_030255.3, etc.);

APOBEC3C: *Homo sapiens* APOBEC3C (protein: GenBank Accession No. NP_055323.2 etc.; gene: GenBank Accession No. NM 014508.2 etc.);

APOBEC3D (including APOBEC3E): *Homo sapiens* APOBEC3D (protein: GenBank Accession No. NP_689639.2, etc.; gene: GenBank Accession No. NM 152426.3 etc.);

APOBEC3F: *Homo sapiens* APOBEC3F (protein: GenBank Accession Nos. NP_660341.2, NP_001006667.1, etc.; gene: GenBank Accession Nos. NM_145298.5, NM_001006666.1, etc.);

APOBEC3G: *Homo sapiens* APOBEC3G (protein: GenBank Accession Nos. NP_068594.1, NP_001336365.1, NP_001336366.1, NP_001336367.1, etc.; gene: GenBank Accession Nos. NM_021822.3, NM_001349436.1, NM_001349437.1, NM_001349438.1, etc.);

APOBEC3H: *Homo sapiens* APOBEC3H (protein: GenBank Accession Nos. NP_001159474.2, NP_001159475.2, NP_001159476.2, NP_861438.3, etc.; gene: GenBank Accession Nos. NM_001166002.2, NM_001166003. 2, NM_001166004.2, NM_181773.4, etc.);

APOBEC4 (including APOBEC3E): *Homo sapiens* APOBEC4 (protein: GenBank Accession No. NP_982279.1, etc.; gene: GenBank Accession No. NM_203454.2 etc.); mouse APOBEC4 (protein: GenBank Accession No. NP_001074666.1, etc.; gene: GenBank Accession No. NM_001081197.1, etc.); and Activation-induced cytidine deaminase (AICDA or AID): *Homo sapiens* AID (Protein: GenBank Accession Nos. NP_001317272.1, NP_065712.1, etc; Genes: GenBank Accession Nos. NM_001330343 0.1, NM_020661.3, etc.); mouse AID (protein: GenBank Accession No. NP_033775.1, etc., gene: GenBank Accession No. NM_009645.2, etc.), and the like.

As used herein, a target-specific nuclease is also referred to as a programmable nuclease, and refers to all types of endonuclease that are capable of recognizing and cleaving a specific target position on a genomic DNA.

For example, the target-specific nuclease may be at least one selected from the group consisting of all nuclases capable of recognizing a particular sequence of a target gene and having a nucleotide-cleavage activity thereby inducing insertion and/or deletion (Indel) on the target gene.

For example, the target-specific nuclease may be at least one selected from the group consisting of, but not limited to:

a transcription activator-like effector nuclease (TALEN) wherein and a cleavage domain and a transcription activator-like effector domain derived from a plant pathogenic gene that is a domain that recognizes a specific target sequence on the genome are fused;

a zinc-finger nuclease;

a meganuclease;

a RGEN (RNA-guided engineered nuclease; e.g., Cas9, Cpf1, etc.) derived from microorganism immune system, CRISPR; and an Ago homolog, DNA-guided endonuclease.

According to an embodiment, the target-specific nuclease may be at least one selected from the group consisting of endonucleases involved in type II and/or type V of the CRISPR (Clustered regularly interspaced short palindromic repeats) system, such as Cas protein (e.g., Cas9 protein (CRISPR associated protein 9)), Cpf1 protein (CRISPR from *Prevotella* and *Francisella* 1), etc. In this regard, the target-specific nuclease may further comprise a target DNA-specific guide RNA for guiding to an on-target site in genomic DNA. The guide RNA may be one transcribed in vitro, for example, from an oligonucleotide duplex or a plasmid template, but is not limited thereto. The target-specific nuclease and the guide RNA may form a ribonucleic acid-protein complex, to act in the form of ribonucleic acid protein (RNP).

Cas9 protein is a main protein component of the CRISPR/Cas system, which can function as an activated endonuclease or nickase.

Cas9 protein or gene information thereof may be acquired from a well-known database such as the GenBank of NCBI (National Center for Biotechnology Information). For example, the Cas9 protein may be at least one selected from the group consisting of, but not limited to:
- a Cas9 protein derived from *Streptococcus* sp., for example, *Streptococcus pyogenes* (e.g., SwissProt Accession number Q99ZW2(NP_269215.1) (encoding gene: SEQ ID NO: 229);
- a Cas9 protein derived from *Campylobacter* sp., for example, *Campylobacter jejuni*;
- a Cas9 protein derived from *Streptococcus* sp., for example, *Streptococcus* thermophiles or Streptocuccus aureus;
- a Cas9 protein derived from *Neisseria meningitidis*;
- a Cas9 protein derived from *Pasteurella* sp., for example, *Pasteurella multocida*; and
- a Cas9 protein derived from *Francisella* sp., for example, *Francisella novicida*.

Cpf1 protein, which is an endonuclease of a new CRISPR system distinguished from the CRISPR/Cas system, is small in size compared to Cas9, requires no tracrRNA, and can function with a single guide RNA. In addition, Cpf1 can recognize thymidine-rich PAM (protospacer-adjacent motif) sequences and produces cohesive double-strand breaks (cohesive end).

For example, the Cpf1 protein may be an endonuclease derived from Candidatus spp., Lachnospira spp., *Butyrivibrio* spp., Peregrinibacteria, Acidominococcus spp., *Porphyromonas* spp., *Prevotella* spp., *Francisella* spp., Candidatus Methanoplasma), or *Eubacterium* spp. Examples of the microorganism from which the Cpf1 protien may be derived include, but are not limited to, Parcubacteria bacterium (GWC2011_GWC2_44_17), Lachnospiraceae bacterium (MC2017), *Butyrivibrio* proteoclasiicus, Peregrinibacteria bacterium (GW2011_GWA_33_10), Acidaminococcus sp. (BV3L6), *Porphyromonas macacae*, Lachnospiraceae bacterium (ND2006), *Porphyromonas* crevioricanis, *Prevotella disiens*, *Moraxella* bovoculi (237), Smiihella sp. (SC_KO8D17), Leptospira inadai, Lachnospiraceae bacterium (MA2020), *Francisella novicida* (U112), Candidatus Methanoplasma *termitum*, Candidatus Paceibacter, and *Eubacterium* eligens.

The target-specific endonuclease may be a microorganism-derived protein or an artificial or non-naturally occurring protein obtained by a recombinant or synthesis method. By way of example, the target-specific endonuclease (e.g., Cas9, Cpf1, and the like) may be a recombinant protein produced with a recombinant DNA. As used herein, the term "recombinant DNA (rDNA)" refers to a DNA molecule artificially made by genetic recombination, such as molecular cloning, to include therein heterogenous or homogenous genetic materials derived from various organisms. For instance, when a target-specific endonuclease is produced in vivo or in vitro by expressing a recombinant DNA in an appropriate organism, the recombinant DNA may have a nucleotide sequence reconstituted with codons selected from among codons encoding the protein of interest in order to be optimal for expression in the organism.

The term "inactivated target-specific endonuclease", as used herein, refers to a target-specific endonuclease that lacks the endonuclease activity of cleaving a DNA duplex. The inactivated target-specific endonuclease may be at least one selected from among inactivated target-specific endonucleases that lack endonuclease activity, but retain nickase activity, and inactivated target-specific endonuclease that lack both endonuclease activity and nickase activity. In an embodiment, the inactivated target-specific endonuclease may retain nickase activity. In this case, when a cytosine base is converted to a uracil base, a nick is introduced into a strand on which cytosine-to-uracil conversion occurs, or an opposite strand thereto simultaneously or sequentially irrespective of order (for example, a nick is introduced at a position between third and fourth nucleotides in the direction toward the 5' end of a PAM sequence on a strand opposite to a strand having the PAM sequence). The modification (mutation) of such target-specific endonucleases may include substitution of a catalytic aspartate residue (for *Streptococcus pyogenes*-derived Cas9 protein, for example, at least one selected from the group consisting of aspartic acid at position 10 (D10)) with a different amino acid, and the different amino acid may be alanine, but is not limited thereto.

As used herein, the expression "different amino acid" may be intended to refer to an amino acid selected from among alanine, isoleucine, leucine, methionine, phenylalanine, proline, tryptophan, valine, asparagine, cysteine, glutamine, glycine, serine, threonine, tyrosine, aspartic acid, glutamic acid, arginine, histidine, lysine, and all known variants thereof, exclusive of the amino acid having a wild-type protein retained at the original substitution position.

In one embodiment, when the inactivated target-specific endonuclease is a modified Cas9 protein, the Cas9 protein may be at least one selected from the group consisting of modified Cas9 that lacks endonuclease activity and retains nickase activity as a result of introducing mutation (for example, substitution with a different amino acid) to D10 of *Streptococcus pyogenes*-derived Cas9 protein (e.g., SwissProt Accession number Q99ZW2(NP_269215.1)), and modified Cas9 protein that lacks both endonuclease activity and nickase activity as a result of introducing mutations (for example, substitution with different mutations) to both D10 and H840 of *Streptococcus pyogenes*-derived Cas9 protein. In Cas9 protein, for example, the mutation at D10 may be D10A mutation (the amino acid D at position 10 in Cas9 protein is substituted with A; below, mutations introduced to Cas9 are expressed in the same manner), and the mutation at H840 may be H840A mutation.

The cytidine deaminase and the inactivated target-specific endonuclease may be used in the form of a fusion protein in which they are fused to each other directly or via a peptide linker (for example, existing in the order of cytidine deaminase-inactivated target-specific endonuclease in the N- to C-terminus direction (i.e., inactivated target-specific endonuclease fused to the C-terminus of cytidine deaminase) or in the order of inactivated target-specific endonuclease-cytidine deaminase in the N- to C-terminus direction (i.e., cytidine deaminase fused to the C-terminus of inactivated target-specific endonuclease) (or may be contained in the composition), a mixture of a purified cytidine deaminase or mRNA coding therefor and an inactivated target-specific endonuclease or mRNA coding therefor (or may be contained in the composition), a plasmid carrying both a cytidine deaminase-encoding gene and an inactivated target-specific endonuclease-encoding gene (e.g., the two genes arranged to encode the fusion protein described above) (or may be contained in the composition), or a mixture of a cytidine deaminase expression plasmid and an inactivated target-specific endonuclease expression plasmid which carry a cytidine deaminase-encoding gene and an inactivated target-specific endonuclease-encoding gene, respectively (or may be contained in the composition). In one embodiment, the cytidine deaminase and the inactivated target-specific endonuclease may be in the form of a fusion protein in which they exist in the order of cytidine deaminase-inactivated target-specific endonuclease in the N- to C-terminus direction or in the order of inactivated target-specific endonuclease-cytidine deaminase in the N- to C-terminus direction, or a single plasmid in which a cytidine deaminase-encoding gene and an inactivated target-specific endonuclease-encoding gene are contained to encode the fusion protein.

So long as it carries the cytidine deaminase-encoding gene and/or the inactivated target-specific endonuclease-encoding gene and contains an expression system capable of expressing the gene in a host cell, any plasmid may be used. The plasmid contains elements for expressing a target gene, which include a replication origin, a promoter, an operator, and a terminator, and may further comprise an enzyme site suitable for introduction into the genome of a host cell (e.g., restriction enzyme site), a selection marker for identifying successful introduction into a host cell, a ribosome binding site (RBS) for translation into a protein, and/or a transcriptional regulatory factor. The plasmid may be one used in the art, for example, at least one selected from the group consisting of, but not limited to, pcDNA series, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19. The host cell may be selected from among cells to which base editing or a double-strand break is intended to introduced by the cytidine deaminase (for example, eukaryotic cells including mammal cells such as human cells) and all cells that can express the cytidine deaminase-encoding gene and/or the inactivated target-specific endonuclease-encoding gene into cytidine deaminase and inactivated target-specific endonuclease, respectively (for example, *E. coli*, etc.).

The guide RNA, which acts to guide a mixture or a fusion protein of the cytidine deaminase and the inactivated target-specific endonuclease to an on-target site, may be at least one selected from the group consisting of CRISPR RNA (crRNA), trans-activating crRNA (tracrRNA), and single guide RNA (sgRNA), and may be, in detail, a crRNA:tracrRNA duplex in which crRNA and tracrRNA is coupled to each other, or a single-strand guide RNA (sgRNA) in which crRNA or a part thereof is connected to tracrRNA or a part thereof via an oligonucleotide linker.

Concrete sequences of the guide RNA may be appropriately selected, depending on kinds of the target-specific endonucleases used, or origin microorganisms thereof, and are an optional matter which could easily be understood by a person skilled in the art.

When a *Streptococcus pyogenes*-derived Cas9 protein is used as a target-specific endonuclease, crRNA may be represented by the following General Formula 1:

(General Formula 1)
(SEQ ID NO: 233)
5'-(N$_{cas9}$)$_l$-(GUUUUAGAGCUA)-(Xcas9)m-3' wherein,
N$_{cas9}$ is a targeting sequence, that is, a region determined according to a sequence at an on-target site in a target gene (i.e., a sequence hybridizable with a sequence of an on-target site), I represents a number of nucleotides included in the targeting sequence and is an integer of 17 to 23 or 18 to 22, for example, 20;

the region including 12 consecutive nucleotides (GUUUUAGAGCUA; SEQ ID NO: 230) adjacent to the 3'-terminus of the targeting sequence is essential for crRNA, X$_{cas9}$ is a region including m nucleotides present at the 3'-terminal site of crRNA (that is, present adjacent to the 3'-terminus of the essential region), and m may be an integer of 8 to 12, for example, 11 wherein the m nucleotides may be the same or different and are independently selected from the group consisting of A, U, C, and G.

In an embodiment, the X$_{cas9}$ may include, but is not limited to, UGCUGUUUUG (SEQ ID NO: 231).

In addition, the tracrRNA may be represented by the following General Formula 2:

(General Formula 2)
(SEQ ID NO: 234)
5'-(Y$_{cas9}$)$_p$-(UAGCAAGUUAAAAUAAGGCUAGUCCGU

UAUCAACUUGAAAAAGUGGCACCGAGUCGGUGC)-3' wherein,
the region represented by 60 nucleotides (UAGCAAGUUAAAAUAAGGCUAGU-CCGUUAUCAACUUGAAAAAGUGGCA CCGA-GUCGGUGC; SEQ ID NO: 232) is essential for tracrRNA, Y$_{cas9}$ is a region including p nucleotides present adjacent to the 3'-terminus of the essential region, and p may be an integer of 6 to 20, for example, 8 to 19 wherein the p nucleotides may be the same or different and are independently selected from the group consisting of A, U, C, and G.

Further, sgRNA may form a hairpin structure (stem-loop structure) in which a crRNA moiety including the targeting sequence and the essential region thereof and a tracrRNA moiety including the essential region (60 nucleotides) thereof are connected to each other via an oligonucleotide linker (responsible for the loop structure). In greater detail, the sgRNA may have a hairpin structure in which a crRNA moiety including the targeting sequence and essential region thereof is coupled with the tracrRNA moiety including the essential region thereof to form a double-strand RNA molecule with connection between the 3' end of the crRNA moiety and the 5' end of the tracrRNA moiety via an oligonucleotide linker.

In one embodiment, sgRNA may be represented by the following General Formula 3:

(General Formula 3)
(SEQ ID NO: 235)
5'-(N$_{cas9}$)$_l$-(GUUUUAGAGCUA)-(oligonucleotide linker)-(UAGCAAGUUAAAAUAAGGCUAGUCCGUUAUCAAC

UUGAAAAAGUGGCACCGAGUCGGUGC)-3' wherein, (N$_{cas9}$)$_l$ is a targeting sequence defined as in General Formula 1.

The oligonucleotide linker included in the sgRNA may be 3-5 nucleotides long, for example 4 nucleotides long in which the nucleotides may be the same or different and are independently selected from the group consisting of A, U, C, and G.

The crRNA or sgRNA may further contain 1 to 3 guanines (G) at the 5' end thereof (that is, the 5' end of the targeting sequence of crRNA).

The tracrRNA or sgRNA may further comprise a terminator inclusive of 5 to 7 uracil (U) residues at the 3' end of the essential region (60 nt long) of tracrRNA.

The target sequence for the guide RNA may be about 17 to about 23 or about 18 to about 22, for example, 20 consecutive nucleotides adjacent to the 5' end of PAM (Protospacer Adjacent Motif (for *S. pyogenes* Cas9, 5'-NGG-3' (N is A, T, G, or C)) on a target DNA.

As used herein, the term "the targeting sequence" of guide RNA hybridizable with the target sequence for the guide RNA refers to a nucleotide sequence having a sequence complementarity of 50% or higher, 60% or higher, 70% or higher, 80% or higher, 90% or higher, 95% or higher, 99% or higher, or 100% to a nucleotide sequence of a complementary strand to a DNA strand on which the target sequence exists (i.e., a DNA strand having a PAM sequence (5'-NGG-3' (N is A, T, G, or C))) and thus can complimentarily couple with a nucleotide sequence of the complementary strand.

In the present specification, a nucleic acid sequence at an on-target site is represented by that of the strand on which a PAM sequence exists among two DNA strands in a region of a target gene. In this regard, the DNA strand to which the guide RNA couples is complementary to a strand on which a PAM sequence exists. Hence, the targeting sequence included in the guide RNA has the same nucleic acid sequence as a sequence at an on-target site, with the exception that U is employed instead of T due to the RNA property. In other words, a targeting sequence of guide RNA and a sequence at the on-target site (or a sequence of a cleavage site) are represented by the same nucleic acid sequence with the exception that T and U are interchanged, in the present specification.

The guide RNA may be used in the form of RNA (or may be contained in the composition) or in the form of a plasmid carrying a DNA coding for the RNA (or may be contained in the composition).

The uracil-specific excision reagent (USER) may include any agent capable of removing uracil that is converted from cytosine by cytosine deaminase and/or introducing DNA cleavage at the position where uracil is removed.

In an embodiment, the uracil-specific excision reagent (USER) may comprise a uracil DNA glycosylase (UDG), endonuclease VIII, or a combination thereof. In an embodiment, the uracil-specific removal reagent may comprise a combination of endonuclease VIII or uracil DNA glycosylase and endonuclease VIII.

The uracil DNA glycosylase (UDG) may refer to an enzyme that acts to remove uracil (U) present in DNA thereby preventing mutagenesis of DNA. It may be at least one selected from the group consisting of enzymes that cleave N-glycosylic bond of uracil to initiate base-excision repair (BER). For example, the uracil DNA glycosylase may be an *Escherichia coli* uracil DNA glycosylase (e.g., GenBank Accession Nos. ADX49788.1, ACT28166.1, EFN36865.1, BAA10923.1, ACA76764.1, ACX38762.1, EFU59768 1, EFU53885.1, EFJ57281.1, EFU47398.1, EFK71412.1, EFJ92376.1, EFJ79936.1, EFO59084.1, EFK47562.1, KXH01728.1, ESE25979.1, ESD99489.1, ESD73882.1, ESD69341.1, etc.), human uracil DNA glycosylase (for example, GenBank Accession Nos. NP_003353.1, NP_550433.1, etc.), mouse uracil DNA glycosylase (for example, GenBank Accession Nos. NP_001035781.1, NP_035807 0.2, etc.), and the like; but not be limited thereto.

The endonuclease VIII functions to remove the uracil-deleted nucleotides. It may be at least one selected from the group consisting of enzymes having N-glycosylase activity to remove uracil damaged by the uracil DNA glycosylase from double-stranded DNA and AP-lyase activity to cut 3' and 5' ends of apurinic site (AP site) which is generated by the removal of damaged uracil. For example, the endonuclease VIII may be human endonuclease VIII (e.g., GenBank Accession Nos. BAC06476.1, NP_001339449.1, NP_001243481.1, NP_078884.2, NP_001339448.1, etc.), mouse endonuclease VIII (e.g., GenBank Accession Nos. BAC06477.1, NP082623.1, etc.), *Escherichia coli* endonuclease VIII (e.g., GenBank Accession Nos. OBZ49008.1, OBZ43214.1, OBZ42025.1, ANJ41661.1, KYL40995.1, KMV55034.1, KMV53379.1, KMV50038.1, KMV40847.1, AQW72152.1, etc.), but not be limited thereto.

In another embodiment, in case of using an inactivated target-specific endonuclease lacking nickase activity as well as endonuclease activity, such as a modified Cas9 which is generated by introducing both of D10A and H840A into Cas9 protien derived from *Streptococcus pyogenes*; for generating double strand cleavage, the composition may further comprise an endonuclease capable of specifically degrading a DNA single strand region generated by removing uracil on one strand among two strands of DNA (the endonuclease may cleave phosphodiester bonds of both ends of DNA single strand region). The endonuclease capable of specifically degrading a single strand region of DNA may be at least one selected from the group consisting of S1 nuclease (derived from *Aspergillus oryzae*; e.g., catalog number M5791 (Promega), etc.), Mung bean nuclease, and the like.

By using a cytosine deaminase, an inactivated target-specific endonuclease, and a uracil-specific excision reagent, a double strand break can be generated at a site where a base conversion (base editing) from cytosine to uracil (C→U) by cytosine deaminase occurs (FIG. 4a). The DNA cleavage fragments generated as above have staggered ends. Thereafter, an end repair process may optionally occur, whereby DNA fragments (double stranded) with blunted ends can be generated (see FIG. 4a).

Another embodiment provides a method of generating double strand break using a cytosine deaminase, the method comprising:
  (i) introducing or contacting (a) a cytosine deaminase and an inactivated target-specific endonuclease, or (b) a cytosine deaminase coding gene and an inactivated target-specific endonuclease coding gene, or (c) a plasmid comprising a cytosine deaminase coding gene and an inactivated target-specific endonuclease coding gene, into a cell or with DNA isolated from a cell, together with a guide RNA; and
  (ii) treating a uracil-specific excision reagent (USER).

By generating (or introducing) a double strand break into DNA using cytosine deaminase, a base editing (i.e., conversion from C to U) site, a base editing efficiency by a cytosine deaminase, and the like can be analyzed, thereby identifying (or measuring) a base editing efficiency at on-target site, specificity to on-target sequence, an off-target sequence, etc., of cytosine deaminase.

Another embodiment provides a method of analyzing nucleic acid sequence of DNA in which a base editing is introduced by cytosine deaminase, comprising:
  (i) introducing or contacting (a) a cytosine deaminase and an inactivated target-specific endonuclease, or (b) a cytosine deaminase coding gene and an inactivated target-specific endonuclease coding gene, or (c) a plasmid comprising a cytosine deaminase coding gene and an inactivated target-specific endonuclease coding gene, into a cell or with DNA isolated from a cell, together with a guide RNA;

(ii) treating a uracil-specific excision reagent (USER), to generate double strand break in the DNA; and (iii) analyzing nucleic acid sequence of the cleaved DNA fragment.

Another embodiment provides a method of identifying (or measuring or detecting) a base editing site, a base editing efficiency at on-target site, an off-target site, and/or a target-specificity, of cytosine deaminase, comprising:

(i) introducing or contacting (a) a cytosine deaminase and an inactivated target-specific endonuclease, or (b) a cytosine deaminase coding gene and an inactivated target-specific endonuclease coding gene, or (c) a plasmid comprising a cytosine deaminase coding gene and an inactivated target-specific endonuclease coding gene, into a cell or with DNA isolated from a cell, together with a guide RNA;

(ii) treating a uracil-specific excision reagent (USER), to generate double strand break in the DNA;

(iii) analyzing nucleic acid sequence of the cleaved DNA fragment; and (iv) identifying the double strand break site in the nucleic acid sequence read obtained by said analysis.

The cytosine deaminase, inactivated target-specific endonuclease, plasmid, guide RNA and uracil-specific excision reagent are as described above.

The method may be carried out in a cell or in vitro, for example, it may be carried out in vitro. More specifically, all steps of the method are carried out in vitro; or step (i) is carried out in a cell, and step (ii) and subsequent steps are carried out in vitro using DNA (e.g., genomic DNA) extracted from the cell used in step (i).

Said step (i) comprises transfecting a cell or contacting (e.g., co-incubating) DNA extracted from the cell with a cytosine deaminase and an inactivated target-specific endonuclease (or coding genes thereof) together with a guide RNA, to induce conversion from cytosine to uracil and generation of DNA nick in a target site targeted by the guide RNA. The cell may be selected from all eukaryotic cells which are desired to be introduced with a base editing by cytosine deaminase, and for example, it may be selected from mammalian cells including human cells. The transfection can be carried out by introducing a plasmid containing a gene encoding a cytosine deaminase and an inactivated target-specific endonuclease into a cell by any conventional means. For example, the plasmid may be introduced into a cell by electroporation, lipofection, and the like, but not be limited thereto.

In one embodiment, step (i) may be performed by culturing DNA extracted from a cell (a cell to which base editing (e.g., a base editing site, base editing efficiency, etc.) by a cytosine deaminase is to be examined) together with a cytosine deaminase and an inactivated target-specific endonuclease (e.g., a fusion protein comprising a cytosine deaminase and an inactivated target-specific endonuclease) and a guide RNA (in vitro). The DNA extracted from the cell may be a genomic DNA or a PCR (polymerase chain reaction) amplification product containing a target gene or a target site.

Said step (ii) may comprise removing a base modified with uracil in the step (i) to generate DNA double strand break. More specifically, step (ii) may comprise treating (contacting) uracil DNA glycosylase (UDG), endonuclease VIII, or a combination thereof to the reaction product obtained in step (i). When both of uracil DNA glycosylase and endonuclease VIII are treated (contacted), they can be treated at the same time or sequentially in any order. The step of contacting (contacting) may be carried out by incubating the reaction product obtained in step (i) with uracil DNA glycosylase and/or endonuclease VIII.

When step (i) is carried out in a cell (i.e., when the cell is transfected), the reaction sample of step (ii) may comprise DNA isolated from the transfected cell. When step (i) is carried out in vitro for DNA extracted (separated) from a cell, the reaction sample of step (ii) may comprise isolated DNA treated with a cytosine deaminase and an inactivated target-specific endonuclease and a guided RNA.

In another embodiment, when an inactivated target-specific endonuclease generated by introducing both of D10A and H840A into Cas9 protien derived from *Streptococcus pyogenes* is used in step (i), since the inactivated target-specific endonuclease lacks nickase activity as well as endonuclease activity, for generating double strand cleavage, the method may further comprise a step (step (ii-1)) of treating an endonuclease capable of specifically degrading a DNA single strand region generated by removing uracil on one strand among two strands of DNA (the endonuclease may cleave phosphodiester bonds of both ends of DNA single strand region), after step (ii) and before step (iii) (FIG. 22(a)). The endonuclease capable of specifically degrading a single strand region of DNA may be S1 nuclease, but not be limited thereto.

Optionally, the method may further comprise a step of removing the cytosine deaminase, inactivated target-specific endonuclease, and/or guide RNA used in step (i), after performing (finishing) step (i) and prior to performing step (ii). The cytidine deaminase and inactivated target-specific endonuclease are used together with a guide RNA, thereby having sequence specificity, and thus, they mostly act on an on-target site; however, if similar sequences to a target sequence of on-target site are present on an off-target site, they may also act on the off-target site. As used herein, the term "off-target site" may refer to a site that is not an on-target site, but to which the cytidine deaminase and inactivated target-specific endonuclease have activity. That is, the off-target site may refer to a site where base editing and/or cleavage by cytidine deaminase and inactivated target-specific endonuclease occurs, besides an on-target site. In an embodiment, the term "off-target site" may used to cover not only sites that are not on-target sites of the cytidine deaminase and inactivated target-specific endonuclease, but also sites having possibility to be off-target sites thereof. The off-target sites may refer to, but not be limited to, any sites that are cleaved by the cytidine deaminase and inactivated target-specific endonuclease in vitro, besides on-target sites.

The activity of cytidine deaminase and inactivated target-specific endonuclease on sites besides an on-target site may be caused by various reasons. For example, a sequence (off-target sequence) other than target sequence having low mismatch level to a target sequence designed for a desired target site and high sequence homology with the target sequence, may act as an on-target sequence of cytidine deaminase and inactivated target-specific endonuclease used. The off-target sequence may be a sequence (gene region) having 1 to 6, 1 to 5, 1 to 4, 1 to 3, 1 to 2, or 1 nucleotide mismatch to a target sequence, but not be limited thereto.

The working of the deaminase and the inactivated target-specific endonuclease in an off-target site may incur undesirable mutation in a genome, which may lead to a significant problem. Hence, a process of accurately detecting and analyzing an off-site sequence may be as very important as the activity of the deaminase and the inactivated target-specific endonuclease at an on-target site. The process may be useful for developing a deaminase and an inactivated target-specific endonuclease which both work specifically only at on-target sites without the off-target effect.

Because the cytidine deaminase and the inactivated target-specific endonuclease have activities in vivo and in vitro for the purpose of the present invention, the enzymes can be used in detecting in vitro an off-target site of DNA (e.g., genomic DNA). When applied in vivo, thus, the enzymes are expected to be active in the same sites (gene loci including off-target sequences) as the detected off-target sites.

Step (iii) is a step of analyzing nucleic acid sequence of DNA fragments cleaved in step (ii), and can be performed by any conventional method for analyzing nucleic acid sequence. For example, when the separate DNA used in step (i) is a genomic DNA, the nucleic acid sequence analysis may be conducted by whole genome sequencing. In contrast to the indirect method in which a sequence having a homology with the sequence at an on-target site is searched for and would be predicted to be off-target site, whole genome sequencing allows for detecting an off-target site actually cleaved by the target-specific nuclease at the level of the entire genome, thereby more accurately detecting an off-target site.

As used herein, the term "whole genome sequencing" (WGS) refers to a method of reading the genome by many multiples such as in 10X, 20X, and 40X formats for whole genome sequencing by next generation sequencing. The term "Next generation sequencing" means a technology that fragments the whole genome or targeted regions of genome in a chip-based and PCR-based paired end format and performs sequencing of the fragments by high throughput on the basis of chemical reaction (hybridization).

In the step (iv), a DNA cleavage site is identified (or determined) using the base sequence data (sequence read) obtained in step (ii). By analyzing the sequencing data, an on-target site and an off-target site can simply be detected. The determination of a site at which DNA is cleaved from the base sequence data can be performed by various approaches. In the specification, various reasonable methods are provided for determining the site. However, they are merely illustrative examples that fall within the technical spirit of the present invention, but are not intended to limit the scope of the present invention.

As an example of determining a cleaved site, when the sequence reads obtained by whole genome sequencing are aligned according to sites on a genome, the site at which the 5' ends are vertically (straightly) aligned may mean the site at which DNA is cleaved. The alignment of the sequence reads according to sites on genomes may be performed using an analysis program (for example, BWA/GATK or ISAAC). As used herein, the term "vertical alignment" refers to an arrangement in which the 5' ends of two more sequence reads start at the same site (nucleotide position) on the genome for each of the adjacent Watson strand and Crick strand when the whole genome sequencing results are analyzed with a program such as BWA/GATK or ISAA. Through this method, the DNA fragments that are cleaved in step (ii) and thus have the same 5' end are each sequenced.

That is, when the cleavage in step (ii) occurs at on-target sites and off-target sites, the alignment of the sequence reads allows the vertical alignment of the common cleaved sites because each of their sites start at the 5' end. However, the 5' end is not present in the uncleaved sites, so that it can be arranged in a staggered manner in alignment. Accordingly, the vertically aligned site may be regarded as a site cleaved in step (i), which means an on-target site or off-target site cleaved by the inactivated target-specific endonuclease.

The term "alignment" means mapping sequence reads to a reference genome and then aligning the bases having identical sites in genomes to fit for each site. Accordingly, so long as it can align sequence reads in the same manner as above, any computer program may be employed. The program may be one already known in the pertinent art or may be selected from among programs tailored to the purpose. In one embodiment, alignment is performed using ISAAC, but is not limited thereto.

As a result of the alignment, the site at which the DNA is cleaved by the deaminase and the inactivated target-specific endonuclease can be determined by a method such as finding a site where the 5' end is vertically aligned as described above, and the cleaved site may be determined as an off-target site if not an on-target site. In other words, a sequence is an on-target site if identical to the base sequence designed as an on-target site of the deaminase and inactivated target-specific endonuclease, and is regarded as an off-target site if not identical to the base sequence. This is obvious according to the definition of an off-target site described above. The off-target site may comprise a sequence having homology with the sequence of on-target site; in particular, a sequence having at least one nucleotide mismatch with the on-target site; more particularly, a sequence having 1 to 6, 1 to 5, 1 to 4, 1 to 3, 1 to 2, or 1 nucleotide mismatch with the on-target site; however, the off-target site does not limited thereto, but includes any site capable of being cleaved by the cytidine deaminase and the inactivated target-specific endonuclease used.

In another example, in addition to finding a vertically aligned position at the 5' end, when the double peak pattern is seen in 5' end plot, the position can be determined as an off-target site if it is not on-target site. When a graph is drawn by counting the number of nucleotides constituting 5' end having the same base for each site in a genomic DNA, a double peak pattern appears at a specific position. This is because the double peak is caused by each strand of a double strand cleaved by a cytidine deaminase and inactivated target-specific endonuclease.

Therefore, the method of identifying an off-target site may further comprise, after the step (iv), determining the cleaved site as an off-target site when the site is not an on-target site.

In an embodiment, the steps (i) and (ii) are conducted with regard to the genomic DNA to induce a double-strand break and after the whole genome analysis (step (iii), the DNA reads are aligned with ISAAC to identify alignment patterns for vertical alignment at cleaved sites and staggered alignment at uncleaved sites. A unique pattern of double peaks may appear at the cleavage sites as represented by a 5' end plot.

Moreover, as a non-limiting examples, a site where two or more sequence reads corresponding to each of Watson strand and Crick strand are aligned vertically may be determined as an off-target site. In addition, a site where 20% or more of sequence reads are vertically aligned and the number of sequence reads having the same 5' end in each of the Watson and Crick strands is 10 or more is determined as an off-target site, that is, a cleavage site.

The process in steps (iii) and (iv) of the method described above may be Digenome-seq (digested-genome sequencing). For greater details, reference may be made to Korean Patent No. 10-2016-0058703 A (this document is herein incorporated by reference in its entirety).

Base editing sites (i.e., double-strand break site) of cytidine deaminase, base editing efficiency at on-target sites or target-specificity (i.e., [base editing frequency at on-target sites]/[base editing frequency over entire sequence]), and/or off-target sites (identified as base editing sites of deaminase, but not on-target sites) can be identified (or measure or detected) by the method described above.

The identification (detection) of an off-target site is performed in vitro by treating a genomic DNA with the deaminase and the inactivated target-specific endonuclease. Thus, it can be identified whether off-target effects are actually produced also in vivo in the off-target site detected by this method. However, this is merely an additional verification process, and thus is not a step that is essentially entailed by the scope of the present invention, and is merely a step that can be additionally performed according to the needs.

In the present specification, the term "off-target effect" is intended to mean a level at which base editing and/or double-strand break occurs at an off-target site. The term "indel" (insertion and/or deletion) is a generic term for a mutation in which some bases are inserted or deleted in the middle of a base sequence of DNA.

In another embodiment, a method for identifying (or measuring or detecting) a base editing site, a base editing efficiency at on-target site, an off-target site, and/or target-specificity of a cytosine deaminase can be conducted by a method other than the Digenome-seq method as described above.

In a concrete embodiment, the method for identifying (or measuring or detecting) a base editing site, a base editing efficiency at on-target site, an off-target site, and/or target-specificity of a cytosine deaminase may be conducted by circle-seq method (FIG. 20a). For example, the method may comprise the following steps of:
  (i) fragmenting and circularizing a genomic DNA extracted from a cell;
  (ii) treating the circularized DNA fragment with a cytosine deaminase and an inactivated target-specific endonuclease, followed by treating with a uracil-specific excision reagent (USER), to generate a double stranded break in the circularized DNA fragment; and
  (iii) constructing a library using the DNA fragment in which double-strand break is generated, and performing next-generation genome sequencing (NGS).

The cytosine deaminase and inactivated target-specific endonuclease in step (ii) may be used together with a guide RNA.

In another concrete embodiment, the method for identifying (or measuring or detecting) a base editing site, a base editing efficiency at on-target site, an off-target site, and/or target-specificity of a cytosine deaminase may be conducted by Bless method (FIG. 20b). For example, the method may comprise the following steps of:
  (i) contacting (a) a cytosine deaminase and an inactivated target-specific endonuclease, or (b) a cytosine deaminase coding gene and an inactivated target-specific endonuclease coding gene, or (c) a plasmid comprising a cytosine deaminase coding gene and an inactivated target-specific endonuclease coding gene, with a cell or DNA isolated from a cell;
  (ii) treating uracil-specific excision reagent (USER), to generate a double stranded break in DNA;
  (iii) labeling an end of the cleaved DNA fragment and capturing the labeled DNA fragment;
  (iv) amplifying the captured DNA fragment and performing next generation dielectric sequencing (NGS).

The cytosine deaminase and inactivated target-specific endonuclease, or a gene encoding the same, or a plasmid comprising the gene in step (i) may be used together with a guide RNA or DNA encoding the guide RNA or a plasmid comprising the DNA.

In another concrete embodiment, the method for identifying (or measuring or detecting) a base editing site, a base editing efficiency at on-target site, an off-target site, and/or target-specificity of a cytosine deaminase may be conducted by DSBCapture method (FIG. 20c). For example, the method may comprise the following steps of:
  (i) contacting (a) a cytosine deaminase and an inactivated target-specific endonuclease, or (b) a cytosine deaminase coding gene and an inactivated target-specific endonuclease coding gene, or (c) a plasmid comprising a cytosine deaminase coding gene and an inactivated target-specific endonuclease coding gene, with a cell or DNA isolated from a cell;
  (ii) treating uracil-specific excision reagent (USER), to generate a double stranded break in DNA;
  (iii) performing an end repair and adaptor ligation for the cleaved DNA fragment; and
  (iv) amplifying the DNA fragment obtained in step (iii) and performing next generation dielectric sequencing (NGS).

The cytosine deaminase and inactivated target-specific endonuclease, or a gene encoding the same, or a plasmid comprising the gene in step (i) may be used together with a guide RNA or DNA encoding the guide RNA or a plasmid comprising the DNA.

Effect of the Invention

The method of generating DNA double-strand break and technologies for analyzing nucleic acid sequence using the method can achieve more accurate and efficient validation of base editing site, a base editing efficiency at on-target site, an off-target site, and/or target-specificity of a cytosine deaminase.

BRIEF DESCRIPTION OF DRAWINGS

FIG. 1a shows the base editing efficiency resulted by BE1 (APOBEC1-dCas9), BE2 (APOBEC1-dCas9-UGI) and BE3 (APOBEC1-nCas9-UGI) (Reference Example 1) on 7 endogenous on-target sites (EMX1, FANCF, HEK2, RNF2, HEK3, HEK4, HBB) in HEK293T cells.

FIG. 1b shows the frequency of Cas9 nuclease-induced mutation measured by targeted deep sequencing at 7 endogenous on-target sites in HEK293T cells.

FIG. 1c is a graph representatively showing base editing efficiency or ranking of indel frequency at 7 endogenous target sites.

FIG. 2a is a graph showing mutation frequency at one of 3 endogenous sites (EMX1) of HEK293T cells which are co-transfected with sgRNA having 0 to 4 mismatches and a plasmid encoding BE3 or Cas9 (wherein the nucleic acid sequences listed are sequentially numbered from SEQ ID NO: 1 to SEQ ID NO: 31 in the downward direction on the graph).

FIG. 2b is a graph showing mutation frequency at one of 3 endogenous sites (HBB) of HEK293T cells which are co-transfected with sgRNA having 0 to 4 mismatches and a plasmid encoding BE3 or Cas9 (wherein the nucleic acid sequences listed are sequentially numbered from SEQ ID NO: 32 to SEQ ID NO: 62 in the downward direction on the graph).

FIG. 2c is a graph showing mutation frequency at one of 3 endogenous sites (RNF2) of HEK293T cells which are co-transfected with sgRNA having 0 to 4 mismatches and a plasmid encoding BE3 or Cas9 (wherein the nucleic acid sequences listed are sequentially numbered from SEQ ID NO: 63 to SEQ ID NO: 93 in the downward direction on the graph).

FIG. 3a is a graph showing Cas9 nuclease associated indel frequency and BE associated base editing frequency at EMX1 site.

FIG. 3b is a graph showing Cas9 nuclease associated indel frequency and BE associated base editing frequency at HBB site.

FIG. 3c is a graph showing Cas9 nuclease associated indel frequency and BE associated base editing frequency at RNF2 site.

FIG. 4a is a schematic view of BE3 Digenome-seq.

FIG. 4b is an electrophoresis image showing the PCR products cleaved by treating BE3 and/or USER.

FIG. 4c is a Sanger sequencing result showing C-to-U conversion by BE3 and DNA cleavage by USER.

FIG. 4d is an IGV image showing straight alignment of the sequence read at on-target site of EMX1.

FIG. 5 is an IGV image showing straight alignment of sequence reads at 6 different on-target sites.

FIGS. 6a (EMX1) and 6b (HBB) are genome-wide circus plots representing DNA cleavage scores obtained with intact genomic DNA (first layer from the center) and genomic DNA digested with BE3 and USER (second layer from the center) or with Cas9 (third layer from the center, only present in FIG. 6b), where the arrow indicates on-target site.

FIGS. 6c (EMX1) and 6d (HBB) show sequence logos obtained via WebLogo using DNA sequences at Digenome-capture sites (Tables 2-8) (DNA cleavage score >2.5).

FIGS. 6e (EMXI) and 6f (HBB) represent scatterplots of BE3-mediated substitution frequencies vs Cas9-mediated indel frequencies determined using targeted deep sequencing, wherein circled dots indicate off-target sites validated by BE3 but invalidated by Cas9.

FIGS. 6g (EMX1) and 6h (HBB) show BE3 off-target sites validated in HEK293T cells by targeted deep sequencing, wherein PAM sequences are the last 3 nucleotides at 3' end, mismatched bases are shown in small letters, and dashes indicate RNA bulges (Error bars indicate s.e.m. (n=3)).

FIG. 7 is a Venn diagram showing the number of sites with DNA cleavage scores 2.5 or higher identified by Digenome-seq of Cas9 nuclease- and Base editor-treated genomic DNA.

FIG. 8 is a graph showing the number of total sites (■) and the number of PAM-containing sites with ten or fewer mismatches (D) for a range of DNA cleavage scores.

FIG. 9 is a Venn diagram showing the number of PAM-containing homologous sites with DNA cleavage scores over 0.1 or higher identified by Digenome-seq of Cas9 nuclease- and Base editor-treated genomic DNA.

FIG. 10 shows fractions of homologous sites captured by Digenome-seq, wherein bars represent the number of homologous sites that differ from on-target sites by up to 6nt, squares (BE3) and triangles (Cas9) represent the fraction of Digenome-seq captured sites for a range of mismatch numbers.

FIGS. 11a and 11b are graphs showing the significant correlation between the number of BE3- and Cas9-associated sites identified by Digenome 1.0 (11a) and Digenome 2.0 (11b).

FIGS. 12a and 12b are graphs showing the significant correlation between the number of BE3-associated sites identified by Digenome 1.0 (12a) or Digenome 2.0 (12b) and the number of sites with 6 or fewer mismatches.

FIG. 13 shows examples of Digenome-captured off-target sites associated only with Cas9, which contain no cytosines at positions 4-9.

FIGS. 14a-14c show base editing efficiencies at Digenome-captured sites associated only with 3 different Cas9 nucleases.

FIGS. 15a-15c show base editing efficiencies of 3 different BE3 deaminases at Digenome-negative sites.

FIG. 16a is a schematic view showing conventional ($gX_{19}$ sgRNA), truncated ($gX_{18}$ or $gX_{17}$ sgRNA), and extended sgRNAs ($gX_{20}$ or $ggX_{20}$ sgRNA).

FIG. 16b shows base-editing frequencies at the HBB on- and off-target sites in HEK293T cells measured by targeted deep sequencing.

FIG. 17 shows the result of reducing BE3 off-target effects using modified sgRNAs, wherein 17a shows a schematic view of conventional sgRNAs ($GX_{19}$ sgRNA) and modified sgRNAs ($GX_{17}$ sgRNA, $gX_{18}$ sgRNA, $gX_{20}$ sgRNA, and $ggX_{20}$ sgRNA), and 17b shows base editing efficiencies (frequencies) measured at the EMX1 on- and off-target sites by targeted deep sequencing in HEK293T cells.

FIG. 18a is a cleavage map of plasmid rAPOBEC1-XTEN-dCas9-NLS.

FIG. 18b is a cleavage map of plasmid rAPOBEC1-XTEN-dCas9-UGI-NLS.

FIG. 18C is a cleavage map of plasmid rAPOBEC1-XTEN-Cas9n-UGI-NLS.

FIG. 19 is a cleavage map of Cas9 expression plasmid.

FIG. 20 is a cleavage map of plasmid pET28b-BE1 encoding His6-rAPOBEC1-XTEN-dCas9.

FIGS. 21a to 21c are schematic overviews of genome-wide off-target profiling by a method other than Digenome-seq, wherein FIG. 21a illustrates a method using circle-seq, FIG. 21b illustrates a method using Bless, and FIG. 21c illustrates a method using DSBCapture.

FIG. 22 shows process and results of BE1 (rAPOBEC1-dCas9)-mediated double strand breaks (DSBs), wherein (a) schematically shows processes to generate DBS using BE1 (rAPOBEC1-dCas9), USER enzyme, and S1 nuclease, and (B) is an agarose gel electrophoresis image showing BE1-mediated DSB results in PCR amplicons obtained after treating BE1/sgRNA, USER enzyme, and S1 nuclease.

DETAILED DESCRIPTION OF THE EMBODIMENTS

Hereinafter, the present invention will be described in more detail with reference to the following examples. However, these are only for illustrating the present invention, and the scope of the present invention is not limited by these examples.

REFERENCE EXAMPLE

1. Cell Culture and Transfection

HEK293T cells (ATCC CRL-11268) were maintained in DMEM (Dulbecco Modified Eagle Medium) supplemented with 10% (w/v) FBS and 1% (w/v) penicillin/streptomycin (Welgene). HEK293T cells ($1.5 \times 10^5$) were seeded on 24-well plates and transfected at ~80% confluency with sgRNA plasmid (500 ng) and Base Editor plasmid (Addgene plasmid #73019 (Expresses BE1 with C-terminal NLS in mammalian cells; rAPOBEC1-XTEN-dCas9-NLS; FIG. 18a), #73020 (Expresses BE2 in mammalian cells; rAPOBEC1-XTEN-dCas9-UGI-NLS; FIG. 18b), #73021

(Expresses BE3 in mammalian cells; rAPOBEC1-XTEN-Cas9n-UGI-NLS; FIG. 18c)) (1.5 µg) or Cas9 expression plasmid (Addgene plasmid #43945; FIG. 19), using Lipofectamine 2000 (Invitrogen). Genomic DNA was isolated using DNeasy Blood & Tissue Kit (Qiagen) at 72 hours after transfection. The cells were not tested for *mycoplasma* contamination. The sgRNA used in the following Examples was constructed by converting T to U on the overall sequence at an on-target site (on-target sequence; see Tables 1-8), except the 5'-terminal PAM sequence (5'-NGG-3'; wherein N is A, T, G, or C), and employing the converted sequence as the targeting sequence '$(N_{cas9})_i$' of the following General Formula 3: 5'-$(N_{cas9})_i$-(GUUUUAGAGCUA)-(GAAA)-(UAGCAAGUUAAAAUAAGGCUAGU-CCGUUAUCAACUUGAAAAAGUGGCA CCGAGUCGGUGC)-3' (General Formula 3; oligonucleotide linker: GAAA) (SEQ ID NO: 235).

2. Protein Purification

The His6-rAPOBEC1-XTEN-dCas9 protein-coding plasmid (pET28b-BE1; Expresses BE1 with N-terminal His6 tag in *E. coli*; FIG. 20) was generously given by David Liu (Addgene plasmid #73018). The His6-rAPOBEC1-XTEN-dCas9 protein-coding plasmid pET28b-BE1 was converted into a His6-rAPOBEC1-nCas9 protein (BE3 delta UGI; BE3 variant lacking a UGI domain)-coding plasmid (pET28b-BE3 delta UGI) by site directed mutagenesis for substituting A840 with H840 in the dCas9.

Rosetta expression cells (Novagen, catalog number: 70954-3CN) were transformed with the prepared pET28b-BE1 or pET28b-BE3 delta UGI and cultured overnight in Luria-Bertani (LB) broth containing 100 µg/ml kanamycin and 50 mg/ml carbenicilin at 37° C. Ten ml of the overnight cultures of Rosetta cells containing pET28b-BE1 or pET28b-BE3 delta UGI was inoculated into 400 ml LB broth containing 100 µg/ml kanamycin and 50 mg/ml carbenicilin and cultured at 30° C. until the OD600 reached 0.5-0.6. The cells were cooled to 16° C. for 1 hour, supplemented with 0.5 mM IPTG (Isopropyl β-D-1-thiogalactopyranoside), and cultured for 14-18 hours.

For protein purification, cells were harvested by centrifugation at 5,000×g for 10 min at 4° C. and lysed by sonication in 5 ml lysis buffer (50 mM $NaH_2PO_4$, 300 mM NaCl, 1 mM DTT, and 10 mM imidazole, pH 8.0) supplemented with lysozyme (Sigma) and a protease inhibitor (Roche complete, EDTA-free). The soluble lysate obtained after centrifugation of the cell lysis mixture at 13,000 rpm. for 30 min at 4° C. was incubated with Ni-NTA agarose resin (Qiagen) for 1 hour at 4° C. The cell lysate/Ni-NTA mixture was applied to a column and washed with a buffer (50 mM $NaH_2PO_4$, 300 mM NaCl, and 20 mM imidazole, pH 8.0). The BE3 protein was eluted with an elution buffer (50 mM $NaH_2PO_4$, 300 mM NaCl, and 250 mM imidazole, pH 8.0). The eluted protein was buffer exchanged with a storage buffer (20 mM HEPES-KOH (pH 7.5), 150 mM KCl, 1 mM DTT, and 20% glycerol) and concentrated with centrifugal filter units (Millipore) to give purified rAPOBEC1-XTEN-dCas9 protein and rAPOBEC1-nCas9 protein.

3. Desamination and USER Treatment of PCR Amplification Products

PCR amplification products (10 µg) containing EMX1 site were incubated with purified rAPOBEC1-nCas9 protein (4 µg) and EMX1-specific sgRNA (3 µg) at 100 µl reaction volume for 1 hour at 37° C. The cultures were then incubated for 30 min at 37° C. in a uracil-specific excitation reagent (6 units) (New England Biolabs; containing a mixture of Uracil DNA glycosylase (UDG) and DNA glycosylase-lyase Endonuclease VIII, 50 mM KCl, 5 mM NaCl, 10 mM Tris-HCl (pH 7.4), 0.1 mM EDTA, 1 mM DTT, BSA 175 mg/ml, and 50% (w/v) glycerol) glycerol) and then subjected to agarose gel electrophoresis.

4. Deamination and USER Treatment of Genomic DNA

Genomic DNA was purified (extracted) from HEK293T cells with a DNeasy Blood & Tissue Kit (Qiagen) according to the manufacturer's instructions. Genomic DNA (10 µg) was incubated with the rAPOBEC1-nCas9 protein (300 nM) purified in Reference Example 2 and an sgRNA (900 nM) in a reaction volume of 500 µL for 8 hours at 37° C. in a buffer (100 mM NaCl, 40 mM Tris-HCl, 10 mM $MgCl_2$, and 100 µg/ml BSA, pH 7.9). After removal of sgRNA using RNase A (50 µg/mL), uracil-containing genomic DNA was purified with a DNeasy Blood & Tissue Kit (Qiagen). The on-target site was amplified by PCR using a SUN-PCR blend and subjected to Sanger sequencing to check BE3-mediated cytosine deamination and USER-mediated DNA cleavage.

5. Sequencing of Whole Genome and Digenome

Genomic DNA (1 µg) was fragmented to the 400- to 500-bp range using the Covaris system (Life Technologies) and blunt-ended using End Repair Mix (Thermo Fischer). Fragmented DNA was ligated with adapters to produce libraries, which were then subjected to WGS (whole genome sequencing) using HiSeq X Ten Sequencer (Illumina) at Macrogen.

6. Targeted Deep Sequencing

On-target and potential off-target sites were amplified with a KAPA HiFi HotStart PCR kit (KAPA Biosystems #KK2501) for deep sequencing library generation. Pooled PCR amplicons were sequenced using MiniSeq (Illumina) or Illumina Miseq (LAS Inc. Korea) with TruSeq HT Dual Index system (Illumina).

Example 1. Comparison of BE3-Associated Base Editing Efficiency and Cas9-Associated Indel Frequency in Human Cells Base editing efficiencies, defined by single-nucleotide substitution frequencies, of three different forms of BEs, at seven genomic loci (EMX1, FANCF, HEK2, RNF2, HEK3, HEK4 and HBB) in HEK293T cells were determined, and compared with genome editing efficiencies, defined by indel frequencies at target sites, of Cas9 nucleases (FIG. 1a,b). FIG. 1a shows the base editing efficiencies resulted from BE1 (APOBEC1-dCas9), BE2 (APOBEC-dCas9-UGI) and BE3 (APOBEC-nCas9-UGI) (Reference Example 1) in seven endogenous target sites (EMX1, FANCF, HEK2, RNF2, HEK3, HEK4, HBB) of HEK293T cells. The base editing efficiency was measured by targeted deep sequencing (Reference Example 6). The efficiency of BE3 [APOBEC-nCas9-UGI (uracil DNA glycosylase inhibitor), 29±6%] is superior to that of BE1 (APOBEC1-dCas9, 5±1%) and BE2 (APOBEC-dCas9-UGI, 8±2%). FIG. 1b shows the Cas9 nuclease-induced mutation frequencies measured by the target deep-sequnctation at 7 endogenous target sites in HEK293T cells (the results were obtained by using the Cas9 expression plasmid of Reference Example 1 (Addgene plasmid #43945; FIG. 19)). These results show that BE3 activity is independent of Cas9 nuclease activity. FIG. 1c is a graph representatively showing the ranking of indel frequency or base editing efficiency at the 7 endogenous on-target sites (see Table 2-8). As shown in FIG. 1c, several sgRNAs exhibit low activity when working together with Cas9, but highly activity when working together with BE3; while some sgRNAs show opposite correlation.

Example 2. Tolerance of BE3 and Cas9 to Mismatched sgRNAs

To assess specificities of BE3 deaminases, it was examined in a cell whether BE3 can tolerate mismatches in small guide RNAs (sgRNAs). To this end, plasmids encoding BE3 or Cas9 (Reference Example 1) eand sgRNAs with one to four mismatches were co-transfected into HEK293T cells, to measure mutation frequencies at three endogenous sites (EMX1, HBB, RNF2).

The used target sites (including the PAM sequence (in bold)) of the sgRNA with 1 to 4 mismatches are summarized in Table 1 below:

TABLE 1

| SEQ ID NO: | EMX1 mismatched sgRNAs | SEQ ID NO: | HBB mismatched sgRNAs | SEQ ID NO: | RNF2 mismatched sgRNAs |
|---|---|---|---|---|---|
| 1 | GgactCGAGCAGAAGAAGAAGGG | 32 | GccatCCCACAGGGCAGTAACGG | 63 | GctgcCTTAGTCATTACCTGAGG |
| 2 | GAGTttagGCAGAAGAAGAAGGG | 33 | GTTGttttACAGGGCAGTAACGG | 64 | GTCActccAGTCATTACCTGAGG |
| 3 | GAGTCCGAatgaAAGAAGAAGGG | 34 | GTTGCCCCgtgaGGCAGTAACGG | 65 | GTCATCTTgactATTACCTGAGG |
| 4 | GAGTCCGAGCAGggagAGAAGGG | 35 | GTTGCCCCACAGaatgGTAACGG | 66 | GTCATCTTAGTCgccgCTGAGG |
| 5 | GAGTCCGAGCAGAAGAgaggGGG | 36 | GTTGCCCCACAGGGCAacggCGG | 67 | GTCATCTTAGTCATTAttcaAGG |
| 6 | GAactCGAGCAGAAGAAGAAGGG | 37 | GTcatCCCACAGGCAGTAACGG | 68 | GTtgcCTTAGTCATTACCTGAGG |
| 7 | GAGTCtagGCAGAAGAAGAAGGG | 38 | GTTGCtttACAGGGCAGTAACGG | 69 | GTCATtccAGTCATTACCTGAGG |
| 8 | GAGTCCGAatgGAAGAAGAAGGG | 39 | GTTGCCCCgtgGGGCAGTAACGG | 70 | GTCATCTTgacCATTACCTGAGG |
| 9 | GAGTCCGAGCAaggGAAGAAGGG | 40 | GTTGCCCCACAaaaCAGTAACGG | 71 | GTCATCTTAGTtgcTACCTGAGG |
| 10 | GAGTCCGAGCAGAAaggGAAGGG | 41 | GTTGCCCCACAGGGtgaTAACGG | 72 | GTCATCTTAGTCATcgtCTGAGG |
| 11 | GAGTCCGAGCAGAAGAAaggGGG | 42 | GTTGCCCCACAGGGCAGcggCGG | 73 | GTCATCTTAGTCATTActcaAGG |
| 12 | GAacCCGAGCAGAAGAAGAAGGG | 43 | GTcaCCCCACAGGGCAGTAACGG | 74 | GTtgTCTTAGTCATTACCTGAGG |
| 13 | GAGTttGAGCAGAAGAAGAAGGG | 44 | GTTGttCCACAGGGCAGTAACGG | 75 | GTCActTTAGTCATTACCTGAGG |
| 14 | GAGTCCagGCAGAAGAAGAAGGG | 45 | GTTGCCttACAGGGCAGTAACGG | 76 | GTCATCccAGTCATTACCTGAGG |
| 15 | GAGTCCGAatAGAAGAAGAAGGG | 46 | GTTGCCCCgtAGGGCAGTAACGG | 77 | GTCATCTTgaTCATTACCTGAGG |
| 16 | GAGTCCGAGCgaAAGAAGAAGGG | 47 | GTTGCCCCACgaGGCAGTAACGG | 78 | GTCATCTTAGctATTACCTGAGG |
| 17 | GAGTCCGAGCAGggGAAGAAGGG | 48 | GTTGCCCCACAGaaCAGTAACGG | 79 | GTCATCTTAGTCgcTACCTGAGG |
| 18 | GAGTCCGAGCAGAAagAGAAGGG | 49 | GTTGCCCCACAGGGtgGTAACGG | 80 | GTCATCTTAGTCATcgCCTGAGG |
| 19 | GAGTCCGAGCAGAAGAgaAAGGG | 50 | GTTGCCCCACAGGGCAacAACGG | 81 | GTCATCTTAGTCATTAttTGAGG |
| 20 | GAGTCCGAGCAGAAGAAggGGG | 51 | GTTGCCCCACAGGGCAGTggCGG | 82 | GTCATCTTAGTCATTACCaAGG |
| 21 | GgGTCCGAGCAGAAGAAGAAGGG | 52 | GcTGCCCCACAGGGCAGTAACGG | 83 | GcCATCTTAGTCATTACCTGAGG |
| 22 | GAGcCCGAGCAGAAGAAGAAGGG | 53 | GTTaCCCCACAGGGCAGTAACGG | 84 | GTCgTCTTAGTCATTACCTGAGG |
| 23 | GAGTCtGAGCAGAAGAAGAAGGG | 54 | GTTGCtCCACAGGGCAGTAACGG | 85 | GTCATtTTAGTCATTACCTGAGG |
| 24 | GAGTCCGgGCAGAAGAAGAAGGG | 55 | GTTGCCCtACAGGGCAGTAACGG | 86 | GTCATCTcAGTCATTACCTGAGG |
| 25 | GAGTCCGAGtAGAAGAAGAAGGG | 56 | GTTGCCCCAtAGGGCAGTAACGG | 87 | GTCATCTTAaTCATTACCTGAGG |
| 26 | GAGTCCGAGCAaAAGAAGAAGGG | 57 | GTTGCCCCACAaGGCAGTAACGG | 88 | GTCATCTTAGTtATTACCTGAGG |
| 27 | GAGTCCGAGCAGAgGAAGAAGGG | 58 | GTTGCCCCACAGGaCAGTAACGG | 89 | GTCATCTTAGTCAcTACCTGAGG |
| 28 | GAGTCCGAGCAGAAGgAGAAGGG | 59 | GTTGCCCCACAGGGCgGTAACGG | 90 | GTCATCTTAGTCATTgCCTGAGG |
| 29 | GAGTCCGAGCAGAAGAAaAAGGG | 60 | GTTGCCCCACAGGGCAGcAACGG | 91 | GTCATCTTAGTCATTActTGAGG |
| 30 | GAGTCCGAGCAGAAGAAGAgGGG | 61 | GTTGCCCCACAGGGCAGTAgCGG | 92 | GTCATCTTAGTCATTACCTaAGG |
| 31 | GAGTCCGAGCAGAAGAAGAAGGG on target sequence | 62 | GTTGCCCCACAGGGCAGTAACGG (on target sequence) | 93 | GTCATCTTAGTCATTACCTGAGG (on target sequence) |

(In Table 1, the base position in a lower-case letter refers to the mismatched site)

The results (Indel frequency and cytosine conversion frequency) obtained in the mismatched sequence and the on-target sequence listed in Table 1 are shown in FIGS. 2a to 2c (2a: EMX1, 2b: HBB and 2c: RNF2; Error bars indicate s.e.m. (n=3)). In FIGS. 2a to 2c, the bars indicated as 'Cn' show a mutation (substitution with other base or deletion) frequency of cytosine (C) at the n-th position from 5' end of mismatched sequence or on-target sequence. The Indel frequency and the cytosine conversion frequency (base editing frequency) were measured using the target deep sequencing (Reference Example 6). The primers used for the target deep sequencing are as follows:

```
EMX1
1st PCR
Forward(5'→3'):
                                    (SEQ ID NO: 94)
AGTGTTGAGGCCCCAGTG;

Reverse(5'→3'):
                                    (SEQ ID NO: 95)
GTGACTGGAGTTCAGACGTGTGCTCTTCCGATCTCAGCAGCAAGCAGCA

CTCT;

2nd PCR
Forward(5'→3'):
                                    (SEQ ID NO: 96)
ACACTCTTTCCCTACACGACGCTCTTCCGATCTGGGCCTCCTGAGTTTC

TCAT;

Reverse(5'→3')
                                    (SEQ ID NO: 97)
GTGACTGGAGTTCAGACGTGTGCTCTTCCGATCTCAGCAGCAAGCAGCA

CTCT;

HBB
1st PCR
Forward(5'→3'):
                                    (SEQ ID NO: 98)
GGCAGAGAGAGTCAGTGCCTA;

Reverse(5'→3'):
                                    (SEQ ID NO: 99)
GTGACTGGAGTTCAGACGTGTGCTCTTCCGATCTCAGGGCTGGGCATAA

AAGT;

2nd PCR
Forward(5'→3'):
                                    (SEQ ID NO: 100)
ACACTCTTTCCCTACACGACGCTCTTCCGATCTGTCTCCACATGCCCAG

TTTC;

Reverse(5'→3')
                                    (SEQ ID NO: 101)
GTGACTGGAGTTCAGACGTGTGCTCTTCCGATCTCAGGGCTGGGCATAA

AAGT;

RNF2
1st PCR
Forward(5'→3'):
                                    (SEQ ID NO: 102)
CCATAGCACTTCCCTTCCAA;

Reverse(5'→3'):
                                    (SEQ ID NO: 103)
GTGACTGGAGTTCAGACGTGTGCTCTTCCGATCTGCCAACATACAGAAG

TCAGGAA;

2nd PCR
Forward(5'→3'):
                                    (SEQ ID NO: 104)
ACACTCTTTCCCTACACGACGCTCTTCCGATCTATTTCCAGCAATGTCT

CAGG;
```

-continued
```
Reverse(5'→3')
                                    (SEQ ID NO: 105)
GTGACTGGAGTTCAGACGTGTGCTCTTCCGATCTGCCAACATACAGAAG

TCAGGAA.
```

In addition, the Cas9 nuclease-associated indel frequency and BE3-associated base editing frequency in EMX1 site (FIG. 3a), HBB site (FIG. 3b), and RNF2 site (FIG. 3c) were measured using mismatched sgRNAs (Table 1), and the obtained results are shown in FIGS. 3a to 3c. As shown in FIGS. 3a-3c, there is a statistically significant correlation (R2=0.70, 0.83, and 0.72 at three sites, respectively) between the Cas9-induced indel frequency and the BE3 induced substitution frequency.

BE3 deaminases and Cas9 nucleases tolerated one-nucleotide (nt) mismatches at almost every position and 2-nt mismatches in the protospacer-adjacent motif (PAM)-distal region but did not tolerate most of the 3-nt or 4-nt mismatches in either the PAM-proximal or distal regions. We noticed, however, that several sgRNAs (indicated by asterisks in FIG. 2) with two or three mismatches were highly active with BE3 but not with Cas9 or vice versa. For example, BE3 with the fully-matched sgRNA or with a 3-nt mismatched sgRNA induced substitutions at comparable frequencies (33% vs. 14%) at the EMX1 site, whereas Cas9 with the same matched and 3-nt mismatched sgRNAs showed widely different indel frequencies (50% vs. 2%) (FIG. 2a). Conversely, BE3 with two 2-nt mismatched sgRNAs was poorly active (substitution frequencies <1%), whereas Cas9 with the same mismatched sgRNAs was highly active (indel frequencies >10%) (FIG. 2a). These results indicate that the tolerance of Cas9 nucleases and BE3 deaminases for mismatched sgRNAs can differ and imply that BE3 and Cas9 could have separate sets of off-target sites in the genome, calling for a method to profile genome-wide specificities of RNA-programmable deaminases.

Example 3. Digenome-Seq for Identifying BE3 Off-Target Sites in Human Genome

Several different cell-based methods, which include GUIDE-seq (Tsai, S.Q. et al. GUIDE-seq enables genome-wide profiling of off-target cleavage by CRISPR-Cas nucleases. Nature biotechnology 33, 187-197 (2015)), HTGTS (Frock, R. L. et al. Genome-wide detection of DNA double-stranded breaks induced by engineered nucleases. Nature biotechnology (2014)), BLESS (Ran, F. A. et al. In vivo genome editing using *Staphylococcus aureus* Cas9. Nature 520, 186-191 (2015)), and IDLV capture(Wang, X. et al. Unbiased detection of비표적 cleavage by CRISPR-Cas9 and TALENs using integrase-defective lentiviral vectors. Nature biotechnology 33, 175-178 (2015)), have been developed for identifying genome-wide off-target sites at which Cas9 nucleases induce DSBs. None of these methods, at least in their present forms, are suitable for assessing the genome-wide specificities of programmable deaminases, simply because deaminases do not yield DSBs. We reasoned that DSBs could be produced at deaminated, uracil-containing sites in vitro using appropriate enzymes and that these DNA cleavage sites could be identified via Digenome-seq (digested-genome sequencing; Kim, D., Kim, S., Kim, S., Park, J. & Kim, J. S. Genome-wide target-specificities of CRISPR-Cas9 nucleases revealed by multiplex Digenome-seq. Genome research 26, 406-415 (2016); Kim, D. et al. Genome-wide analysis reveals specificities of Cpf1 endo-nucleases in human cells. Nature biotechnology 34, 863-868

(2016); Kim, D. et al. Digenome-seq: genome-wide profiling of CRISPR-Cas9 off-target effects in human cells. Nature methods 12, 237-243, 231 p following 243 (2015)), an in vitro method used for assessing genome-wide specificities of Cas9 and Cpf1 nucleases.

To test this idea, a PCR amplicon containing a target sequence was incubated (1) with the recombinant rAPOBEC1-nCas9 protein (Reference Example 2), a derivative of BE3 with no UGI domain, and its sgRNA in vitro to induce C-to-U conversions and a nick in the Watson and Crick strands, respectively, and then (2) with USER (Uracil-Specific Excision Reagent), a mixture of *E. coli* Uracil DNA glycosylase (UDG) and DNA glycosylase-lyase Endonuclease VIII, to generate a gap at the location of the uracils, giving rise to a composite DSB (FIG. 4a). Next it was investigated whether Digenome-seq could be used to assess genome-wide target-specificities of BE3 deaminases. Human genomic DNA, purified from HEK293T cells, was incubated with each of 7 different BE3 ribonucleoproteins (RNPs) (300 nM rAPOBEC1-nCas9 protein and 900 nM sgRNA each) for 7 hours three times, and then with USER for 3 hours (FIG. 4a).

FIG. 4a shows an outline of the BE3 Digenome-seq, showing the BE3-mediated cleavage of uracil-containing site by USER, a mixture of *E. coli* Uracil DNA glycosylase (UDG) and DNA glycosylase-lyase Endonuclease VIII. FIG. 4b is an electrophoresis image showing the PCR products cleaved by treating BE3 and/or USER. As shown in FIG. 4b, the PCR amplicon was cleaved, when incubated with both BE3 and USER.

C-to-U conversions induced by BE3 and uracil removal by USER were confirmed by Sanger sequencing (FIG. 4c). FIG. 4c is a Sanger sequencing result showing C-to-U conversion by BE3 and DNA cleavage by USER. Each genomic DNA sample was subjected to whole genome sequencing (WGS) after end repair and adaptor ligation (FIG. 4a).

After sequence alignment to the human reference genome (hg19), we used Integrative Genomics Viewer (IGV) to monitor alignment patterns at each on-target site, and the results are shown in FIGS. 4d and 5, respectively. After sequencing for the human reference genome (hg19), an alignment pattern at the target position was monitored using an Integrative Genomics Viewer (IGV) FIG. 4d is an IGV image showing straight alignment of the sequence read at on-target site of EMX1, and FIG. 5 is an IGV image showing straight alignment of sequence reads at 6 different on-target sites. As shown in FIGS. 4d and 5, uniform alignments of sequence reads, signature patterns associated with DSBs produced in vitro, were observed at all 7 on-target sites.

Example 4. Genome-Wide BE3 Off-Target Sites Revealed by Digenome-Seq

To identify BE3 off-target sites in the human genome, a DNA cleavage score was assigned, based on the number of sequence reads whose 5' ends aligned at a given position, to each nt position across the genome and listed all the sites with scores over 2.5, a cutoff value that was used for finding off-target sites of Cas9 nucleases with the same set of 7 sgRNAs in the inventor's previous study (Kim, D., Kim, S., Kim, S., Park, J. & Kim, J. S. Genome-wide target-specificities of CRISPR-Cas9 nucleases revealed by multiplex Digenome-seq. Genome research 26, 406-415 (2016)) (FIG. 6a-d and Tables 2-8).

The DNA cleavage score at site i of each nucleotide (i.e., the nucleotide position on genomic DNA) was calculated by the following formula:

$$\text{Score at the } i \text{ site} = \sum_{a=1}^{5} \frac{C(F_i - 1)}{D_i} \times \frac{C(R_{i-4+a} - 1)}{D_{i-4+a}} \times (F_i + R_{i-4+a} - 2) +$$

$$\sum_{a=1}^{5} \frac{C(R_{i-1} - 1)}{D_{i-1}} \times \frac{C(F_{i-3+a} - 1)}{D_{i-3+a}} \times (R_{i-a} + F_{i-3+a} - 2)$$

$F_i$: Number of forward sequence reads starting at the i site
$R_i$: Number of reverse sequence reads starting at the i site
$D_i$: Sequencing depth at the i site
C: Arbitrary constant In the above formula, the number of nucleotide sequence data means the number of nucleotide leads, the sequencing depth means the number of sequencing leads at a specific site, and the C value is 1.

Digenome-captured sites (cleavage site+PAM) and DNA cleavage score are shown in Tables 2 to 8 below:

TABLE 2

(On target: EMX1_4)
EMX1

| ID | Chr | Position | DNA cleavage Score | DNA seq at a cleavage sites | SEQ ID NO | Bulge |
|---|---|---|---|---|---|---|
| EMX1_1 | chr15 | 44109763 | 30.53 | GAGTCtaAGCAG AAGAAGAAGAG | 106 | x |
| EMX1_2 | chr11 | 62365273 | 26.44 | GAaTCCaAGCAG AAGAAGAgAAG | 107 | x |
| EMX1_3 | chr5 | 9227162 | 23.66 | aAGTCtGAGCAc AAGAAGAATGG | 108 | x |
| EMX1_4 | chr2 | 73160998 | 14.55 | GAGTCCGAGCAG AAGAAGAAGGG | 31 | x |
| EMX1_5 | chr4 | 131662222 | 11.14 | GAaTCCaAG-AG AAGAAGAATGG | 109 | RNA bulge |
| EMX1_6 | chr8 | 128801258 | 9.60 | GAGTCCtAGCAG gAGAAGAAGAG | 110 | x |

TABLE 2-continued (On target: EMX1_4)
EMX1

| ID | Chr | Position | DNA cleavage Score | DNA seq at a cleavage sites | SEQ ID NO | Bulge |
|---|---|---|---|---|---|---|
| EMX1_7 | chr19 | 24250503 | 8.35 | GAGTCCaAGCAG tAGAgGAAGGG | 111 | x |
| EMX1_8 | chr1 | 4515013 | 8.12 | GtGTCCtAG-AG AAGAAGAAGGG | 112 | RNA bulge |
| EMX1_9 | chr1 | 23720618 | 5.96 | aAGTCCGAGgAG AgGAAGAAAGG | 113 | x |
| EMX1_10 | chr2 | 219845072 | 5.47 | GAGgCCGAGCAG AAGAAagACGG | 114 | x |
| EMX1_11 | chr8 | 102244551 | 4.70 | agtTCCaAGCAG AAGAAGcATGG | 115 | x |
| EMX1_12 | chr3 | 45605387 | 3.11 | GAGTCCacaCAG AAGAAGAAAGA | 116 | x |
| EMX1_13 | chr16 | 12321159 | 3.01 | GAGTCCaAG-AG AAGAAGtgAGG | 117 | RNA bulge |
| EMX1_14 | chr9 | 111348573 | 1.56 | GAGTCCttG-AG AAGAAGgAAGG | 118 | RNA bulge |
| EMX1_15 | chr3 | 5031614 | 1.50 | GAaTCCaAGCAG gAGAAGAAGGA | 119 | x |
| EMX1_16 | chr14 | 31216733 | 1.34 | GtacCaGAG-AG AAGAAGAgAGG | 120 | RNA bulge |
| EMX1_17 | chr14 | 48932119 | 1.16 | GAGTCCcAGCAa AAGAAGAAAAG | 121 | x |
| EMX1_18 | chr11 | 107812992 | 1.04 | aAGTCCaAGt-G AAGAAGAAAGG | 122 | RNA bulge |
| EMX1_19 | chr12 | 106646090 | 1.03 | aAGTCCatGCAG AAGAgGAAGGG | 123 | x |
| EMX1_20 | chr2 | 71969823 | 0.80 | GAGTCCtAG-AG AAGAAaAAGGG | 124 | RNA bulge |
| EMX1_21 | chr3 | 145057362 | 0.48 | GAGTCCct-CAG gAGAAGAAAGG | 125 | RNA bulge |
| EMX1_22 | chr6 | 9118799 | 0.45 | acGTCtGAGCAG AAGAAGAATGG | 126 | x |
| EMX1_23 | chr1 | 59750259 | 0.27 | GAGTtCcAGaAG AAGAAGAAGAG | 127 | x |
| EMX1_24 | chr11 | 79484079 | 0.22 | GAGTCCtAa-AG AAGAAGcAGGG | 128 | RNA bulge |
| EMX1_25 | chr9 | 135663403 | 0.21 | cAGTCCaAaCAG AAGAgGAATGG | 129 | x |

TABLE 3

(On target sequence: FANCF_2)
FANCF

| ID | Chr | Position | DNA Cleavage Score | DNA seq at a cleavage sites | SEQ ID NO | Bulge |
|---|---|---|---|---|---|---|
| FANCF_1 | chr10 | 73463135 | 13.34 | tGAATCCCaTCT cCAGCACCAGG | 130 | x |
| FANCF_2 | chr11 | 22647338 | 7.04 | GGAATCCCTTCT GCAGCACCTGG | 131 | x |
| FANCF_3 | chr10 | 43410030 | 6.53 | GGAgTCCCTcCT aCAGCACCAGG | 132 | x |
| FANCF_4 | chr10 | 37953199 | 5.67 | GGAgTCCCTcCT aCAGCACCAGG | 133 | x |
| FANCF_5 | chr11 | 47554037 | 5.13 | GGAATCCCTTCT aCAGCAtCCTG | 134 | x |
| FANCF_6 | chr16 | 49671025 | 3.00 | GGAgTCCCTcCT GCAGCACCTGA | 135 | x |
| FANCF_7 | chr18 | 8707528 | 1.26 | GGAAcCCCgTCT GCAGCACCAGG | 136 | x |
| FANCF_8 | chr7 | 44076496 | 0.95 | GtctcCCCTTCT GCAGCACCAGG | 137 | x |
| FANCF_9 | chr9 | 113162294 | 0.46 | aaAATCCCTTCc GCAGCACCTAG | 138 | x |
| FANCF_10 | chr15 | 49119756 | 0.42 | tGtATttCTTCT GCctCAggCTG | 139 | x |
| FANCF_11 | chr2 | 54853314 | 0.39 | GGAATatCTTCT GCAGCcCCAGG | 140 | x |
| FANCF_12 | chr8 | 21374810 | 0.37 | GagtgCCCTgaa GCctCAgCTGG | 141 | x |
| FANCF_13 | chrX | 86355179 | 0.35 | accATCCCTcCT GCAGCACCAGG | 142 | x |
| FANCF_14 | chr3 | 35113165 | 0.20 | tGAATCCtaaCT GCAGCACCAGG | 143 | x |
| FANCF_15 | chr10 | 3151994 | 0.13 | ctctgtCCTTCT GCAGCACCTGG | 144 | x |

TABLE 4

(On target sequence: RNF2_1)
RNF2

| ID | Chr | Position | DNA Cleavage Score | DNA seq at a cleavage sites | SEQ ID NO | Bulge |
|---|---|---|---|---|---|---|
| RNF2_1 | chr1 | 185056773 | 27.66 | GTCATCTTAGTC ATTACCTGAGG | 93 | x |

TABLE 5

(On target sequence: HBB_1)
HBB

| ID | Chr | Position | DNA Cleavage Score | DNA seq at a cleavage sites | SEQ ID NO | Bulge |
|---|---|---|---|---|---|---|
| HBB_1 | chr11 | 5248214 | 17.68 | CTTGCCCCACAG GGCAGTAACGG | 145 | x |
| HBB_2 | chr17 | 8370252 | 13.64 | tTgctCCCCACAG GGCAGTAAACG | 146 | x |
| HBB_3 | chr12 | 124803834 | 10.88 | gcTGCCCCACAG GGCAGcAAAGG | 147 | x |
| HBB_4 | chrX | 75006256 | 2.34 | gTgGCCCCACAG GGCAGgAATGG | 148 | x |
| HBB_5 | chr12 | 93549201 | 0.55 | aTTGCCCCACgG GGCAGTgACGG | 149 | x |
| HBB_6 | chr10 | 95791920 | 0.27 | acTctCCCACAa GGCAGTAAGGG | 150 | x |
| HBB_7 | chr9 | 104595883 | 0.18 | tcaGCCCCACAG GGCAGTAAGGG | 151 | x |

TABLE 6

(On target sequence: HEK2_2)
HEK2

| ID | Chr | Position | DNA Cleavage Score | DNA seq at a cleavage sites | SEQ ID NO | Bulge |
|---|---|---|---|---|---|---|
| HEK2_1 | chr4 | 90522183 | 18.27 | GAACACAAtGCA TAGAtTGCCGG | 152 | x |
| HEK2_2 | chr5 | 87240613 | 7.54 | GAACACAAAGCA TAGACTGCGGG | 153 | x |
| HEK2_3 | chr2 | 19844956 | 0.93 | aActcCAAAGCA TAtACTGCTGG | 154 | x |

TABLE 7

(On target sequence: HEK3_2)
HEK3

| ID | Chr | Position | DNA Cleavage Score | DNA seq at a cleavage sites | SEQ ID NO | Bulge |
|---|---|---|---|---|---|---|
| HEK3_1 | chr1 | 47005705 | 29.27 | aGCtCAGACTGA GCAaGTGAGGG | 155 | x |
| HEK3_2 | chr9 | 110184636 | 11.38 | GGCCCAGACTGA GCACGTGATGG | 156 | x |
| HEK3_3 | chr19 | 882560 | 10.90 | GGCCCAGA--GA GCACGTGtGGG | 157 | RNA bulge |
| HEK3_4 | chr15 | 79749930 | 3.03 | caCCCAGACTGA GCACGTGcTGG | 158 | x |

TABLE 7-continued (On target sequence: HEK3_2)
HEK3

| ID | Chr | Position | DNA Cleavage Score | DNA seq at a cleavage sites | SEQ ID NO | Bulge |
|---|---|---|---|---|---|---|
| HEK3_5 | chr17 | 34954539 | 2.10 | GGCCCa-ACTGA GCAaGTGATGG | 159 | RNA bulge |
| HEK3_6 | chrX | 114764149 | 1.66 | aGaCCAGACTGA GCAaGaGAGGG | 160 | x |
| HEK3_7 | chr6 | 73097166 | 0.15 | GGCCactcaTGg cCACaTacTGG | 161 | x |

TABLE 8

(On target sequence: HEK4_1)
HEK4

| ID | Chr | Position | DNA Cleavage Score | DNA seq at a cleavage sites | SEQ ID NO | Bulge |
|---|---|---|---|---|---|---|
| HEK4_1 | chr20 | 31349772 | 19.26 | GGCACTGCGGCT GGAGGTGGGGG | 162 | x |
| HEK4_2 | chr6 | 160517881 | 15.45 | GGCACTGCtGCT GGgGGTGGTGG | 163 | x |
| HEK4_3 | chr6 | 168787137 | 15.37 | GGCACTGCa-CT GGAGGTtGTGG | 164 | RNA bulge |
| HEK4_4 | chr19 | 33382081 | 13.83 | GGCtCTGCGGCT GGAGGgGGTGG | 165 | x |
| HEK4_5 | chr20 | 60080553 | 12.71 | aGCACTGCaGaT GGAGGaGGCGG | 166 | x |
| HEK4_6 | chr5 | 141232853 | 10.87 | GGCACTGCGGCa GGgaGgaGGGG | 167 | x |
| HEK4_7 | chr20 | 60010562 | 10.51 | tGCACTGCGGCc GGAGGaGGTGG | 168 | x |
| HEK4_8 | chr13 | 70136736 | 8.76 | GGCACT-gGGCT GaAGGTaGAGG | 169 | RNA bulge |
| HEK4_9 | chr20 | 1151854 | 8.41 | GGCACTGtGGCT GcAGGTGGAGG | 170 | x |
| HEK4_10 | chr15 | 71686928 | 7.70 | tGCtCTGCGGCa GGAGGaGGAGG | 171 | x |
| HEK4_11 | chr7 | 1397398 | 6.71 | aGCACTGCaGCT GGgaGTGGAGG | 172 | x |
| HEK4_12 | chr20 | 45343010 | 6.57 | GGCACTGaGGgT GGAGGTGGGGG | 173 | x |
| HEK4_13 | chr8 | 20854500 | 5.57 | GGCACTGgGGCT GGAGacGGGGG | 174 | x |
| HEK4_14 | chr7 | 54561437 | 5.40 | aGgACTGCGGCT GGgGGTGGTGG | 175 | x |
| HEK4_15 | chr15 | 60790561 | 5.29 | GGCACTGCaaCT GGAaGTGaTGG | 176 | x |
| HEK4_16 | chr13 | 27629410 | 4.40 | GGCACTGgGGtT GGAGGTGGGGG | 177 | x |
| HEK4_17 | chr7 | 110143150 | 3.69 | GcCACTGCaGCT aGAGGTGGAGG | 178 | x |

TABLE 8-continued (On target sequence: HEK4_1)
HEK4

| ID | Chr | Position | DNA Cleavage Score | DNA seq at a cleavage sites | SEQ ID NO | Bulge |
|---|---|---|---|---|---|---|
| HEK4_18 | chr7 | 139244406 | 3.59 | GcCACTGCGaCT GGAGGaGGGGG | 179 | x |
| HEK4_19 | chr19 | 2474643 | 3.56 | GGCACTG-GGCT GGAGGcGGGGG | 180 | RNA bulge |
| HEK4_20 | chr2 | 6961255 | 3.17 | aGCtCTGCGGCa GGAGtTGGAGG | 181 | x |
| HEK4_21 | chr17 | 75429280 | 2.90 | GaCACcaCGGCT GGAGaTGGTGG | 182 | x |
| HEK4_22 | chr7 | 17979717 | 2.66 | GcactgGCaGCc GGAGGTGGTGG | 183 | DNA bulge |
| HEK4_23 | chr9 | 5020590 | 2.64 | tGCACTGCaGCT GcAGGTGGAGG | 184 | x |
| HEK4_24 | chrX | 122479548 | 2.52 | GGCACTG-GGCT GGAGaTGGAGG | 185 | RNA bulge |
| HEK4_25 | chr12 | 104739608 | 2.48 | ccttCTGCGGCT GGAaGTGGTGG | 186 | x |
| HEK4_26 | chr17 | 40693638 | 2.38 | GcactgcaGGCa GGAGGTGaGTG | 187 | DNA bulge |
| HEK4_27 | chr8 | 144781301 | 2.38 | GaCACTGCaGCT GGAGGTGGGGT | 188 | x |
| HEK4_28 | chr9 | 74103955 | 2.36 | GGCACTGCaGCa GGgGaTGGGGG | 189 | x |
| HEK4_29 | chr18 | 37194558 | 2.31 | GGCACTGCGGgT GGAGGcGGGGG | 190 | x |
| HEK4_30 | chr20 | 60895671 | 2.12 | GGCACaGCaGCT GGAGGTGcTGG | 191 | x |
| HEK4_31 | chr12 | 113935460 | 1.63 | GGCcCTGCGGCT GGAGaTatGGG | 192 | x |
| HEK4_32 | chrX | 70597642 | 1.57 | GaCACTGC-tCT GGAGGTGGTGG | 193 | RNA bulge |
| HEK4_33 | chr15 | 41044242 | 1.31 | GGCgGGAGCTGC GGCgGTGGAGG | 194 | x |
| HEK4_34 | chr17 | 176302 | 1.18 | tGCACTGtGGCT GGAGaTGGGGG | 195 | x |
| HEK4_35 | chr10 | 77103119 | 1.15 | GGCAtcaCGGCT GGAGGTGGAGG | 196 | x |
| HEK4_36 | chr7 | 134872032 | 0.93 | aGCACTGtGGCT GGgGGaGGCGG | 197 | x |
| HEK4_37 | chr9 | 133039175 | 0.86 | GtCACTGCaGCT GGAGGaGGGGG | 198 | x |
| HEK4_38 | chr10 | 73435248 | 0.79 | GtaACTGCGGCT GGcGGTGGTGG | 199 | x |
| HEK4_39 | chr14 | 21993455 | 0.78 | GGtACaGCGGCT GGgGGaGGCGG | 200 | x |
| HEK4_40 | chr17 | 29815563 | 0.59 | GGCgCTGCGGCc GGAGGTGGGGC | 201 | x |
| HEK4_41 | chr16 | 50300346 | 0.56 | aGCACTGtGGCT GGgGGaGGGGG | 202 | x |

TABLE 8-continued (On target sequence: HEK4_1)
HEK4

| ID | Chr | Position | DNA Cleavage Score | DNA seq at a cleavage sites | SEQ ID NO | Bulge |
|---|---|---|---|---|---|---|
| HEK4_42 | chr11 | 78127584 | 0.53 | tGCACTGCaGCT GGAGGcaaCGG | 203 | x |
| HEK4_43 | chr19 | 1295086 | 0.52 | GaCACTGaGGCa GGAGGTGGGGG | 204 | x |
| HEK4_44 | chr2 | 162283033 | 0.51 | GGCAtctgGGTG GCTGGgaGGGG | 205 | x |
| HEK4_45 | chr20 | 24376056 | 0.47 | GGCACTGaGaCc aGAGGTGGTGG | 206 | x |
| HEK4_46 | chr16 | 1029977 | 0.42 | GGCACTGCaGac GGAGGTGtGGG | 207 | x |
| HEK4_47 | chr19 | 47503406 | 0.39 | GGCACTG-GGCT GGAGGgGaGAG | 208 | RNA bulge |
| HEK4_48 | chr2 | 231467380 | 0.39 | GGCACTGCaGCT GGgGGTtGGTG | 209 | x |
| HEK4_49 | chr10 | 13692636 | 0.38 | GGCACTGgGGCT GGgGGaGGGGG | 210 | x |
| HEK4_50 | chr1 | 32471659 | 0.34 | GGCACTtCaGCT GGAGGcaGAGG | 211 | x |
| HEK4_51 | chr17 | 8634933 | 0.33 | GGCACat-GGaT GGAGGTGGAGG | 212 | RNA bulge |
| HEK4_52 | chr6 | 83388605 | 0.30 | aGCACTGtGG-T GGAGGTGGAGG | 213 | RNA bulge |
| HEK4_53 | chr10 | 27700491 | 0.29 | GGCACTG-GGtT GGgGGTGGTGG | 214 | RNA bulge |
| HEK4_54 | chr1 | 143662284 | 0.27 | GGCACat-GGCT GGgGGTGGTGG | 215 | RNA bulge |
| HEK4_55 | chr16 | 49777696 | 0.22 | tGCACTGCGaCT GGAGGgaGAGG | 216 | x |
| HEK4_56 | chr19 | 38616186 | 0.19 | GGCACTGaGaCT GGgGGTGGGGG | 217 | x |
| HEK4_57 | chr10 | 126752487 | 0.18 | GGCACTGCaGCc tGgGGgtGGGG | 218 | x |
| HEK4_58 | chr16 | 28266968 | 0.17 | GGCtCTtCGGCT GGAGGTaGCGG | 219 | x |
| HEK4_59 | chr2 | 149886210 | 0.15 | GaCACTG-GGCT GGAGGTtGCGG | 220 | RNA bulge |
| HEK4_60 | chr20 | 37471343 | 0.15 | aGCACTGtGcCT GGgGGTGGGGG | 221 | x |
| HEK4_61 | chr12 | 53453556 | 0.13 | tGgACTGCGGCT GGAGagGGAGG | 222 | x |
| HEK4_62 | chr15 | 30501337 | 0.13 | GGCACTG-GGCT GGAtGTGGTGG | 223 | RNA bulge |
| HEK4_63 | chr5 | 139284047 | 0.12 | GGCACTGaGGCT GcAGGcGGCGG | 224 | x |
| HEK4_64 | chr8 | 119227145 | 0.12 | GGCACaatGGCT GGAGGTGaAGG | 225 | x |

TABLE 8-continued (On target sequence: HEK4_1)
HEK4

| ID | Chr | Position | DNA Cleavage Score | DNA seq at a cleavage sites | SEQ ID NO | Bulge |
|---|---|---|---|---|---|---|
| HEK4_65 | chr14 | 95761249 | 0.11 | GGCACTctGGCT GGAGcTGGGGG | 226 | x |
| HEK4_66 | chr3 | 23651529 | 0.11 | GGCACaGCaGgT GGAGGTGGAGG | 227 | x |
| HEK4_67 | chr12 | 9287415 | 0.10 | GGCtCTGCaGCc aGgGGTGGAGG | 228 | x |

(In Tables 2 to 8, the bases in lower case letters represent mismatched bases)

FIGS. 6a and 6b are genome-wide circus plots representing DNA cleavage scores obtained with intact genomic DNA (first layer from the center) and genomic DNA digested with BE3 and USER (second layer from the center) or with Cas9 (third layer from the center, only present in FIG. 6b), where the arrow indicates on-target site. FIGS. 6c and 6d show sequence logos obtained via WebLogo using DNA sequences at Digenome-capture sites (Tables 2-8) (DNA cleavage score >2.5). FIGS. 6e and 6f represent scatterplots of BE3-mediated substitution frequencies vs Cas9-mediated indel frequencies determined using targeted deep sequencing, wherein circled dots indicate off-target sites validated by BE3 but invalidated by Cas9. FIGS. 6g and 6h show BE3 off-target sites validated in HEK293T cells by targeted deep sequencing, wherein PAM sequences are the last 3 nucleotides at 3' end, mismatched bases are shown in small letters, and dashes(-) indicate RNA bulges (Error bars indicate s.e.m. (n=3)).

The primers used in the deep sequencing are summarized in Tables 9 to 15 below:

TABLE 9

EMX1

| | 1st PCR | | | | 2nd PCR | | | |
|---|---|---|---|---|---|---|---|---|
| ID | SEQ ID NO: | Forward (5'to3') | SEQ ID NO: | Reverse (5'to3') | SEQ ID NO: | Forward (5'to3') | SEQ ID NO: | Reverse (5'to3') |
| EMX1_1 | 236 | GCCTTTTTCCG GACACATAA | 237 | GTGACTGGAGT TCAGACGTGTG CTCTTCCGATCT GCCTCATTATCA TCAGTGTTGG | 238 | ACACTCTTTCCC TACACGACGCT CTTCCGATCTAT CTCACCTGGGC GAGAAAG | 239 | GTGACTGGAGT TCAGACGTGTG CTCTTCCGATCT GCCTCATTATCA TCAGTGTTGG |
| EMX1_2 | 240 | ACACTCTTTCCC TACACGACGCT CTTCCGATCTGT CCCAGACCTTC ATCTCCA | 241 | GTCTCTGTGAAT GGCGTCAC | 242 | ACACTCTTTCCC TACACGACGCT CTTCCGATCTGT CCCAGACCTTC ATCTCCA | 243 | GTGACTGGAGT TCAGACGTGTG CTCTTCCGATCT CACTGTCTGCA GGGCTCTCT |
| EMX1_3 | 244 | ACACTCTTTCCC TACACGACGCT CTTCCGATCTTT GGTCCCACAGG TGAATAAC | 245 | TCAAATTGTTTA ATAGCTCTGTTG TT | 246 | ACACTCTTTCCC TACACGACGCT CTTCCGATCTTT GGTCCCACAGG TGAATAAC | 247 | GTGACTGGAGT TCAGACGTGTG CTCTTCCGATCT TTTTTGGTCAAT ATCTGAAAGGTT |
| EMX1_4 (on target) | 248 | AGTGTTGAGGC CCCAGTG | 249 | GTGACTGGAGT TCAGACGTGTG CTCTTCCGATCT CAGCAGCAAGC AGCACTCT | 250 | ACACTCTTTCCC TACACGACGCT CTTCCGATCTG GGCCTCCTGAG TTTCTCAT | 251 | GTGACTGGAGT TCAGACGTGTG CTCTTCCGATCT CAGCAGCAAGC AGCACTCT |
| EMX1_5 | 252 | ACACTCTTTCCC TACACGACGCT CTTCCGATCTCT GAAAATTTATGA CAATTTACTACC A | 253 | AAAAGATGTGG TATATACATACG ATGG | 254 | ACACTCTTTCCC TACACGACGCT CTTCCGATCTCT GAAAATTTATGA CAATTTACTACC A | 255 | GTGACTGGAGT TCAGACGTGTG CTCTTCCGATCT CAAACAAAGAA GGAAAGTCCTC A |
| EMX1_6 | 256 | ACACTCTTTCCC TACACGACGCT CTTCCGATCTG CTTGCCTGTGT GACTTGAC | 257 | TGTCTCATTGGC TTTTTCTTTTC | 258 | ACACTCTTTCCC TACACGACGCT CTTCCGATCTG CTTGCCTGTGT GACTTGAC | 259 | GTGACTGGAGT TCAGACGTGTG CTCTTCCGATCT GCCCAGCTGTG CATTCTATC |

TABLE 9-continued

| | EMX1 | | | | | | | |
|---|---|---|---|---|---|---|---|---|
| | 1st PCR | | | | 2nd PCR | | | |
| ID | SEQ ID NO: | Forward (5'to3') | SEQ ID NO: | Reverse (5'to3') | SEQ ID NO: | Forward (5'to3') | SEQ ID NO: | Reverse (5'to3') |
| EMX1_7 | 260 | ACACTCTTTCCCTACACGACGCTCTTCCGATCTTGAGCCCTATGAAAAGATTGC | 261 | CCCAGCTACACGTCACAATG | 262 | ACACTCTTTCCCTACACGACGCTCTTCCGATCTTGAGCCCTATGAAAAGATTGC | 263 | GTGACTGGAGTTCAGACGTGTGCTCTTCCGATCTTAGGGTCCAGGCAAGAGAAA |
| EMX1_8 | 264 | ACACTCTTTCCCTACACGACGCTCTTCCGATCTACATTGCTACCCCTTGGTGA | 265 | TCTGTCTGGCAGATGATACCC | 266 | ACACTCTTTCCCTACACGACGCTCTTCCGATCTACATTGCTACCCCTTGGTGA | 267 | GTGACTGGAGTTCAGACGTGTGCTCTTCCGATCTATCTGCTTCCTCGTGGTCAT |
| EMX1_9 | 268 | ACACTCTTTCCCTACACGACGCTCTTCCGATCTCGGTTCCGGTACTTCATGTC | 269 | GATCTGATCTTACCCCAGAAGC | 270 | ACACTCTTTCCCTACACGACGCTCTTCCGATCTCGGTTCCGGTACTTCATGTC | 271 | GTGACTGGAGTTCAGACGTGTGCTCTTCCGATCTCTGCTACTTGGCTGACCACA |
| EMX1_10 | 272 | CTCCTCCGACCAGCAGAG | 273 | GTGACTGGAGTTCAGACGTGTGCTCTTCCGATCTTCCCTCAGCCACTTTATTTCA | 274 | ACACTCTTTCCCTACACGACGCTCTTCCGATCTAAGGAGGTGCAGGAGCTAGA | 275 | GTGACTGGAGTTCAGACGTGTGCTCTTCCGATCTTCCCTCAGCCACTTTATTTCA |
| EMX1_11 | 276 | GGTGCTGTGGGGGCATAG | 277 | GTGACTGGAGTTCAGACGTGTGCTCTTCCGATCTACAGGCGAACAGAACAGACA | 278 | ACACTCTTTCCCTACACGACGCTCTTCCGATCTCCTTGATTTGGAGGGGTCTT | 279 | GTGACTGGAGTTCAGACGTGTGCTCTTCCGATCTACAGGCGAACAGAACAGACA |
| EMX1_12 | 280 | CCCTTTCTTAATAAATTACCCAGTTTC | 281 | GTGACTGGAGTTCAGACGTGTGCTCTTCCGATCTAAAAAGATAGGCAAACATAGGAAAA | 282 | ACACTCTTTCCCTACACGACGCTCTTCCGATCTTGGACTAAAACACTGCCCAAG | 283 | GTGACTGGAGTTCAGACGTGTGCTCTTCCGATCTAAAAAGATAGGCAAACATAGGAAAA |
| EMX1_13 | 284 | GCTTTTCTGGGGACATAGCA | 285 | GTGACTGGAGTTCAGACGTGTGCTCTTCCGATCTAAGAATTCCAGGCAGTTAACCA | 286 | ACACTCTTTCCCTACACGACGCTCTTCCGATCTACTTCCCTTGTCATCCCACA | 287 | GTGACTGGAGTTCAGACGTGTGCTCTTCCGATCTAAGAATTCCAGGCAGTTAACCA |
| EMX1_14 | 288 | CACAGGAATGTCTTGGGTCA | 289 | GTGACTGGAGTTCAGACGTGTGCTCTTCCGATCTCTCTTCAATCCATCGCCAGT | 290 | ACACTCTTTCCCTACACGACGCTCTTCCGATCTCTTAGCCTGGGTCATGCACT | 291 | GTGACTGGAGTTCAGACGTGTGCTCTTCCGATCTCTCTTCAATCCATCGCCAGT |
| EMX1_15 | 292 | ACACTCTTTCCCTACACGACGCTCTTCCGATCTTGAGGAGGCAAAAGGGAATA | 293 | GCACTTGTTGGCCATTTGTA | 294 | ACACTCTTTCCCTACACGACGCTCTTCCGATCTTGAGGAGGCAAAAGGGAATA | 295 | GTGACTGGAGTTCAGACGTGTGCTCTTCCGATCTTTTTGAATATGTTTTAAATTCTCCACA |
| EMX1_16 | 296 | ACACTCTTTCCCTACACGACGCTCTTCCGATCTAAGGCTAGCCCAGAGTCTCC | 297 | GCACAGAGGGTTGTTTGCTT | 298 | ACACTCTTTCCCTACACGACGCTCTTCCGATCTAAGGCTAGCCCAGAGTCTCC | 299 | GTGACTGGAGTTCAGACGTGTGCTCTTCCGATCTTTCATCCTTTTGTGGGGTTC |
| EMX1_17 | 300 | GGAATCAATCAATGAAGTTGAAGA | 301 | GTGACTGGAGTTCAGACGTGTGCTCTTCCGATCTTTTGCAATTTGCTTAGTTATTGAA | 302 | ACACTCTTTCCCTACACGACGCTCTTCCGATCTGCAATCTGAAGAACAAAGAGCA | 303 | GTGACTGGAGTTCAGACGTGTGCTCTTCCGATCTTTTGCAATTTGCTTAGTTATTGAA |
| EMX1_18 | 304 | ACACTCTTTCCCTACACGACGCTCTTCCGATCTTGACATTTGATAGAACAGATGGGTA | 305 | TCAAGAGACTGTTGTTTTAGATTGTC | 306 | ACACTCTTTCCCTACACGACGCTCTTCCGATCTTGACATTTGATAGAACAGATGGGTA | 307 | GTGACTGGAGTTCAGACGTGTGCTCTTCCGATCTCCCAGTCCAATGGCTGTAGT |

TABLE 9-continued

| | EMX1 | | | | | | | |
|---|---|---|---|---|---|---|---|---|
| | 1st PCR | | | | 2nd PCR | | | |
| ID | SEQ ID NO: | Forward (5'to3') | SEQ ID NO: | Reverse (5'to3') | SEQ ID NO: | Forward (5'to3') | SEQ ID NO: | Reverse (5'to3') |
| EMX1_19 | 308 | CCCTGCAAATT GAGTACGTG | 309 | GTGACTGGAGT TCAGACGTGTG CTCTTCCGATCT GTCCCGAAGTG CTGGAATTA | 310 | ACACTCTTTCCC TACACGACGCT CTTCCGATCTTG GGGGCCATTCT TTATAGTT | 311 | GTGACTGGAGT TCAGACGTGTG CTCTTCCGATCT GTCCCGAAGTG CTGGAATTA |
| EMX1_20 | 312 | GACAGTCCTGG GCTAGGTGA | 313 | GTGACTGGAGT TCAGACGTGTG CTCTTCCGATCT CTCTGGACTCA GCTCCCATC | 314 | ACACTCTTTCCC TACACGACGCT CTTCCGATCTGA GAGTCAGGAGT GCCCAGT | 315 | GTGACTGGAGT TCAGACGTGTG CTCTTCCGATCT CTCTGGACTCA GCTCCCATC |
| EMX1_21 | 316 | ACACTCTTTCCC TACACGACGCT CTTCCGATCTCC TCTCATTTCTAC | 317 | AGATGAATGCA GGGAGCTGT CACCATTG | 318 | ACACTCTTTCCC TACACGACGCT CTTCCGATCTCC TCTCATTTCTAC CACCATTG | 319 | GTGACTGGAGT TCAGACGTGTG CTCTTCCGATCT TTCTGAATTAAA AATGGAAAGAA CTG |
| EMX1_22 | 320 | ACAATTTCAGTA GTAGCATTAAG GAAT | 321 | GTGACTGGAGT TCAGACGTGTG CTCTTCCGATCT TTGTGACAAACT GCCCTCTG | 322 | ACACTCTTTCCC TACACGACGCT CTTCCGATCTGA ATGCCAGTTCT GGGTTGT | 323 | GTGACTGGAGT TCAGACGTGTG CTCTTCCGATCT TTGTGACAAACT GCCCTCTG |
| EMX1_23 | 324 | ACACTCTTTCCC TACACGACGCT CTTCCGATCTAA TTTCTGAACCCA AAGACAGG | 325 | CAAAAATCAACT CAAGATGGATTA AA | 326 | ACACTCTTTCCC TACACGACGCT CTTCCGATCTAA TTTCTGAACCCA AAGACAGG | 327 | GTGACTGGAGT TCAGACGTGTG CTCTTCCGATCT GAGAACCTAGG GAAAACTCTTCTG |
| EMX1_24 | 328 | ACACTCTTTCCC TACACGACGCT CTTCCGATCTCC AAGCTATTTAAC TGGTATGCAC | 329 | CTTGTGGATCAT GGGTACTGAG | 330 | ACACTCTTTCCC TACACGACGCT CTTCCGATCTCC AAGCTATTTAAC TGGTATGCAC | 331 | GTGACTGGAGT TCAGACGTGTG CTCTTCCGATCT TGGGCCTTGGT ATTAGAGCA |
| EMX1_25 | 332 | ACACTCTTTCCC TACACGACGCT CTTCCGATCTTC AAGGGGGTATA TAAAAGGAAGA | 333 | TGCTTTTTCACT TGTCTAGTTTTC TT | 334 | ACACTCTTTCCC TACACGACGCT CTTCCGATCTTC AAGGGGGTATA TAAAAGGAAGA | 335 | GTGACTGGAGT TCAGACGTGTG CTCTTCCGATCT AACAATTTCCCA CAAAGTCCA |

TABLE 10

| | FANCF | | | | | | | |
|---|---|---|---|---|---|---|---|---|
| | 1st PCR | | | | 2nd PCR | | | |
| ID | SEQ ID NO: | Forward (5'to3') | SEQ ID NO: | Reverse (5'to3') | SEQ ID NO: | Forward (5'to3') | SEQ ID NO: | Reverse (5'to3') |
| FANCF_1 | 336 | CTGAAGGTGCT GGTTTAGGG | 337 | GTGACTGGAGT TCAGACGTGTG CTCTTCCGATCT TGTCTGATTGAG TCCCCACA | 338 | ACACTCTTTCCC TACACGACGCT CTTCCGATCTTG ACATCCAGGGT TTCAAGTC | 339 | GTGACTGGAGT TCAGACGTGTG CTCTTCCGATCT TGTCTGATTGAG TCCCCACA |
| FANCF_2 (on target) | 340 | ACACTCTTTCCC TACACGACGCT CTTCCGATCTAT GGATGTGGCGC AGGTAG | 341 | TGACATGCATTT CGACCAAT | 342 | ACACTCTTTCCC TACACGACGCT CTTCCGATCTAT GGATGTGGCGC AGGTAG | 343 | GTGACTGGAGT TCAGACGTGTG CTCTTCCGATCT AGCATTGCAGA GAGGCGTAT |
| FANCF_3 | 344 | CCTCAGGGATG GATGAAGTG | 345 | GTGACTGGAGT TCAGACGTGTG CTCTTCCGATCT TCCCAGTGAGA CCAGTTTGA | 346 | ACACTCTTTCCC TACACGACGCT CTTCCGATCTCC CTTACCAGATG GAGGACA | 347 | GTGACTGGAGT TCAGACGTGTG CTCTTCCGATCT TCCCAGTGAGA CCAGTTTGA |

TABLE 10-continued

FANCF

| ID | SEQ ID NO: | 1st PCR Forward (5'to3') | SEQ ID NO: | 1st PCR Reverse (5'to3') | SEQ ID NO: | 2nd PCR Forward (5'to3') | SEQ ID NO: | 2nd PCR Reverse (5'to3') |
|---|---|---|---|---|---|---|---|---|
| FANCF_4 | 348 | CCCTTACCAGAT GGAGGACA | 349 | GTGACTGGAGT TCAGACGTGTG CTCTTCCGATCT ACCTTGAGTTTT GCCCAGTG | 350 | ACACTCTTTCCC TACACGACGCT CTTCCGATCTGT GACCCAGGTCC AGTGTTT | 351 | GTGACTGGAGT TCAGACGTGTG CTCTTCCGATCT ACCTTGAGTTTT GCCCAGTG |
| FANCF_5 | 352 | AGCTTTAAAATG GGGAATCCA | 353 | GTGACTGGAGT TCAGACGTGTG CTCTTCCGATCT TTCCCAGCACT GTTCTGTTG | 354 | ACACTCTTTCCC TACACGACGCT CTTCCGATCTCT CCAGTACAGGG GCTTTTG | 355 | GTGACTGGAGT TCAGACGTGTG CTCTTCCGATCT TTCCCAGCACT GTTCTGTTG |
| FANCF_6 | 356 | ACACAGGGTGC AGTGGTACA | 357 | GTGACTGGAGT TCAGACGTGTG CTCTTCCGATCT TGGGGAGTATC CTTGCAATC | 358 | ACACTCTTTCCC TACACGACGCT CTTCCGATCTAG GTGCTTCTGCA GGTCATC | 359 | GTGACTGGAGT TCAGACGTGTG CTCTTCCGATCT TGGGGAGTATC CTTGCAATC |
| FANCF_7 | 360 | ACGCCAGCACT TTCTAAGGA | 361 | GTGACTGGAGT TCAGACGTGTG CTCTTCCGATCT CACAGATTGAT GCCACTGGA | 362 | ACACTCTTTCCC TACACGACGCT CTTCCGATCTG CCTGCTGCACT CTCTGAGTA | 363 | GTGACTGGAGT TCAGACGTGTG CTCTTCCGATCT CACAGATTGAT GCCACTGGA |
| FANCF_8 | 364 | ACACTCTTTCCC TACACGACGCT CTTCCGATCTTT TCCTCAACCTTT TCTGCTG | 365 | ACACCTCCGAG GCCTTCT | 366 | ACACTCTTTCCC TACACGACGCT CTTCCGATCTTT TCCTCAACCTTT TCTGCTG | 367 | GTGACTGGAGT TCAGACGTGTG CTCTTCCGATCT CAGGTCCTCCT CTCCCAGTT |
| FANCF_9 | 368 | ACACTCTTTCCC TACACGACGCT CTTCCGATCTCC TGAATAACTAAA TGACAACATGG | 369 | GCCAGGATTTC CTCAAACAA | 370 | ACACTCTTTCCC TACACGACGCT CTTCCGATCTCC TGAATAACTAAA TGACAACATGG | 371 | GTGACTGGAGT TCAGACGTGTG CTCTTCCGATCT GCCAAGTTCCC ATAAGCAAA |
| FANCF_10 | 372 | GCTCTCAAATG GCTCCAAAC | 373 | GTGACTGGAGT TCAGACGTGTG CTCTTCCGATCT CAGAGTGGCCT GCTTACAATC | 374 | ACACTCTTTCCC TACACGACGCT CTTCCGATCTTC CTCCATCTCATT CCCATC | 375 | GTGACTGGAGT TCAGACGTGTG CTCTTCCGATCT CAGAGTGGCCT GCTTACAATC |
| FANCF_11 | 376 | GCCGAGAATTA CCACGACAT | 377 | GTGACTGGAGT TCAGACGTGTG CTCTTCCGATCT GGCACACAGCT | 378 | ACACTCTTTCCC TACACGACGCT CTTCCGATCTTC ACAGCGAGGAA | 379 | GTGACTGGAGT TCAGACGTGTG CTCTTCCGATCT GGCACACAGCT |
| FANCF_12 | 380 | ACACTCTTTCCC TACACGACGCT CTTCCGATCTG GAGCTCTCAGT TGGACTGG | 381 | GTACGTAGG CTCCTCAGTGG GTGAAGTCC | 382 | GGACAAT ACACTCTTTCCC TACACGACGCT CTTCCGATCTG GAGCTCTCAGT TGGACTGG | 383 | GTACGTAGG GTGACTGGAGT TCAGACGTGTG CTCTTCCGATCT ACGGAGAGGTC ACATGAAGG |
| FANCF_13 | 384 | TGAAAAGCAGT CTAGGACACAA A | 385 | GTGACTGGAGT TCAGACGTGTG CTCTTCCGATCT CAACTCTGCCAT GTGCCTTA | 386 | ACACTCTTTCCC TACACGACGCT CTTCCGATCTTG GCAGGCTAGGT TTAGAGC | 387 | GTGACTGGAGT TCAGACGTGTG CTCTTCCGATCT CAACTCTGCCAT GTGCCTTA |
| FANCF_14 | 388 | CACATATGAAAT ATTAAATTTGAA CCA | 389 | GTGACTGGAGT TCAGACGTGTG CTCTTCCGATCT GGGAATATAGA AAAATCAAGAGA TGG | 390 | ACACTCTTTCCC TACACGACGCT CTTCCGATCTTG AACCATGTTACC TTTTGACC | 391 | GTGACTGGAGT TCAGACGTGTG CTCTTCCGATCT GGGAATATAGA AAAATCAAGAGA TGG |
| FANCF_15 | 392 | CGTCTTCGCTCT TTGGTTTT | 393 | GTGACTGGAGT TCAGACGTGTG CTCTTCCGATCT CACCCTGTAGA TCTCTCTCACG | 394 | ACACTCTTTCCC TACACGACGCT CTTCCGATCTTG TGGCACATAGT CGTAACCTC | 395 | GTGACTGGAGT TCAGACGTGTG CTCTTCCGATCT CACCCTGTAGA TCTCTCTCACG |

TABLE 11

| | RNF2 | | | | | | | |
|---|---|---|---|---|---|---|---|---|
| | 1st PCR | | | | 2nd PCR | | | |
| ID | SEQ ID NO: | Forward (5'to3') | SEQ ID NO: | Reverse (5'to3') | SEQ ID NO: | Forward (5'to3') | SEQ ID NO: | Reverse (5'to3') |
| RNF2_1 (on target) | 396 | CCATAGCACTTC CCTTCCAA | 397 | GTGACTGGAGTT CAGACGTGTGCT CTTCCGATCTGC CAACATACAGAA GTCAGGAA | 398 | ACACTCTTTCCC TACACGACGCTC TTCCGATCTATTT CCAGCAATGTCT CAGG | 399 | GTGACTGGAGTT CAGACGTGTGCT CTTCCGATCTGC CAACATACAGAA GTCAGGAA |

TABLE 12

| | HBB | | | | | | | |
|---|---|---|---|---|---|---|---|---|
| | 1st PCR | | | | 2nd PCR | | | |
| ID | SEQ ID NO: | Forward (5'to3') | SEQ ID NO: | Reverse (5'to3') | SEQ ID NO: | Forward (5'to3') | SEQ ID NO: | Reverse (5'to3') |
| HBB_1 (on target) | 400 | GGCAGAGAGAG TCAGTGCCTA | 401 | GTGACTGGAGTT CAGACGTGTGCT CTTCCGATCTCA GGGCTGGGCAT AAAAGT | 402 | ACACTCTTTCCC TACACGACGCTC TTCCGATCTGTC TCCACATGCCCA GTTTC | 403 | GTGACTGGAGTT CAGACGTGTGCT CTTCCGATCTCA GGGCTGGGCAT AAAAGT |
| HBB_2 | 404 | ACACTCTTTCCC TACACGACGCTC TTCCGATCTCCT ACAGCCTGCGA GGAATA | 405 | GTGGGTGTCCTG GGTTGTT | 406 | ACACTCTTTCCC TACACGACGCTC TTCCGATCTCCT ACAGCCTGCGA GGAATA | 407 | GTGACTGGAGTT CAGACGTGTGCT CTTCCGATCTCA CCTGGAGGCTA GGCACT |
| HBB_3 | 408 | CCCACACAGGTT TTCTCCTC | 409 | GTGACTGGAGTT CAGACGTGTGCT CTTCCGATCTCT AGGCCTTCACCT GGAACC | 410 | ACACTCTTTCCC TACACGACGCTC TTCCGATCTCTT CCCTAGACCTGC CTCCT | 411 | GTGACTGGAGTT CAGACGTGTGCT CTTCCGATCTCT AGGCCTTCACCT GGAACC |
| HBB_4 | 412 | ACACTCTTTCCC TACACGACGCTC TTCCGATCTTTG TGTAACAGCCAC TCACCA | 413 | CAGAAAATAAAG CAGCTGACTCAC | 414 | ACACTCTTTCCC TACACGACGCTC TTCCGATCTTTG TGTAACAGCCAC TCACCA | 415 | GTGACTGGAGTT CAGACGTGTGCT CTTCCGATCTCC TGGCAAAAGTGT TTGGAT |
| HBB_5 | 416 | TTTGCATTCCTTT TAGCTTCTTTT | 417 | GTGACTGGAGTT CAGACGTGTGCT CTTCCGATCTAG CTACCACGGTGA CAGTAACA | 418 | ACACTCTTTCCC TACACGACGCTC TTCCGATCTATG GCTGTTATTCAG GGAAA | 419 | GTGACTGGAGTT CAGACGTGTGCT CTTCCGATCTAG CTACCACGGTGA CAGTAACA |
| HBB_6 | 420 | ACACTCTTTCCC TACACGACGCTC TTCCGATCTTCC ACTTTGTTAGTC AGGAGATTC | 421 | AAATGGTAAAAA GAAACTCAAATG C | 422 | ACACTCTTTCCC TACACGACGCTC TTCCGATCTTCC ACTTTGTTAGTC AGGAGATTC | 423 | GTGACTGGAGTT CAGACGTGTGCT CTTCCGATCTGG ATACCACTGGGC TTCTGA |
| HBB_7 | 424 | TTCAAATCTGGA AAATAATCTATCA CC | 425 | GTGACTGGAGTT CAGACGTGTGCT CTTCCGATCTAT TTCCAGGCTATG CTTCCA | 426 | ACACTCTTTCCC TACACGACGCTC TTCCGATCTTTTT CATACCCTTTCC CGTTC | 427 | GTGACTGGAGTT CAGACGTGTGCT CTTCCGATCTAT TTCCAGGCTATG CTTCCA |

TABLE 13

EK2

| ID | 1st PCR | | | | 2nd PCR | | | |
|---|---|---|---|---|---|---|---|---|
| | SEQ ID NO: | Forward (5'to3') | SEQ ID NO: | Reverse (5'to3') | SEQ ID NO: | Forward (5'to3') | SEQ ID NO: | Reverse (5'to3') |
| HEK2_1 | 428 | ACACTCTTTCCC TACACGACGCTC TTCCGATCTCGT ACTATGCAAGCC ACATTG | 429 | TTTTCTTGTGAA ACAGAAATGTCA | 430 | ACACTCTTTCCC TACACGACGCTC TTCCGATCTCGT ACTATGCAAGCC ACATTG | 431 | GTGACTGGAGTT CAGACGTGTGCT CTTCCGATCTAA TGCTCCCACACC ATTTTT |
| HEK2_2 (on target) | 432 | ACACTCTTTCCC TACACGACGCTC TTCCGATCTAGG ACGTCTGCCCAA TATGT | 433 | TTCCCAAGTGAG AAGCCAGT | 434 | ACACTCTTTCCC TACACGACGCTC TTCCGATCTAGG ACGTCTGCCCAA TATGT | 435 | GTGACTGGAGTT CAGACGTGTGCT CTTCCGATCTAA AATTGTCCAGCC CCATCT |
| HEK2_3 | 436 | ATTTACAAAACTT AGGAGAATCAAA GG | 437 | GTGACTGGAGTT CAGACGTGTGCT CTTCCGATCTCA GCTGCTGTTATC CTTCCTC | 438 | ACACTCTTTCCC TACACGACGCTC TTCCGATCTTCA AAGGAAAAGCAA CGTGA | 439 | GTGACTGGAGTT CAGACGTGTGCT CTTCCGATCTCA GCTGCTGTTATC CTTCCTC |

TABLE 14

HEK3

| ID | 1st PCR | | | | 2nd PCR | | | |
|---|---|---|---|---|---|---|---|---|
| | SEQ ID NO: | Forward (5'to3') | SEQ ID NO: | Reverse (5'to3') | SEQ ID NO: | Forward (5'to3') | SEQ ID NO: | Reverse (5'to3') |
| HEK3_1 | 440 | GCAGTTGCTTG ACTAGAGGTAG C | 441 | GTGACTGGAGT TCAGACGTGTG CTCTTCCGATCT AGTGATGTGGG AGGTTCCTG | 442 | ACACTCTTTCCC TACACGACGCT CTTCCGATCTTC CAGATTCCTGGT CCAAAG | 443 | GTGACTGGAGT TCAGACGTGTG CTCTTCCGATCT AGTGATGTGGG AGGTTCCTG |
| HEK3_2 (on target) | 444 | AAGGCATGGAT GAGAGAAGC | 445 | GTGACTGGAGT TCAGACGTGTG CTCTTCCGATCT CTCCCTAGGTG CTGGCTTC | 446 | ACACTCTTTCCC TACACGACGCT CTTCCGATCTAA ACGCCCATGCA ATTAGTC | 447 | GTGACTGGAGT TCAGACGTGTG CTCTTCCGATCT CTCCCTAGGTG CTGGCTTC |
| HEK3_3 | 448 | CTCAGGAGGCT GAGGTAGGA | 449 | GTGACTGGAGT TCAGACGTGTG CTCTTCCGATCT ACGTGTCTGCG GTTAGCAG | 450 | ACACTCTTTCCC TACACGACGCT CTTCCGATCTAG GAAGATGAGGC TGCAGTG | 451 | GTGACTGGAGT TCAGACGTGTG CTCTTCCGATCT ACGTGTCTGCG GTTAGCAG |
| HEK3_4 | 452 | TTATGCGGCAAA ACAAAATG | 453 | GTGACTGGAGT TCAGACGTGTG CTCTTCCGATCT TCGTCGCTGAC AATTTCTGA | 454 | ACACTCTTTCCC TACACGACGCT CTTCCGATCTGA TCTCATCCCCTG TTGACC | 455 | GTGACTGGAGT TCAGACGTGTG CTCTTCCGATCT TCGTCGCTGAC AATTTCTGA |
| HEK3_5 | 456 | TGTTATCAACTG GGGGTTGC | 457 | GTGACTGGAGT TCAGACGTGTG CTCTTCCGATCT TCCTTCATGGAC TGGTAGGC | 458 | ACACTCTTTCCC TACACGACGCT CTTCCGATCTAG AGGGGCATCTC GTGTAGA | 459 | GTGACTGGAGT TCAGACGTGTG CTCTTCCGATCT TCCTTCATGGAC TGGTAGGC |
| HEK3_6 | 460 | ACACTCTTTCCC TACACGACGCT CTTCCGATCTTG TGTGCATGGTTC ATCCC | 461 | AAGCTATGATGT GATGTGACTGG | 462 | ACACTCTTTCCC TACACGACGCT CTTCCGATCTTG TGTGCATGGTTC ATCCC | 463 | GTGACTGGAGT TCAGACGTGTG CTCTTCCGATCT CATGGTGTCTCA CCCCTGTA |
| HEK3_7 | 464 | GCCATGATCCT CGTGATTTT | 465 | GTGACTGGAGT TCAGACGTGTG CTCTTCCGATCT ACTTACCGAAG GCAGGGACT | 466 | ACACTCTTTCCC TACACGACGCT CTTCCGATCTTC TCATGCTGTCTT GGATAAACA | 467 | GTGACTGGAGT TCAGACGTGTG CTCTTCCGATCT ACTTACCGAAG GCAGGGACT |

TABLE 15

| | HEK4 | | | | | | | |
|---|---|---|---|---|---|---|---|---|
| | 1st PCR | | | | 2nd PCR | | | |
| ID | SEQ ID NO: | Forward (5'to3') | SEQ ID NO: | Reverse (5'to3') | SEQ ID NO: | Forward (5'to3') | SEQ ID NO: | Reverse (5'to3') |
| HEK4_1 (on target) | 468 | ACACTCTTTCCCTACACGACGCTCTTCCGATCTCTCCCTTCAAGATGGCTGAC | 469 | GACGTCCAAAACCAGACTCC | 470 | ACACTCTTTCCCTACACGACGCTCTTCCGATCTCTCCCTTCAAGATGGCTGAC | 471 | GTGACTGGAGTTCAGACGTGTGCTCTTCCGATCTACTCCTTCTGGGGCCTTTT |
| HEK4_2 | 472 | TCCCCAATGTTTTCTTGTGA | 473 | GTGACTGGAGTTCAGACGTGTGCTCTTCCGATCTGATTACACAGAGGAGGCACCA | 474 | ACACTCTTTCCCTACACGACGCTCTTCCGATCTTAGAAGCGGACCCCACATAG | 475 | GTGACTGGAGTTCAGACGTGTGCTCTTCCGATCTGATTACACAGAGGAGGCACCA |
| HEK4_3 | 476 | TGAGAGAACATGGTGCTTTG | 477 | GTGACTGGAGTTCAGACGTGTGCTCTTCCGATCTAGGCTGTGGTAGGGACTCAC | 478 | ACACTCTTTCCCTACACGACGCTCTTCCGATCTGAATGTGGACAGCATTGCAT | 479 | GTGACTGGAGTTCAGACGTGTGCTCTTCCGATCTAGGCTGTGGTAGGGACTCAC |
| HEK4_4 | 480 | ACACTCTTTCCCTACACGACGCTCTTCCGATCTCCAGAAGAGTGTGGTGCAGT | 481 | AACCAACATGGTGGGACACT | 482 | ACACTCTTTCCCTACACGACGCTCTTCCGATCTCCAGAAGAGTGTGGTGCAGT | 483 | GTGACTGGAGTTCAGACGTGTGCTCTTCCGATCTAGGCTGTGGTGAAGAGGATG |
| HEK4_5 | 484 | GGAGTTAGGCGTAGCTTCAGG | 485 | GTGACTGGAGTTCAGACGTGTGCTCTTCCGATCTCCTGGCACAGACCTTCCTAA | 486 | ACACTCTTTCCCTACACGACGCTCTTCCGATCTAATCCAATCAATGGGAGCAT | 487 | GTGACTGGAGTTCAGACGTGTGCTCTTCCGATCTCCTGGCACAGACCTTCCTAA |
| HEK4_6 | 488 | ACACTCTTTCCCTACACGACGCTCTTCCGATCTAAAGCCCAGCTCTGCTGATA | 489 | GCTGGTCATGCAGTGTCTGT | 490 | ACACTCTTTCCCTACACGACGCTCTTCCGATCTAAAGCCCAGCTCTGCTGATA | 491 | GTGACTGGAGTTCAGACGTGTGCTCTTCCGATCTCCCCATTTCTGCCTGATTT |
| HEK4_7 | 492 | ACACTCTTTCCCTACACGACGCTCTTCCGATCTGGGCATGGCTTCTGAGACT | 493 | TGGGCTCAACCCAGGTGT | 494 | ACACTCTTTCCCTACACGACGCTCTTCCGATCTGGGCATGGCTTCTGAGACT | 495 | GTGACTGGAGTTCAGACGTGTGCTCTTCCGATCTCCGGATGATTCTCCTACTTCC |
| HEK4_8 | 496 | ACACTCTTTCCCTACACGACGCTCTTCCGATCTGCCAACTAGAGGCAGACAGG | 497 | AGTTGTGGGGTTTTCTGCTG | 498 | ACACTCTTTCCCTACACGACGCTCTTCCGATCTGCCAACTAGAGGCAGACAGG | 499 | GTGACTGGAGTTCAGACGTGTGCTCTTCCGATCTATTCTGGAGGCAACTCCTCA |
| HEK4_9 | 500 | GGCAAAACCCATTCCAGAAG | 501 | GTGACTGGAGTTCAGACGTGTGCTCTTCCGATCTTGTTAGGAGCTCCCCATCAC | 502 | ACACTCTTTCCCTACACGACGCTCTTCCGATCTACCACGTCAGGACTTGTGTG | 503 | GTGACTGGAGTTCAGACGTGTGCTCTTCCGATCTTGTTAGGAGCTCCCCATCAC |
| HEK4_10 | 504 | ATGTTAGCCGGGATGGTCTA | 505 | GTGACTGGAGTTCAGACGTGTGCTCTTCCGATCTTCCAGGGTATCAGGAAAGGTT | 506 | ACACTCTTTCCCTACACGACGCTCTTCCGATCTGATCTCTTGACTTGGTGATCCA | 507 | GTGACTGGAGTTCAGACGTGTGCTCTTCCGATCTTCCAGGGTATCAGGAAAGGTT |
| HEK4_11 | 508 | ACACTCTTTCCCTACACGACGCTCTTCCGATCTAAATCCTCAGCACACGACAA | 509 | CACAGCCCATCTCTCCACTC | 510 | ACACTCTTTCCCTACACGACGCTCTTCCGATCTAAATCCTCAGCACACGACAA | 511 | GTGACTGGAGTTCAGACGTGTGCTCTTCCGATCTTGGGCTCCAACCTCTTCTAA |
| HEK4_12 | 512 | CCCTGGTGAGCAAACACAC | 513 | GTGACTGGAGTTCAGACGTGTGCTCTTCCGATCTCAGGTCCTGTGCCACCTC | 514 | ACACTCTTTCCCTACACGACGCTCTTCCGATCTCCCACGTGGTATTCACCTCT | 515 | GTGACTGGAGTTCAGACGTGTGCTCTTCCGATCTCAGGTCCTGTGCCACCTC |

TABLE 15-continued

| | | HEK4 | | | | | | |
|---|---|---|---|---|---|---|---|---|
| | | 1st PCR | | | | 2nd PCR | | |
| ID | SEQ ID NO: | Forward (5'to3') | SEQ ID NO: | Reverse (5'to3') | SEQ ID NO: | Forward (5'to3') | SEQ ID NO: | Reverse (5'to3') |
| HEK4_13 | 516 | GCCATCTAATCA CAGCCACA | 517 | GTGACTGGAGTT CAGACGTGTGCT CTTCCGATCTGC ATCTTGTCCCTT CTCAGC | 518 | ACACTCTTTCCC TACACGACGCTC TTCCGATCTCTC CTGGGTGCTCAG ACTTC | 519 | GTGACTGGAGTT CAGACGTGTGCT CTTCCGATCTGC ATCTTGTCCCTT CTCAGC |
| HEK4_14 | 520 | ACACTCTTTCCC TACACGACGCTC TTCCGATCTGTT GAGAAGCAGCAA GGTGA | 521 | CACCATGCCTGG CTAATTTT | 522 | ACACTCTTTCCC TACACGACGCTC TTCCGATCTGTT GAGAAGCAGCAA GGTGA | 523 | GTGACTGGAGTT CAGACGTGTGCT CTTCCGATCTTT AGTAGGGACGG GGTTTCA |
| HEK4_15 | 524 | CAGAACCCAAGG CTCTTGAC | 525 | GTGACTGGAGTT CAGACGTGTGCT CTTCCGATCTAT TTTGCTCAGACC CAGCAT | 526 | ACACTCTTTCCC TACACGACGCTC TTCCGATCTTCC AAGATGCCTTCT GCTCT | 527 | GTGACTGGAGTT CAGACGTGTGCT CTTCCGATCTAT TTTGCTCAGACC CAGCAT |
| HEK4_16 | 528 | ACACTCTTTCCC TACACGACGCTC TTCCGATCTAAC AGAGCCCTGCA GAACAT | 529 | TTTCTCACGATG ACATTTTGG | 530 | ACACTCTTTCCC TACACGACGCTC TTCCGATCTAAC AGAGCCCTGCA GAACAT | 531 | GTGACTGGAGTT CAGACGTGTGCT CTTCCGATCTCG GAGGAGGTAGAT TGGAGA |
| HEK4_17 | 532 | ACACTCTTTCCC TACACGACGCTC TTCCGATCTCAT GTATGCAGCTGC TTTTGA | 533 | TGTTCCTAGAGC AACCTTCACA | 534 | ACACTCTTTCCC TACACGACGCTC TTCCGATCTCAT GTATGCAGCTGC TTTTGA | 535 | GTGACTGGAGTT CAGACGTGTGCT CTTCCGATCTGG AGAGCCAGAGT GGCTAAA |
| HEK4_18 | 536 | CTGAAAGAGGGA GGGGAGAC | 537 | GTGACTGGAGTT CAGACGTGTGCT CTTCCGATCTCT TCGCCAGGTCTT CTGTTC | 538 | ACACTCTTTCCC TACACGACGCTC TTCCGATCTCTC GGGAGAGAGGA AAGGAC | 539 | GTGACTGGAGTT CAGACGTGTGCT CTTCCGATCTCT TCGCCAGGTCTT CTGTTC |
| HEK4_19 | 540 | ACACTCTTTCCC TACACGACGCTC TTCCGATCTCCC GGCCGATTTAAC TTTTA | 541 | GACGCATCCCAC CTCCTC | 542 | ACACTCTTTCCC TACACGACGCTC TTCCGATCTCCC GGCCGATTTAAC TTTTA | 543 | GTGACTGGAGTT CAGACGTGTGCT CTTCCGATCTCT GGGGCACGAAA TGTCC |
| HEK4_20 | 544 | CCAGGAACAGA GGGACCAT | 545 | GTGACTGGAGTT CAGACGTGTGCT CTTCCGATCTCC TGGTTCCAGTCA CCTCTC | 546 | ACACTCTTTCCC TACACGACGCTC TTCCGATCTCCA GGTCCAGAGACA AGACG | 547 | GTGACTGGAGTT CAGACGTGTGCT CTTCCGATCTCC TGGTTCCAGTCA CCTCTC |

FIG. 7 is a Venn diagram showing the number of sites with DNA cleavage scores 2.5 or higher identified by Digenome-seq of Cas9 nuclease- and Base editor-treated genomic DNA.

As can be seen from the above results, seven BE3 deaminases plus USER cleaved human genomic DNA in vitro at just 1-24 (8±3) sites, far fewer than did Cas9 nucleases with the same set of sgRNAs (70±30 sites) in a multiplex Digenome-seq analysis (Kim, D., Kim, S., Kim, S., Park, J. & Kim, J. S. Genome-wide target-specificities of CRISPR-Cas9 nucleases revealed by multiplex Digenome-seq. Genome research 26, 406-415 (2016)) (FIG. 7). This means that BE3 has far fewer potential, not necessarily genuine, off-target sites than does Cas9. Sequence logos, obtained by comparing Digenome-identified sites, showed that both the PAM-distal and PAM-proximal regions contributed to the specificities of BE3 deaminases (FIG. 6c, d). The inventors further improved the computer program (termed Digenome 2.0) to identify potential off-target sites more comprehensively. The inventors counted the number of positions whose DNA cleavage scores were over a cutoff value that ranged from 0.0001 to 10 and the number of PAM (5'-NGN-3' or 5'-NNG-3')-containing sites with 10 or fewer mismatches, compared to the on-target site, among the positions with scores over the cutoff value (FIG. 8). FIG. 8 is a graph showing the number of total sites (■) and the number of PAM-containing sites with ten or fewer mismatches (□) for a range of DNA cleavage scores. Such result was obtained by performing whole genome sequencing (WGS) for intact human genomic DNA (left) and human genomic DNA (right) cleaved by BE3 and USER. Cutoff score of 0.1 was selected, because WGS data obtained using intact genomic DNA, which had not been treated with BE3 and USER and thus served as a negative control, did not yield any false-positive sites with this cutoff score 0.1 (FIG. 8). Based on these results, in determining off-target sites by Digenome 2.0, sites with DNA cleavage score of 0.1 or more and 10 or less mismatch and having PAM (5'-NGN-3' or 5'-NNG-3') are determined as a off-target sites. In determining off-target sites by Digenome 2.0, sites with DNA cleavage score of 2.5 or more are determined as off-target sites. On the other hand, in the off-target localization by Digenome 1.0, a site with a DNA cleavage score of 2.5 or more is determined as off-target site candidates.

With Digenome 2.0, it was able to identify many additional BE3- and Cas9-associated DNA cleavage sites, including two sites that had been missed in the previous study ((Kim, D., Kim, S., Kim, S., Park, J. & Kim, J. S. Genome-wide target-specificities of CRISPR-Cas9 nucleases revealed by multiplex Digenome-seq. Genome Res (2016)) but had been captured by both HTGTS and GUIDE-seq using EMX1-specific Cas9. FIG. 9 is a Venn diagram showing the number of PAM-containing homologous sites with DNA cleavage scores over 0.1 or higher identified by Digenome-seq of Cas9 nuclease- and Base editor-treated genomic DNA. BE3 deaminases induced base conversions in vitro at 1-67 (18±9) sites, whereas Cas9 nucleases cleaved genomic DNA at 30-241 (90±30) sites.

Example 5. Fraction of Homologous Sites Captured by Digenome-Seq

The inventors examined the BE3- and Cas9-associated sites as shown in FIGS. 7 and 9. FIG. 10 shows fractions of homologous sites captured by Digenome-seq, wherein bars represent the number of homologous sites that differ from on-target sites by up to 6nt, squares (BE3) and triangles (Cas9) represent the fraction of Digenome-seq captured sites for a range of mismatch numbers. As shown in FIG. 10, regardless of the number of mismatches, fewer homologous sites were identified by Digenome-seq when BE3 was used than when Cas9 was used.

FIGS. 11a and 11b are graphs showing the significant correlation between the number of BE3- and Cas9-associated sites identified by Digenome 1.0 (11a) and Digenome 2.0 (11b). As shown in FIGS. 11a and 11b, there was a statistically significant correlation [$R^2=0.97$ (Score >2.5, Digenome 1.0) or 0.86 (Digenome 2.0)] between the number of Cas9- and BE3-associated sites. These results suggest that sgRNAs were the primary determinants of both Cas9 and BE3 specificities.

FIGS. 12a and 12b show the correlation between the number of BE3-associated sites identified by Digenome 1.0 (12a) or Digenome 2.0 (12b) and the number of sites with 6 or fewer mismatches. As shown in FIGS. 12a and 12b, a strong correlation [$R^2=0.94$ (Digenome 1.0) or 0.95 (Digenome 2.0)] was observed between the number of BE3-associated, Digenome-captured sites and the number of homologous sites with 6 mismatches in the human genome (defined as "orthogonality"). Of particular interest are those associated with BE3 alone or Cas9 alone. Interestingly, 69% (=18/26) of sites associated with BE3 alone had missing or extra nucleotides, compared to their respective on-target sites, producing, respectively, an RNA or DNA bulge at the DNA-gRNA interface (Table 1). By contrast, these bulge-type off-target sites were rare among Cas9-associated sites. Just 4% (=25/647) of sites associated with Cas9 had missing or extra nucleotides.

FIG. 13 shows examples of Digenome-captured off-target sites associated only with Cas9, which contain no cytosines at positions 4-9. Thirteen % (=73/548) of sites associated with Cas9 alone had no cytosines at positions 4-8 (numbered 1-20 in the 5' to 3' direction), the window of BE3-mediated deamination.

To validate off-target effects at BE3-associated sites identified by Digenome-seq, the inventors performed targeted deep sequencing and measured BE3-induced substitution frequencies and Cas9-induced indel frequencies in HEK293T cells. The results are shown in 6e to 6h as above and Table 16 as below.

TABLE 16

Mutation frequencies of Cas9 and BE3 in on-target and off-target sites captured by Digenome-seq EMX1
Base editing efficiency (%)

| | SEQ ID NO. | | G | A | G | T | C | C | G | A | G | C | A | G | A | A | G | A | A | G | A | A | G | G | G |
|---|---|---|---|---|---|---|---|---|---|---|---|---|---|---|---|---|---|---|---|---|---|---|---|---|---|
| On-target (EMX1_4) | SEQ ID NO: 31 | | G | A | G | T | C | C | G | A | G | C | A | G | A | A | G | A | A | G | A | A | G | G | G |
| | C->other bases | Untreated | | | | | 0.04 | 0.06 | | | | 0.15 | | | | | | | | | | | | | |
| | | (+)jBE1 | | | | | 8.49 | 4.72 | | | | 0.08 | | | | | | | | | | | | | |
| | | (+)jBE2 | | | | | 11.08 | 10.72 | | | | 0.09 | | | | | | | | | | | | | |
| | | (+)jBE3 | | | | | 49.17 | 45.06 | | | | 0.10 | | | | | | | | | | | | | |
| EMX1_1 | SEQ ID NO: 106 | | G | A | G | T | C | t | a | A | G | C | A | G | A | A | G | A | A | G | A | A | G | G | G |
| | C->other bases | Untreated | | | | | 0.04 | | | | | 0.05 | | | | | | | | | | | | | |
| | | (+)jBE1 | | | | | 3.13 | | | | | 0.05 | | | | | | | | | | | | | |
| | | (+)jBE2 | | | | | 0.75 | | | | | 0.05 | | | | | | | | | | | | | |
| | | (+)jBE3 | | | | | 15.57 | | | | | 0.07 | | | | | | | | | | | | | |
| EMX1_2 | SEQ ID NO: 107 | | G | A | G | T | C | C | a | A | G | C | A | G | A | A | G | A | A | G | A | A | G | A | G |
| | C->other bases | Untreated | | | | | 0.08 | 0.08 | | | | 0.07 | | | | | | | | | | | | | |
| | | (+)jBE1 | | | | | 0.65 | 0.31 | | | | 0.06 | | | | | | | | | | | | | |
| | | (+)jBE2 | | | | | 0.32 | 0.32 | | | | 0.07 | | | | | | | | | | | | | |
| | | (+)jBE3 | | | | | 0.84 | 0.81 | | | | 0.07 | | | | | | | | | | | | | |
| EMX1_3 | SEQ ID NO: 108 | | a | A | G | T | C | t | G | A | G | C | A | G | A | A | G | A | A | G | A | A | G | T | G |
| | C->other bases | Untreated | | | | | 0.02 | | | | | 0.07 | 0.06 | | | | | | | | | | | | |
| | | (+)jBE1 | | | | | 0.02 | | | | | 0.07 | 0.04 | | | | | | | | | | | | |
| | | (+)jBE2 | | | | | 0.02 | | | | | 0.05 | 0.05 | | | | | | | | | | | | |
| | | (+)jBE3 | | | | | 0.13 | | | | | 0.07 | 0.05 | | | | | | | | | | | | |
| EMX1_5 | SEQ ID NO: 109 | | G | A | G | T | C | C | a | A | G | — | A | G | A | A | G | A | A | G | A | A | G | T | G |
| | C->other bases | Untreated | | | | | 0.06 | 0.10 | | | | | | | | | | | | | | | | | |
| | | (+)jBE1 | | | | | 0.63 | 0.24 | | | | | | | | | | | | | | | | | |
| | | (+)jBE2 | | | | | 0.32 | 0.34 | | | | | | | | | | | | | | | | | |
| | | (+)jBE3 | | | | | 0.96 | 0.96 | | | | | | | | | | | | | | | | | |

TABLE 16-continued

Mutation frequencies of Cas9 and BE3 in on-target and off-target sites captured by Digenome-seq

| | | | | | | | | | | | | | | | | | | | | | C->other bases |
|---|---|---|---|---|---|---|---|---|---|---|---|---|---|---|---|---|---|---|---|---|---|
| EMX1_6 | SEQ ID NO: 110 | G | A | T | C | C | t | A | G | 9 | A | G | A | A | G | A | A | A | G | | |
| | Untreated | | | | 0.02 | 0.04 | | | | | | | | | | | | | | | 0.04 |
| | (+)BE1 | | | | 0.06 | 0.07 | | | | | | | | | | | | | | | 0.07 |
| | (+)BE2 | | | | 0.07 | 0.08 | | | | | | | | | | | | | | | 0.05 |
| | (+)BE3 | | | | 2.43 | 12.40 | | | | | | | | | | | | | | | 0.04 |
| EMX1_7 | SEQ ID NO: 111 | G | A | T | C | C | a | A | G | t | A | G | A | A | G | A | A | G | G | | |
| | Untreated | | | | 0.03 | 0.06 | | | | | | | | | | | | | | | 0.06 |
| | (+)BE1 | | | | 0.07 | 0.10 | | | | | | | | | | | | | | | 0.07 |
| | (+)BE2 | | | | 0.03 | 0.06 | | | | | | | | | | | | | | | 0.09 |
| | (+)BE3 | | | | 0.05 | 0.09 | | | | | | | | | | | | | | | 0.07 |
| EMX1_8 | SEQ ID NO: 112 | G | t | G | T | C | C | t | A | G | — | A | G | A | A | G | A | A | A | G | |
| | Untreated | | | | | 0.05 | 0.03 | | | | | | | | | | | | | | — |
| | (+)BE1 | | | | | 0.64 | 0.57 | | | | | | | | | | | | | | |
| | (+)BE2 | | | | | 0.54 | 0.39 | | | | | | | | | | | | | | |
| | (+)BE3 | | | | | 0.37 | 0.34 | | | | | | | | | | | | | | |
| EMX1_9 | SEQ ID NO: 113 | a | A | G | T | C | C | G | A | G | A | A | A | g | G | G | A | A | G | | |
| | Untreated | | | | | 0.05 | 0.16 | | | | | | | | | | | | | | g |
| | (+)BE1 | | | | | 0.06 | 0.18 | | | | | | | | | | | | | | |
| | (+)BE2 | | | | | 0.06 | 0.17 | | | | | | | | | | | | | | |
| | (+)BE3 | | | | | 0.09 | 0.25 | | | | | | | | | | | | | | |
| EMX1_10 | SEQ ID NO: 114 | G | A | g | T | C | C | a | A | G | A | A | A | G | A | A | A | G | G | | |
| | Untreated | | | | | 0.14 | 0.10 | | | | | | | | | | | | 0.13 | | |
| | (+)BE1 | | | | | 0.44 | 0.24 | | | | | | | | | | | | 0.16 | | |
| | (+)BE2 | | | | | 0.51 | 0.48 | | | | | | | | | | | | 0.15 | | |
| | (+)BE3 | | | | | 3.45 | 3.70 | | | | | | | | | | | | 0.17 | | |
| EMX1_11 | SEQ ID NO: 115 | a | g | T | C | C | t | A | G | A | A | A | G | A | A | G | c | A | T | G | G |
| | Untreated | | | | 0.06 | 0.05 | | | | | | | | | | | | 0.07 | | | 0.06 |
| | (+)BE1 | | | | 1.19 | 0.44 | | | | | | | | | | | | 0.08 | | | 0.07 |
| | (+)BE2 | | | | 0.46 | 0.43 | | | | | | | | | | | | 0.05 | | | 0.07 |
| | (+)BE3 | | | | 0.74 | 0.62 | | | | | | | | | | | | 0.06 | | | 0.07 |

TABLE 16-continued

Mutation frequencies of Cas9 and BE3 in on-target and off-target sites captured by Digenome-seq

| | | | | | | | | | | | | | | | | | | | | |
|---|---|---|---|---|---|---|---|---|---|---|---|---|---|---|---|---|---|---|---|---|
| EMX1_12 | SEQ ID NO: 116 | G | A | G | T | C | C | a | C | A | G | A | A | G | A | A | A | G | A |
| | Untreated | | | | 0.08 | 0.26 | | 0.11 | 0.11 | | | | | | | | | | |
| | (+)BE1 | | | | 0.08 | 0.24 | | 0.11 | 0.11 | | | | | | | | | | |
| | (+)BE2 | | | | 0.08 | 0.23 | | 0.10 | 0.10 | | | | | | | | | | |
| | (+)BE3 | | | | 0.17 | 0.33 | | 0.17 | 0.10 | | | | | | | | | | |
| C->other bases | | | | | | | | | | | | | | | | | | | |
| EMX1_13 | SEQ ID NO: 117 | G | A | G | T | C | C | a | C | A | G | A | A | G | A | A | g | A | G |
| | Untreated | | | | | 0.08 | 0.12 | | | | | | | | | | | | |
| | (+)BE1 | | | | | 0.07 | 0.11 | | | | | | | | | | | | |
| | (+)BE2 | | | | | 0.07 | 0.11 | | | | | | | | | | | | |
| | (+)BE3 | | | | | 0.08 | 0.13 | | | | | | | | | | | | |
| C->other bases | | | | | | | | | | | | | | | | | | | |
| EMX1_14 | SEQ ID NO: 118 | G | A | G | T | C | C | t | G | A | G | A | A | G | A | A | g | A | G |
| | Untreated | | | | | 0.06 | 0.13 | | | | | | | | | | | | |
| | (+)BE1 | | | | | 0.09 | 0.17 | | | | | | | | | | | | |
| | (+)BE2 | | | | | 0.05 | 0.10 | | | | | | | | | | | | |
| | (+)BE3 | | | | | 0.05 | 0.13 | | | | | | | | | | | | |
| C->other bases | | | | | | | | | | | | | | | | | | | |
| EMX1_15 | SEQ ID NO: 119 | G | A | a | T | C | C | a | A | G | A | g | A | G | A | A | A | G | A |
| | Untreated | | | | | 0.04 | 0.07 | | | | | | 0.05 | | | | | | |
| | (+)BE1 | | | | | 0.03 | 0.08 | | | | | | 0.06 | | | | | | |
| | (+)BE2 | | | | | 0.04 | 0.07 | | | | | | 0.06 | | | | | | |
| | (+)BE3 | | | | | 0.14 | 0.18 | | | | | | 0.05 | | | | | | |
| C->other bases | | | | | | | | | | | | | | | | | | | |
| EMX1_16 | SEQ ID NO: 120 | G | t | a | c | C | C | c | G | A | G | A | A | G | a | A | A | A | G |
| | Untreated | | | 0.06 | 0.06 | | | | | | | | | | | | | | |
| | (+)BE1 | | | 0.05 | 0.05 | | | | | | | | | | | | | | |
| | (+)BE2 | | | 0.05 | 0.05 | | | | | | | | | | | | | | |
| | (+)BE3 | | | 0.05 | 0.05 | | | | | | | | | | | | | | |
| C->other bases | | | | | | | | | | | | | | | | | | | |
| EMX1_17 | SEQ ID NO: 121 | G | A | G | T | C | C | C | C | A | G | A | A | G | A | A | A | A | G |
| | Untreated | | | | | 0.10 | 0.19 | 0.09 | 0.07 | | | | | | | | | | |
| | (+)BE1 | | | | | 0.13 | 0.17 | 0.09 | 0.05 | | | | | | | | | | |
| | (+)BE2 | | | | | 0.10 | 0.20 | 0.06 | 0.03 | | | | | | | | | | |
| | (+)BE3 | | | | | 0.11 | 0.20 | 0.07 | 0.07 | | | | | | | | | | |
| C->other bases | | | | | | | | | | | | | | | | | | | |

TABLE 16-continued

Mutation frequencies of Cas9 and BE3 in on-target and off-target sites captured by Digenome-seq

| | | | | a | A | G | T | C | C | a | A | G | t | — | G | A | A | A | G | A | A | G |
|---|---|---|---|---|---|---|---|---|---|---|---|---|---|---|---|---|---|---|---|---|---|---|
| EMX1_18 | | SEQ ID NO: 122 | | | | | | | | | | | | | | | | | | | | | |
| | C->other bases | Untreated (+)BE1 (+)BE2 (+)BE3 | | | | | | 0.05 0.08 0.08 0.09 | 0.09 0.09 0.10 0.11 | | | | | | | | | | | | | |
| EMX1_19 | | SEQ ID NO: 123 | | a | A | G | T | C | C | a | t | G | C | A | G | A | A | A | G | A | A | G |
| | C->other bases | Untreated (+)BE1 (+)BE2 (+)BE3 | | | | | | 0.03 0.17 0.09 0.24 | 0.07 0.10 0.14 0.30 | | | | 0.10 0.12 0.08 0.12 | | | | | | | | | |
| EMX1_20 | | SEQ ID NO: 124 | | G | A | G | T | C | C | t | A | G | — | A | G | A | A | a | G | A | A | G |
| | C->other bases | Untreated (+)BE1 (+)BE2 (+)BE3 | | | | | | 0.05 0.28 0.39 0.50 | 0.12 0.24 0.42 0.57 | | | | | | | | | | | | | |
| EMX1_21 | | SEQ ID NO: 125 | | G | A | G | T | C | C | c | t | G | C | A | G | A | A | A | G | A | A | G |
| | C->other bases | Untreated (+)BE1 (+)BE2 (+)BE3 | | | | | | 0.16 0.15 0.20 0.20 | 0.08 0.10 0.13 0.12 | 0.07 0.06 0.11 0.10 | | | 0.03 0.04 0.05 0.06 | | | | | | | | | |
| EMX1_22 | | SEQ ID NO: 126 | | a | c | G | T | C | t | G | A | G | C | A | G | A | A | A | G | A | T | G |
| | C->other bases | Untreated (+)BE1 (+)BE2 (+)BE3 | | | 0.14 0.17 0.13 0.15 | | | 0.04 0.36 0.14 0.62 | | | | | 0.11 0.10 0.11 0.12 | | | | | | | | | |
| EMX1_23 | | SEQ ID NO: 127 | | G | A | G | T | C | C | c | A | G | a | A | G | A | A | A | G | A | A | G |
| | C->other bases | Untreated (+)BE1 (+)BE2 (+)BE3 | | | | | | 0.06 0.09 0.06 0.06 | 0.06 0.09 0.06 0.06 | 0.08 0.13 0.10 0.09 | | | | | | | | | | | | |

TABLE 16-continued

Mutation frequencies of Cas9 and BE3 in on-target and off-target sites captured by Digenome-seq

| | | | G | A | G | T | C | C | t | A | a | T | A | C | G | A | A | G | A | c | A | G | G |
|---|---|---|---|---|---|---|---|---|---|---|---|---|---|---|---|---|---|---|---|---|---|---|---|
| EMX1_24 | C->other bases | SEQ ID NO: 128 | | | | | | | | | | | | | | | | | | | | | |
| | | Untreated | | | | | 0.05 | 0.18 | | | | | | | | | | | | 0.11 | | | |
| | | (+)jBE1 | | | | | 0.04 | 0.18 | | | | | | | | | | | | 0.12 | | | |
| | | (+)jBE2 | | | | | 0.05 | 0.19 | | | | | | | | | | | | 0.11 | | | |
| | | (+)jBE3 | | | | | 0.05 | 0.22 | | | | | | | | | | | | 0.12 | | | |

| | | | c | A | G | T | C | C | a | A | a | C | A | G | A | A | g | G | A | A | T | G | G |
|---|---|---|---|---|---|---|---|---|---|---|---|---|---|---|---|---|---|---|---|---|---|---|---|
| EMX1_25 | C->other bases | SEQ ID NO: 129 | 0.11 | | | | 0.05 | 0.11 | | | | 0.11 | | | | | | | | | | | | |
| | | Untreated | 0.08 | | | | 0.10 | 0.10 | | | | 0.10 | | | | | | | | | | | | |
| | | (+)jBE1 | 0.10 | | | | 0.06 | 0.10 | | | | 0.11 | | | | | | | | | | | | |
| | | (+)jBE2 | 0.11 | | | | 0.07 | 0.13 | | | | 0.11 | | | | | | | | | | | | |
| | | (+)jBE3 | | | | | | | | | | | | | | | | | | | | | | |

FANCF

Base editing efficiency (%)

| | | | G | A | A | T | C | C | t | C | T | — | A | C | G | A | C | A | G | C | C | T | G |
|---|---|---|---|---|---|---|---|---|---|---|---|---|---|---|---|---|---|---|---|---|---|---|---|
| On-target (FANCF_2) | C->other bases | SEQ ID NO: 131 | | | | | | 0.06 | 0.10 | 0.04 | | | 0.03 | | 0.13 | 0.12 | | 0.13 | | | 0.05 | 0.04 | | |
| | | Untreated | | | | | | 0.81 | 10.39 | 0.42 | | | 0.07 | | 0.12 | 0.13 | | 0.13 | | | 0.06 | 0.03 | | |
| | | (+)jBE1 | | | | | | 2.11 | 12.06 | 1.97 | | | 0.39 | | 0.14 | 0.09 | | 0.09 | | | 0.07 | 0.02 | | |
| | | (+)jBE2 | | | | | | 10.26 | 9.44 | 9.28 | | | 4.12 | | 0.18 | 0.12 | | 0.12 | | | 0.05 | 0.04 | | |

| | | | t | A | G | A | C | C | C | C | T | T | c | C | T | c | C | A | G | C | C | C | G |
|---|---|---|---|---|---|---|---|---|---|---|---|---|---|---|---|---|---|---|---|---|---|---|---|
| FNACF_1 | C->other bases | SEQ ID NO: 130 | | | | | | 0.07 | 0.10 | 0.08 | | | 0.03 | 0.04 | 0.03 | 0.04 | 0.04 | | 0.07 | | 0.04 | 0.07 | | |
| | | Untreated | | | | | | 0.07 | 0.10 | 0.09 | | | 0.03 | 0.05 | 0.03 | 0.05 | 0.05 | | 0.09 | | 0.03 | 0.06 | | |
| | | (+)jBE1 | | | | | | 0.10 | 0.10 | 0.12 | | | 0.03 | 0.02 | 0.03 | 0.02 | 0.06 | | 0.07 | | 0.02 | 0.08 | | |
| | | (+)jBE2 | | | | | | 0.16 | 0.16 | 0.18 | | | 0.06 | 0.05 | 0.06 | 0.05 | 0.07 | | 0.09 | | 0.03 | 0.07 | | |

| | | | G | A | G | T | C | C | C | C | T | c | a | C | T | a | C | A | G | C | C | A | G |
|---|---|---|---|---|---|---|---|---|---|---|---|---|---|---|---|---|---|---|---|---|---|---|---|
| FNACF_3 | C->other bases | SEQ ID NO: 132 | | | | | | 0.06 | 0.09 | 0.05 | | | 0.05 | 0.06 | 0.08 | | 0.07 | | 0.07 | | 0.06 | 0.14 | | |
| | | Untreated | | | | | | 0.06 | 0.09 | 0.06 | | | 0.03 | 0.06 | 0.08 | | 0.06 | | 0.06 | | 0.07 | 0.13 | | |
| | | (+)jBE1 | | | | | | 0.06 | 0.10 | 0.05 | | | 0.04 | 0.05 | 0.08 | | 0.05 | | 0.07 | | 0.07 | 0.15 | | |
| | | (+)jBE2 | | | | | | 0.20 | 0.23 | 0.18 | | | 0.06 | 0.08 | 0.16 | | 0.08 | | 0.06 | | 0.07 | 0.18 | | |

TABLE 16-continued

Mutation frequencies of Cas9 and BE3 in on-target and off-target sites captured by Digenome-seq

| | | SEQ ID | | | | | | | | | | | | | | | | | | | | | | |
|---|---|---|---|---|---|---|---|---|---|---|---|---|---|---|---|---|---|---|---|---|---|---|---|---|
| FNACF_4 | | NO: 133 | G | G | A | g | T | C | C | C | c | C | T | a | C | A | G | C | A | C | C | | | |
| | C->other bases | Untreated | | | | | | 0.06 | 0.05 | 0.06 | 0.05 | 0.06 | | | 0.06 | | | 0.03 | | 0.03 | 0.06 | | | |
| | | (+)BE1 | | | | | | 0.06 | 10.05 | 0.05 | 0.02 | 0.07 | | | 0.07 | | | 0.03 | | 0.03 | 0.05 | | | |
| | | (+)BE2 | | | | | | 0.07 | 10.06 | 0.03 | 0.05 | 0.06 | | | 0.07 | | | 0.02 | | 0.04 | 0.06 | | | |
| | | (+)BE3 | | | | | | 0.11 | 0.09 | 0.12 | 0.05 | 0.06 | | | 0.07 | | | 0.04 | | 0.04 | 0.04 | | | |
| FNACF_5 | | SEQ ID NO: 134 | G | G | A | A | T | C | C | C | T | C | T | a | C | A | G | C | A | C | C | | | |
| | C->other bases | Untreated | | | | | | 0.09 | 10.07 | 0.05 | | 0.03 | | | 0.07 | | | 0.03 | | 0.03 | 0.03 | | | |
| | | (+)BE1 | | | | | | 0.07 | 0.06 | 0.04 | | 0.03 | | | 0.07 | | | 0.03 | | 0.03 | 0.03 | | | |
| | | (+)BE2 | | | | | | 0.08 | 0.05 | 10.06 | | 0.03 | | | 0.06 | | | 0.05 | | 0.03 | 0.03 | | | |
| | | (+)BE3 | | | | | | 0.10 | 10.07 | 0.05 | | 0.03 | | | 0.07 | | | 0.03 | | 0.03 | 0.02 | | | |
| FNACF_6 | | SEQ ID NO: 135 | G | G | A | g | T | C | C | C | c | C | T | G | C | A | G | C | A | C | C | T | G | A |
| | C->other bases | Untreated | | | | | | 0.04 | 0.04 | | 0.02 | 0.04 | | | 0.09 | | | 0.06 | | 0.02 | 0.04 | | | |
| | | (+)BE1 | | | | | | 0.05 | 0.05 | 0.02 | 0.02 | 0.04 | | | 0.12 | | | 0.04 | | 0.05 | 0.05 | | | |
| | | (+)BE2 | | | | | | 0.04 | 0.05 | 0.05 | 0.03 | 0.06 | | | 0.11 | | | 0.06 | | 0.05 | 0.05 | | | |
| | | (+)BE3 | | | | | | 0.13 | 0.09 | 0.09 | 0.05 | 0.06 | | | 0.12 | | | 0.06 | | 0.05 | 0.03 | | | |
| FNACF_7 | | SEQ ID NO: 136 | G | G | A | A | c | C | C | C | T | T | g | G | C | A | G | C | A | C | C | | | |
| | C->other bases | Untreated | 0.03 | | | | | 0.07 | 0.07 | 0.06 | | 0.03 | | | 0.20 | | | 0.05 | | 0.03 | 0.07 | | | |
| | | (+)BE1 | 0.05 | | | | | 0.06 | 0.04 | 0.07 | | 0.01 | | | 0.21 | | | 0.05 | | 0.02 | 0.05 | | | |
| | | (+)BE2 | 0.04 | | | | | 0.08 | 10.05 | 0.08 | | 0.02 | | | 0.23 | | | 0.06 | | 0.02 | 0.05 | | | |
| | | (+)BE3 | 1.06 | | | | | 1.07 | 1.07 | 1.02 | | 0.71 | | | 0.22 | | | 0.07 | | 0.03 | 0.07 | | | |
| FNACF_8 | | SEQ ID NO: 137 | G | t | c | t | T | C | C | C | c | C | T | C | C | A | G | C | A | C | C | | | |
| | C->other bases | Untreated | | 0.02 | | 0.03 | | 0.02 | 0.02 | 0.05 | | 0.03 | | | 0.11 | | | 0.03 | | 0.02 | 0.03 | | | |
| | | (+)BE1 | | 0.02 | | 0.02 | | 0.03 | 0.04 | 0.05 | | 0.03 | | | 0.08 | | | 0.04 | | 0.02 | 0.04 | | | |
| | | (+)BE2 | | 0.01 | | 0.02 | | 0.02 | 10.05 | 0.05 | | 0.02 | | | 0.09 | | | 0.03 | | 0.02 | 0.04 | | | |
| | | (+)BE3 | | 0.02 | | 0.02 | | 0.04 | 0.04 | 0.08 | | 0.03 | | | 0.10 | | | 0.03 | | 0.03 | 0.03 | | | |
| FNACF_9 | | SEQ ID NO: 138 | a | | A | A | T | C | C | C | T | C | c | G | C | A | G | C | A | C | C | T | A | G |
| | C->other bases | Untreated | | | | | | 0.07 | 0.02 | 0.04 | 0.05 | 0.05 | 0.06 | | 0.05 | | | 0.04 | | 0.05 | 0.06 | | | |
| | | (+)BE1 | | | | | | 0.08 | 0.03 | 0.04 | 0.04 | 0.04 | 0.07 | | 0.04 | | | 0.04 | | 0.05 | 0.04 | | | |
| | | (+)BE2 | | | | | | 0.08 | 0.02 | 0.03 | 0.03 | 0.03 | 0.07 | | 0.04 | | | 0.04 | | 0.04 | 0.06 | | | |
| | | (+)BE3 | | | | | | 0.10 | 0.04 | 0.05 | 0.05 | 0.05 | 0.06 | | 0.06 | | | 0.04 | | 0.05 | 0.03 | | | |

TABLE 16-continued

Mutation frequencies of Cas9 and BE3 in on-target and off-target sites captured by Digenome-seq

| | | SEQ ID | t | G | t | A | T | t | t | C | T | T | G | C | c | t | C | A | g | c | T | G |
|---|---|---|---|---|---|---|---|---|---|---|---|---|---|---|---|---|---|---|---|---|---|---|---|
| FNACF_10 | C->other bases | SEQ ID NO: 139 | | | | | | | | | | | | | | | | | | | | |
| | | Untreated (+)BE1 (+)BE2 (+)BE3 | | | | | | | | | | | | | | | | | | | | |
| FNACF_11 | C->other bases | SEQ ID NO: 140 | G | G | A | A | T | a | t | C | T | T | G | C | A | G | C | A | g | C | C | G |
| | | Untreated (+)BE1 (+)BE2 (+)BE3 | | | 0.06 0.07 0.07 0.08 | | | 0.04 0.07 0.04 0.15 | 0.04 0.04 0.03 0.15 | 0.03 0.03 0.03 0.04 | | 0.06 0.06 0.06 0.13 | 0.05 0.04 0.04 0.03 | 0.22 0.23 0.21 0.21 | | | 0.03 0.03 0.03 0.02 | 0.05 0.06 0.06 0.06 | 0.05 0.05 0.07 0.05 | 0.10 0.09 0.09 0.09 | | |
| FNACF_12 | C->other bases | SEQ ID NO: 141 | G | a | g | t | g | C | C | C | T | a | G | c | t | C | | | | C | T | G |
| FNACF_13 | C->other bases | SEQ ID NO: 142 | a | c | c | A | T | C | C | C | T | c | C | A | G | C | A | g | c | C | A | G |
| | | Untreated (+)BE1 (+)BE2 (+)BE3 | | 0.07 0.14 0.11 0.13 | 0.06 0.07 0.07 0.08 | | | 0.04 0.04 0.03 0.15 | 0.04 0.04 0.04 0.15 | 0.04 0.05 0.04 0.14 | | 0.06 0.06 0.06 0.13 | 0.05 0.04 0.04 0.09 | 0.10 0.10 0.12 0.10 | | | 0.03 0.04 0.04 0.04 | 0.03 0.04 0.04 0.04 | 0.08 0.06 0.05 0.06 | 0.04 0.05 0.05 0.04 | | |
| FNACF_14 | C->other bases | SEQ ID NO: 143 | t | | | A | T | C | a | t | a | C | T | G | C | A | G | C | A | g | c | T | G |
| | | Untreated (+)BE1 (+)BE2 (+)BE3 | | | | | | 0.09 0.09 0.07 0.10 | 0.05 10.04 0.05 0.08 | | | | | | 0.09 0.10 0.07 0.11 | | | 0.04 0.05 0.04 0.03 | 0.06 0.06 0.06 0.07 | 0.06 0.06 0.06 0.07 | 0.08 0.10 0.09 0.10 | 0.06 0.07 0.06 0.07 | | |
| FNACF_15 | C->other bases | SEQ ID NO: 144 | c | t | c | t | g | C | C | C | T | C | T | G | C | A | G | C | A | g | c | T | G |
| | | Untreated (+)BE1 (+)BE2 (+)BE3 | 0.03 0.03 0.04 0.03 | | 0.04 0.02 0.03 0.02 | | | 0.05 0.04 0.04 0.07 | 0.05 0.04 0.04 0.07 | 0.02 0.02 0.03 0.03 | | | 0.02 0.02 0.02 0.02 | 0.06 0.06 0.05 0.05 | | | 0.02 0.03 0.03 0.03 | 0.02 0.03 0.03 0.03 | 0.01 0.02 0.02 0.02 | 0.03 0.04 0.04 0.04 | | |

TABLE 16-continued

Mutation frequencies of Cas9 and BE3 in on-target and off-target sites captured by Digenome-seq

RNF2

Base editing efficiency (%)

| | | SEQ ID NO: 93 | G | T | C | A | T | C | T | A | G | T | C | A | T | A | C | C | T | G | A | G | G |
|---|---|---|---|---|---|---|---|---|---|---|---|---|---|---|---|---|---|---|---|---|---|---|---|
| On-target (RNF2_1) | C->other bases | Untreated (+)BE1 (+)BE2 (+)BE3 | 0.05 0.04 0.08 0.10 | | | | | 0.07 2.90 3.89 31.12 | | | | | 0.06 0.08 0.62 3.45 | | | | 0.03 0.03 0.05 0.16 | 0.07 0.07 0.08 0.08 | | | | |

HBB

Base editing efficiency (%)

| | | SEQ ID NO: 145 | C | T | T | G | A | T | C | T | A | C | G | T | C | A | T | A | C | T | A | C | G | G |
|---|---|---|---|---|---|---|---|---|---|---|---|---|---|---|---|---|---|---|---|---|---|---|---|---|---|
| On-target (HBB_1) | C->other bases | Untreated (+)BE1 (+)BE2 (+)BE3 | | | | | | | 0.08 0.08 0.56 3.01 | 0.03 0.14 0.80 4.51 | | 0.05 0.17 0.83 4.88 | 0.04 0.08 0.80 4.64 | | 0.04 0.05 0.07 0.14 | | | 0.08 0.07 0.06 0.08 | | | | | | | |

| | | SEQ ID NO: 146 | t | T | g | c | G | A | G | A | C | A | C | C | T | A | G | C | T | A | A | C | G |
|---|---|---|---|---|---|---|---|---|---|---|---|---|---|---|---|---|---|---|---|---|---|---|---|---|
| HBB_2 | C->other bases | Untreated (+)BE1 (+)BE2 (+)BE3 | | | | 0.07 0.07 0.14 0.42 | | | | | 0.06 0.09 0.24 0.89 | | 0.04 0.07 0.22 0.84 | 0.05 0.07 0.22 0.86 | | 0.04 0.04 0.05 0.07 | | | 0.06 0.07 0.06 0.06 | | | | | | |

| | | SEQ ID NO: 147 | g | c | T | G | G | A | G | A | C | A | C | C | C | A | G | C | A | A | A | G | G |
|---|---|---|---|---|---|---|---|---|---|---|---|---|---|---|---|---|---|---|---|---|---|---|---|---|
| HBB_3 | C->other bases | Untreated (+)BE1 (+)BE2 (+)BE3 | | | 0.07 0.08 0.09 0.09 | | | | | | 0.06 0.06 0.15 0.86 | | 0.11 0.10 0.17 0.87 | 0.03 0.03 0.09 0.75 | | 0.07 0.05 0.05 0.07 | | | 0.14 0.10 0.12 0.11 | | | | 0.09 0.08 0.09 0.09 | | |

| | | SEQ ID NO: 148 | g | T | g | G | A | G | A | C | A | C | C | C | A | G | C | A | T | G | G |
|---|---|---|---|---|---|---|---|---|---|---|---|---|---|---|---|---|---|---|---|---|
| HBB_4 | C->other bases | Untreated (+)BE1 (+)BE2 (+)BE3 | | | | | | | | 0.07 0.09 0.09 0.14 | 0.13 0.14 0.15 0.20 | | 0.06 0.07 0.08 0.13 | 0.09 0.08 0.12 0.16 | | 0.04 0.05 0.04 0.07 | | | 0.06 0.08 0.07 0.08 | | | |

TABLE 16-continued

Mutation frequencies of Cas9 and BE3 in on-target and off-target sites captured by Digenome-seq

| | | SEQ ID NO: 149 | a | T | A | T | G | C | C | C | C | A | C | g | G | G | C | A | G | T | g | A | C | G | G |
|---|---|---|---|---|---|---|---|---|---|---|---|---|---|---|---|---|---|---|---|---|---|---|---|---|---|
| HBB_5 | C->other bases | Untreated | | | | | | 0.12 | 0.19 | 0.73 | 0.40 | | 0.16 | | | | 0.20 | | | | | | | | |
| | | (+)BE1 | | | | | | 0.16 | 0.20 | 0.76 | 0.47 | | 0.19 | | | | 0.25 | | | | | | | | |
| | | (+)BE2 | | | | | | 0.14 | 0.16 | 0.77 | 0.51 | | 0.17 | | | | 0.28 | | | | | | | | |
| | | (+)BE3 | | | | | | 0.36 | 0.42 | 0.95 | 0.73 | | 0.20 | | | | 0.21 | | | | | | | | |
| | | SEQ ID NO: 150 | a | c | T | c | t | C | C | C | A | C | A | a | G | C | A | G | T | A | G | G | G |
| HBB_6 | C->other bases | Untreated | | 0.11 | | 0.08 | | 0.12 | 0.08 | 0.11 | 0.20 | 0.08 | 0.05 | | | | 0.17 | | | | | | | | |
| | | (+)BE1 | | 0.10 | | 0.10 | | 0.16 | 0.10 | 0.09 | 0.20 | 0.10 | 0.04 | | | | 0.14 | | | | | | | | |
| | | (+)BE2 | | 0.08 | | 0.11 | | 0.16 | 0.11 | 0.11 | 0.21 | 0.11 | 0.05 | | | | 0.20 | | | | | | | | |
| | | (+)BE3 | | 0.10 | | 0.13 | | 0.14 | 0.13 | 0.13 | 0.22 | 0.13 | 0.05 | | | | 0.17 | | | | | | | | |
| | | SEQ ID NO: 151 | t | c | T | c | a | C | C | C | A | C | A | A | G | C | A | G | T | A | G | G | G |
| HBB_7 | C->other bases | Untreated | | 0.03 | | 0.07 | | | 0.07 | 0.09 | 0.05 | | 0.05 | | | | 0.08 | | | | | | | | |
| | | (+)BE1 | | 0.14 | | 0.09 | | | 0.09 | 0.11 | 0.08 | | 0.06 | | | | 0.14 | | | | | | | | |
| | | (+)BE2 | | 0.27 | | 0.09 | | | 0.22 | 0.25 | 0.19 | | 0.05 | | | | 0.09 | | | | | | | | |
| | | (+)BE3 | | 2.82 | | 0.80 | | | 2.89 | 4.01 | 4.20 | | 0.14 | | | | 0.09 | | | | | | | | |

HEK2

Base editing efficiency (%)

| | | SEQ ID NO: 153 | G | A | A | C | A | A | A | t | A | A | C | A | T | A | G | A | CT | G | T | G | C | G |
|---|---|---|---|---|---|---|---|---|---|---|---|---|---|---|---|---|---|---|---|---|---|---|---|---|
| On-target (HEK2_2) | C->other bases | Untreated | | | | | 0.05 | | | | | 0.04 | | | | | | 0.16 | | | | | | |
| | | (+)BE1 | | | | 0.65 | 10.29 | | | | | 0.04 | | | | | | 0.18 | | | | | | |
| | | (+)BE2 | | | | 7.32 | 14.69 | | | | | 0.03 | | | | | | 0.17 | | | | | | |
| | | (+)BE3 | | | | 11.74 | 33.30 | | | | | 0.07 | | | | | | 0.18 | | | | | | |
| | | SEQ ID NO: 152 | G | A | A | C | A | A | A | t | A | A | C | A | T | A | G | A | t | G | C | G | C | G |
| HEK2_1 | C->other bases | Untreated | | | | 0.10 | 0.00 | | | | | 0.11 | | | | | | | | | | 0.18 | | |
| | | (+)BE1 | | | | 0.10 | 0.10 | | | | | 0.13 | | | | | | | | | | 0.21 | | |
| | | (+)BE2 | | | | 0.13 | 0.12 | | | | | 0.11 | | | | | | | | | | 0.16 | | |
| | | (+)BE3 | | | | 0.17 | 0.21 | | | | | 0.11 | | | | | | | | | | 0.19 | | |

TABLE 16-continued

Mutation frequencies of Cas9 and BE3 in on-target and off-target sites captured by Digenome-seq

HEK2_3 — SEQ ID NO: 154

| | a | A | c | t | C | C | A | G | c | A | T | A | C | T | G | G |
|---|---|---|---|---|---|---|---|---|---|---|---|---|---|---|---|---|
| C->other bases | | | | | | | | | | | | | | | | |
| Untreated | 0.08 | | 0.09 | | 0.09 | | | | 0.25 | | | | 0.34 | | | 0.09 |
| (+)BE1 | 0.09 | | 0.08 | | 0.07 | | | | 0.24 | | | | 0.37 | | | 0.08 |
| (+)BE2 | 0.09 | | 0.09 | | 0.07 | | | | 0.19 | | | | 0.38 | | | 0.08 |
| (+)BE3 | 0.08 | | 0.09 | | 0.07 | | | | 0.24 | | | | 0.38 | | | 0.07 |

HEK3

Base editing efficiency (%)

On-target (HEK3_2) — SEQ ID NO: 156

| | G | G | C | C | C | A | G | A | C | T | G | C | T | A | C | G | T | G | G |
|---|---|---|---|---|---|---|---|---|---|---|---|---|---|---|---|---|---|---|---|
| C->other bases | | | | | | | | | | | | | | | | | | | |
| Untreated | | | 0.13 | 0.46 | 0.42 | | | | 0.14 | | | 0.10 | | 0.07 | | | | | |
| (+)BE1 | | | 0.38 | 6.45 | 8.56 | | | | 0.59 | | | 0.14 | | 0.08 | | | | | |
| (+)BE2 | | | 0.37 | 6.27 | 8.17 | | | | 0.41 | | | 0.20 | | 0.06 | | | | | |
| (+)BE3 | | | 1.00 | 24.71 | 31.39 | | | | 0.76 | | | 0.09 | | 0.10 | | | | | |

HEK3_1 — SEQ ID NO: 155

| | a | G | a | t | C | C | A | G | A | C | T | G | C | A | G | G |
|---|---|---|---|---|---|---|---|---|---|---|---|---|---|---|---|---|
| C->other bases | | | | | | | | | | | | | | | | |
| Untreated | | | | | 0.12 | 0.04 | | | | 0.04 | | | 0.14 | | | |
| (+)BE1 | | | | | 0.12 | 0.04 | | | | 0.07 | | | 0.13 | | | |
| (+)BE2 | | | | | 0.13 | 0.05 | | | | 0.08 | | | 0.17 | | | |
| (+)BE3 | | | | | 0.13 | 0.09 | | | | 0.05 | | | 0.13 | | | |

HEK3_3 — SEQ ID NO: 157

| | c | G | g | g | C | c | c | G | A | C | T | G | C | A | t | G | G |
|---|---|---|---|---|---|---|---|---|---|---|---|---|---|---|---|---|---|
| C->other bases | | | | | | | | | | | | | | | | | |
| Untreated | | | | | | 0.07 | 0.06 | | | 0.07 | | | 0.12 | | | | |
| (+)BE1 | | | | | | 0.08 | 0.05 | | | 0.10 | | | 0.09 | | | | |
| (+)BE2 | | | | | | 0.08 | 0.05 | | | 0.06 | | | 0.11 | | | | |
| (+)BE3 | | | | | | 0.07 | 0.05 | | | 0.07 | | | 0.10 | | | | |

HEK3_4 — SEQ ID NO: 158

| | c | c | C | C | C | A | G | A | C | T | G | C | A | c | T | G | G |
|---|---|---|---|---|---|---|---|---|---|---|---|---|---|---|---|---|---|
| C->other bases | | | | | | | | | | | | | | | | | |
| Untreated | 0.08 | 0.07 | 0.07 | 0.05 | 0.05 | | | | 0.01 | | | 0.14 | | 0.06 | | | 0.04 |
| (+)BE1 | 0.09 | 0.06 | 0.08 | 0.06 | 0.06 | | | | 0.03 | | | 0.13 | | 0.04 | | | 0.04 |
| (+)BE2 | 0.09 | 0.07 | 0.07 | 0.06 | 0.06 | | | | 0.02 | | | 0.10 | | 0.05 | | | 0.05 |
| (+)BE3 | 0.08 | 0.05 | 0.08 | 0.06 | 0.06 | | | | 0.02 | | | 0.13 | | 0.05 | | | 0.05 |

TABLE 16-continued

Mutation frequencies of Cas9 and BE3 in on-target and off-target sites captured by Digenome-seq

| | | | | | | | | | | | | | | | | | | | | | | |
|---|---|---|---|---|---|---|---|---|---|---|---|---|---|---|---|---|---|---|---|---|---|---|
| HEK3_5 | | SEQ ID NO: 159 | c | G | g | C | C | c | a | A | C | T | G | A | C | A | a | G | T | G | A | T | G |
| | C->other bases | Untreated (+)BE1 (+)BE2 (+)BE3 | 0.16 0.19 0.16 0.16 | | 0.08 0.11 0.08 0.08 | 0.13 0.14 0.13 0.13 | 0.10 0.07 0.09 0.09 | | | 0.06 0.06 0.05 0.05 | 0.06 0.06 0.05 0.05 | | | 0.19 0.21 0.16 0.20 | | | | | | | | |
| HEK3_6 | | SEQ ID NO: 160 | a | G | a | C | C | A | G | A | C | T | G | A | C | A | a | G | a | G | A | G | G |
| | C->other bases | Untreated (+)BE1 (+)BE2 (+)BE3 | | | 0.08 0.09 0.08 0.10 | 0.10 0.12 0.12 0.11 | | | | 0.06 0.06 0.06 0.05 | 0.06 0.06 0.06 0.05 | | | 0.20 0.19 0.19 0.16 | | | | | | | | |
| HEK3_7 | | SEQ ID NO: 161 | G | G | C | a | C | c | t | c | a | T | g | C | A | T | a | c | T | G | G |
| | C->other bases | Untreated (+)BE1 (+)BE2 (+)BE3 | | | 0.15 0.16 0.17 0.16 | 0.45 0.45 0.47 0.44 | 0.05 0.08 0.00 0.08 | | 0.19 0.19 0.19 0.19 | | | | 0.29 0.30 0.31 0.29 | 0.26 0.28 0.24 0.26 | | | | 0.06 0.06 0.06 0.06 | | |

HEK4

Base editing efficiency (%)

| | | | | | | | | | | | | | | | | | | | | | | |
|---|---|---|---|---|---|---|---|---|---|---|---|---|---|---|---|---|---|---|---|---|---|---|
| On-target (HEK4_1) | | SEQ ID NO: 162 | G | G | A | C | T | G | G | t | C | G | C | T | T | A | G | G | T | G | G | G |
| | C->other bases | Untreated (+)BE1 (+)BE2 (+)BE3 | | | 0.16 0.17 0.65 2.34 | 0.11 6.18 10.35 41.18 | | | | 0.20 0.25 0.84 0.80 | 0.07 0.07 0.06 0.07 | | | | | | | | | | | |
| HEK4_2 | | SEQ ID NO: 163 | G | G | A | C | T | G | G | C | g | G | G | T | C | G | G | G | T | G | G |
| | C->other bases | Untreated (+)BE1 (+)BE2 (+)BE3 | | | 0.11 0.13 0.16 0.31 | 0.05 0.38 0.46 5.93 | | | | 0.15 0.14 0.13 0.22 | 0.98 0.98 0.93 1.07 | | | | | | | | | | | |

TABLE 16-continued

Mutation frequencies of Cas9 and BE3 in on-target and off-target sites captured by Digenome-seq

HEK4_3

| | SEQ ID NO: 164 | G | G | C | A | C | T | G | C | a | C | — | C | G | A | G | G | T | t | G | T | G | G |
|---|---|---|---|---|---|---|---|---|---|---|---|---|---|---|---|---|---|---|---|---|---|---|---|
| C->other bases | Untreated | | | 0.08 | | 0.05 | | | 0.07 | | 0.05 | | | | | | | | | | | | |
| | (+)BE1 | | | 0.10 | | 0.22 | | | 0.09 | | 0.05 | | | | | | | | | | | | |
| | (+)BE2 | | | 0.11 | | 0.22 | | | 0.07 | | 0.05 | | | | | | | | | | | | |
| | (+)BE3 | | | 0.09 | | 0.39 | | | 0.08 | | 0.03 | | | | | | | | | | | | |

HEK4_4

| | SEQ ID NO: 165 | G | G | C | t | C | T | G | C | G | C | G | C | G | A | G | g | T | G | G |
|---|---|---|---|---|---|---|---|---|---|---|---|---|---|---|---|---|---|---|---|---|
| C->other bases | Untreated | | | 0.04 | | 0.05 | | | 0.34 | | 0.13 | | | | | | | | | |
| | (+)BE1 | | | 0.05 | | 0.26 | | | 0.35 | | 0.13 | | | | | | | | | |
| | (+)BE2 | | | 0.06 | | 0.19 | | | 0.35 | | 0.15 | | | | | | | | | |
| | (+)BE3 | | | 0.07 | | 2.07 | | | 0.34 | | 0.17 | | | | | | | | | |

HEK4_5

| | SEQ ID NO: 166 | a | G | C | A | C | T | G | C | a | G | a | T | G | G | A | G | a | T | G | G |
|---|---|---|---|---|---|---|---|---|---|---|---|---|---|---|---|---|---|---|---|---|---|
| C->other bases | Untreated | | | 0.08 | | 0.07 | | | 0.11 | | | | | | | | | | | | |
| | (+)BE1 | | | 0.09 | | 0.11 | | | 0.11 | | | | | | | | | | | | |
| | (+)BE2 | | | 0.09 | | 0.07 | | | 0.10 | | | | | | | | | | | | |
| | (+)BE3 | | | 0.10 | | 0.52 | | | 0.20 | | | | | | | | | | | | |

HEK4_6

| | SEQ ID NO: 167 | G | G | C | A | C | T | G | C | G | C | G | G | G | a | G | a | G | C | G | G |
|---|---|---|---|---|---|---|---|---|---|---|---|---|---|---|---|---|---|---|---|---|---|

HEK4_7

| | SEQ ID NO: 168 | t | G | C | A | C | T | G | C | G | C | c | G | G | A | G | a | T | G | T | G | G |
|---|---|---|---|---|---|---|---|---|---|---|---|---|---|---|---|---|---|---|---|---|---|---|
| C->other bases | Untreated | | | 0.21 | | 0.12 | | | 0.36 | | 0.14 | 0.09 | | | | | | | | | | |
| | (+)BE1 | | | 0.15 | | 0.53 | | | 0.31 | | 0.13 | 0.08 | | | | | | | | | | |
| | (+)BE2 | | | 0.19 | | 1.25 | | | 0.32 | | 0.11 | 0.14 | | | | | | | | | | |
| | (+)BE3 | | | 0.37 | | 10.75 | | | 0.41 | | 0.12 | 0.07 | | | | | | | | | | |

HEK4_8

| | SEQ ID NO: 169 | G | G | C | A | C | T | — | g | G | C | T | a | A | G | T | a | G | G |
|---|---|---|---|---|---|---|---|---|---|---|---|---|---|---|---|---|---|---|---|
| C->other bases | Untreated | | | 0.09 | | 0.05 | | | | | 0.08 | | | | | | | | |
| | (+)BE1 | | | 0.07 | | 0.15 | | | | | 0.05 | | | | | | | | |
| | (+)BE2 | | | 0.08 | | 0.17 | | | | | 0.07 | | | | | | | | |
| | (+)BE3 | | | 0.07 | | 0.18 | | | | | 0.06 | | | | | | | | |

TABLE 16-continued

Mutation frequencies of Cas9 and BE3 in on-target and off-target sites captured by Digenome-seq

| | | | | | | | | | | | | | | | | | | | | | | |
|---|---|---|---|---|---|---|---|---|---|---|---|---|---|---|---|---|---|---|---|---|---|---|
| HEK4_9 | SEQ ID NO: 170 | | G | G | C | A | C | T | G | c | C | T | G | G | A | G | T | G | G |
| | C->other bases | Untreated | | | 0.09 | | 0.03 | | | 0.02 | 0.04 | | | | | | | | |
| | | (+)BE1 | | | 0.08 | | 0.04 | | | 0.04 | 0.03 | | | | | | | | |
| | | (+)BE2 | | | 0.12 | | 0.03 | | | 0.04 | 0.03 | | | | | | | | |
| | | (+)BE3 | | | 0.12 | | 0.02 | | | 0.04 | 0.05 | | | | | | | | |
| HEK4_10 | SEQ ID NO: 171 | | t | G | C | t | C | T | G | C | C | a | G | G | A | G | T | G | G |
| | C->other bases | Untreated | | | 0.08 | | 0.17 | | | 0.06 | | | | | | | | | |
| | | (+)BE1 | | | 0.07 | | 0.17 | | | 0.06 0.05 | | | | | | | | | |
| | | (+)BE2 | | | 0.08 | | 0.18 | | | 0.07 0.07 | | | | | | | | | |
| | | (+)BE3 | | | 0.08 | | 0.19 | | | 0.07 0.07 | | | | | | | | | |
| HEK4_11 | SEQ ID NO: 172 | | a | G | C | A | C | T | G | C | C | g | G | A | G | T | G | A | G |
| | C->other bases | Untreated | | | 0.16 | | 0.05 | | | 0.13 0.07 | | | | | | | | | |
| | | (+)BE1 | | | 0.12 | | 0.47 | | | 0.12 0.07 | | | | | | | | | |
| | | (+)BE2 | | | 0.13 | | 0.64 | | | 0.14 0.08 | | | | | | | | | |
| | | (+)BE3 | | | 0.19 | | 1.83 | | | 0.18 0.08 | | | | | | | | | |
| HEK4_12 | SEQ ID NO: 173 | | G | G | C | A | C | T | G | C | C | a | G | A | G | T | G | G |
| | C->other bases | Untreated | | | 0.10 | | 0.03 | | | 0.03 | | | | | | | | | |
| | | (+)BE1 | | | 0.07 | | 0.65 | | | 0.07 | | | | | | | | | |
| | | (+)BE2 | | | 0.10 | | 0.47 | | | 0.08 | | | | | | | | | |
| | | (+)BE3 | | | 0.09 | | 0.99 | | | 0.08 | | | | | | | | | |
| HEK4_13 | SEQ ID NO: 174 | | G | G | g | A | C | T | G | C | C | a | G | A | G | T | G | G |
| | C->other bases | Untreated | | | 0.13 | | 0.15 | | | 0.13 | | | | | 0.23 | | | | |
| | | (+)BE1 | | | 0.12 | | 0.14 | | | 0.11 | | | | | 0.18 | | | | |
| | | (+)BE2 | | | 0.10 | | 0.13 | | | 0.09 | | | | | 0.15 | | | | |
| | | (+)BE3 | | | 0.11 | | 0.12 | | | 0.12 | | | | | 0.18 | | | | |
| HEK4_14 | SEQ ID NO: 175 | | a | G | g | A | C | T | G | C | C | g | G | A | G | T | G | T | G |
| | C->other bases | Untreated | | | 0.06 | | 0.28 | | | 0.05 | | | | | | | | | |
| | | (+)BE1 | | | 0.50 | | 0.37 | | | 0.03 | | | | | | | | | |
| | | (+)BE2 | | | 0.63 | | 0.38 | | | 0.04 | | | | | | | | | |
| | | (+)BE3 | | | 5.20 | | 0.50 | | | 0.04 | | | | | | | | | |

TABLE 16-continued

Mutation frequencies of Cas9 and BE3 in on-target and off-target sites captured by Digenome-seq

| | | SEQ ID | G | G | C | A | C | T | G | G | A | G | C | T | a | G | G |
|---|---|---|---|---|---|---|---|---|---|---|---|---|---|---|---|---|---|
| HEK4_15 | C->other bases | SEQ ID NO: 176 Untreated (+)BE1 (+)BE2 (+)BE3 | | | 0.11 0.10 0.08 0.10 | | 0.06 0.08 0.08 0.26 | | | | | 0.12 0.07 0.08 0.09 | 0.03 0.02 0.02 0.03 | | | | |
| HEK4_16 | C->other bases | SEQ ID NO: 177 Untreated (+)BE1 (+)BE2 (+)BE3 | G | G | 0.17 0.14 0.17 0.38 | A | 0.16 1.01 0.58 3.41 | T | G | G | A | G | | T | | G | G |
| HEK4_17 | C->other bases | SEQ ID NO: 178 Untreated (+)BE1 (+)BE2 (+)BE3 | G | c | 0.05 0.06 0.10 0.34 | A | 0.07 0.24 0.27 3.12 | T | G | G | A | G | 0.20 0.13 0.14 0.22 | T | a | G | G |
| HEK4_18 | C->other bases | SEQ ID NO: 179 Untreated (+)BE1 (+)BE2 (+)BE3 | G | c | 0.14 0.10 0.12 0.10 | A | 0.06 0.08 0.05 0.12 | T | G | G | A | G | 0.03 0.04 0.04 0.04 | T | a | G | G |
| HEK4_19 | C->other bases | SEQ ID NO: 180 Untreated (+)BE1 (+)BE2 (+)BE3 | G | G | 0.07 0.05 0.03 0.08 | A | 0.06 0.08 0.05 0.12 | T | G | G | A | G | 60.77 61.73 60.63 60.98 | — | G | G | G |
| HEK4_20 | C->other bases | SEQ ID NO: 181 Untreated (+)BE1 (+)BE2 (+)BE3 | a | G | 0.06 0.07 0.08 0.08 | t | 0.06 0.04 0.06 0.05 | T | G | G | A | G | 0.04 0.03 0.05 0.04 | T | G | G | G |
| | | | | | 0.24 0.21 0.21 0.23 | | 0.02 0.03 0.02 0.02 | | | | | | 0.05 0.06 0.04 0.07 | | | 0.12 0.11 0.10 0.09 | |
| | | | | | | | | | | | | | 0.20 0.20 0.17 0.22 | | | 0.12 0.08 0.08 0.11 | | A | G |

TABLE 16-continued

Mutation frequencies of Cas9 and BE3 in on-target and off-target sites captured by Digenome-seq

| | Indel frequency (%) | | Validation | |
|---|---|---|---|---|
| | (−) | (+) RGEN | BE3 | Cas9 |
| EMX1 | | | | |
| On-target (EMX1_4) | 0.15 | 61.59 | Validated | Validated |
| EMX1_1 | 0.29 | 38.25 | Validated | Validated |
| EMX1_2 | 0.00 | 0.01 | Validated | Validated |
| EMX1_3 | 0.10 | 3.45 | Validated | Validated |
| EMX1_5 | 0.01 | 0.01 | Validated | Invalidated |
| EMX1_6 | 0.00 | 8.63 | Validated | Validated |
| EMX1_7 | 0.01 | 0.01 | Validated | Invalidated |
| EMX1_8 | 0.08 | 0.08 | Validated | Invalidated |
| EMX1_9 | 0.01 | 0.23 | Validated | Validated |
| EMX1_10 | 0.00 | 7.94 | Validated | Invalidated |
| EMX1_11 | 0.00 | 0.01 | Validated | Invalidated |
| EMX1_12 | 0.00 | 0.00 | Invalidated | Invalidated |
| EMX1_13 | 0.00 | 0.00 | Invalidated | Invalidated |
| EMX1_14 | 0.01 | 0.01 | Invalidated | Invalidated |
| EMX1_15 | 0.46 | 0.89 | Validated | Validated |
| EMX1_16 | 0.00 | 0.00 | Invalidated | Invalidated |
| EMX1_17 | 0.01 | 0.00 | Invalidated | Invalidated |
| EMX1_18 | 0.01 | 0.01 | Invalidated | Invalidated |
| EMX1_19 | 0.01 | 0.02 | Validated | Invalidated |
| EMX1_20 | 0.27 | 0.25 | Validated | Invalidated |
| EMX1_21 | 0.00 | 0.00 | Invalidated | Invalidated |
| EMX1_22 | 0.02 | 0.17 | Validated | Validated |
| EMX1_23 | 0.01 | 0.01 | Invalidated | Invalidated |
| EMX1_24 | 0.00 | 0.00 | Invalidated | Invalidated |
| EMX1_25 | 1.06 | 1.04 | Validated | Invalidated |
| FANCF | | | | |
| | Indel frequency (%) | | Validation | |
| | (−) | (+) RGEN | BE3 | Cas9 |
| On-target (FANCF_2) | 0.01 | 44.48 | Validated | Validated |
| FNACF_1 | 0.00 | 0.02 | Validated | Validated |
| FNACF_3 | 0.01 | 0.37 | Validated | Validated |
| FNACF_4 | 0.01 | 0.22 | Validated | Validated |
| FNACF_5 | 0.00 | 0.00 | Invalidated | Invalidated |
| FNACF_6 | 0.00 | 0.28 | Validated | Validated |
| FNACF_7 | 0.01 | 12.06 | Validated | Validated |
| FNACF_8 | 0.03 | 0.05 | Invalidated | Invalidated |
| FNACF_9 | 0.00 | 0.08 | Validated | Validated |
| FNACF_10 | | | | |

TABLE 16-continued

Mutation frequencies of Cas9 and BE3 in
on-target and off-target sites captured by Digenome-seq

| | Indel frequency (%) | | Validation | |
|---|---|---|---|---|
| | (−) | (+) IRGEN | BE3 | Cas9 |
| FNACF_11 | 0.02 | 0.03 | Invalidated | Invalidated |
| FNACF_12 | 0.01 | 0.03 | Validated | Validated |
| FNACF_13 | 0.00 | 0.00 | Invalidated | Invalidated |
| FNACF_14 | | | Invalidated | Invalidated |
| FNACF_15 | 0.02 | 0.00 | | |

RNF2

| | Indel frequency (%) | | Validation | |
|---|---|---|---|---|
| | (−) | (+) IRGEN | BE3 | Cas9 |
| On-target (RNF2_1) | 0.03 | 66.13 | Validated | Validated |

HBB

| | Indel frequency (%) | | Validation | |
|---|---|---|---|---|
| | (−) RGEN | (+) RGEN | BE3 | Cas9 |
| On-target (HB8_1) | 0.02 | 38.35 | Validated | Validated |
| HBB_2 | 0.02 | 0.01 | Validated | Invalidated |
| HBB_3 | 0.01 | 3.57 | Validated | Validated |
| HBB_4 | 0.00 | 0.70 | Validated | Validated |
| HBB_5 | 0.00 | 0.35 | Invalidated | Invalidated |
| HBB_6 | 0.02 | 0.01 | Invalidated | Validated |
| HBB_7 | 0.00 | 20.92 | Validated | |

HEK2

| | Indel frequency (%) | | Validation | |
|---|---|---|---|---|
| | (−) RGEN | (+) RGEN | BE3 | Cas9 |
| On-target (HEK2_2) | 0.00 | 43.28 | Validated | Validated |
| HEK2_1 | 0.00 | 1.01 | Validated | Validated |
| HEK2_3 | 0.00 | 0.00 | Invalidated | Invalidated |

HEK3

| | Indel frequency (%) | | Validation | |
|---|---|---|---|---|
| | (−) RGEN | (+) RGEN | BE3 | Cas9 |
| On-target (HEK3_2) | 0.00 | 60.16 | Validated | Validated |
| HEK3_1 | 0.00 | 2.93 | Invalidated | Validated |

TABLE 16-continued

Mutation frequencies of Cas9 and BE3 in on-target and off-target sites captured by Digenome-seq

| | Indel frequency (%) | | | Validation | |
|---|---|---|---|---|---|
| | (−) RGEN | (+) RGEN | | BE3 | Cas9 |
| HEK3_3 | 0.00 | 0.00 | | Invalidated | Invalidated |
| HEK3_4 | 0.00 | 4.16 | | Invalidated | Validated |
| HEK3_5 | 0.00 | 0.00 | | Invalidated | Invalidated |
| HEK3_6 | 0.00 | 0.02 | | Invalidated | Invalidated |
| HEK3_7 | 0.00 | 0.00 | | Invalidated | Invalidated |

HEK4

| | (−) RGEN | (+) RGEN | | BE3 | Cas9 |
|---|---|---|---|---|---|
| On-target (HEK4_1) | 0.00 | 59.38 | | Validated | Validated |
| HEK4_2 | 0.02 | 35.65 | | Validated | Validated |
| HEK4_3 | 0.00 | 0.00 | | Validated | Validated |
| HEK4_4 | 0.07 | 29.61 | | Validated | Validated |
| HEK4_5 | 0.00 | 0.08 | | Validated | Validated |
| HEK4_6 | | | | | |
| HEK4_7 | 0.02 | 35.87 | | Validated | Validated |
| HEK4_8 | 0.04 | 0.04 | | Validated | Invalidated |
| HEK4_9 | 0.02 | 25.09 | | Invalidated | Validated |
| HEK4_10 | 2.67 | 3.08 | | Invalidated | Validated |
| HEK4_11 | 0.04 | 8.97 | | Validated | Validated |
| HEK4_12 | 0.08 | 10.38 | | Validated | Validated |
| HEK4_13 | 0.11 | 0.69 | | Invalidated | Validated |
| HEK4_14 | 0.38 | 46.26 | | Validated | Validated |
| HEK4_15 | 0.01 | 0.14 | | Validated | Validated |
| HEK4_16 | 0.12 | 25.87 | | Validated | Validated |
| HEK4_17 | 0.01 | 2.93 | | Validated | Validated |
| HEK4_18 | 0.16 | 0.37 | | Validated | Validated |
| HEK4_19 | 0.10 | 0.11 | | Invalidated | Invalidated |
| HEK4_20 | 0.02 | 0.07 | | Invalidated | Validated |

The inventors analyzed a total of 75 sites identified using 7 sgRNAs and observed BE3-induced point mutations at 50 sites, including all 7 on-target sites, with frequencies above noise levels caused by sequencing errors (typically in the range of 0.1-2%), resulting in a validation rate of 67%. It is possible that BE3 can still induce mutagenesis at the other BE3-associated, Digenome-positive sites with frequencies below background noise levels. Importantly, we were able to identify BE3 off-target sites at which base editing was detected with a frequency of 0.1%, demonstrating that Digenome-seq is a highly sensitive method. Cas9 nucleases detectably induced indels at 70% (=44/63) of the sites associated with both Cas9 and BE3 but failed to do so at each of the 12 sites associated with BE3 alone (Tables 2-8).

Figure 14A:
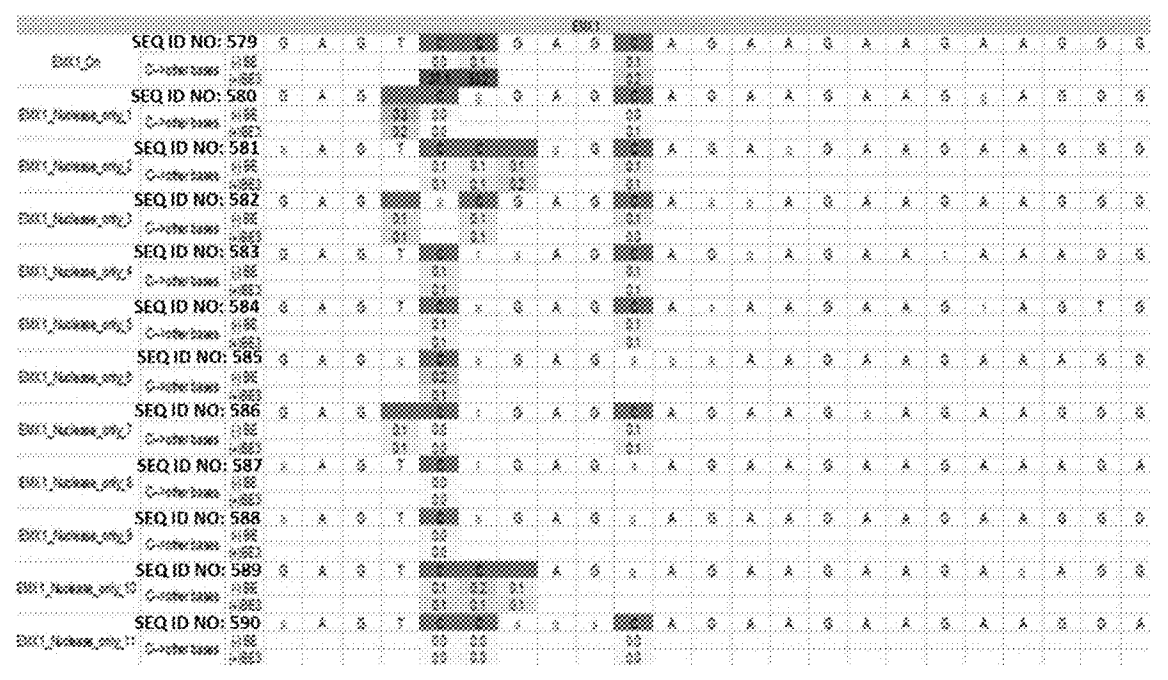
Figure 14B:
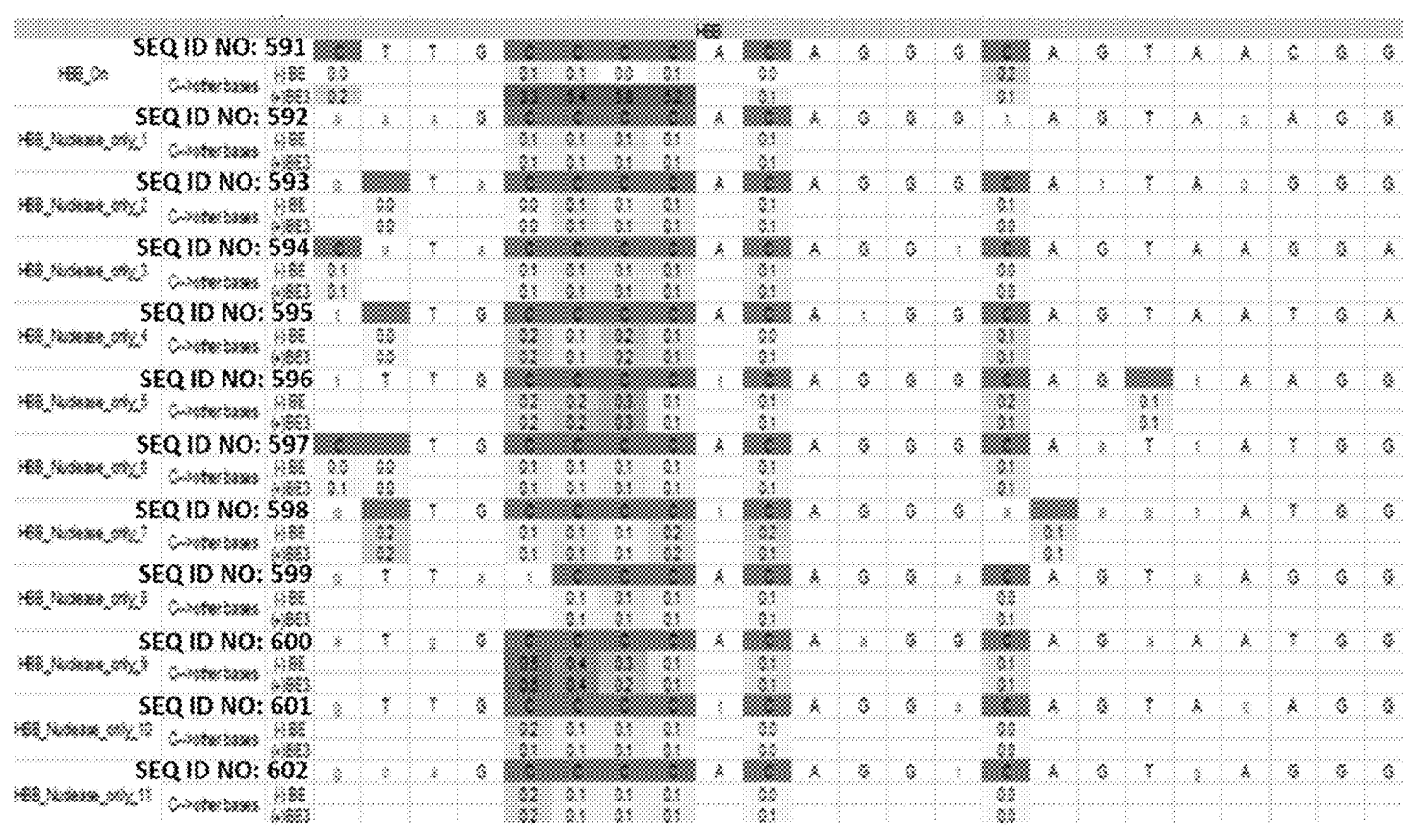

FIGS. 14a-14c show base editing efficiencies at Digenome-captured sites associated only with 3 different Cas9 nucleases. As shown in FIGS. 14a-14c, BE3 did not detectably cause substitutions at 24 Digenome-positive sites associated with 3 different Cas9 nucleases alone. Furthermore, FIGS. 15a-15c show base editing efficiencies of 3 different BE3 deaminases at Digenome-negative sites. As shown in FIGS. 15a-15c, the 3 BE3 deaminases did not induce base editing at 28 Digenome-negative sites with ≤3 mismatches, identified using Cas-OFFinder (Bae, S., Park, J. & Kim, J. S. Cas-OFFinder: A fast and versatile algorithm that searches for potential off-target sites of Cas9 RNA-guided endonucleases. Bioinformatics (2014)) (FIGS. 15a-15c). Frequencies of BE3-induced substitutions were well-correlated with those of Cas9-mediated indels [$R^2$=0.92 (EMX1) or 0.89 (HBB)] (FIG. 6e, f). Nevertheless, there were many off-target sites validated by BE3 but not by Cas9. 64% (=7/11) of these validated, BE3-exclusive off-target sites had a missing nt, compared to their respective on-target sites. These results show that Cas9 and BE3 off-target sites largely overlap with each other but that there are off-target sites exclusively associated with Cas9 alone or BE3 alone (FIG. 10).

Example 6. Reducing BE3 Off-Target Effects Via Modified sgRNAs

To reduce BE3 off-target effects, the inventors replaced conventional sgRNAs (termed $gX_{19}$ or $GX_{19}$; "g" and "G" represent, respectively, a mismatched and matched guanine) with truncated sgRNAs (termed $gX_{18}$ or $gX_{17}$) or extended sgRNAs containing one or two extra guanines at the 5' terminus (termed $gX_{20}$ or $ggX_{20}$) and measured on-target and off-target base-editing frequencies in HEK293T cells. The results are shown in FIGS. 16-17 and Table 3.

TABLE 17

Analysis of BE3 off-target effect via modified sgRNAs

EMX1

| | | SEQ ID NO: 31 | G | A | G | T | C | C | G | A | G | C | A | G | A | A | G | A | A | G | A | A | G | G | G |
|---|---|---|---|---|---|---|---|---|---|---|---|---|---|---|---|---|---|---|---|---|---|---|---|---|---|
| On-target (EMX1_4) | C-> other bases | Untreated | | | | | 0.04 | 0.06 | | | | 0.15 | | | | | | | | | | | | | |
| | | ggX20 | | | | | 49.01 | 46.36 | | | | 0.10 | | | | | | | | | | | | | |
| | | gX20 | | | | | 54.78 | 50.04 | | | | 0.14 | | | | | | | | | | | | | |
| | | GX19 | | | | | 49.17 | 45.06 | | | | 0.10 | | | | | | | | | | | | | |
| | | gX18 | | | | | 48.68 | 37.61 | | | | 0.09 | | | | | | | | | | | | | |
| | | GX17 | | | | | 48.71 | 37.70 | | | | 0.14 | | | | | | | | | | | | | |

| | | SEQ ID NO: 106 | G | A | G | t | C | C | G | A | G | C | A | G | A | A | G | A | A | G | A | A | G | A | G |
|---|---|---|---|---|---|---|---|---|---|---|---|---|---|---|---|---|---|---|---|---|---|---|---|---|---|
| EMX1_1 | C-> other bases | Untreated | | | | | 0.04 | | | | | 0.05 | | | | | | | | | | | | | |
| | | ggX20 | | | | | 1.26 | | | | | 0.05 | | | | | | | | | | | | | |
| | | gX20 | | | | | 8.50 | | | | | 0.06 | | | | | | | | | | | | | |
| | | GX19 | | | | | 15.57 | | | | | 0.07 | | | | | | | | | | | | | |
| | | gX18 | | | | | 0.06 | | | | | 0.05 | | | | | | | | | | | | | |
| | | GX17 | | | | | 0.07 | | | | | 0.05 | | | | | | | | | | | | | |

| | | SEQ ID NO: 107 | G | A | G | a | C | c | G | A | G | C | A | G | A | A | G | A | A | G | A | A | G | A | G |
|---|---|---|---|---|---|---|---|---|---|---|---|---|---|---|---|---|---|---|---|---|---|---|---|---|---|
| EMX1_2 | C-> other bases | Untreated | | | | | 0.08 | 0.08 | | | | 0.07 | | | | | | | | | | | | | |
| | | ggX20 | | | | | 0.40 | 0.36 | | | | 0.05 | | | | | | | | | | | | | |
| | | gX20 | | | | | 0.80 | 0.75 | | | | 0.07 | | | | | | | | | | | | | |
| | | GX19 | | | | | 0.84 | 0.81 | | | | 0.07 | | | | | | | | | | | | | |
| | | gX18 | | | | | 0.22 | 0.23 | | | | 0.08 | | | | | | | | | | | | | |
| | | GX17 | | | | | 0.16 | 0.17 | | | | 0.06 | | | | | | | | | | | | | |

| | | SEQ ID NO: 108 | a | A | G | t | C | c | G | A | G | C | A | G | A | A | c | A | A | G | A | A | A | G | G |
|---|---|---|---|---|---|---|---|---|---|---|---|---|---|---|---|---|---|---|---|---|---|---|---|---|---|
| EMX1_3 | c-> other bases | Untreated | | | | | 0.02 | | | | | 0.07 | | | | | 0.06 | | | | | | | | |
| | | ggX20 | | | | | 0.03 | | | | | 0.06 | | | | | 0.06 | | | | | | | | |
| | | gX20 | | | | | 0.03 | | | | | 0.07 | | | | | 0.05 | | | | | | | | |
| | | GX19 | | | | | 0.13 | | | | | 0.07 | | | | | 0.05 | | | | | | | | |
| | | gX18 | | | | | 0.02 | | | | | 0.07 | | | | | 0.05 | | | | | | | | |
| | | GX17 | | | | | 0.02 | | | | | 0.08 | | | | | 0.04 | | | | | | | | |

| | | SEQ ID NO: 109 | G | A | G | c | C | c | G | A | G | C | A | G | A | A | G | A | A | G | A | A | T | G | G |
|---|---|---|---|---|---|---|---|---|---|---|---|---|---|---|---|---|---|---|---|---|---|---|---|---|---|
| EMX1_5 | C-> other bases | Untreated | | | | | 0.11 | 0.05 | | | | | | | | | | | | | | | | | |
| | | ggX20 | | | | | 1.09 | 1.11 | | | | | | | | | | | | | | | | | |
| | | gX20 | | | | | 2.31 | 2.27 | | | | | | | | | | | | | | | | | |
| | | GX19 | | | | | 0.96 | 0.96 | | | | | | | | | | | | | | | | | |
| | | gX18 | | | | | 0.06 | 0.11 | | | | | | | | | | | | | | | | | |
| | | GX17 | | | | | 0.08 | 0.12 | | | | | | | | | | | | | | | | | |

TABLE 17-continued

Analysis of BE3 off-target effect via modified sgRNAs

| EMX1_6 | SEQ ID NO: 110 | G | A | G | T | C | C | t | A | G | g | A | G | A | A | G | A | A | G |
|---|---|---|---|---|---|---|---|---|---|---|---|---|---|---|---|---|---|---|---|
| C->other bases | Untreated | | | | | 0.02 | 0.04 | | | | | | | | | | | | |
| | ggX20 | | | | | 0.34 | 0.35 | | | | | | | | | | | | |
| | gX20 | | | | | 1.69 | 1.71 | | | | | | | | | | | | |
| | GX19 | | | | | 2.43 | 2.40 | | | | | | | | | | | | |
| | gX18 | | | | | 0.02 | 0.02 | | | | | | | | | | | | |
| | GX17 | | | | | 0.02 | 0.04 | | | | | | | | | | | | |

| EMX1_7 | SEQ ID NO: 111 | G | A | G | T | C | C | a | A | G | t | A | G | A | A | G | A | G | G |
|---|---|---|---|---|---|---|---|---|---|---|---|---|---|---|---|---|---|---|---|
| C->other bases | Untreated | | | | | 0.03 | 0.06 | | | | | | | | | | | | |
| | ggX20 | | | | | 0.03 | 0.06 | | | | | | | | | | | | |
| | gX20 | | | | | 0.04 | 0.08 | | | | | | | | | | | | |
| | GX19 | | | | | 0.07 | 0.10 | | | | | | | | | | | | |
| | gX18 | | | | | 0.03 | 0.05 | | | | | | | | | | | | |
| | GX17 | | | | | 0.03 | 0.05 | | | | | | | | | | | | |

| EMX1_8 | SEQ ID NO: 112 | G | t | G | T | C | C | t | A | G | — | A | G | A | A | G | A | G | G |
|---|---|---|---|---|---|---|---|---|---|---|---|---|---|---|---|---|---|---|---|
| C->other bases | Untreated | | | | | 0.05 | 0.03 | | | | | | | | | | | | |
| | ggX20 | | | | | 0.10 | 0.09 | | | | | | | | | | | | |
| | gX20 | | | | | 0.38 | 0.35 | | | | | | | | | | | | |
| | GX19 | | | | | 0.64 | 0.57 | | | | | | | | | | | | |
| | gX18 | | | | | 0.60 | 0.56 | | | | | | | | | | | | |
| | GX17 | | | | | 0.62 | 0.60 | | | | | | | | | | | | |

| EMX1_9 | SEQ ID NO: 113 | a | A | G | T | C | C | G | A | G | A | A | G | A | A | G | A | A | G |
|---|---|---|---|---|---|---|---|---|---|---|---|---|---|---|---|---|---|---|---|
| C->other bases | Untreated | | | | | 0.05 | 0.16 | | | | | | | | | | | | |
| | ggX20 | | | | | 0.04 | 0.14 | | | | | | | | | | | | |
| | gX20 | | | | | 0.05 | 0.17 | | | | | | | | | | | | |
| | GX19 | | | | | 0.06 | 0.18 | | | | | | | | | | | | |
| | gX18 | | | | | 0.05 | 0.18 | | | | | | | | | | | | |
| | GX17 | | | | | 0.05 | 0.16 | | | | | | | | | | | | |

| EMX1_10 | SEQ ID NO: 114 | G | A | G | T | C | C | G | A | G | g | A | G | A | A | G | A | C | G |
|---|---|---|---|---|---|---|---|---|---|---|---|---|---|---|---|---|---|---|---|
| C->other bases | Untreated | | | | | 0.14 | 0.10 | | | | 0.13 | | | | | | | | |
| | ggX20 | | | | | 0.26 | 0.21 | | | | 0.12 | | | | | | | | |
| | gX20 | | | | | 0.44 | 0.39 | | | | 0.19 | | | | | | | | |
| | GX19 | | | | | 3.45 | 3.70 | | | | 0.17 | | | | | | | | |
| | gX18 | | | | | 0.17 | 0.10 | | | | 0.15 | | | | | | | | |
| | GX17 | | | | | 0.18 | 0.09 | | | | 0.16 | | | | | | | | |

| EMX1_11 | SEQ ID NO: 115 | a | g | t | T | C | C | a | A | G | A | A | G | a | A | G | A | T | G |
|---|---|---|---|---|---|---|---|---|---|---|---|---|---|---|---|---|---|---|---|
| C->other bases | Untreated | | | | | 0.06 | 0.05 | | | | 0.07 | | | | c 0.06 | | | | |
| | ggX20 | | | | | 0.27 | 0.28 | | | | 0.07 | | | | 0.07 | | | | |
| | gX20 | | | | | 0.74 | 0.70 | | | | 0.07 | | | | 0.08 | | | | |
| | GX19 | | | | | 0.74 | 0.62 | | | | 0.06 | | | | 0.07 | | | | |

TABLE 17-continued

Analysis of BE3 off-target effect via modified sgRNAs

| | | SEQ ID NO: 116 | G | A | G | T | C | C | a | C | a | c | A | A | A | A | G | A | A | A |
|---|---|---|---|---|---|---|---|---|---|---|---|---|---|---|---|---|---|---|---|
| EMX1_12 | C-> other bases | Untreated<br>ggx20<br>gx20<br>GX19<br>gx18<br>GX17 | | | | | 0.08<br>0.07<br>0.09<br>0.17<br>0.07<br>0.08 | 0.26<br>0.21<br>0.23<br>0.33<br>0.25<br>0.23 | | 0.11<br>0.12<br>0.09<br>0.17<br>0.10<br>0.11 | | 0.11<br>0.11<br>0.11<br>0.10<br>0.13<br>0.11 | | | | | 0.06<br>0.07 | 0.05<br>0.06 | 0.06<br>0.07 | |
| | | SEQ ID NO: 117 | G | A | G | T | C | C | a | A | G | — | A | A | A | A | G | t | g | A |
| EMX1_13 | C-> other bases | Untreated<br>ggX20<br>gX20<br>GX19<br>gX18<br>GX17 | | | | | 0.08<br>0.06<br>0.07<br>0.08<br>0.08<br>0.07 | 0.12<br>0.11<br>0.11<br>0.13<br>0.13<br>0.13 | | | | | | | | | | | | |
| | | SEQ ID NO: 118 | G | A | G | T | C | C | a | A | G | — | A | A | A | A | G | g | A | G |
| EMX1_14 | C-> other bases | Untreated<br>ggX20<br>gX20<br>GX19<br>gX18<br>GX17 | | | | | 0.06<br>0.07<br>0.07<br>0.05<br>0.06<br>0.05 | 0.13<br>0.19<br>0.17<br>0.13<br>0.12<br>0.14 | | | | | | | | | g | | | |
| | | SEQ ID NO: 119 | G | A | a | T | C | C | a | A | G | C | A | A | G | A | G | A | A | A |
| EMX1_15 | C-> other bases | Untreated<br>ggX20<br>gX20<br>GX19<br>gX18<br>GX17 | | | | | 0.04<br>0.09<br>0.54<br>0.14<br>0.04<br>0.01 | 0.07<br>0.15<br>0.60<br>0.18<br>0.07<br>0.07 | | | | 0.05<br>0.04<br>0.08<br>0.05<br>0.05<br>0.06 | | | | | | | | |
| | | SEQ ID NO: 120 | G | t | a | c | C | a | G | A | G | — | A | A | G | A | G | g | G | G |
| EMX1_16 | C-> other bases | Untreated<br>ggX20<br>gX20<br>GX19<br>gX18<br>GX17 | | | | 0.06<br>0.05<br>0.06<br>0.05<br>0.06<br>0.06 | 0.06<br>0.05<br>0.05<br>0.05<br>0.04<br>0.05 | | | | | | | | | | | | | |

TABLE 17-continued

Analysis of BE3 off-target effect via modified sgRNAs

EMX1_17, SEQ ID NO: 121

| | G | A | G | T | C | C | C | A | G | C | A | G | G | A | A | A | A | A | A | A | G |
|---|---|---|---|---|---|---|---|---|---|---|---|---|---|---|---|---|---|---|---|---|---|
| C->other bases | | | | | | | | | | | | | | | | | | | | | |
| Untreated | | | | | 0.10 | 0.19 | 0.09 | | | 0.07 | | | | | | | | | | | |
| ggX20 | | | | | 0.10 | 0.16 | 0.10 | | | 0.07 | | | | | | | | | | | |
| gX20 | | | | | 0.19 | 0.24 | 0.13 | | | 0.05 | | | | | | | | | | | |
| GX19 | | | | | 0.11 | 0.20 | 0.07 | | | 0.07 | | | | | | | | | | | |
| gX18 | | | | | 0.12 | 0.24 | 0.09 | | | 0.06 | | | | | | | | | | | |
| GX17 | | | | | 0.12 | 0.20 | 0.07 | | | 0.06 | | | | | | | | | | | |

EMX1_18, SEQ ID NO: 122

| | G | a | A | G | T | C | C | a | A | G | C | A | G | — | G | A | A | A | G | A | A | G |
|---|---|---|---|---|---|---|---|---|---|---|---|---|---|---|---|---|---|---|---|---|---|---|
| C->other bases | | | | | | | | | | | | | | | | | | | | | | |
| Untreated | | | | | | 0.06 | 0.09 | | | | | | | | | | | | | | | |
| ggX20 | | | | | | 0.05 | 0.09 | | | | | | | | | | | | | | | |
| gX20 | | | | | | 0.05 | 0.08 | | | | | | | | | | | | | | | |
| GX19 | | | | | | 0.09 | 0.11 | | | | | | | | | | | | | | | |
| gX18 | | | | | | 0.05 | 0.08 | | | | | | | | | | | | | | | |
| GX17 | | | | | | 0.05 | 0.09 | | | | | | | | | | | | | | | |

EMX1_19, SEQ ID NO: 123

| | a | t | A | G | C | C | C | A | G | t | G | C | A | G | — | A | A | A | A | G | A | A | G |
|---|---|---|---|---|---|---|---|---|---|---|---|---|---|---|---|---|---|---|---|---|---|---|---|
| C->other bases | | | | | | | | | | | | | | | | | | | | | | | |
| Untreated | | | | | 0.03 | 0.07 | 0.10 | | | | | 0.09 | | | | | | | | | | | |
| ggX20 | | | | | 0.05 | 0.07 | 0.09 | | | | | 0.07 | | | | | | | | | | | |
| gX20 | | | | | 0.03 | 0.08 | 0.12 | | | | | 0.08 | | | | | | | | | | | |
| GX19 | | | | | 0.24 | 0.30 | 0.12 | | | | | 0.12 | | | | | | | | | | | |
| gX18 | | | | | 0.03 | 0.08 | 0.10 | | | | | 0.10 | | | | | | | | | | | |
| GX17 | | | | | 0.05 | 0.07 | 0.09 | | | | | 0.09 | | | | | | | | | | | |

EMX1_20, SEQ ID NO: 124

| | G | A | G | T | C | t | A | G | C | t | G | A | G | — | A | A | a | A | G | A | A | G |
|---|---|---|---|---|---|---|---|---|---|---|---|---|---|---|---|---|---|---|---|---|---|---|
| C->other bases | | | | | | | | | | | | | | | | | | | | | | |
| Untreated | | | | | 0.05 | | | | 0.12 | | | | | | | | | | | | | |
| ggX20 | | | | | 0.21 | | | | 0.26 | | | | | | | | | | | | | |
| gX20 | | | | | 0.43 | | | | 0.50 | | | | | | | | | | | | | |
| GX19 | | | | | 0.50 | | | | 0.57 | | | | | | | | | | | | | |
| gX18 | | | | | 0.06 | | | | 0.12 | | | | | | | | | | | | | |
| GX17 | | | | | 0.05 | | | | 0.12 | | | | | | | | | | | | | |

EMX1_21, SEQ ID NO: 125

| | G | A | G | T | C | C | c | t | G | A | G | C | A | G | g | A | A | A | A | G | A | G |
|---|---|---|---|---|---|---|---|---|---|---|---|---|---|---|---|---|---|---|---|---|---|---|
| C->other bases | | | | | | | | | | | | | | | | | | | | | | |
| Untreated | | | | | 0.16 | 0.08 | 0.07 | 0.03 | | | | | | | | | | | | | | |
| ggX20 | | | | | 0.12 | 0.07 | 0.06 | 0.04 | | | | | | | | | | | | | | |
| gX20 | | | | | 0.15 | 0.11 | 0.08 | 0.04 | | | | | | | | | | | | | | |
| GX19 | | | | | 0.24 | 0.17 | 0.16 | 0.06 | | | | | | | | | | | | | | |
| gX18 | | | | | 0.12 | 0.09 | 0.07 | 0.04 | | | | | | | | | | | | | | |
| GX17 | | | | | 0.14 | 0.08 | 0.06 | 0.02 | | | | | | | | | | | | | | |

EMX1_22, SEQ ID NO: 126

| | a | c | G | A | T | G | A | G | C | A | G | C | A | G | g | A | A | A | T | G | G |
|---|---|---|---|---|---|---|---|---|---|---|---|---|---|---|---|---|---|---|---|---|---|
| C->other bases | | | | | | | | | | | | | | | | | | | | | | |
| Untreated | | 0.14 | | | | | | | 0.04 | | | 0.11 | | | | | | | | | |
| ggX20 | | 0.14 | | | | | | | 0.16 | | | 0.13 | | | | | | | | | |
| gX20 | | 0.15 | | | | | | | 0.20 | | | 0.16 | | | | | | | | | |
| GX19 | | 0.15 | | | | | | | 0.62 | | | 0.12 | | | | | | | | | |

TABLE 17-continued

Analysis of BE3 off-target effect via modified sgRNAs

| EMX1_23 | C->other bases | gX18 | | | | | | | | | | | | | | | | | | | 1.24 | | | | | | | | | 0.22 | 0.12 |
| | | GX17 | | | | | | | | | | | | | | | | | | | 4.49 | | | | | | | | | 0.13 | 0.11 |

| | SEQ ID NO: 127 | G | A | G | T | C | c | A | G | A | A | A | G | A | A | A | A | G | A | A | G | A | A |
| EMX1_24 | C->other bases | Untreated | | | | 0.06 | 0.08 | | | | | | | | | | | | | | | | | |
| | | ggX20 | | | | 0.06 | 0.09 | | | | | | | | | | | | | | | | | |
| | | gX20 | | | | 0.09 | 0.13 | | | | | | | | | | | | | | | | | |
| | | GX19 | | | | 0.06 | 0.09 | | | | | | | | | | | | | | | | | |
| | | gX18 | | | | 0.07 | 0.11 | | | | | | | | | | | | | | | | | |
| | | GX17 | | | | 0.07 | 0.09 | | | | | | | | | | | | | | | | | |

| | SEQ ID NO: 128 | G | A | G | T | C | C | A | — | A | G | A | A | A | A | G | A | c | A |
| EMX1_25 | C->other bases | Untreated | | | | 0.18 | | | | | | | | | | | | 0.11 | |
| | | ggX20 | | | | 0.20 | | | | | | | | | | | | 0.16 | |
| | | gX20 | | | | 0.19 | | | | | | | | | | | | 0.12 | |
| | | GX19 | | | | 0.22 | | | | | | | | | | | | 0.12 | |
| | | gX18 | | | | 0.19 | | | | | | | | | | | | 0.15 | |
| | | GX17 | | | | 0.18 | | | | | | | | | | | | 0.12 | |

| | SEQ ID NO: 129 | c | A | G | T | C | t | A | a | C | A | a | C | A | a | g | G | A | A | T | G | G |
| On-target (FANCF_2) | C->other bases | Untreated | 0.11 | | | 0.05 | 0.18 | | | | 0.11 | | 0.05 | 0.08 | | | | | | | | | |
| | | ggX20 | 0.11 | | | 0.08 | 0.20 | | | | 0.12 | | 0.08 | 0.08 | | | | | | | | | |
| | | gX20 | 0.10 | | | 0.05 | 0.19 | | | | 0.10 | | 0.05 | 0.05 | | | | | | | | | |
| | | GX19 | 0.11 | | | 0.07 | 0.22 | | | | 0.13 | | 0.07 | 0.07 | | | | | | | | | |
| | | gX18 | 0.13 | | | 0.05 | 0.19 | | | | 0.14 | | 0.05 | 0.05 | | | | | | | | | |
| | | GX17 | 0.10 | | | 0.04 | 0.18 | | | | 0.13 | | 0.07 | 0.07 | | | | | | | | | |

FANCF

| | SEQ ID NO: 131 | G | G | A | T | C | C | C | T | c | G | C | A | G | C | A | C | A | G |
| FANCF_1 | C->other bases | Untreated | | | | 0.06 | 0.10 | 0.04 | 0.03 | | 0.04 | 0.13 | 0.13 | 0.07 | 0.13 | 0.05 | 0.04 | 0.04 | |
| | | ggX20 | | | | 9.20 | 8.19 | 7.94 | 4.25 | | 0.03 | 0.12 | 0.12 | 0.11 | 0.12 | 0.06 | 0.04 | 0.04 | |
| | | gX20 | | | | 8.12 | 7.31 | 6.89 | 3.01 | | 0.02 | 0.13 | 0.12 | 0.09 | 0.12 | 0.05 | 0.03 | 0.03 | |
| | | GX19 | | | | 10.26 | 9.44 | 9.28 | 4.12 | | 0.05 | 0.18 | 0.13 | 0.12 | 0.15 | 0.05 | 0.05 | 0.03 | |
| | | gX18 | | | | 9.74 | 8.81 | 8.16 | 3.14 | | 0.13 | 0.15 | 0.14 | 0.14 | 0.18 | 0.06 | 0.02 | 0.04 | |
| | | GX17 | | | | 3.36 | 2.80 | 2.77 | 1.14 | | 0.03 | 0.12 | 0.12 | 0.12 | 0.12 | 0.05 | 0.04 | 0.04 | |

| | SEQ ID NO: 130 | t | G | A | A | T | C | C | C | a | T | c | C | A | G | C | A | C | A | G |
| FANCF_1 | C->other bases | Untreated | | | | 0.07 | 0.10 | 0.08 | 0.03 | | 0.04 | 0.07 | 0.07 | 0.04 | 0.07 | 0.04 | 0.07 | |
| | | ggX20 | | | | 0.06 | 0.11 | 0.07 | 0.03 | | 0.05 | 0.11 | 0.11 | 0.05 | 0.06 | 0.03 | 0.06 | |
| | | gX20 | | | | 0.09 | 0.10 | 0.09 | 0.04 | | 0.05 | 0.09 | 0.09 | 0.05 | 0.09 | 0.03 | 0.09 | |
| | | GX19 | | | | 0.16 | 0.16 | 0.18 | 0.06 | | 0.07 | 0.09 | 0.09 | 0.07 | 0.09 | 0.04 | 0.07 | |
| | | gX18 | | | | 0.80 | 0.79 | 0.79 | 0.25 | | 0.08 | 0.10 | 0.10 | 0.08 | 0.10 | 0.03 | 0.06 | |
| | | GX17 | | | | 0.08 | 0.10 | 0.09 | 0.02 | | 0.06 | 0.09 | 0.09 | 0.06 | 0.09 | 0.02 | 0.07 | |

TABLE 17-continued

Analysis of BE3 off-target effect via modified sgRNAs

| | | SEQ ID NO: 132 | G | G | A | g | T | C | C | C | T | c | T | a | C | A | C | A | C | C | A | G |
|---|---|---|---|---|---|---|---|---|---|---|---|---|---|---|---|---|---|---|---|---|---|---|
| FANCF_3 | C->other bases | Untreated | | | | | | 0.09 | 0.06 | 0.05 | | 0.08 | | | 0.06 | | 0.07 | | 0.06 | 0.06 | | 0.14 |
| | | ggX20 | | | | | | 0.08 | 0.05 | 0.04 | | 0.07 | | | 0.06 | | 0.05 | | 0.07 | 0.07 | | 0.15 |
| | | gX20 | | | | | | 0.13 | 0.07 | 0.08 | | 0.10 | | | 0.07 | | 0.06 | | 0.07 | 0.15 | | 0.15 |
| | | GX19 | | | | | | 0.23 | 0.09 | 0.12 | | 0.16 | | | 0.08 | | 0.06 | | 0.07 | 0.18 | | 0.18 |
| | | GX18 | | | | | | 0.09 | 0.07 | 0.05 | | 0.08 | | | 0.05 | | 0.06 | | 0.08 | 0.17 | | 0.17 |
| | | gX17 | | | | | | 0.08 | 0.05 | 0.04 | | 0.11 | | | 0.06 | | 0.07 | | 0.09 | 0.15 | | 0.15 |

| | | SEQ ID NO: 133 | G | G | A | g | T | C | C | C | T | c | T | a | C | A | C | A | C | C | A | G |
|---|---|---|---|---|---|---|---|---|---|---|---|---|---|---|---|---|---|---|---|---|---|---|
| FANCF_4 | C->other bases | Untreated | | | | | | 0.06 | 0.05 | 0.05 | | 0.05 | | | 0.06 | | 0.03 | | 0.03 | 0.06 | | 0.06 |
| | | ggX20 | | | | | | 0.05 | 0.05 | 0.05 | | 0.04 | | | 0.07 | | 0.04 | | 0.03 | 0.04 | | 0.04 |
| | | gX20 | | | | | | 0.08 | 0.07 | 0.06 | | 0.06 | | | 0.06 | | 0.02 | | 0.02 | 0.06 | | 0.06 |
| | | GX19 | | | | | | 0.09 | 0.09 | 0.12 | | 0.08 | | | 0.07 | | 0.04 | | 0.04 | 0.04 | | 0.04 |
| | | GX18 | | | | | | 0.07 | 0.07 | 0.06 | | 0.06 | | | 0.05 | | 0.04 | | 0.03 | 0.07 | | 0.07 |
| | | gX17 | | | | | | 0.05 | 0.05 | 0.04 | | 0.04 | | | 0.07 | | 0.03 | | 0.02 | 0.06 | | 0.06 |

| | | SEQ ID NO: 134 | G | G | A | T | | | | | | | | | | | | | | | | |
|---|---|---|---|---|---|---|---|---|---|---|---|---|---|---|---|---|---|---|---|---|---|---|
| FANCF_5 | C->other bases | Untreated | | | | | | | | | | | | | | | | | | | | |

| | | SEQ ID NO: 135 | G | G | A | g | T | C | C | C | T | c | T | a | C | A | C | A | C | C | T | G |
|---|---|---|---|---|---|---|---|---|---|---|---|---|---|---|---|---|---|---|---|---|---|---|
| | | Untreated | | | | | | 0.07 | 0.05 | 0.05 | | 0.03 | | | 0.07 | | 0.03 | | 0.03 | 0.03 | | 0.03 |
| | | ggX20 | | | | | | 0.06 | 0.04 | 0.04 | | 0.04 | | | 0.06 | | 0.03 | | 0.03 | 0.02 | | 0.02 |
| | | gX20 | | | | | | 0.05 | 0.06 | 0.06 | | 0.04 | | | 0.05 | | 0.04 | | 0.02 | 0.03 | | 0.03 |
| | | GX19 | | | | | | 0.07 | 0.07 | 0.05 | | 0.03 | | | 0.07 | | 0.03 | | 0.04 | 0.02 | | 0.02 |
| | | GX18 | | | | | | 0.06 | 0.06 | 0.06 | | 0.04 | | | 0.08 | | 0.04 | | 0.03 | 0.03 | | 0.03 |
| | | gX17 | | | | | | 0.05 | 0.05 | 0.05 | | 0.05 | | | 0.08 | | 0.04 | | 0.02 | 0.02 | | 0.02 |

| | | SEQ ID NO: 136 | G | G | A | g | T | C | C | C | T | c | T | G | C | A | C | A | C | C | T | A |
|---|---|---|---|---|---|---|---|---|---|---|---|---|---|---|---|---|---|---|---|---|---|---|
| FANCF_6 | C->other bases | Untreated | | | | | | 0.04 | 0.04 | 0.04 | | 0.02 | | | 0.09 | | 0.06 | | 0.02 | 0.04 | | 0.04 |
| | | ggX20 | | | | | | 0.03 | 0.04 | 0.04 | | 0.04 | | | 0.12 | | 0.05 | | 0.03 | 0.06 | | 0.06 |
| | | gX20 | | | | | | 0.06 | 0.06 | 0.05 | | 0.03 | | | 0.11 | | 0.07 | | 0.06 | 0.04 | | 0.04 |
| | | GX19 | | | | | | 0.09 | 0.09 | 0.09 | | 0.05 | | | 0.12 | | 0.06 | | 0.05 | 0.03 | | 0.03 |
| | | GX18 | | | | | | 0.05 | 0.05 | 0.04 | | 0.03 | | | 0.08 | | 0.07 | | 0.04 | 0.05 | | 0.05 |
| | | gX17 | | | | | | 0.05 | 0.04 | 0.04 | | 0.04 | | | 0.14 | | 0.05 | | 0.05 | 0.04 | | 0.04 |

| | | SEQ ID NO: 137 | G | t | c | c | g | T | C | C | T | c | T | G | C | A | C | A | C | C | A | G |
|---|---|---|---|---|---|---|---|---|---|---|---|---|---|---|---|---|---|---|---|---|---|---|
| FANCF_7 | C->other bases | Untreated | | | | 0.03 | | 0.07 | 0.06 | 0.03 | | 0.03 | | | 0.20 | | 0.05 | | 0.03 | 0.07 | | 0.07 |
| | | ggX20 | 0.02 | | | 0.27 | | 0.29 | 0.32 | 0.10 | | 0.10 | | | 0.21 | | 0.05 | | 0.02 | 0.07 | | 0.07 |
| | | gX20 | 0.02 | | | 1.46 | | 1.50 | 1.48 | 0.80 | | 0.20 | | | 0.20 | | 0.04 | | 0.06 | 0.06 | | 0.06 |
| | | GX19 | 0.01 | | | 1.06 | | 1.07 | 1.02 | 0.71 | | 0.22 | | | 0.22 | | 0.07 | | 0.05 | 0.07 | | 0.07 |
| | | GX18 | 0.02 | | | 0.04 | | 0.07 | 0.09 | 0.01 | | 0.08 | | | 0.17 | | 0.04 | | 0.04 | 0.06 | | 0.06 |
| | | gX17 | | | | 0.04 | | 0.06 | 0.09 | 0.01 | | 0.14 | | | 0.17 | | 0.05 | | 0.05 | 0.04 | | 0.04 |

| | | SEQ ID NO: 138 | G | t | c | c | g | T | C | C | T | c | T | G | C | A | C | A | C | C | A | G |
|---|---|---|---|---|---|---|---|---|---|---|---|---|---|---|---|---|---|---|---|---|---|---|
| FANCF_8 | C->other bases | Untreated | | | | 0.03 | | 0.02 | 0.04 | 0.05 | | 0.03 | | | 0.11 | | 0.03 | | 0.02 | 0.03 | | 0.03 |
| | | ggX20 | 0.02 | | | 0.01 | | 0.05 | 0.03 | 0.05 | | 0.01 | | | 0.08 | | 0.02 | | 0.02 | 0.02 | | 0.04 |
| | | gX20 | 0.01 | | | 0.02 | | 0.04 | 0.04 | 0.04 | | 0.02 | | | 0.08 | | 0.02 | | 0.03 | 0.03 | | 0.03 |
| | | GX19 | 0.02 | | | 0.02 | | 0.04 | 0.04 | 0.08 | | 0.03 | | | 0.10 | | 0.03 | | 0.02 | 0.03 | | 0.03 |

TABLE 17-continued

Analysis of BE3 off-target effect via modified sgRNAs

| | | | | | | | | | | | | | | | | | | | | | | |
|---|---|---|---|---|---|---|---|---|---|---|---|---|---|---|---|---|---|---|---|---|---|---|
| | | GX18 | | | | | | | | | 0.04 | | 0.09 | 0.09 | 0.07 | 0.09 | 0.10 | 0.13 | 0.04 | | 0.05 | 0.10 | 0.05 | | | 0.04 | | 0.03 | 0.03 |
| | | gX17 | | | | | | | | | 0.04 | | 0.09 | 0.11 | 0.08 | 0.11 | 0.11 | 0.13 | 0.04 | | 0.07 | 0.11 | | | 0.05 | | 0.02 | 0.04 |
| FANCF_9 | | SEQ ID NO: 138 | a | a | A | T | C | C | C | G | A | T | C | G | A | C | T | G |
| | C->other bases | Untreated<br>ggX20<br>gX20<br>gX19<br>gX18<br>gX17 | | | | | 0.07<br>0.08<br>0.09<br>0.10<br>0.10<br>0.06 | 0.02<br>0.03<br>0.03<br>0.04<br>0.06<br>0.06 | 0.04<br>0.04<br>0.04<br>0.05<br>0.07<br>0.06 | | 0.05<br>0.03<br>0.04<br>0.05<br>0.06<br>0.05 | 0.06<br>0.06<br>0.05<br>0.06<br>0.05<br>0.06 | | 0.05<br>0.06<br>0.05<br>0.06<br>0.07<br>0.04 | 0.04<br>0.05<br>0.04<br>0.04<br>0.03<br>0.03 | | | 0.05<br>0.05<br>0.06<br>0.05<br>0.06<br>0.05 | 0.06<br>0.04<br>0.04<br>0.05<br>0.04<br>0.06 |
| FANCF_10 | | SEQ ID NO: 139 | t | G | t | A | T | C | T | G | c | t | C | T | G |
| | C->other bases | Untreated<br>ggX20<br>gX20<br>gX19<br>gX18<br>gX17 | | | | | | | | | | | | | | |
| FANCF_11 | | SEQ ID NO: 140 | G | G | A | A | C | T | T | G | A | G | C | c | C | A | G |
| | C->other bases | Untreated<br>ggX20<br>gX20<br>gX19<br>gX18<br>gX17 | | | | | | 0.03<br>0.03<br>0.03<br>0.04<br>0.03<br>0.04 | 0.05<br>0.05<br>0.03<br>0.03<br>0.04<br>0.05 | | 0.22<br>0.23<br>0.23<br>0.21<br>0.20<br>0.24 | | 0.03<br>0.02<br>0.03<br>0.02<br>0.02<br>0.02 | | 0.05<br>0.06<br>0.05<br>0.06<br>0.04<br>0.06 | 0.10<br>0.09<br>0.10<br>0.09<br>0.07<br>0.08 |
| FANCF_12 | | SEQ ID NO: 141 | G | a | t | A | C | C | T | G | c | a | C | c | A | g | G |
| FANCF_13 | | SEQ ID NO: 142 | a | c | c | T | C | C | T | c | C | T | C | A | C | C | G |
| | C->other bases | Untreated<br>ggX20<br>gX20<br>gX19<br>gX18<br>gX17 | | 0.07<br>0.13<br>0.10<br>0.13<br>0.14<br>0.15 | 0.06<br>0.07<br>0.08<br>0.08<br>0.12<br>0.15 | | 0.04<br>0.05<br>0.04<br>0.15<br>1.03<br>2.04 | 0.04<br>0.04<br>0.04<br>0.15<br>0.99<br>1.96 | 0.04<br>0.05<br>0.04<br>0.14<br>0.94<br>1.94 | 0.06<br>0.05<br>0.06<br>0.13<br>0.40<br>0.75 | 0.05<br>0.02<br>0.04<br>0.09<br>0.14<br>0.26 | | 0.10<br>0.08<br>0.09<br>0.10<br>0.09<br>0.10 | | 0.03<br>0.04<br>0.04<br>0.04<br>0.04<br>0.04 | | 0.08<br>0.03<br>0.07<br>0.06<br>0.05<br>0.06 | 0.04<br>0.06<br>0.04<br>0.04<br>0.05<br>0.04 |

TABLE 17-continued

Analysis of BE3 off-target effect via modified sgRNAs

| | | SEQ ID NO: 143 | t | G | A | A | T | C | C | t | a | C | T | G | C | A | C | A | C | C | G |
|---|---|---|---|---|---|---|---|---|---|---|---|---|---|---|---|---|---|---|---|---|---|
| FANCF_14 | C->other bases | Untreated | | | | | | 0.09 | 0.05 | | | 0.04 | | 0.09 | | 0.06 | 0.08 | 0.06 | | |
| | | ggX20 | 0.03 | | 0.04 | | | 0.10 | 0.05 | | | 0.04 | | 0.08 | | 0.07 | 0.11 | 0.07 | | |
| | | gX20 | 0.03 | | 0.03 | | | 0.08 | 0.05 | | | 0.05 | | 0.12 | | 0.07 | 0.09 | 0.06 | | |
| | | gX19 | 0.04 | | 0.03 | | | 0.10 | 0.08 | | | 0.03 | | 0.11 | | 0.07 | 0.10 | 0.07 | | |
| | | gX18 | 0.03 | | 0.02 | | | 0.46 | 0.42 | | | 0.04 | | 0.13 | | 0.05 | 0.08 | 0.06 | | |
| | | gX17 | 0.03 | | 0.02 | | | 0.10 | 0.05 | | | 0.03 | | 0.11 | | 0.06 | 0.09 | 0.07 | | |

| | | SEQ ID NO: 144 | c | t | c | t | g | t | C | T | T | T | C | C | A | C | T | C | C | G |
|---|---|---|---|---|---|---|---|---|---|---|---|---|---|---|---|---|---|---|---|---|---|
| FANCF_15 | C->other bases | Untreated | | | | | | 0.05 | 0.02 | | | 0.02 | | 0.06 | | 0.02 | 0.01 | 0.03 | | |
| | | ggX20 | 0.03 | | 0.04 | | | 0.04 | 0.03 | | | 0.03 | | 0.07 | | 0.01 | 0.02 | 0.04 | | |
| | | gX20 | 0.04 | | 0.03 | | | 0.06 | 0.03 | | | 0.02 | | 0.05 | | 0.02 | 0.03 | 0.04 | | |
| | | gX19 | 0.03 | | 0.02 | | | 0.07 | 0.03 | | | 0.02 | | 0.05 | | 0.03 | 0.02 | 0.04 | | |
| | | gX18 | 0.03 | | 0.04 | | | 0.05 | 0.03 | | | 0.03 | | 0.05 | | 0.02 | 0.02 | 0.02 | | |
| | | gX17 | 0.03 | | 0.02 | | | 0.10 | 0.04 | | | 0.03 | | 0.06 | | 0.04 | 0.02 | 0.02 | | |

| | | SEQ ID NO: 93 | G | T | C | A | T | C | T | T | A | G | T | C | A | T | T | G | G |
|---|---|---|---|---|---|---|---|---|---|---|---|---|---|---|---|---|---|---|---|
| On-target (RNF2_1) | C->other bases | Untreated | | | 0.06 | | | 0.07 | | | | | 0.06 | | | | 0.03 | | |
| | | ggX20 | | | 22.35 | | | 29.23 | | | | | 3.10 | | | | 0.10 | | |
| | | gX20 | | | 20.82 | | | 28.93 | | | | | 3.23 | | | | 0.10 | | |
| | | gX19 | | | 19.23 | | | 31.12 | | | | | 3.45 | | | | 0.16 | | |
| | | gX18 | | | 9.19 | | | 19.16 | | | | | 1.61 | | | | 0.07 | | |
| | | gX17 | | | 2.34 | | | 7.73 | | | | | 0.95 | | | | 0.06 | | |

| | | SEQ ID NO: 145 | C | T | C | A | C | C | T | G | A | C | T | C | A | G | T | A | C | G |
|---|---|---|---|---|---|---|---|---|---|---|---|---|---|---|---|---|---|---|---|---|
| On-target (HBB_1) | C->other bases | Untreated | 0.05 | 0.08 | 0.03 | | | 0.05 | 0.04 | | 0.04 | 0.05 | | 0.08 | | | 0.07 | | | |
| | | ggX20 | 0.30 | 4.68 | 6.16 | | | 6.49 | 5.84 | | 0.15 | 6.06 | | 0.08 | | | 0.08 | | | |
| | | gX20 | 0.09 | 2.76 | 3.27 | | | 3.37 | 3.07 | | 0.11 | 0.07 | | 0.07 | | | 0.07 | | | |
| | | gX19 | 0.10 | 3.01 | 4.51 | | | 4.88 | 4.64 | | 0.14 | 0.84 | | 0.08 | | | 0.08 | | | |
| | | gX18 | 0.08 | 2.20 | 6.12 | | | 6.80 | 6.30 | | 0.15 | 0.10 | | 0.07 | | | 0.07 | | | |
| | | gX17 | 0.08 | 0.63 | 3.27 | | | 4.07 | 3.74 | | 0.10 | 0.05 | | 0.10 | | | 0.10 | | | |

| | | SEQ ID NO: 146 | t | T | G | C | C | C | T | G | A | C | C | C | A | G | T | A | A | G |
|---|---|---|---|---|---|---|---|---|---|---|---|---|---|---|---|---|---|---|---|---|
| HBB_2 | C->other bases | Untreated | | | | | | 0.06 | 0.04 | | 0.04 | 0.05 | | | | | 0.06 | | | |
| | | ggX20 | | | | | | 0.08 | 0.04 | | 0.04 | 0.06 | | | | | 0.09 | | | |
| | | gX20 | | | | | | 0.09 | 0.07 | | 0.03 | 0.08 | | | | | 0.05 | | | |
| | | gX19 | | | | | | 0.89 | 0.84 | | 0.07 | 0.11 | | | | | 0.06 | | | |
| | | gX18 | | | | | | 0.12 | 0.10 | | 0.05 | 0.06 | | | | | 0.06 | | | |
| | | gX17 | | | | | | 0.08 | 0.05 | | 0.05 | | | | | | 0.08 | | | |

| | | SEQ ID NO: 147 | g | c | T | G | C | C | C | T | C | C | C | A | C | A | C | C | A | G |
|---|---|---|---|---|---|---|---|---|---|---|---|---|---|---|---|---|---|---|---|---|
| HBB_3 | C->other bases | Untreated | 0.07 | | | 0.06 | 0.06 | 0.11 | 0.03 | | 0.07 | | | 0.14 | | | 0.09 | | | |
| | | ggX20 | 0.10 | | | 0.09 | 0.11 | 0.14 | 0.08 | | 0.07 | | | 0.15 | | | 0.07 | | | |
| | | gX20 | 0.10 | | | 0.74 | 0.77 | 0.79 | 0.70 | | 0.09 | | | 0.13 | | | 0.08 | | | |
| | | gX19 | 0.09 | | | 0.80 | 0.86 | 0.87 | 0.75 | | 0.07 | | | 0.11 | | | 0.09 | | | |

TABLE 17-continued

Analysis of BE3 off-target effect via modified sgRNAs

| | | gX18 | | | | | | 0.46 | 0.64 | 0.64 | | 0.53 | | | | | | 0.11 | | | | | | 0.10 | |
| --- | --- | --- | --- | --- | --- | --- | --- | --- | --- | --- | --- | --- | --- | --- | --- | --- | --- | --- | --- | --- | --- | --- | --- | --- | --- |
| | | gX17 | | | 0.12 | | | 0.16 | 0.19 | 0.24 | | 0.18 | | | | | | 0.14 | | | | | | 0.09 | |
| | | SEQ ID NO: 148 | G | a | A | g | T | C | C | C | A | C | A | G | G | C | A | G | A | g | | | | |
| HBB_4 | C- >other bases | Untreated<br>ggX20<br>gX20<br>gX19<br>gX18<br>gX17 | | | | | | 0.07<br>0.10<br>0.08<br>0.14<br>0.10<br>0.84 | 0.13<br>0.11<br>0.12<br>0.20<br>0.24<br>1.61 | 0.06<br>0.06<br>0.07<br>0.13<br>0.17<br>1.58 | | 0.09<br>0.10<br>0.09<br>0.16<br>0.20<br>1.53 | | 0.04<br>0.05<br>0.04<br>0.07<br>0.08<br>0.16 | | | | 0.06<br>0.04<br>0.06<br>0.08<br>0.06<br>0.05 | | | | | | |
| | | SEQ ID NO: 149 | a | c | T | T | G | C | C | C | A | C | g | G | G | C | A | G | T | g | A | A | T | G |
| HBB_5 | C- >other bases | Untreated<br>ggX20<br>gX20<br>gX19<br>gX18<br>gX17 | | | | | | 0.12<br>0.16<br>0.20<br>0.36<br>0.24<br>0.17 | 0.19<br>0.20<br>0.23<br>0.42<br>0.32<br>0.20 | 0.73<br>0.73<br>0.80<br>0.95<br>0.89<br>0.75 | | 0.40<br>0.48<br>0.47<br>0.73<br>0.60<br>0.49 | | 0.16<br>0.19<br>0.14<br>0.20<br>0.20<br>0.20 | | | | 0.20<br>0.25<br>0.21<br>0.21<br>0.24<br>0.22 | | | | | | |
| | | SEQ ID NO: 150 | a | c | A | t | c | C | C | C | A | C | A | G | G | C | A | G | T | A | A | G | G | G |
| HBB_6 | C- >other bases | Untreated<br>ggX20<br>gX20<br>gX19<br>gX18<br>gX17 | | | 0.11<br>0.09<br>0.12<br>0.10<br>0.12<br>0.10 | | 0.12<br>0.14<br>0.13<br>0.14<br>0.15<br>0.16 | 0.11<br>0.09<br>0.13<br>0.13<br>0.14<br>0.11 | 0.20<br>0.24<br>0.23<br>0.22<br>0.26<br>0.24 | 0.08<br>0.09<br>0.14<br>0.09<br>0.11<br>0.10 | | 0.05<br>0.05<br>0.04<br>0.05<br>0.06<br>0.04 | | | | | 0.17<br>0.19<br>0.22<br>0.17<br>0.22<br>0.19 | | | | | | | |
| | | SEQ ID NO: 151 | t | c | A | a | G | C | A | C | A | C | A | G | G | C | A | G | T | A | A | G | G | G |
| HBB_7 | C- >other bases | Untreated<br>ggX20<br>gX20<br>gX19<br>gX18<br>gX17 | | 0.03<br>1.37<br>2.47<br>2.82<br>3.34<br>3.86 | | | 0.07<br>0.17<br>0.41<br>0.80<br>1.71<br>1.68 | 0.05<br>47.30<br>44.99<br>34.66<br>45.27<br>30.94 | 0.07<br>0.76<br>1.72<br>2.89<br>5.48<br>5.97 | 0.09<br>0.99<br>2.24<br>4.01<br>7.00<br>7.44 | 0.09<br>1.08<br>2.30<br>4.20<br>7.65<br>7.65 | | 0.05<br>0.08<br>0.15<br>0.14<br>0.30<br>0.15 | | | | | 0.08<br>0.09<br>0.08<br>0.09<br>0.08<br>0.10 | | | | | | | |
| | | | | | | | | | | HEK2 | | | | | | | | | | | | | | | |
| | | SEQ ID NO: 153 | G | A | C | A | C | C | A | A | A | C | A | T | G | A | C | T | A | C | G | G | |
| On-target (HEK2_2) | C- >other bases | Untreated<br>ggX20<br>gX20<br>GX19<br>gX18<br>gX17 | | | 0.05<br>30.30<br>36.76<br>11.89<br>2.02<br>2.77 | | 0.05<br>47.30<br>44.99<br>34.66<br>45.27<br>30.94 | | | | | | | | | | 0.03<br>0.03<br>0.08<br>0.05<br>0.02<br>0.02 | | | 0.03<br>0.14<br>0.13<br>0.27<br>0.03<br>0.03 | | | 0.19<br>0.15<br>0.16<br>0.15<br>0.19<br>0.18 | |

TABLE 17-continued

Analysis of BE3 off-target effect via modified sgRNAs

HEK2_1 — SEQ ID NO: 152

| | G | A | A | A | C | A | C | A | A | C | A | | | A | T | G | C | C | G | G |
|---|---|---|---|---|---|---|---|---|---|---|---|---|---|---|---|---|---|---|---|---|
| C->other bases | | | | | | | | | | | | | | | | | | | | | |
| Untreated | | | | | | | | | | | | | | | | | | | | | |
| ggX20 | | | 0.11 | | 0.09 | | 0.07 | | | 0.09 | | | | | | | 0.09 | | 0.16 | | |
| GX20 | | | 0.12 | | 0.09 | | 0.09 | | | 0.08 | | | | | | | 0.14 | | 0.18 | | |
| GX19 | | | 0.17 | | 0.14 | | 0.08 | | | 0.08 | | | | | | | 0.13 | | 0.19 | | |
| GX18 | | | 0.19 | | 0.22 | | 0.08 | | | 0.08 | | | | | | | 0.12 | | 0.18 | | |
| gX17 | | | 0.12 | | 0.10 | | 0.08 | | | 0.08 | | | | | | | 0.11 | | 0.20 | | |
| | | | 0.11 | | 0.09 | | 0.06 | | | 0.06 | | | | | | | 0.13 | | 0.20 | | |

HEK2_3 — SEQ ID NO: 154

| | a | A | A | c | t | C | A | A | A | G | C | A | C | T | G | C | G |
|---|---|---|---|---|---|---|---|---|---|---|---|---|---|---|---|---|---|
| C->other bases | | | | | | | | | | | | | | | | | |
| Untreated | | | | | | | | | | | | | | | | | |
| ggX20 | | 0.07 | 0.09 | | | 0.37 | | | | | 0.24 | | | | | 0.24 | |
| GX20 | | 0.09 | 0.08 | | | 0.39 | | | | | 0.24 | | | | | 0.30 | |
| GX19 | | 0.08 | 0.08 | | | 0.38 | | | | | 0.25 | | | | | 0.28 | |
| GX18 | | 0.08 | 0.08 | | | 0.38 | | | | | 0.24 | | | | | 0.27 | |
| gX17 | | 0.08 | 0.08 | | | 0.39 | | | | | 0.24 | | | | | 0.30 | |
| | | 0.06 | 0.06 | | | 0.36 | | | | | 0.23 | | | | | 0.28 | |

On-target (HEX3_2) — SEQ ID NO: 156

| | G | G | C | C | A | G | C | T | G | A | A | G | C | A | G | C | T | A | T | G | G |
|---|---|---|---|---|---|---|---|---|---|---|---|---|---|---|---|---|---|---|---|---|---|
| C->other bases | | | | | | | | | | | | | | | | | | | | | |
| Untreated | 0.15 | | 0.47 | 0.39 | | | | | | | | | 0.15 | | | 0.08 | | 0.06 | | | |
| ggX20 | 6.89 | | 25.21 | 26.19 | | | | | | | | | 0.61 | | | 0.07 | | 0.05 | | | |
| gX20 | 6.36 | | 32.68 | 37.05 | | | | | | | | | 1.76 | | | 0.06 | | 0.11 | | | |
| GX19 | 0.93 | | 25.39 | 32.09 | | | | | | | | | 0.75 | | | 0.09 | | 0.13 | | | |
| GX18 | 0.95 | | 14.23 | 21.59 | | | | | | | | | 1.68 | | | 0.09 | | 0.10 | | | |
| gX17 | 0.14 | | 0.65 | 0.85 | | | | | | | | | 0.40 | | | 0.10 | | 0.06 | | | |

HEK3_1 — SEQ ID NO: 155

| | a | G | C | C | A | t | T | G | C | C | A | G | A | g | G | A | T | G | T | G |
|---|---|---|---|---|---|---|---|---|---|---|---|---|---|---|---|---|---|---|---|---|
| C->other bases | | | | | | | | | | | | | | | | | | | | |
| Untreated | | | 0.13 | 0.18 | 0.04 | | | | 0.06 | | | | | | | 0.12 | | | | |
| ggX20 | | | 0.13 | 0.15 | 0.05 | | | | 0.05 | | | | | | | 0.14 | | | | |
| gX20 | | | 0.12 | 0.14 | 0.04 | | | | 0.04 | | | | | | | 0.15 | | | | |
| GX19 | | | 0.14 | 0.15 | 0.09 | | | | 0.04 | | | | | | | 0.17 | | | | |
| GX18 | | | 0.14 | 0.14 | 0.04 | | | | 0.06 | | | | | | | 0.13 | | | | |
| gX17 | | | 0.11 | 0.14 | 0.04 | | | | 0.05 | | | | | | | 0.12 | | | | |

HEK3_7 — SEQ ID NO: 161

| | G | G | C | C | A | t | c | G | C | c | A | g | C | A | G | A | T | a | G | G |
|---|---|---|---|---|---|---|---|---|---|---|---|---|---|---|---|---|---|---|---|---|
| c->other bases | | | | | | | | | | | | | | | | | | | | |
| Untreated | | | 0.38 | 0.18 | 0.08 | 0.18 | 0.06 | | 0.07 | 0.30 | | 0.30 | | | | 0.07 | | | 0.06 | |
| ggX20 | | | 0.42 | 0.15 | 48.84 | 0.20 | 0.07 | | 0.07 | 0.27 | | 0.28 | | | | 0.08 | | | 0.05 | |
| gX20 | | | 0.39 | 0.14 | 44.02 | 0.15 | 0.08 | | 0.08 | 0.21 | | 0.28 | | | | 0.08 | | | 0.06 | |
| GX19 | | | 0.44 | 0.15 | 0.09 | 0.17 | 0.07 | | 0.08 | 0.26 | | 0.28 | | | | 0.08 | | | 0.06 | |
| GX18 | | | 0.45 | 0.14 | 0.04 | 0.16 | 0.07 | | 0.06 | 0.26 | | 0.25 | | | | 0.06 | | | 0.05 | |
| gX17 | | | 0.42 | 0.14 | 0.04 | 0.19 | 0.07 | | 0.07 | 0.26 | | 0.26 | | | | 0.07 | | | 0.04 | |

On-target (HEK4_1) — SEQ ID NO: 162

| | G | G | C | A | C | T | G | C | G | G |
|---|---|---|---|---|---|---|---|---|---|---|
| C->other bases | | | | | | | | | | |
| Untreated | | | 0.17 | 0.08 | 0.23 | | | 0.07 | | |
| ggX20 | | | 1.97 | 48.84 | 1.50 | | | 0.08 | | |
| gX20 | | | 1.20 | 44.02 | 1.39 | | | 0.06 | | |
| GX19 | | | 1.38 | 41.26 | 0.50 | | | 0.10 | | |

TABLE 17-continued

Analysis of BE3 off-target effect via modified sgRNAs

| | | | | | | | | | | | | | |
|---|---|---|---|---|---|---|---|---|---|---|---|---|---|
| HEK4_2 | C->other bases | GX18 | | 0.27 | 1.43 | 0.11 | | 39.88 | 0.27 | | | | 0.07 |
| | | gX17 | | 0.23 | 1.10 | | | 5.72 | 0.23 | | | | 0.35 |

| | | SEQ ID NO: 163 | G | G | C | A | C | G | T | G | C | t | G | c | C | G | G | T | G | G |
|---|---|---|---|---|---|---|---|---|---|---|---|---|---|---|---|---|---|---|---|---|

| HEK4_3 | C->other bases | Untreated | | 0.14 | 0.11 | 0.04 | | | | | 0.91 | | | |
| | | ggX20 | | 0.17 | 0.13 | 0.39 | | | | | 0.93 | | | |
| | | gX20 | | 0.21 | 0.15 | 1.86 | | | | | 1.11 | | | |
| | | GX19 | | 0.27 | 0.25 | 6.55 | | | | | 0.99 | | | |
| | | GX18 | | 0.16 | 0.14 | 0.11 | | | | | 0.90 | | | |
| | | gX17 | | 0.15 | 0.10 | 0.06 | | | | | 0.93 | | | |

| | | SEQ ID NO: 164 | G | G | C | A | C | T | G | t | G | a | C | G | G | T | G | G |
|---|---|---|---|---|---|---|---|---|---|---|---|---|---|---|---|---|---|---|

| HEK4_3 | C->other bases | Untreated | | 0.09 | 0.07 | 0.05 | | | | | 0.05 | | | |
| | | ggX20 | | 0.08 | 0.09 | 0.10 | | | 0.06 | | 0.04 | | | |
| | | gX20 | | 0.10 | 0.09 | 0.26 | | | 0.08 | | 0.06 | | | |
| | | GX19 | | 0.09 | 0.09 | 0.27 | | | 0.07 | | 0.04 | | | |
| | | GX18 | | 0.08 | 0.06 | 0.05 | | | 0.07 | | 0.05 | | | |
| | | gX17 | | 0.08 | 0.07 | 0.04 | | | 0.07 | | 0.05 | | | |

| | | SEQ ID NO: 161 | G | G | C | C | a | c | t | g | T | a | G | g | c | C | A | G | T | G | G |
|---|---|---|---|---|---|---|---|---|---|---|---|---|---|---|---|---|---|---|---|---|---|

HEK4

| HEK3_7 | C->other bases | Untreated | | 0.38 | 0.18 | | 0.06 | 0.18 | | | 0.23 | 0.30 | 0.30 | 0.07 | | | 0.06 |
| | | ggX20 | | 0.42 | 0.15 | | 0.07 | 0.20 | | | 1.50 | 0.28 | 0.27 | 0.07 | | | 0.05 |
| | | gX20 | | 0.39 | 0.14 | | 0.08 | 0.15 | | | 1.39 | 0.28 | 0.21 | 0.08 | | | 0.06 |
| | | GX19 | | 0.44 | 0.15 | | 0.07 | 0.17 | | | 0.50 | 0.28 | 0.26 | 0.08 | | | 0.06 |
| | | GX18 | | 0.45 | 0.14 | | 0.07 | 0.16 | | | 1.43 | 0.25 | 0.25 | 0.06 | | | 0.05 |
| | | gX17 | | 0.42 | 0.14 | | 0.07 | 0.19 | | | 1.10 | 0.26 | 0.26 | 0.07 | | | 0.04 |

| | | SEQ ID NO: 162 | G | G | C | A | C | T | G | t | G | C | G | A | G | T | G | G |
|---|---|---|---|---|---|---|---|---|---|---|---|---|---|---|---|---|---|---|

| On-target (HEK4_1) | C->other bases | Untreated | | 0.17 | 0.08 | | | 0.23 | | | 0.07 | | | | 0.11 |
| | | ggX20 | | 1.97 | 48.84 | | | 1.50 | | | 0.08 | | | | |
| | | gX20 | | 1.20 | 44.02 | | | 1.39 | | | 0.06 | | | | |
| | | GX19 | | 1.38 | 41.26 | | | 0.50 | | | 0.10 | | | | |
| | | GX18 | | 0.27 | 39.88 | | | 1.43 | | | 0.07 | | | | |
| | | gX17 | | 0.23 | 5.72 | | | 1.10 | | | 0.35 | | | | |

| | | SEQ ID NO: 163 | G | G | C | A | C | T | G | C | G | G | T | G | G |
|---|---|---|---|---|---|---|---|---|---|---|---|---|---|---|---|

| HEK4_2 | C->other bases | Untreated | | 0.14 | 0.04 | | | 0.11 | | | 0.91 | | | |
| | | ggX20 | | 0.17 | 0.39 | | | 0.13 | | | 0.93 | | | |
| | | gX20 | | 0.21 | 1.85 | | | 0.15 | | | 1.11 | | | |
| | | GX19 | | 0.27 | 6.55 | | | 0.25 | | | 0.99 | | | |
| | | GX18 | | 0.15 | 0.11 | | | 0.14 | | | 0.90 | | | |
| | | gX17 | | 0.15 | 0.06 | | | 0.10 | | | 0.93 | | | |

TABLE 17-continued

Analysis of BE3 off-target effect via modified sgRNAs

HEK4_3

| C->other bases | SEQ ID NO: 164 | G | G | C | A | G | C | T | G | — | C | G | G | A | G | G | T | G | G |
|---|---|---|---|---|---|---|---|---|---|---|---|---|---|---|---|---|---|---|---|
| | Untreated | | | 0.09 | | | 0.05 | | | | 0.07 | | | | | | | | |
| | ggX20 | | | 0.08 | | | 0.10 | | | | 0.09 | | | | | | | | |
| | gX20 | | | 0.10 | | | 0.26 | | | | 0.09 | | | | | | | | |
| | GX19 | | | 0.09 | | | 0.27 | | | | 0.09 | | | | | | | | |
| | GX18 | | | 0.08 | | | 0.05 | | | | 0.06 | | | | | | | | |
| | gX17 | | | 0.08 | | | 0.04 | | | | 0.07 | | | | | | | | |

HEK4_4

| C->other bases | SEQ ID NO: 163 | G | G | C | t | C | T | G | G | G | C | a | — | G | A | G | G | T | G | G |
|---|---|---|---|---|---|---|---|---|---|---|---|---|---|---|---|---|---|---|---|---|
| | Untreated | | | 0.05 | | 0.05 | | | | | 0.29 | | | | | | | | | |
| | ggX20 | | | 0.13 | | 2.87 | | | | | 0.34 | | | | | | | | | |
| | gX20 | | | 0.11 | | 2.94 | | | | | 0.38 | | | | | | | | | |
| | GX19 | | | 0.10 | | 2.53 | | | | | 0.35 | | | | | | | | | |
| | GX18 | | | 0.04 | | 0.13 | | | | | 0.30 | | | | | | | | | |
| | gX17 | | | 0.05 | | 0.05 | | | | | 0.29 | | | | | | | | | |

HEK4_5

| C->other bases | SEQ ID NO: 166 | a | G | C | A | C | T | G | a | G | C | a | G | G | A | G | G | a | G | G |
|---|---|---|---|---|---|---|---|---|---|---|---|---|---|---|---|---|---|---|---|---|
| | Untreated | | | 0.09 | | 0.03 | | | | | 0.14 | | | | | | | | | |
| | ggX20 | | | 0.11 | | 0.03 | | | | | 0.13 | | | | | | | | | |
| | gX20 | | | 0.08 | | 0.07 | | | | | 0.14 | | | | | | | | | |
| | GX19 | | | 0.15 | | 0.58 | | | | | 0.15 | | | | | | | | | |
| | GX18 | | | 0.08 | | 0.03 | | | | | 0.12 | | | | | | | | | |
| | gX17 | | | 0.06 | | 0.03 | | | | | 0.13 | | | | | | | | | |

HEK4_6

| C->other bases | SEQ ID NO: 167 | G | G | C | A | C | T | G | G | G | C | a | G | G | A | G | G | a | G | G |
|---|---|---|---|---|---|---|---|---|---|---|---|---|---|---|---|---|---|---|---|---|
| | Untreated | | | | | | | | | | | | | | | | | | | |
| | ggX20 | | | | | | | | | | | | | | | | | | | |
| | gX20 | | | | | | | | | | | | | | | | | | | |
| | GX19 | | | | | | | | | | | | | | | | | | | |
| | GX18 | | | | | | | | | | | | | | | | | | | |
| | gX17 | | | | | | | | | | | | | | | | | | | |

HEK4_7

| C->other bases | SEQ ID NO: 168 | t | G | C | A | C | T | G | C | G | C | a | G | G | A | G | G | a | G | G |
|---|---|---|---|---|---|---|---|---|---|---|---|---|---|---|---|---|---|---|---|---|
| | Untreated | | | 0.24 | | 0.10 | | | 0.38 | | 0.14 | | | | | | | 0.08 | | |
| | ggX20 | | | 0.18 | | 0.38 | | | 0.29 | | 0.13 | | | | | | | 0.05 | | |
| | gX20 | | | 0.19 | | 1.64 | | | 0.36 | | 0.14 | | | | | | | 0.09 | | |
| | GX19 | | | 0.43 | | 9.74 | | | 0.32 | | 0.13 | | | | | | | 0.08 | | |
| | GX18 | | | 1.01 | | 11.33 | | | 0.56 | | 0.11 | | | | | | | 0.08 | | |
| | gX17 | | | 0.18 | | 0.16 | | | 0.26 | | 0.13 | | | | | | | 0.08 | | |

HEK4_8

| C->other bases | SEQ ID NO: 169 | G | G | C | A | C | T | g | G | — | C | G | a | G | A | G | G | T | A | G |
|---|---|---|---|---|---|---|---|---|---|---|---|---|---|---|---|---|---|---|---|---|
| | Untreated | | | 0.08 | | 0.03 | | | | | 0.09 | | | | | | | | | |
| | ggX20 | | | 0.18 | | 0.64 | | | | | 0.05 | | | | | | | | | |
| | gX20 | | | 0.18 | | 0.62 | | | | | 0.05 | | | | | | | | | |
| | GX19 | | | 0.07 | | 0.16 | | | | | 0.06 | | | | | | | | | |

TABLE 17-continued

Analysis of BE3 off-target effect via modified sgRNAs

| | | | | | | | | | | | | | | | | | | | | | | |
|---|---|---|---|---|---|---|---|---|---|---|---|---|---|---|---|---|---|---|---|---|---|---|
| HEK4_9 | C->other bases | GX18 | | | | | | | | | | 0.08 | | | 0.03 | | 0.11 | 0.08 | | | 0.03 | 0.08 |
| | | gX17 | | | | | | | | | | 0.06 | | | 0.03 | | 0.10 | 0.07 | | | 0.03 | 0.06 |
| | | SEQ ID NO: 170 | G | G | G | C | A | T | G | c | A | G | T | G | G | G | | | | | | |
| HEK4_10 | C->other bases | Untreated | | | | 0.04 | | | | 0.07 | 0.03 | | 0.07 | | | | 0.08 | | | 0.03 | 0.04 | 0.03 |
| | | ggX20 | | | | 0.02 | | | | 0.07 | 0.04 | | 0.06 | | | | 0.07 | | | 0.04 | 0.03 | 0.04 |
| | | gX20 | | | | 0.03 | | | | 0.05 | 0.03 | | 0.06 | | | | 0.09 | | | 0.03 | 0.03 | 0.03 |
| | | gX19 | | | | 0.04 | | | | 0.07 | 0.02 | | 0.09 | | | | 0.06 | | | 0.04 | 0.02 | 0.04 |
| | | gX18 | | | | 0.03 | | | | 0.06 | 0.03 | | 0.07 | | | | 0.07 | | | 0.03 | 0.03 | 0.03 |
| | | gX17 | | | | 0.03 | | | | 0.04 | 0.02 | | 0.02 | | | | 0.06 | | | 0.03 | 0.02 | 0.03 |
| | | SEQ ID NO: 171 | t | G | t | C | T | G | C | C | t | G | C | G | a | G | T | G | G | G | | |
| HEK4_11 | C->other bases | Untreated | | | | 0.16 | | | | 0.18 | 0.05 | | 0.15 | | | | 0.08 | | | 0.16 | | G |
| | | ggX20 | | | | 0.11 | | | | 0.17 | 0.17 | | 0.10 | | | | 0.08 | | | 0.10 | | |
| | | gX20 | | | | 0.15 | | | | 0.16 | 0.35 | | 0.16 | | | | 0.08 | | | 0.17 | | |
| | | gX19 | | | | 0.19 | | | | 0.16 | 1.78 | | 0.27 | | | | 0.11 | | | 0.27 | | |
| | | gX18 | | | | 0.13 | | | | 0.17 | 0.33 | | 0.12 | | | | 0.08 | | | 0.12 | | |
| | | gX17 | | | | 0.14 | | | | 0.06 | 0.07 | | 0.10 | | | | 0.09 | | | 0.10 | | |
| | | SEQ ID NO: 172 | a | G | C | A | T | G | C | C | g | G | a | G | T | G | G | G | | | | |
| HEK4_12 | C->other bases | Untreated | | | | 0.07 | | | | 0.04 | | | | | | | | | | | | |
| | | ggX20 | | | | 0.27 | | | | 1.09 | | | | | | | | | | | | |
| | | gX20 | | | | 0.30 | | | | 1.94 | | | | | | | | | | | | |
| | | gX19 | | | | 0.07 | | | | 1.09 | | | | | | | | | | | | |
| | | gX18 | | | | 0.07 | | | | 0.04 | | | | | | | | | | | | |
| | | gX17 | | | | 0.10 | | | | 0.03 | | | | | | | | | | | | |
| | | SEQ ID NO: 173 | G | G | C | A | T | G | G | C | T | G | A | G | T | G | G | G | | | | |
| HEK4_13 | C->other bases | Untreated | | | | 0.12 | | | | 0.13 | | | 0.12 | | | | 0.12 | | | a | G | G |
| | | ggX20 | | | | 0.10 | | | | 0.15 | | | 0.10 | | | | 0.10 | | | 0.14 | | |
| | | gX20 | | | | 0.12 | | | | 0.15 | | | 0.12 | | | | 0.12 | | | 0.20 | | |
| | | gX19 | | | | 0.12 | | | | 0.19 | | | 0.11 | | | | 0.12 | | | 0.19 | | |
| | | gX18 | | | | 0.12 | | | | 0.14 | | | 0.13 | | | | 0.12 | | | 0.19 | | |
| | | gX17 | | | | 0.12 | | | | 0.13 | | | 0.10 | | | | 0.12 | | | 0.18 | | |
| | | SEQ ID NO: 174 | G | G | C | A | T | G | C | C | a | G | c | G | a | G | G | G | | | | |

TABLE 17-continued

Analysis of BE3 off-target effect via modified sgRNAs

HEK4_14 — SEQ ID NO: 175

| C->other bases | G | a | G | g | A | C | T | G | C | G | G | C | T | G | G | G |
|---|---|---|---|---|---|---|---|---|---|---|---|---|---|---|---|---|
| Untreated | | | | | | 0.05 | | | 0.29 | | | 0.03 | | | | |
| ggX20 | | | | | | 1.37 | | | 0.31 | | | 0.04 | | | | |
| gX20 | | | | | | 1.03 | | | 0.44 | | | 0.05 | | | | |
| GX19 | | | | | | 4.70 | | | 0.38 | | | 0.06 | | | | |
| GX18 | | | | | | 1.67 | | | 0.29 | | | 0.04 | | | | |
| GX17 | | | | | | 6.06 | | | 0.88 | | | 0.07 | | | | |

HEK4_15 — SEQ ID NO: 176

| C->other bases | G | a | G | C | A | C | T | G | C | G | G | C | T | G | G | G |
|---|---|---|---|---|---|---|---|---|---|---|---|---|---|---|---|---|
| Untreated | | | | 0.11 | | 0.06 | | | 0.11 | | | 0.02 | | | | |
| ggX20 | | | | 0.10 | | 0.10 | | | 0.08 | | | 0.02 | | | | |
| gX20 | | | | 0.08 | | 0.16 | | | 0.08 | | | 0.03 | | | | |
| GX19 | | | | 0.10 | | 0.32 | | | 0.09 | | | 0.02 | | | | |
| GX18 | | | | 0.08 | | 0.06 | | | 0.06 | | | 0.01 | | | | |
| GX17 | | | | 0.10 | | 0.04 | | | 0.09 | | | 0.02 | | | | |

HEK4_16 — SEQ ID NO: 177

| C->other bases | G | G | C | A | C | T | G | C | G | G | t | G | G | a | G | G |
|---|---|---|---|---|---|---|---|---|---|---|---|---|---|---|---|---|
| Untreated | | | 0.16 | | 0.18 | | | 0.16 | | | | | | | | |
| ggX20 | | | 0.69 | | 2.90 | | | 0.69 | | | | | | | | |
| gX20 | | | 0.87 | | 3.94 | | | 0.87 | | | | | | | | |
| GX19 | | | 0.29 | | 3.17 | | | 0.29 | | | | | | | | |
| GX18 | | | 0.18 | | 0.21 | | | 0.18 | | | | | | | | |
| GX17 | | | 0.15 | | 0.15 | | | 0.15 | | | | | | | | |

HEK4_17 — SEQ ID NO: 178

| C->other bases | G | c | C | A | C | T | G | C | G | G | C | T | G | a | G | G |
|---|---|---|---|---|---|---|---|---|---|---|---|---|---|---|---|---|
| Untreated | | | 0.11 | | 0.05 | | | 0.16 | | | 0.05 | | | | | |
| ggX20 | | | 0.11 | | 0.69 | | | 0.17 | | | 0.04 | | | | | |
| gX20 | | | 0.11 | | 1.46 | | | 0.17 | | | 0.04 | | | | | |
| GX19 | | | 0.11 | | 3.27 | | | 0.28 | | | 0.04 | | | | | |
| GX18 | | | 0.13 | | 0.69 | | | 0.15 | | | 0.04 | | | | | |
| GX17 | | | 0.12 | | 0.23 | | | 0.18 | | | 0.03 | | | | | |

HEK4_18 — SEQ ID NO: 179

| C->other bases | G | c | C | A | C | T | G | C | G | G | a | G | G | A | G | G |
|---|---|---|---|---|---|---|---|---|---|---|---|---|---|---|---|---|
| Untreated | | | 0.16 | | 0.06 | | | 0.06 | 61.49 | | | | | | | |
| ggX20 | | | 0.12 | | 0.06 | | | 0.06 | 60.75 | | | | | | | |
| gX20 | | | 0.10 | | 0.06 | | | 0.07 | 60.11 | | | | | | | |
| GX19 | | | 0.12 | | 0.11 | | | 0.08 | 61.02 | | | | | | | |
| GX18 | | | 0.14 | | 0.08 | | | 0.08 | 60.97 | | | | | | | |
| GX17 | | | 0.12 | | 0.08 | | | 0.07 | 60.12 | | | | | | | |

HEK4_19 — SEQ ID NO: 180

| C->other bases | G | G | C | A | C | T | G | — | G | G | a | G | G | A | G | G |
|---|---|---|---|---|---|---|---|---|---|---|---|---|---|---|---|---|
| Untreated | | | 0.03 | | 0.06 | | | | | | | | | | | |
| ggX20 | | | 0.04 | | 0.11 | | | | | | | | | | | |
| gX20 | | | 0.04 | | 0.10 | | | | | | | | | | | | with additional values: 0.05 c 0.08, 0.08, 0.05 0.08, 0.05 0.11

TABLE 17-continued

Analysis of BE3 off-target effect via modified sgRNAs

| SEQ ID NO. 181 | a | G | a | G | G | C | t | C | T | G | C | G | G | a | G | G | A | G | G | T | G | G | G |
|---|---|---|---|---|---|---|---|---|---|---|---|---|---|---|---|---|---|---|---|---|---|---|---|
| GX19 | | | | | | 0.05 | | 0.05 | | | | | | 0.09 | | | | | | 0.08 | | | |
| GX18 | | | | | | 0.03 | | 0.05 | | | | | | 0.07 | | | | | | 0.09 | | | |
| gX17 | | | | | | 0.01 | | 0.03 | | | | | | 0.02 | | | | | | 0.06 | | | |
| HEK4_20 C->other bases Untreated | | | | | | 0.22 | 0.03 | 0.22 | 0.03 | | | | | | | | | | | | | | 0.10 |
| ggX20 | | | | | | 0.25 | 0.02 | 0.20 | 0.02 | | | | | | | | | | | | | | 0.10 |
| gX20 | | | | | | 0.23 | 0.02 | 0.21 | 0.02 | | | | | | | | | | | | | | 0.10 |
| GX19 | | | | | | 0.22 | 0.02 | 0.20 | 0.02 | | | | | | | | | | | | | | 0.09 |
| GX18 | | | | | | 0.23 | 0.02 | 0.16 | 0.02 | | | | | | | | | | | | | | 0.09 |
| gX17 | | | | | | 0.25 | 0.02 | 0.23 | 0.02 | | | | | | | | | | | | | | 0.10 |

FIG. 16a schematically shows a conventional sgRNA (gX19 sgRNA), a truncated sgRNA (gX18 or gX17 sgRNA) and an extended sgRNA (gX20 or ggX20 sgRNA). FIG. 16b shows base-editing frequencies at the HBB on- and off-target sites in HEK293T cells measured by targeted deep sequencing. Specificity ratios were calculated by dividing the base-editing frequency at the on-target site with that at off-target sites. The heatmap represents relative specificities of modified sgRNAs, compared to that of conventional sgRNA.

FIG. 17 shows the result of reducing BE3 off-target effects using modified sgRNAs, wherein 17a shows a schematic view of conventional sgRNAs ($GX_{19}$ sgRNA) and modified sgRNAs ($GX_{17}$ sgRNA, $gX_{18}$ sgRNA, $gX_{20}$ sgRNA, and $ggX_{20}$ sgRNA), and 17b shows base editing efficiencies (frequencies) measured at the EMX1 on- and off-target sites by targeted deep sequencing in HEK293T cells.

As shown in FIGS. 16a, 16b, 17a, and 17b, truncated sgRNAs reduced off-target effects at many sites but exacerbated them at sites with mismatches at the 5' terminus (shown by asterisks in FIGS. 16b and 17b). Extended sgRNAs reduced off-target effects at almost every site without sacrificing on-target effects. Interestingly, some extended sgRNAs were more active at on-target sites than conventional sgRNAs (Table 17). Use of attenuated Cas9 variants or delivery of BE3 RNPs rather than plasmids may further improve the genome-wide specificity of base editing.

In summary, the results obtained using mismatched sgRNAs, Digenome-seq, and targeted deep sequencing showed that BE3 deaminases were highly specific, catalyzing C-to-U conversions in vitro and base editing in human cells at a limited number of sites in the human genome. It was also found that BE3 and Cas9 off-target sites were not always coincidental, justifying independent assessments of each tool. It is expect that the above results and methods will accelerate broad use of RNA-guided programmable deaminases in research and medicine.

Example 7. BE1 (rAPOBEC1-dCas9)-Mediated Double Strand Breaks (DSBs)

A PCR amplicon containing a target sequence (ENX1 on-target sequence; SEQ ID NO: 31) was incubated with BE1 (rAPOBEC1-dCas9; Example 2) and its sgRNA (sgRNA targeting SEQ ID NO: 31) in vitro to induce Cytidine to Uracil conversions. Uracil, which is induced by rAPOBEC1, was removed by USER (Uracil-Specific Excision Reagent) Enzyme (New England Biolabs). Then, S1 nuclease (Catalog #M5761; Promega) was treated to cleave phosphodiester bonds in a single-strand DNA, producing a DSB at the cytosine-deaminated site (FIG. 22(a)).

The above-obtained PCR amplicon was subjected to electrophoresis, to confirm that they are cleaved by the treatment of BE1/sgRNA, USER, and S1 Nuclease (FIG. 22(b)).

From the above description, it will be understood by those skilled in the art that the present invention may be embodied in other specific forms without departing from the spirit or essential characteristics thereof. In this regard, it should be understood that the above-described embodiments are to be considered in all respects as illustrative and not restrictive. The scope of the present invention should be construed as being included in the scope of the present invention without departing from the scope of the present invention as defined by the appended claims.

The invention claimed is:

1. A method of analyzing nucleic acid sequence of DNA in which a base editing is introduced by cytosine deaminase, comprising:
   (i) introducing or contacting (a) a cytosine deaminase and an inactivated target-specific endonuclease, or (b) a cytosine deaminase coding gene and an inactivated target-specific endonuclease coding gene, or (c) a plasmid comprising a cytosine deaminase coding gene and an inactivated target-specific endonuclease coding gene, into a cell or with DNA isolated from a cell, together with a guide RNA;
   (ii) treating the DNA with a uracil-specific excision reagent (USER) and generating double strand cleavage in DNA; and
   (iii) analyzing nucleic acid sequence of the cleaved DNA fragment,
   wherein the DNA isolated from a cell in step (i) is a genomic DNA, and the nucleic acid sequence analysis of step (iii) is performed by whole genome sequencing,
   wherein the uracil-specific excision reagent (USER) comprises uracil DNA glycosylase (UDG) and endonuclease VIII, and
   wherein the inactivated target-specific endonuclease is a Cas9 protein derived from *Streptococcus pyogenes* wherein amino acid residue D10 is substituted with alanine.

2. The method of claim 1, wherein the cytosine deaminase and inactivated target-specific endonuclease are in a form of a fusion protein, or the cytosine deaminase coding gene and inactivated target-specific endonuclease coding gene encode a fusion protein comprising the cytosine deaminase and inactivated target-specific endonuclease.

3. The method of claim 1, wherein amino acid residue H840 of the inactive target-specific endonuclease is substituted with alanine, and wherein generating double strand cleavage in DNA comprises treating the DNA with an endonuclease specifically cleaving a single strand region of DNA.

4. The method of claim 1, wherein the guide RNA is a crRNA:tracrRNA duplex in which crRNA and tracrRNA is coupled to each other, or a single-strand guide RNA (sgRNA).

5. The method of claim 1, which is performed in vitro.

6. A method of identifying a base editing site of cytosine deaminase, comprising:
   (i) introducing or contacting (a) a cytosine deaminase and an inactivated target-specific endonuclease, or (b) a cytosine deaminase coding gene and an inactivated target-specific endonuclease coding gene, or (c) a plasmid comprising a cytosine deaminase coding gene and an inactivated target-specific endonuclease coding gene, into a cell or with DNA isolated from a cell, together with a guide RNA;
   (ii) treating the DNA with a uracil-specific excision reagent (USER) and generating double strand cleavage in DNA;
   (iii) analyzing nucleic acid sequence of the cleaved DNA fragment; and
   (iv) identifying the double strand cleavage site in the nucleic acid sequence read obtained by the analysis,
   wherein the DNA isolated from a cell in step (i) is a genomic DNA, and the nucleic acid sequence analysis of step (iii) is performed by whole genome sequencing,
   wherein the uracil-specific excision reagent (USER) comprises uracil DNA glycosylase (UDG) and endonuclease VIII, and
   wherein the inactivated target-specific endonuclease is a Cas9 protein derived from *Streptococcus pyogenes* wherein amino acid residue D10 is substituted with alanine.

7. The method of claim 6, wherein the cytosine deaminase and inactivated target-specific endonuclease are in a form of a fusion protein, or the cytosine deaminase coding gene and inactivated target-specific endonuclease coding gene encode a fusion protein comprising the cytosine deaminase and inactivated target-specific endonuclease.

8. The method of claim 6, wherein amino acid residue H840 of the inactive target-specific endonuclease is substituted with alanine, and wherein generating double strand cleavage in DNA comprises treating the DNA with an endonuclease specifically cleaving a single strand region of DNA.

9. The method of claim 6, wherein the guide RNA is a crRNA:tracrRNA duplex in which crRNA and tracrRNA is coupled to each other, or a single-strand guide RNA (sgRNA).

10. The method of claim 6, which is performed in vitro.

* * * * *

SEQUENCE LISTING

<160> NUMBER OF SEQ ID NOS: 676

<210> SEQ ID NO 1
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 1
ggactcgagc agaagaagaa ggg                                           23

<210> SEQ ID NO 2
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 2
gagtttaggc agaagaagaa ggg                                           23

<210> SEQ ID NO 3
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

```
<400> SEQUENCE: 3
gagtccgaat gaaagaagaa ggg                                              23

<210> SEQ ID NO 4
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 4
gagtccgagc agggagagaa ggg                                              23

<210> SEQ ID NO 5
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 5
gagtccgagc agaagagagg ggg                                              23

<210> SEQ ID NO 6
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 6
gaactcgagc agaagaagaa ggg                                              23

<210> SEQ ID NO 7
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 7
gagtctaggc agaagaagaa ggg                                              23

<210> SEQ ID NO 8
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 8
gagtccgaat ggaagaagaa ggg                                              23

<210> SEQ ID NO 9
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 9
```
gagtccgagc aagggaagaa ggg                                        23

<210> SEQ ID NO 10
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 10
gagtccgagc agaaagggaa ggg                                        23

<210> SEQ ID NO 11
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 11
gagtccgagc agaagaaagg ggg                                        23

<210> SEQ ID NO 12
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 12
gaacccgagc agaagaagaa ggg                                        23

<210> SEQ ID NO 13
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 13
gagtttgagc agaagaagaa ggg                                        23

<210> SEQ ID NO 14
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 14
gagtccaggc agaagaagaa ggg                                        23

<210> SEQ ID NO 15
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 15
gagtccgaat agaagaagaa ggg                                       23

<210> SEQ ID NO 16
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 16
gagtccgagc gaaagaagaa ggg                                       23

<210> SEQ ID NO 17
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 17
gagtccgagc agggaagaa ggg                                        23

<210> SEQ ID NO 18
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 18
gagtccgagc agaaagagaa ggg                                       23

<210> SEQ ID NO 19
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 19
gagtccgagc agaagagaaa ggg                                       23

<210> SEQ ID NO 20
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 20
gagtccgagc agaagaaggg ggg                                       23

<210> SEQ ID NO 21
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 21
gggtccgagc agaagaagaa ggg                                       23

```
<210> SEQ ID NO 22
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 22
gagcccgagc agaagaagaa ggg                                              23

<210> SEQ ID NO 23
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 23
gagtctgagc agaagaagaa ggg                                              23

<210> SEQ ID NO 24
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 24
gagtccgggc agaagaagaa ggg                                              23

<210> SEQ ID NO 25
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 25
gagtccgagt agaagaagaa ggg                                              23

<210> SEQ ID NO 26
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 26
gagtccgagc aaaagaagaa ggg                                              23

<210> SEQ ID NO 27
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 27
gagtccgagc agaggaagaa ggg                                              23
```

```
<210> SEQ ID NO 28
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 28
gagtccgagc agaaggagaa ggg                                              23

<210> SEQ ID NO 29
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 29
gagtccgagc agaagaaaaa ggg                                              23

<210> SEQ ID NO 30
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (off-target sequence)

<400> SEQUENCE: 30
gagtccgagc agaagaagag ggg                                              23

<210> SEQ ID NO 31
<211> LENGTH: 23
<212> TYPE: DNA
<213> ORGANISM: Artificial Sequence
<220> FEATURE:
<223> OTHER INFORMATION: Target sequence of EMX1 mismatched sgRNAs
      (on-target sequence)

<400> SEQUENCE: 31
gagtccgagc agaagaagaa ggg                                              23

<210> SEQ ID NO 32
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 32
gccatcccac agggcagtaa cgg                                              23

<210> SEQ ID NO 33
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 33
gttgttttac agggcagtaa cgg                                              23
```

```
<210> SEQ ID NO 34
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 34
gttgccccgt gaggcagtaa cgg                                            23

<210> SEQ ID NO 35
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 35
gttgccccac agaatggtaa cgg                                            23

<210> SEQ ID NO 36
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 36
gttgccccac agggcaacgg cgg                                            23

<210> SEQ ID NO 37
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 37
gtcatcccac agggcagtaa cgg                                            23

<210> SEQ ID NO 38
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 38
gttgctttac agggcagtaa cgg                                            23

<210> SEQ ID NO 39
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 39
gttgccccgt ggggcagtaa cgg                                            23

<210> SEQ ID NO 40
```

-continued

```
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 40
gttgccccac aaaacagtaa cgg                                              23

<210> SEQ ID NO 41
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 41
gttgccccac agggtgataa cgg                                              23

<210> SEQ ID NO 42
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 42
gttgccccac agggcagcgg cgg                                              23

<210> SEQ ID NO 43
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 43
gtcaccccac agggcagtaa cgg                                              23

<210> SEQ ID NO 44
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 44
gttgttccac agggcagtaa cgg                                              23

<210> SEQ ID NO 45
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 45
gttgccttac agggcagtaa cgg                                              23

<210> SEQ ID NO 46
<211> LENGTH: 23
```

```
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 46
gttgccccgt agggcagtaa cgg                                          23

<210> SEQ ID NO 47
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 47
gttgccccac gaggcagtaa cgg                                          23

<210> SEQ ID NO 48
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 48
gttgccccac agaacagtaa cgg                                          23

<210> SEQ ID NO 49
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 49
gttgccccac agggtggtaa cgg                                          23

<210> SEQ ID NO 50
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 50
gttgccccac agggcaacaa cgg                                          23

<210> SEQ ID NO 51
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 51
gttgccccac agggcagtgg cgg                                          23

<210> SEQ ID NO 52
<211> LENGTH: 23
<212> TYPE: DNA
```

<210> SEQ ID NO 52
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 52
gctgccccac agggcagtaa cgg					23

<210> SEQ ID NO 53
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 53
gttaccccac agggcagtaa cgg					23

<210> SEQ ID NO 54
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 54
gttgctccac agggcagtaa cgg					23

<210> SEQ ID NO 55
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 55
gttgccctac agggcagtaa cgg					23

<210> SEQ ID NO 56
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 56
gttgccccat agggcagtaa cgg					23

<210> SEQ ID NO 57
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 57
gttgccccac aaggcagtaa cgg					23

<210> SEQ ID NO 58
<211> LENGTH: 23
<212> TYPE: DNA
<213> ORGANISM: Artificial Sequence

```
<220> FEATURE:
<223> OTHER INFORMATION: Target sequence of HBB mismatched sgRNAs
      (off-target sequence)

<400> SEQUENCE: 58
gttgccccac aggacagtaa cgg                                              23

<210> SEQ ID NO 59
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 59
gttgccccac agggcggtaa cgg                                              23

<210> SEQ ID NO 60
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 60
gttgccccac agggcagcaa cgg                                              23

<210> SEQ ID NO 61
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (off-target sequence)

<400> SEQUENCE: 61
gttgccccac agggcagtag cgg                                              23

<210> SEQ ID NO 62
<211> LENGTH: 23
<212> TYPE: DNA
<213> ORGANISM: Artificial Sequence
<220> FEATURE:
<223> OTHER INFORMATION: Target sequence of HBB mismatched sgRNAs
      (on-target sequence)

<400> SEQUENCE: 62
gttgccccac agggcagtaa cgg                                              23

<210> SEQ ID NO 63
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 63
gctgccttag tcattacctg agg                                              23

<210> SEQ ID NO 64
<211> LENGTH: 23
<212> TYPE: DNA
<213> ORGANISM: Artificial Sequence
<220> FEATURE:
```

```
<223> OTHER INFORMATION: Target sequence of RNF2 mismatched sgRNAs
      (off-target sequence)

<400> SEQUENCE: 64
gtcactccag tcattacctg agg                                             23

<210> SEQ ID NO 65
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 65
gtcatcttga ctattacctg agg                                             23

<210> SEQ ID NO 66
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 66
gtcatcttag tcgccgcctg agg                                             23

<210> SEQ ID NO 67
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 67
gtcatcttag tcattattca agg                                             23

<210> SEQ ID NO 68
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 68
gttgccttag tcattacctg agg                                             23

<210> SEQ ID NO 69
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 69
gtcattccag tcattacctg agg                                             23

<210> SEQ ID NO 70
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
```

(off-target sequence)

<400> SEQUENCE: 70
gtcatcttga ccattacctg agg                                              23

<210> SEQ ID NO 71
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 71
gtcatcttag ttgctacctg agg                                              23

<210> SEQ ID NO 72
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 72
gtcatcttag tcatcgtctg agg                                              23

<210> SEQ ID NO 73
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 73
gtcatcttag tcattactca agg                                              23

<210> SEQ ID NO 74
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 74
gttgtcttag tcattacctg agg                                              23

<210> SEQ ID NO 75
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 75
gtcactttag tcattacctg agg                                              23

<210> SEQ ID NO 76
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

```
<400> SEQUENCE: 76
gtcatcccag tcattacctg agg                                              23

<210> SEQ ID NO 77
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 77
gtcatcttga tcattacctg agg                                              23

<210> SEQ ID NO 78
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 78
gtcatcttag ctattacctg agg                                              23

<210> SEQ ID NO 79
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 79
gtcatcttag tcgctacctg agg                                              23

<210> SEQ ID NO 80
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 80
gtcatcttag tcatcgcctg agg                                              23

<210> SEQ ID NO 81
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 81
gtcatcttag tcattatttg agg                                              23

<210> SEQ ID NO 82
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)
```

```
<400> SEQUENCE: 82
gtcatcttag tcattaccca agg                                                  23

<210> SEQ ID NO 83
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 83
gccatcttag tcattacctg agg                                                  23

<210> SEQ ID NO 84
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 84
gtcgtcttag tcattacctg agg                                                  23

<210> SEQ ID NO 85
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 85
gtcattttag tcattacctg agg                                                  23

<210> SEQ ID NO 86
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 86
gtcatctcag tcattacctg agg                                                  23

<210> SEQ ID NO 87
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 87
gtcatcttaa tcattacctg agg                                                  23

<210> SEQ ID NO 88
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 88
```

```
gtcatcttag ttattacctg agg                                          23
```

<210> SEQ ID NO 89
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 89

```
gtcatcttag tcactacctg agg                                          23
```

<210> SEQ ID NO 90
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 90

```
gtcatcttag tcattgcctg agg                                          23
```

<210> SEQ ID NO 91
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 91

```
gtcatcttag tcattacttg agg                                          23
```

<210> SEQ ID NO 92
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (off-target sequence)

<400> SEQUENCE: 92

```
gtcatcttag tcattaccta agg                                          23
```

<210> SEQ ID NO 93
<211> LENGTH: 23
<212> TYPE: DNA
<213> ORGANISM: Artificial Sequence
<220> FEATURE:
<223> OTHER INFORMATION: Target sequence of RNF2 mismatched sgRNAs
      (on-target sequence)

<400> SEQUENCE: 93

```
gtcatcttag tcattacctg agg                                          23
```

<210> SEQ ID NO 94
<211> LENGTH: 18
<212> TYPE: DNA
<213> ORGANISM: Artificial Sequence
<220> FEATURE:
<223> OTHER INFORMATION: Forward primer for 1st PCR of EMX1

<400> SEQUENCE: 94

```
agtgttgagg ccccagtg                                                18
```

-continued

<210> SEQ ID NO 95
<211> LENGTH: 53
<212> TYPE: DNA
<213> ORGANISM: Artificial Sequence
<220> FEATURE:
<223> OTHER INFORMATION: Reverse primer for 1st PCR of EMX1

<400> SEQUENCE: 95
gtgactggag ttcagacgtg tgctcttccg atctcagcag caagcagcac tct        53

<210> SEQ ID NO 96
<211> LENGTH: 53
<212> TYPE: DNA
<213> ORGANISM: Artificial Sequence
<220> FEATURE:
<223> OTHER INFORMATION: Forward primer for 2nd PCR of EMX1

<400> SEQUENCE: 96
acactctttc cctacacgac gctcttccga tctgggcctc ctgagtttct cat        53

<210> SEQ ID NO 97
<211> LENGTH: 53
<212> TYPE: DNA
<213> ORGANISM: Artificial Sequence
<220> FEATURE:
<223> OTHER INFORMATION: Reverse primer for 2nd PCR of EMX1

<400> SEQUENCE: 97
gtgactggag ttcagacgtg tgctcttccg atctcagcag caagcagcac tct        53

<210> SEQ ID NO 98
<211> LENGTH: 21
<212> TYPE: DNA
<213> ORGANISM: Artificial Sequence
<220> FEATURE:
<223> OTHER INFORMATION: Forward primer for 1st PCR of HBB

<400> SEQUENCE: 98
ggcagagaga gtcagtgcct a                                            21

<210> SEQ ID NO 99
<211> LENGTH: 53
<212> TYPE: DNA
<213> ORGANISM: Artificial Sequence
<220> FEATURE:
<223> OTHER INFORMATION: Reverse primer for 1st PCR of HBB

<400> SEQUENCE: 99
gtgactggag ttcagacgtg tgctcttccg atctcagggc tgggcataaa agt        53

<210> SEQ ID NO 100
<211> LENGTH: 53
<212> TYPE: DNA
<213> ORGANISM: Artificial Sequence
<220> FEATURE:
<223> OTHER INFORMATION: Forward primer for 2nd PCR of HBB

<400> SEQUENCE: 100
acactctttc cctacacgac gctcttccga tctgtctcca catgcccagt ttc        53

<210> SEQ ID NO 101
<211> LENGTH: 53
<212> TYPE: DNA
<213> ORGANISM: Artificial Sequence
<220> FEATURE:

<223> OTHER INFORMATION: Reverse primer for 2nd PCR of HBB

<400> SEQUENCE: 101
gtgactggag ttcagacgtg tgctcttccg atctcagggc tgggcataaa agt        53

<210> SEQ ID NO 102
<211> LENGTH: 20
<212> TYPE: DNA
<213> ORGANISM: Artificial Sequence
<220> FEATURE:
<223> OTHER INFORMATION: Forward primer for 1st PCR of RNF2

<400> SEQUENCE: 102
ccatagcact tcccttccaa        20

<210> SEQ ID NO 103
<211> LENGTH: 56
<212> TYPE: DNA
<213> ORGANISM: Artificial Sequence
<220> FEATURE:
<223> OTHER INFORMATION: Reverse primer for 1st PCR of RNF2

<400> SEQUENCE: 103
gtgactggag ttcagacgtg tgctcttccg atctgccaac atacagaagt caggaa        56

<210> SEQ ID NO 104
<211> LENGTH: 53
<212> TYPE: DNA
<213> ORGANISM: Artificial Sequence
<220> FEATURE:
<223> OTHER INFORMATION: Forward primer for 2nd PCR of RNF2

<400> SEQUENCE: 104
acactctttc cctacacgac gctcttccga tctatttcca gcaatgtctc agg        53

<210> SEQ ID NO 105
<211> LENGTH: 56
<212> TYPE: DNA
<213> ORGANISM: Artificial Sequence
<220> FEATURE:
<223> OTHER INFORMATION: Reverse primer for 2nd PCR of RNF2

<400> SEQUENCE: 105
gtgactggag ttcagacgtg tgctcttccg atctgccaac atacagaagt caggaa        56

<210> SEQ ID NO 106
<211> LENGTH: 23
<212> TYPE: DNA
<213> ORGANISM: Artificial Sequence
<220> FEATURE:
<223> OTHER INFORMATION: Digenome-captured site of EMX1

<400> SEQUENCE: 106
gagtctaagc agaagaagaa gag        23

<210> SEQ ID NO 107
<211> LENGTH: 23
<212> TYPE: DNA
<213> ORGANISM: Artificial Sequence
<220> FEATURE:
<223> OTHER INFORMATION: Digenome-captured site of EMX1

<400> SEQUENCE: 107
gaatccaagc agaagaagag aag        23

```
<210> SEQ ID NO 108
<211> LENGTH: 23
<212> TYPE: DNA
<213> ORGANISM: Artificial Sequence
<220> FEATURE:
<223> OTHER INFORMATION: Digenome-captured site of EMX1

<400> SEQUENCE: 108
aagtctgagc acaagaagaa tgg                                              23

<210> SEQ ID NO 109
<211> LENGTH: 22
<212> TYPE: DNA
<213> ORGANISM: Artificial Sequence
<220> FEATURE:
<223> OTHER INFORMATION: Digenome-captured site of EMX1

<400> SEQUENCE: 109
gaatccaaga gaagaagaat gg                                               22

<210> SEQ ID NO 110
<211> LENGTH: 23
<212> TYPE: DNA
<213> ORGANISM: Artificial Sequence
<220> FEATURE:
<223> OTHER INFORMATION: Digenome-captured site of EMX1

<400> SEQUENCE: 110
gagtcctagc aggagaagaa gag                                              23

<210> SEQ ID NO 111
<211> LENGTH: 23
<212> TYPE: DNA
<213> ORGANISM: Artificial Sequence
<220> FEATURE:
<223> OTHER INFORMATION: Digenome-captured site of EMX1

<400> SEQUENCE: 111
gagtccaagc agtagaggaa ggg                                              23

<210> SEQ ID NO 112
<211> LENGTH: 22
<212> TYPE: DNA
<213> ORGANISM: Artificial Sequence
<220> FEATURE:
<223> OTHER INFORMATION: Digenome-captured site of EMX1

<400> SEQUENCE: 112
gtgtcctaga gaagaagaag gg                                               22

<210> SEQ ID NO 113
<211> LENGTH: 23
<212> TYPE: DNA
<213> ORGANISM: Artificial Sequence
<220> FEATURE:
<223> OTHER INFORMATION: Digenome-captured site of EMX1

<400> SEQUENCE: 113
aagtccgagg agaggaagaa agg                                              23

<210> SEQ ID NO 114
<211> LENGTH: 23
<212> TYPE: DNA
<213> ORGANISM: Artificial Sequence
<220> FEATURE:
<223> OTHER INFORMATION: Digenome-captured site of EMX1
```

<400> SEQUENCE: 114
gaggccgagc agaagaaaga cgg					23

<210> SEQ ID NO 115
<211> LENGTH: 23
<212> TYPE: DNA
<213> ORGANISM: Artificial Sequence
<220> FEATURE:
<223> OTHER INFORMATION: Digenome-captured site of EMX1

<400> SEQUENCE: 115
agttccaagc agaagaagca tgg					23

<210> SEQ ID NO 116
<211> LENGTH: 23
<212> TYPE: DNA
<213> ORGANISM: Artificial Sequence
<220> FEATURE:
<223> OTHER INFORMATION: Digenome-captured site of EMX1

<400> SEQUENCE: 116
gagtccacac agaagaagaa aga					23

<210> SEQ ID NO 117
<211> LENGTH: 22
<212> TYPE: DNA
<213> ORGANISM: Artificial Sequence
<220> FEATURE:
<223> OTHER INFORMATION: Digenome-captured site of EMX1

<400> SEQUENCE: 117
gagtccaaga gaagaagtga gg					22

<210> SEQ ID NO 118
<211> LENGTH: 22
<212> TYPE: DNA
<213> ORGANISM: Artificial Sequence
<220> FEATURE:
<223> OTHER INFORMATION: Digenome-captured site of EMX1

<400> SEQUENCE: 118
gagtccttga gaagaaggaa gg					22

<210> SEQ ID NO 119
<211> LENGTH: 23
<212> TYPE: DNA
<213> ORGANISM: Artificial Sequence
<220> FEATURE:
<223> OTHER INFORMATION: Digenome-captured site of EMX1

<400> SEQUENCE: 119
gaatccaagc aggagaagaa gga					23

<210> SEQ ID NO 120
<211> LENGTH: 22
<212> TYPE: DNA
<213> ORGANISM: Artificial Sequence
<220> FEATURE:
<223> OTHER INFORMATION: Digenome-captured site of EMX1

<400> SEQUENCE: 120
gtaccagaga gaagaagaga gg					22

<210> SEQ ID NO 121
<211> LENGTH: 23

```
<212> TYPE: DNA
<213> ORGANISM: Artificial Sequence
<220> FEATURE:
<223> OTHER INFORMATION: Digenome-captured site of EMX1

<400> SEQUENCE: 121
gagtcccagc aaaagaagaa aag                                            23

<210> SEQ ID NO 122
<211> LENGTH: 22
<212> TYPE: DNA
<213> ORGANISM: Artificial Sequence
<220> FEATURE:
<223> OTHER INFORMATION: Digenome-captured site of EMX1

<400> SEQUENCE: 122
aagtccaagt gaagaagaaa gg                                             22

<210> SEQ ID NO 123
<211> LENGTH: 23
<212> TYPE: DNA
<213> ORGANISM: Artificial Sequence
<220> FEATURE:
<223> OTHER INFORMATION: Digenome-captured site of EMX1

<400> SEQUENCE: 123
aagtccatgc agaagaggaa ggg                                            23

<210> SEQ ID NO 124
<211> LENGTH: 22
<212> TYPE: DNA
<213> ORGANISM: Artificial Sequence
<220> FEATURE:
<223> OTHER INFORMATION: Digenome-captured site of EMX1

<400> SEQUENCE: 124
gagtcctaga gaagaaaaag gg                                             22

<210> SEQ ID NO 125
<211> LENGTH: 22
<212> TYPE: DNA
<213> ORGANISM: Artificial Sequence
<220> FEATURE:
<223> OTHER INFORMATION: Digenome-captured site of EMX1

<400> SEQUENCE: 125
gagtccctca ggagaagaaa gg                                             22

<210> SEQ ID NO 126
<211> LENGTH: 23
<212> TYPE: DNA
<213> ORGANISM: Artificial Sequence
<220> FEATURE:
<223> OTHER INFORMATION: Digenome-captured site of EMX1

<400> SEQUENCE: 126
acgtctgagc agaagaagaa tgg                                            23

<210> SEQ ID NO 127
<211> LENGTH: 23
<212> TYPE: DNA
<213> ORGANISM: Artificial Sequence
<220> FEATURE:
<223> OTHER INFORMATION: Digenome-captured site of EMX1

<400> SEQUENCE: 127
```

```
gagttccaga agaagaagaa gag                                          23

<210> SEQ ID NO 128
<211> LENGTH: 22
<212> TYPE: DNA
<213> ORGANISM: Artificial Sequence
<220> FEATURE:
<223> OTHER INFORMATION: Digenome-captured site of EMX1

<400> SEQUENCE: 128
gagtcctaaa gaagaagcag gg                                           22

<210> SEQ ID NO 129
<211> LENGTH: 23
<212> TYPE: DNA
<213> ORGANISM: Artificial Sequence
<220> FEATURE:
<223> OTHER INFORMATION: Digenome-captured site of EMX1

<400> SEQUENCE: 129
cagtccaaac agaagaggaa tgg                                          23

<210> SEQ ID NO 130
<211> LENGTH: 23
<212> TYPE: DNA
<213> ORGANISM: Artificial Sequence
<220> FEATURE:
<223> OTHER INFORMATION: Digenome-captured site of FANCF

<400> SEQUENCE: 130
tgaatcccat ctccagcacc agg                                          23

<210> SEQ ID NO 131
<211> LENGTH: 23
<212> TYPE: DNA
<213> ORGANISM: Artificial Sequence
<220> FEATURE:
<223> OTHER INFORMATION: Digenome-captured site of FANCF

<400> SEQUENCE: 131
ggaatccctt ctgcagcacc tgg                                          23

<210> SEQ ID NO 132
<211> LENGTH: 23
<212> TYPE: DNA
<213> ORGANISM: Artificial Sequence
<220> FEATURE:
<223> OTHER INFORMATION: Digenome-captured site of FANCF

<400> SEQUENCE: 132
ggagtccctc ctacagcacc agg                                          23

<210> SEQ ID NO 133
<211> LENGTH: 23
<212> TYPE: DNA
<213> ORGANISM: Artificial Sequence
<220> FEATURE:
<223> OTHER INFORMATION: Digenome-captured site of FANCF

<400> SEQUENCE: 133
ggagtccctc ctacagcacc agg                                          23

<210> SEQ ID NO 134
<211> LENGTH: 23
<212> TYPE: DNA
<213> ORGANISM: Artificial Sequence
```

```
<220> FEATURE:
<223> OTHER INFORMATION: Digenome-captured site of FANCF

<400> SEQUENCE: 134
ggaatcccct ctacagcatc ctg                                              23

<210> SEQ ID NO 135
<211> LENGTH: 23
<212> TYPE: DNA
<213> ORGANISM: Artificial Sequence
<220> FEATURE:
<223> OTHER INFORMATION: Digenome-captured site of FANCF

<400> SEQUENCE: 135
ggagtccctc ctgcagcacc tga                                              23

<210> SEQ ID NO 136
<211> LENGTH: 23
<212> TYPE: DNA
<213> ORGANISM: Artificial Sequence
<220> FEATURE:
<223> OTHER INFORMATION: Digenome-captured site of FANCF

<400> SEQUENCE: 136
ggaaccccgt ctgcagcacc agg                                              23

<210> SEQ ID NO 137
<211> LENGTH: 23
<212> TYPE: DNA
<213> ORGANISM: Artificial Sequence
<220> FEATURE:
<223> OTHER INFORMATION: Digenome-captured site of FANCF

<400> SEQUENCE: 137
gtctcccctt ctgcagcacc agg                                              23

<210> SEQ ID NO 138
<211> LENGTH: 23
<212> TYPE: DNA
<213> ORGANISM: Artificial Sequence
<220> FEATURE:
<223> OTHER INFORMATION: Digenome-captured site of FANCF

<400> SEQUENCE: 138
aaaatccctt ccgcagcacc tag                                              23

<210> SEQ ID NO 139
<211> LENGTH: 23
<212> TYPE: DNA
<213> ORGANISM: Artificial Sequence
<220> FEATURE:
<223> OTHER INFORMATION: Digenome-captured site of FANCF

<400> SEQUENCE: 139
tgtatttctt ctgcctcagg ctg                                              23

<210> SEQ ID NO 140
<211> LENGTH: 23
<212> TYPE: DNA
<213> ORGANISM: Artificial Sequence
<220> FEATURE:
<223> OTHER INFORMATION: Digenome-captured site of FANCF

<400> SEQUENCE: 140
ggaatatctt ctgcagcccc agg                                              23
```

```
<210> SEQ ID NO 141
<211> LENGTH: 23
<212> TYPE: DNA
<213> ORGANISM: Artificial Sequence
<220> FEATURE:
<223> OTHER INFORMATION: Digenome-captured site of FANCF

<400> SEQUENCE: 141
gagtgccctg aagcctcagc tgg                                              23

<210> SEQ ID NO 142
<211> LENGTH: 23
<212> TYPE: DNA
<213> ORGANISM: Artificial Sequence
<220> FEATURE:
<223> OTHER INFORMATION: Digenome-captured site of FANCF

<400> SEQUENCE: 142
accatccctc ctgcagcacc agg                                              23

<210> SEQ ID NO 143
<211> LENGTH: 23
<212> TYPE: DNA
<213> ORGANISM: Artificial Sequence
<220> FEATURE:
<223> OTHER INFORMATION: Digenome-captured site of FANCF

<400> SEQUENCE: 143
tgaatcctaa ctgcagcacc agg                                              23

<210> SEQ ID NO 144
<211> LENGTH: 23
<212> TYPE: DNA
<213> ORGANISM: Artificial Sequence
<220> FEATURE:
<223> OTHER INFORMATION: Digenome-captured site of FANCF

<400> SEQUENCE: 144
ctctgtcctt ctgcagcacc tgg                                              23

<210> SEQ ID NO 145
<211> LENGTH: 23
<212> TYPE: DNA
<213> ORGANISM: Artificial Sequence
<220> FEATURE:
<223> OTHER INFORMATION: Digenome-captured site of HBB (on-target site)

<400> SEQUENCE: 145
cttgccccac agggcagtaa cgg                                              23

<210> SEQ ID NO 146
<211> LENGTH: 23
<212> TYPE: DNA
<213> ORGANISM: Artificial Sequence
<220> FEATURE:
<223> OTHER INFORMATION: Digenome-captured site of HBB

<400> SEQUENCE: 146
ttgctcccac agggcagtaa acg                                              23

<210> SEQ ID NO 147
<211> LENGTH: 23
<212> TYPE: DNA
<213> ORGANISM: Artificial Sequence
<220> FEATURE:
<223> OTHER INFORMATION: Digenome-captured site of HBB
```

-continued

<400> SEQUENCE: 147
gctgccccac agggcagcaa agg                                              23

<210> SEQ ID NO 148
<211> LENGTH: 23
<212> TYPE: DNA
<213> ORGANISM: Artificial Sequence
<220> FEATURE:
<223> OTHER INFORMATION: Digenome-captured site of HBB

<400> SEQUENCE: 148
gtggccccac agggcaggaa tgg                                              23

<210> SEQ ID NO 149
<211> LENGTH: 23
<212> TYPE: DNA
<213> ORGANISM: Artificial Sequence
<220> FEATURE:
<223> OTHER INFORMATION: Digenome-captured site of HBB

<400> SEQUENCE: 149
attgccccac ggggcagtga cgg                                              23

<210> SEQ ID NO 150
<211> LENGTH: 23
<212> TYPE: DNA
<213> ORGANISM: Artificial Sequence
<220> FEATURE:
<223> OTHER INFORMATION: Digenome-captured site of HBB

<400> SEQUENCE: 150
actctcccac aaggcagtaa ggg                                              23

<210> SEQ ID NO 151
<211> LENGTH: 23
<212> TYPE: DNA
<213> ORGANISM: Artificial Sequence
<220> FEATURE:
<223> OTHER INFORMATION: Digenome-captured site of HBB

<400> SEQUENCE: 151
tcagccccac agggcagtaa ggg                                              23

<210> SEQ ID NO 152
<211> LENGTH: 23
<212> TYPE: DNA
<213> ORGANISM: Artificial Sequence
<220> FEATURE:
<223> OTHER INFORMATION: Digenome-captured site of HEK2

<400> SEQUENCE: 152
gaacacaatg catagattgc cgg                                              23

<210> SEQ ID NO 153
<211> LENGTH: 23
<212> TYPE: DNA
<213> ORGANISM: Artificial Sequence
<220> FEATURE:
<223> OTHER INFORMATION: Digenome-captured site of HEK2 (on-target site)

<400> SEQUENCE: 153
gaacacaaag catagactgc ggg                                              23

<210> SEQ ID NO 154

```
<211> LENGTH: 23
<212> TYPE: DNA
<213> ORGANISM: Artificial Sequence
<220> FEATURE:
<223> OTHER INFORMATION: Digenome-captured site of HEK2

<400> SEQUENCE: 154
aactccaaag catatactgc tgg                                              23

<210> SEQ ID NO 155
<211> LENGTH: 23
<212> TYPE: DNA
<213> ORGANISM: Artificial Sequence
<220> FEATURE:
<223> OTHER INFORMATION: Digenome-captured site of HEK3

<400> SEQUENCE: 155
agctcagact gagcaagtga ggg                                              23

<210> SEQ ID NO 156
<211> LENGTH: 23
<212> TYPE: DNA
<213> ORGANISM: Artificial Sequence
<220> FEATURE:
<223> OTHER INFORMATION: Digenome-captured site of HEK3 (on-target site)

<400> SEQUENCE: 156
ggcccagact gagcacgtga tgg                                              23

<210> SEQ ID NO 157
<211> LENGTH: 21
<212> TYPE: DNA
<213> ORGANISM: Artificial Sequence
<220> FEATURE:
<223> OTHER INFORMATION: Digenome-captured site of HEK3

<400> SEQUENCE: 157
ggcccagaga gcacgtgtgg g                                                21

<210> SEQ ID NO 158
<211> LENGTH: 23
<212> TYPE: DNA
<213> ORGANISM: Artificial Sequence
<220> FEATURE:
<223> OTHER INFORMATION: Digenome-captured site of HEK3

<400> SEQUENCE: 158
cacccagact gagcacgtgc tgg                                              23

<210> SEQ ID NO 159
<211> LENGTH: 22
<212> TYPE: DNA
<213> ORGANISM: Artificial Sequence
<220> FEATURE:
<223> OTHER INFORMATION: Digenome-captured site of HEK3

<400> SEQUENCE: 159
ggcccaactg agcaagtgat gg                                               22

<210> SEQ ID NO 160
<211> LENGTH: 23
<212> TYPE: DNA
<213> ORGANISM: Artificial Sequence
<220> FEATURE:
<223> OTHER INFORMATION: Digenome-captured site of HEK3

<400> SEQUENCE: 160
```
agaccagact gagcaagaga ggg                                              23

<210> SEQ ID NO 161
<211> LENGTH: 23
<212> TYPE: DNA
<213> ORGANISM: Artificial Sequence
<220> FEATURE:
<223> OTHER INFORMATION: Digenome-captured site of HEK3

<400> SEQUENCE: 161
ggccactcat ggccacatac tgg                                              23

<210> SEQ ID NO 162
<211> LENGTH: 23
<212> TYPE: DNA
<213> ORGANISM: Artificial Sequence
<220> FEATURE:
<223> OTHER INFORMATION: Digenome-captured site of HEK4 (on-target site)

<400> SEQUENCE: 162
ggcactgcgg ctggaggtgg ggg                                              23

<210> SEQ ID NO 163
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 163
ggcactgctg ctgggggtgg tgg                                              23

<210> SEQ ID NO 164
<211> LENGTH: 22
<212> TYPE: DNA
<213> ORGANISM: Artificial Sequence
<220> FEATURE:
<223> OTHER INFORMATION: Digenome-captured site of HEK4

<400> SEQUENCE: 164
ggcactgcac tggaggttgt gg                                               22

<210> SEQ ID NO 165
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 165
ggctctgcgg ctggaggggg tgg                                              23

<210> SEQ ID NO 166
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 166
agcactgcag atggaggagg cgg                                              23

<210> SEQ ID NO 167
<211> LENGTH: 23
<212> TYPE: DNA

```
<213> ORGANISM: Artificial Sequence
<220> FEATURE:
<223> OTHER INFORMATION: Digenome-captured site of HEK4

<400> SEQUENCE: 167
ggcactgcgg cagggaggag ggg                                              23

<210> SEQ ID NO 168
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 168
tgcactgcgg ccggaggagg tgg                                              23

<210> SEQ ID NO 169
<211> LENGTH: 22
<212> TYPE: DNA
<213> ORGANISM: Artificial Sequence
<220> FEATURE:
<223> OTHER INFORMATION: Digenome-captured site of HEK4

<400> SEQUENCE: 169
ggcactgggc tgaaggtaga gg                                               22

<210> SEQ ID NO 170
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 170
ggcactgtgg ctgcaggtgg agg                                              23

<210> SEQ ID NO 171
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 171
tgctctgcgg caggaggagg agg                                              23

<210> SEQ ID NO 172
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 172
agcactgcag ctgggagtgg agg                                              23

<210> SEQ ID NO 173
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 173
ggcactgagg gtggaggtgg ggg                                              23
```

<210> SEQ ID NO 174
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 174
ggcactgggg ctggagacgg ggg                                    23

<210> SEQ ID NO 175
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 175
aggactgcgg ctggggtgg tgg                                     23

<210> SEQ ID NO 176
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 176
ggcactgcaa ctggaagtga tgg                                    23

<210> SEQ ID NO 177
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 177
ggcactgggg ttggaggtgg ggg                                    23

<210> SEQ ID NO 178
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 178
gccactgcag ctagaggtgg agg                                    23

<210> SEQ ID NO 179
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 179
gccactgcga ctggaggagg ggg                                    23

<210> SEQ ID NO 180
<211> LENGTH: 22
<212> TYPE: DNA
<213> ORGANISM: Artificial Sequence
<220> FEATURE:

```
<223> OTHER INFORMATION: Digenome-captured site of HEK4

<400> SEQUENCE: 180
ggcactgggc tggaggcggg gg                                      22

<210> SEQ ID NO 181
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 181
agctctgcgg caggagttgg agg                                     23

<210> SEQ ID NO 182
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 182
gacaccacgg ctggagatgg tgg                                     23

<210> SEQ ID NO 183
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 183
gcactggcag ccggaggtgg tgg                                     23

<210> SEQ ID NO 184
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 184
tgcactgcag ctgcaggtgg agg                                     23

<210> SEQ ID NO 185
<211> LENGTH: 22
<212> TYPE: DNA
<213> ORGANISM: Artificial Sequence
<220> FEATURE:
<223> OTHER INFORMATION: Digenome-captured site of HEK4

<400> SEQUENCE: 185
ggcactgggc tggagatgga gg                                      22

<210> SEQ ID NO 186
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 186
ccttctgcgg ctggaagtgg tgg                                     23
```

```
<210> SEQ ID NO 187
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 187
gcactgcagg caggaggtga gtg                                              23

<210> SEQ ID NO 188
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 188
gacactgcag ctggaggtgg ggt                                              23

<210> SEQ ID NO 189
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 189
ggcactgcag cagggatgg ggg                                               23

<210> SEQ ID NO 190
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 190
ggcactgcgg gtggaggcgg ggg                                              23

<210> SEQ ID NO 191
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 191
ggcacagcag ctggaggtgc tgg                                              23

<210> SEQ ID NO 192
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 192
ggccctgcgg ctggagatat ggg                                              23

<210> SEQ ID NO 193
<211> LENGTH: 22
<212> TYPE: DNA
<213> ORGANISM: Artificial Sequence
<220> FEATURE:
<223> OTHER INFORMATION: Digenome-captured site of HEK4
```

```
<400> SEQUENCE: 193
gacactgctc tggaggtggt gg                                          22

<210> SEQ ID NO 194
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 194
ggcgctgcgg cgggaggtgg agg                                         23

<210> SEQ ID NO 195
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 195
tgcactgtgg ctggagatgg ggg                                         23

<210> SEQ ID NO 196
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 196
ggcatcacgg ctggaggtgg agg                                         23

<210> SEQ ID NO 197
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 197
agcactgtgg ctgggggagg cgg                                         23

<210> SEQ ID NO 198
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 198
gtcactgcag ctggaggagg ggg                                         23

<210> SEQ ID NO 199
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 199
gtaactgcgg ctggcggtgg tgg                                         23

<210> SEQ ID NO 200
<211> LENGTH: 23
```

```
-continued

<212> TYPE: DNA
<213> ORGANISM: Artificial Sequence
<220> FEATURE:
<223> OTHER INFORMATION: Digenome-captured site of HEK4

<400> SEQUENCE: 200
ggtacagcgg ctgggggagg cgg                                              23

<210> SEQ ID NO 201
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 201
ggcgctgcgg ccggaggtgg ggc                                              23

<210> SEQ ID NO 202
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 202
agcactgtgg ctgggggagg ggg                                              23

<210> SEQ ID NO 203
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 203
tgcactgcag ctggaggcaa cgg                                              23

<210> SEQ ID NO 204
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 204
gacactgagg caggaggtgg ggg                                              23

<210> SEQ ID NO 205
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 205
ggcatctggg ctgggggtag ggg                                              23

<210> SEQ ID NO 206
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 206
```
ggcactgaga ccagaggtgg tgg                                              23

<210> SEQ ID NO 207
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 207
ggcactgcag acggaggtgt ggg                                              23

<210> SEQ ID NO 208
<211> LENGTH: 22
<212> TYPE: DNA
<213> ORGANISM: Artificial Sequence
<220> FEATURE:
<223> OTHER INFORMATION: Digenome-captured site of HEK4

<400> SEQUENCE: 208
ggcactgggc tggagggag ag                                                22

<210> SEQ ID NO 209
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 209
ggcactgcag ctgggggttg gtg                                              23

<210> SEQ ID NO 210
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 210
ggcactgggg ctgggggagg ggg                                              23

<210> SEQ ID NO 211
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 211
ggcacttcag ctggaggcag agg                                              23

<210> SEQ ID NO 212
<211> LENGTH: 22
<212> TYPE: DNA
<213> ORGANISM: Artificial Sequence
<220> FEATURE:
<223> OTHER INFORMATION: Digenome-captured site of HEK4

<400> SEQUENCE: 212
ggcacatgga tggaggtgga gg                                               22

<210> SEQ ID NO 213
<211> LENGTH: 22
<212> TYPE: DNA
<213> ORGANISM: Artificial Sequence

```
<220> FEATURE:
<223> OTHER INFORMATION: Digenome-captured site of HEK4

<400> SEQUENCE: 213
agcactgtgg tggaggtgga gg                                              22

<210> SEQ ID NO 214
<211> LENGTH: 22
<212> TYPE: DNA
<213> ORGANISM: Artificial Sequence
<220> FEATURE:
<223> OTHER INFORMATION: Digenome-captured site of HEK4

<400> SEQUENCE: 214
ggcactgggt tggggtggt gg                                               22

<210> SEQ ID NO 215
<211> LENGTH: 22
<212> TYPE: DNA
<213> ORGANISM: Artificial Sequence
<220> FEATURE:
<223> OTHER INFORMATION: Digenome-captured site of HEK4

<400> SEQUENCE: 215
ggcacatggc tggggtggt gg                                               22

<210> SEQ ID NO 216
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 216
tgcactgcga ctggagggag agg                                             23

<210> SEQ ID NO 217
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 217
ggcactgaga ctggggtgg ggg                                              23

<210> SEQ ID NO 218
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 218
ggcactgcag cctggggtg ggg                                              23

<210> SEQ ID NO 219
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 219
ggctcttcgg ctggaggtag cgg                                             23
```

```
<210> SEQ ID NO 220
<211> LENGTH: 22
<212> TYPE: DNA
<213> ORGANISM: Artificial Sequence
<220> FEATURE:
<223> OTHER INFORMATION: Digenome-captured site of HEK4

<400> SEQUENCE: 220
gacactgggc tggaggttgc gg                                              22

<210> SEQ ID NO 221
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 221
agcactgtgc ctggggtgg ggg                                              23

<210> SEQ ID NO 222
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 222
tggactgcgg ctggagaggg agg                                             23

<210> SEQ ID NO 223
<211> LENGTH: 22
<212> TYPE: DNA
<213> ORGANISM: Artificial Sequence
<220> FEATURE:
<223> OTHER INFORMATION: Digenome-captured site of HEK4

<400> SEQUENCE: 223
ggcactgggc tggatgtggt gg                                              22

<210> SEQ ID NO 224
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 224
ggcactgagg ctgcaggcgg cgg                                             23

<210> SEQ ID NO 225
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 225
ggcacaatgg ctggaggtga agg                                             23

<210> SEQ ID NO 226
<211> LENGTH: 23
<212> TYPE: DNA
<213> ORGANISM: Artificial Sequence
<220> FEATURE:
<223> OTHER INFORMATION: Digenome-captured site of HEK4
```

<400> SEQUENCE: 226
ggcactctgg ctggagctgg ggg                                           23

<210> SEQ ID NO 227
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 227
ggcacagcag gtggaggtgg agg                                           23

<210> SEQ ID NO 228
<211> LENGTH: 23
<212> TYPE: DNA
<213> ORGANISM: Artificial Sequence
<220> FEATURE:
<223> OTHER INFORMATION: Digenome-captured site of HEK4

<400> SEQUENCE: 228
ggctctgcag ccaggggtgg agg                                           23

<210> SEQ ID NO 229
<211> LENGTH: 4107
<212> TYPE: DNA
<213> ORGANISM: Artificial Sequence
<220> FEATURE:
<223> OTHER INFORMATION: Gene encoding Streptococcus pyogenes Cas9

<400> SEQUENCE: 229

```
atggacaaga agtacagcat cggcctggac atcggtacca acagcgtggg ctgggccgtg      60
atcaccgacg agtacaaggt gcccagcaag aagttcaagg tgctgggcaa caccgaccgc     120
cacagcatca agaagaacct gatcggcgcc ctgctgttcg acagcggcga gaccgccgag     180
gccacccgcc tgaagcgcac cgcccgccgc cgctacaccc gccgcaagaa ccgcatctgc     240
tacctgcagg agatcttcag caacgagatg gccaaggtgg acgacagctt cttccaccgc     300
ctggaggaga gcttcctggt ggaggaggac aagaagcacg agcgccaccc catcttcggc     360
aacatcgtgg acgaggtggc ctaccacgag aagtacccca ccatctacca cctgcgcaag     420
aagctggtgg acagcaccga caaggccgac ctgcgcctga tctacctggc cctggcccac     480
atgatcaagt tccgcggcca cttcctgatc gagggcgacc tgaaccccga caacagcgac     540
gtggacaagc tgttcatcca gctggtgcag acctacaacc agctgttcga ggagaacccc     600
atcaacgcca gcggcgtgga cgccaaggcc atcctgagcg cccgcctgag caagagccgc     660
cgcctggaga acctgatcgc ccagctgccc ggcgagaaga gaacggcct gttcggcaac     720 ctgatcgccc tgagcctggg cctgaccccc aacttcaaga gcaacttcga cctggccgag     780
gacgccaagc tgcagctgag caaggacacc tacgacgacg acctggacaa cctgctggcc     840
cagatcggcg accagtacgc cgacctgttc ctggccgcca gaacctgag cgacgccatc     900 ctgctgagcg acatcctgcg cgtgaacacc gagatcacca aggcccccct gagcgccagc     960
atgatcaagc gctacgacga gcaccaccag gacctgaccc tgctgaaggc cctggtgcgc    1020
cagcagctgc ccgagaagta caaggagatc ttcttcgacc agagcaagaa cggctacgcc    1080
ggctacatcg acggcggcgc cagccaggag gagttctaca agttcatcaa gcccatcctg    1140
gagaagatgg acggcaccga ggagctgctg gtgaagctga accgcgagga cctgctgcgc    1200
```

```
aagcagcgca ccttcgacaa cggcagcatc ccccaccaga tccacctggg cgagctgcac   1260
gccatcctgc gccgccagga ggacttctac cccttcctga aggacaaccg cgagaagatc   1320
gagaagatcc tgaccttccg catcccctac tacgtgggcc cctggcccg cggcaacagc    1380 cgcttcgcct ggatgacccg caagagcgag gagaccatca ccccctggaa cttcgaggag   1440
gtggtggaca agggcgccag cgcccagagc ttcatcgagc gcatgaccaa cttcgacaag   1500
aacctgccca cgagaaggt gctgcccaag cacagcctgc tgtacgagta cttcaccgtg    1560
tacaacgagc tgaccaaggt gaagtacgtg accgagggca tgcgcaagcc cgccttcctg   1620
agcggcgagc agaagaaggc catcgtggac ctgctgttca agaccaaccg caaggtgacc   1680
gtgaagcagc tgaaggagga ctacttcaag aagatcgagt gcttcgacag cgtggagatc   1740
agcggcgtgg aggaccgctt caacgccagc ctgggcacct accacgacct gctgaagatc   1800
atcaaggaca aggacttcct ggacaacgag gagaacgagg acatcctgga ggacatcgtg   1860 ctgacccctga ccctgttcga ggaccgcgag atgatcgagg agcgcctgaa gacctacgcc   1920
cacctgttcg acgacaaggt gatgaagcag ctgagcgcc gccgctacac cggctggggc    1980
cgcctgagcc gcaagcttat caacggcatc cgcgacaagc agagcggcaa gaccatcctg   2040
gacttcctga gagcgacgg cttcgccaac cgcaacttca tgcagctgat ccacgacgac   2100
agcctgacct tcaaggagga catccagaag gcccaggtga gcggccaggg cgacagcctg   2160
cacgagcaca tcgccaacct ggccggcagc cccgccatca gaagggcat cctgcagacc    2220 gtgaaggtgg tggacgagct ggtgaaggtg atgggccgcc acaagcccga gaacatcgtg   2280
atcgagatgg cccgcgagaa ccagaccacc cagaagggcc agaagaacag ccgcgagcgc   2340
atgaagcgca tcgaggaggg catcaaggag ctgggcagcc agatcctgaa ggagcacccc   2400
gtggagaaca cccagctgca gaacgagaag ctgtacctgt actacctgca gaacggccgc   2460
gacatgtacg tggaccagga gctggacatc aaccgcctga gcgactacga cgtggaccac   2520
atcgtgcccc agagcttcct gaaggacgac agcatcgaca caaggtgct gacccgcagc    2580 gacaagaacc gcggcaagag cgacaacgtg cccagcgagg aggtggtgaa gaagatgaag   2640
aactactggc gccagctgct gaacgccaag ctgatcaccc agcgcaagtt cgacaacctg   2700
accaaggccg agcgcggcgg cctgagcgag ctggacaagg ccggcttcat caagcgccag   2760
ctggtggaga cccgccagat caccaagcac gtggcccaga tcctggacag ccgcatgaac   2820
accaagtacg acgagaacga caagctgatc cgcgaggtga aggtgatcac cctgaagagc   2880
aagctggtga cgacttccg caaggacttc cagttctaca aggtgcgcga tcaacaac     2940 taccaccacg cccacgacgc ctacctgaac gccgtggtgg gcaccgccct gatcaagaag   3000
taccccaagc tggagagcga gttcgtgtac ggcgactaca aggtgtacga cgtgcgcaag   3060
atgatcgcca agagcgagca ggagatcggc aaggccaccg ccaagtactt cttctacagc   3120
aacatcatga acttcttcaa gaccgagatc accctggcca cggcgagat ccgcaagcgc    3180 cccctgatcg agaccaacgg cgagaccggc gagatcgtgt gggacaaggg ccgcgacttc   3240
gccaccgtgc gcaaggtgct gagcatgccc caggtgaaca tcgtgaagaa gaccgaggtg   3300
cagaccggcg gcttcagcaa ggagagcatc ctgcccaagc gcaacagcga caagctgatc   3360
gcccgcaaga aggactggga ccccaagaag tacgcggct tcgacagccc caccgtggcc    3420
tacagcgtgc tggtggtggc caaggtggag aagggcaaga gcaagaagct gaagagcgtg   3480
aaggagctgc tgggcatcac catcatggag cgcagcagct tcgagaagaa ccccatcgac   3540
ttcctggagg ccaagggcta caaggaggtg aagaaggacc tgatcatcaa gctgcccaag   3600
```

-continued

```
tacagcctgt tcgagctgga gaacggccgc aagcgcatgc tggccagcgc cggcgagctg    3660
cagaagggca cgagctggcc cctgcccagc aagtacgtga acttcctgta cctggccagc    3720
cactacgaga agctgaaggg cagccccgag acaacgagc agaagcagct gttcgtggag     3780
cagcacaagc actacctgga cgagatcatc gagcagatca gcgagttcag caagcgcgtg    3840
atcctggccg acgccaacct ggacaaggtg ctgagcgcct acaacaagca ccgcgacaag    3900
cccatccgcg agcaggccga gaacatcatc cacctgttca ccctgaccaa cctgggcgcc    3960
cccgccgcct tcaagtactt cgacaccacc atcgaccgca agcgctacac cagcaccaag    4020
gaggtgctgg acgccaccct gatccaccag agcatcaccg gtctgtacga acccgcatc     4080 gacctgagcc agctgggcgg cgactaa                                         4107
```

<210> SEQ ID NO 230
<211> LENGTH: 12
<212> TYPE: RNA
<213> ORGANISM: Artificial Sequence
<220> FEATURE:
<223> OTHER INFORMATION: Synthetic (Essential part of crRNA)

<400> SEQUENCE: 230
guuuuagagc ua                                                          12

<210> SEQ ID NO 231
<211> LENGTH: 10
<212> TYPE: RNA
<213> ORGANISM: Artificial Sequence
<220> FEATURE:
<223> OTHER INFORMATION: Synthetic (3' end part of crRNA)

<400> SEQUENCE: 231
ugcuguuuug                                                             10

<210> SEQ ID NO 232
<211> LENGTH: 60
<212> TYPE: RNA
<213> ORGANISM: Artificial Sequence
<220> FEATURE:
<223> OTHER INFORMATION: Synthetic (Essential part of tracrRNA)

<400> SEQUENCE: 232
uagcaaguua aaauaaggcu aguccguuau caacuugaaa aaguggcacc gagucggugc    60

<210> SEQ ID NO 233
<211> LENGTH: 14
<212> TYPE: RNA
<213> ORGANISM: Artificial Sequence
<220> FEATURE:
<223> OTHER INFORMATION: General formula of SpCas9 crRNA
<220> FEATURE:
<221> NAME/KEY: misc_feature
<222> LOCATION: (1)
<223> OTHER INFORMATION: n is targeting sequence comprising 15-30 or 20
      nucleotides
<220> FEATURE:
<221> NAME/KEY: misc_feature
<222> LOCATION: (14)
<223> OTHER INFORMATION: n comprises 8-12 or 11 nucleotides, each of
      which is A, U, C, or G

<400> SEQUENCE: 233
nguuuuagag cuan                                                        14

<210> SEQ ID NO 234

```
<211> LENGTH: 61
<212> TYPE: RNA
<213> ORGANISM: Artificial Sequence
<220> FEATURE:
<223> OTHER INFORMATION: General formula of SpCas9 tracrRNA
<220> FEATURE:
<221> NAME/KEY: misc_feature
<222> LOCATION: (1)
<223> OTHER INFORMATION: n comprises 6-20 or 8-19 nucleotides, each of
      which is A, U, C, or G

<400> SEQUENCE: 234
nuagcaaguu aaaauaaggc uaguccguua ucaacuugaa aaaguggcac cgagucggug    60
c                                                                    61

<210> SEQ ID NO 235
<211> LENGTH: 80
<212> TYPE: RNA
<213> ORGANISM: Artificial Sequence
<220> FEATURE:
<223> OTHER INFORMATION: General formula of SpCas9 sgRNA
<220> FEATURE:
<221> NAME/KEY: misc_feature
<222> LOCATION: (1)
<223> OTHER INFORMATION: n is targeting sequence comprising 15-30 or 20
      nucleotides
<220> FEATURE:
<221> NAME/KEY: misc_feature
<222> LOCATION: (14)
<223> OTHER INFORMATION: n is a linker comprising 3-5 or 4 nucleotides

<400> SEQUENCE: 235
nguuucaguu gcunaugcuc uguaaucauu uaaaaguauu uugaacggac cucuguuuga    60
cacgucugaa uaacuaaaaa                                                80

<210> SEQ ID NO 236
<211> LENGTH: 20
<212> TYPE: DNA
<213> ORGANISM: Artificial Sequence
<220> FEATURE:
<223> OTHER INFORMATION: synthetic_EMX1_1 1st PCR forward(5' to 3')

<400> SEQUENCE: 236 gccttttttcc ggacacataa                                               20

<210> SEQ ID NO 237
<211> LENGTH: 56
<212> TYPE: DNA
<213> ORGANISM: Artificial Sequence
<220> FEATURE:
<223> OTHER INFORMATION: synthetic_EMX1_1 1st PCR reverse(5' to 3')

<400> SEQUENCE: 237
gtgactggag ttcagacgtg tgctcttccg atctgcctca ttatcatcag tgttgg        56

<210> SEQ ID NO 238
<211> LENGTH: 53
<212> TYPE: DNA
<213> ORGANISM: Artificial Sequence
<220> FEATURE:
<223> OTHER INFORMATION: synthetic_EMX1_1 2nd PCR forward(5' to 3')

<400> SEQUENCE: 238
acactctttc cctacacgac gctcttccga tctatctcac ctgggcgaga aag           53

<210> SEQ ID NO 239
<211> LENGTH: 56
```

```
<212> TYPE: DNA
<213> ORGANISM: Artificial Sequence
<220> FEATURE:
<223> OTHER INFORMATION: synthetic_EMX1_1 2nd PCR reverse(5' to 3')

<400> SEQUENCE: 239
gtgactggag ttcagacgtg tgctcttccg atctgcctca ttatcatcag tgttgg        56

<210> SEQ ID NO 240
<211> LENGTH: 53
<212> TYPE: DNA
<213> ORGANISM: Artificial Sequence
<220> FEATURE:
<223> OTHER INFORMATION: synthetic_EMX1_2 1st PCR forward(5' to 3')

<400> SEQUENCE: 240
acactctttc cctacacgac gctcttccga tctgtcccag accttcatct cca           53

<210> SEQ ID NO 241
<211> LENGTH: 20
<212> TYPE: DNA
<213> ORGANISM: Artificial Sequence
<220> FEATURE:
<223> OTHER INFORMATION: synthetic_EMX1_2 1st PCR reverse(5' to 3')

<400> SEQUENCE: 241
gtctctgtga atggcgtcac                                                20

<210> SEQ ID NO 242
<211> LENGTH: 53
<212> TYPE: DNA
<213> ORGANISM: Artificial Sequence
<220> FEATURE:
<223> OTHER INFORMATION: synthetic_EMX1_2 2nd PCR forward(5' to 3')

<400> SEQUENCE: 242
acactctttc cctacacgac gctcttccga tctgtcccag accttcatct cca           53

<210> SEQ ID NO 243
<211> LENGTH: 54
<212> TYPE: DNA
<213> ORGANISM: Artificial Sequence
<220> FEATURE:
<223> OTHER INFORMATION: synthetic_EMX1_2 2nd PCR reverse(5' to 3')

<400> SEQUENCE: 243
gtgactggag ttcagacgtg tgctcttccg atctcactgt ctgcagggct ctct          54

<210> SEQ ID NO 244
<211> LENGTH: 54
<212> TYPE: DNA
<213> ORGANISM: Artificial Sequence
<220> FEATURE:
<223> OTHER INFORMATION: synthetic_EMX1_3 1st PCR forward(5' to 3')

<400> SEQUENCE: 244
acactctttc cctacacgac gctcttccga tctttggtcc cacaggtgaa taac          54

<210> SEQ ID NO 245
<211> LENGTH: 26
<212> TYPE: DNA
<213> ORGANISM: Artificial Sequence
<220> FEATURE:
<223> OTHER INFORMATION: synthetic_EMX1_3 1st PCR reverse(5' to 3')

<400> SEQUENCE: 245
```
tcaaattgtt taatagctct gttgtt                                            26

<210> SEQ ID NO 246
<211> LENGTH: 54
<212> TYPE: DNA
<213> ORGANISM: Artificial Sequence
<220> FEATURE:
<223> OTHER INFORMATION: synthetic_EMX1_3 2nd PCR forward(5' to 3')

<400> SEQUENCE: 246
acactctttc cctacacgac gctcttccga tctttggtcc cacaggtgaa taac            54

<210> SEQ ID NO 247
<211> LENGTH: 58
<212> TYPE: DNA
<213> ORGANISM: Artificial Sequence
<220> FEATURE:
<223> OTHER INFORMATION: synthetic_EMX1_3 2nd PCR reverse(5' to 3')

<400> SEQUENCE: 247
gtgactggag ttcagacgtg tgctcttccg atcttttttg gtcaatatct gaaaggtt       58

<210> SEQ ID NO 248
<211> LENGTH: 18
<212> TYPE: DNA
<213> ORGANISM: Artificial Sequence
<220> FEATURE:
<223> OTHER INFORMATION: synthetic_EMX1_4 (on target) 1st PCR forward(5'
      to 3')

<400> SEQUENCE: 248
agtgttgagg ccccagtg                                                    18

<210> SEQ ID NO 249
<211> LENGTH: 53
<212> TYPE: DNA
<213> ORGANISM: Artificial Sequence
<220> FEATURE:
<223> OTHER INFORMATION: synthetic_EMX1_4 (on target) 1st PCR reverse(5'
      to 3')

<400> SEQUENCE: 249
gtgactggag ttcagacgtg tgctcttccg atctcagcag caagcagcac tct             53

<210> SEQ ID NO 250
<211> LENGTH: 53
<212> TYPE: DNA
<213> ORGANISM: Artificial Sequence
<220> FEATURE:
<223> OTHER INFORMATION: synthetic_EMX1_4 (on target) 2nd PCR forward(5'
      to 3')

<400> SEQUENCE: 250
acactctttc cctacacgac gctcttccga tctgggcctc ctgagtttct cat             53

<210> SEQ ID NO 251
<211> LENGTH: 53
<212> TYPE: DNA
<213> ORGANISM: Artificial Sequence
<220> FEATURE:
<223> OTHER INFORMATION: synthetic_EMX1_4 (on target) 2nd PCR reverse(5'
      to 3')

<400> SEQUENCE: 251
gtgactggag ttcagacgtg tgctcttccg atctcagcag caagcagcac tct             53

```
<210> SEQ ID NO 252
<211> LENGTH: 60
<212> TYPE: DNA
<213> ORGANISM: Artificial Sequence
<220> FEATURE:
<223> OTHER INFORMATION: synthetic_EMX1_5 1st PCR forward(5' to 3')

<400> SEQUENCE: 252
acactctttc cctacacgac gctcttccga tctctgaaaa tttatgacaa tttactacca      60

<210> SEQ ID NO 253
<211> LENGTH: 27
<212> TYPE: DNA
<213> ORGANISM: Artificial Sequence
<220> FEATURE:
<223> OTHER INFORMATION: synthetic_EMX1_5 1st PCR reverse(5' to 3')

<400> SEQUENCE: 253
aaaagatgtg gtatatacat acgatgg                                         27

<210> SEQ ID NO 254
<211> LENGTH: 60
<212> TYPE: DNA
<213> ORGANISM: Artificial Sequence
<220> FEATURE:
<223> OTHER INFORMATION: synthetic_EMX1_5 2nd PCR forward(5' to 3')

<400> SEQUENCE: 254
acactctttc cctacacgac gctcttccga tctctgaaaa tttatgacaa tttactacca      60

<210> SEQ ID NO 255
<211> LENGTH: 57
<212> TYPE: DNA
<213> ORGANISM: Artificial Sequence
<220> FEATURE:
<223> OTHER INFORMATION: synthetic_EMX1_5 2nd PCR reverse(5' to 3')

<400> SEQUENCE: 255
gtgactggag ttcagacgtg tgctcttccg atctcaaaca aagaaggaaa gtcctca        57

<210> SEQ ID NO 256
<211> LENGTH: 53
<212> TYPE: DNA
<213> ORGANISM: Artificial Sequence
<220> FEATURE:
<223> OTHER INFORMATION: synthetic_EMX1_6 1st PCR forward(5' to 3')

<400> SEQUENCE: 256
acactctttc cctacacgac gctcttccga tctgcttgcc tgtgtgactt gac             53

<210> SEQ ID NO 257
<211> LENGTH: 23
<212> TYPE: DNA
<213> ORGANISM: Artificial Sequence
<220> FEATURE:
<223> OTHER INFORMATION: synthetic_EMX1_6 1st PCR reverse(5' to 3')

<400> SEQUENCE: 257
tgtctcattg gcttttttctt ttc                                            23

<210> SEQ ID NO 258
<211> LENGTH: 53
<212> TYPE: DNA
<213> ORGANISM: Artificial Sequence
<220> FEATURE:
<223> OTHER INFORMATION: synthetic_EMX1_6 2nd PCR forward(5' to 3')
```

<400> SEQUENCE: 258
acactctttc cctacacgac gctcttccga tctgcttgcc tgtgtgactt gac    53

<210> SEQ ID NO 259
<211> LENGTH: 54
<212> TYPE: DNA
<213> ORGANISM: Artificial Sequence
<220> FEATURE:
<223> OTHER INFORMATION: synthetic_EMX1_6 2nd PCR reverse(5' to 3')

<400> SEQUENCE: 259
gtgactggag ttcagacgtg tgctcttccg atctgcccag ctgtgcattc tatc    54

<210> SEQ ID NO 260
<211> LENGTH: 54
<212> TYPE: DNA
<213> ORGANISM: Artificial Sequence
<220> FEATURE:
<223> OTHER INFORMATION: synthetic_EMX1_7 1st PCR forward(5' to 3')

<400> SEQUENCE: 260
acactctttc cctacacgac gctcttccga tcttgagccc tatgaaaaga ttgc    54

<210> SEQ ID NO 261
<211> LENGTH: 20
<212> TYPE: DNA
<213> ORGANISM: Artificial Sequence
<220> FEATURE:
<223> OTHER INFORMATION: synthetic_EMX1_7 1st PCR reverse(5' to 3')

<400> SEQUENCE: 261
cccagctaca cgtcacaatg    20

<210> SEQ ID NO 262
<211> LENGTH: 54
<212> TYPE: DNA
<213> ORGANISM: Artificial Sequence
<220> FEATURE:
<223> OTHER INFORMATION: synthetic_EMX1_7 2nd PCR forward(5' to 3')

<400> SEQUENCE: 262
acactctttc cctacacgac gctcttccga tcttgagccc tatgaaaaga ttgc    54

<210> SEQ ID NO 263
<211> LENGTH: 54
<212> TYPE: DNA
<213> ORGANISM: Artificial Sequence
<220> FEATURE:
<223> OTHER INFORMATION: synthetic_EMX1_7 2nd PCR reverse(5' to 3')

<400> SEQUENCE: 263
gtgactggag ttcagacgtg tgctcttccg atcttagggt ccaggcaaga gaaa    54

<210> SEQ ID NO 264
<211> LENGTH: 53
<212> TYPE: DNA
<213> ORGANISM: Artificial Sequence
<220> FEATURE:
<223> OTHER INFORMATION: synthetic_EMX1_8 1st PCR forward(5' to 3')

<400> SEQUENCE: 264
acactctttc cctacacgac gctcttccga tctacattgc taccccttgg tga    53

<210> SEQ ID NO 265
<211> LENGTH: 21

```
<212> TYPE: DNA
<213> ORGANISM: Artificial Sequence
<220> FEATURE:
<223> OTHER INFORMATION: synthetic_EMX1_8 1st PCR reverse(5' to 3')

<400> SEQUENCE: 265
tctgtctggc agatgatacc c                                              21

<210> SEQ ID NO 266
<211> LENGTH: 53
<212> TYPE: DNA
<213> ORGANISM: Artificial Sequence
<220> FEATURE:
<223> OTHER INFORMATION: synthetic_EMX1_8 2nd PCR forward(5' to 3')

<400> SEQUENCE: 266
acactctttc cctacacgac gctcttccga tctacattgc taccccttgg tga           53

<210> SEQ ID NO 267
<211> LENGTH: 54
<212> TYPE: DNA
<213> ORGANISM: Artificial Sequence
<220> FEATURE:
<223> OTHER INFORMATION: synthetic_EMX1_8 2nd PCR reverse(5' to 3')

<400> SEQUENCE: 267
gtgactggag ttcagacgtg tgctcttccg atctatctgc ttcctcgtgg tcat          54

<210> SEQ ID NO 268
<211> LENGTH: 53
<212> TYPE: DNA
<213> ORGANISM: Artificial Sequence
<220> FEATURE:
<223> OTHER INFORMATION: synthetic_EMX1_9 1st PCR forward(5' to 3')

<400> SEQUENCE: 268
acactctttc cctacacgac gctcttccga tctcggttcc ggtacttcat gtc           53

<210> SEQ ID NO 269
<211> LENGTH: 22
<212> TYPE: DNA
<213> ORGANISM: Artificial Sequence
<220> FEATURE:
<223> OTHER INFORMATION: synthetic_EMX1_9 1st PCR reverse(5' to 3')

<400> SEQUENCE: 269
gatctgatct taccccagaa gc                                             22

<210> SEQ ID NO 270
<211> LENGTH: 53
<212> TYPE: DNA
<213> ORGANISM: Artificial Sequence
<220> FEATURE:
<223> OTHER INFORMATION: synthetic_EMX1_9 2nd PCR forward(5' to 3')

<400> SEQUENCE: 270
acactctttc cctacacgac gctcttccga tctcggttcc ggtacttcat gtc           53

<210> SEQ ID NO 271
<211> LENGTH: 54
<212> TYPE: DNA
<213> ORGANISM: Artificial Sequence
<220> FEATURE:
<223> OTHER INFORMATION: synthetic_EMX1_9 2nd PCR reverse(5' to 3')

<400> SEQUENCE: 271
```
gtgactggag ttcagacgtg tgctcttccg atctctgcta cttggctgac caca      54

<210> SEQ ID NO 272
<211> LENGTH: 18
<212> TYPE: DNA
<213> ORGANISM: Artificial Sequence
<220> FEATURE:
<223> OTHER INFORMATION: synthetic_EMX1_10 1st PCR forward(5' to 3')

<400> SEQUENCE: 272
ctcctccgac cagcagag                                              18

<210> SEQ ID NO 273
<211> LENGTH: 55
<212> TYPE: DNA
<213> ORGANISM: Artificial Sequence
<220> FEATURE:
<223> OTHER INFORMATION: synthetic_EMX1_10 1st PCR reverse(5' to 3')

<400> SEQUENCE: 273
gtgactggag ttcagacgtg tgctcttccg atcttccctc agccacttta tttca     55

<210> SEQ ID NO 274
<211> LENGTH: 53
<212> TYPE: DNA
<213> ORGANISM: Artificial Sequence
<220> FEATURE:
<223> OTHER INFORMATION: synthetic_EMX1_10 2nd PCR forward(5' to 3')

<400> SEQUENCE: 274
acactctttc cctacacgac gctcttccga tctaaggagg tgcaggagct aga       53

<210> SEQ ID NO 275
<211> LENGTH: 55
<212> TYPE: DNA
<213> ORGANISM: Artificial Sequence
<220> FEATURE:
<223> OTHER INFORMATION: synthetic_EMX1_10 2nd PCR reverse(5' to 3')

<400> SEQUENCE: 275
gtgactggag ttcagacgtg tgctcttccg atcttccctc agccacttta tttca     55

<210> SEQ ID NO 276
<211> LENGTH: 18
<212> TYPE: DNA
<213> ORGANISM: Artificial Sequence
<220> FEATURE:
<223> OTHER INFORMATION: synthetic_EMX1_11 1st PCR forward(5' to 3')

<400> SEQUENCE: 276
ggtgctgtgg gggcatag                                              18

<210> SEQ ID NO 277
<211> LENGTH: 54
<212> TYPE: DNA
<213> ORGANISM: Artificial Sequence
<220> FEATURE:
<223> OTHER INFORMATION: synthetic_EMX1_11 1st PCR reverse(5' to 3')

<400> SEQUENCE: 277
gtgactggag ttcagacgtg tgctcttccg atctacaggc gaacagaaca gaca      54

<210> SEQ ID NO 278
<211> LENGTH: 53
<212> TYPE: DNA
<213> ORGANISM: Artificial Sequence

```
<220> FEATURE:
<223> OTHER INFORMATION: synthetic_EMX1_11 2nd PCR forward(5' to 3')

<400> SEQUENCE: 278
acactctttc cctacacgac gctcttccga tctccttgat ttggaggggt ctt          53

<210> SEQ ID NO 279
<211> LENGTH: 54
<212> TYPE: DNA
<213> ORGANISM: Artificial Sequence
<220> FEATURE:
<223> OTHER INFORMATION: synthetic_EMX1_11 2nd PCR reverse(5' to 3')

<400> SEQUENCE: 279
gtgactggag ttcagacgtg tgctcttccg atctacaggc aacagaaca gaca           54

<210> SEQ ID NO 280
<211> LENGTH: 27
<212> TYPE: DNA
<213> ORGANISM: Artificial Sequence
<220> FEATURE:
<223> OTHER INFORMATION: synthetic_EMX1_12 1st PCR forward(5' to 3')

<400> SEQUENCE: 280
ccctttctta ataaattacc cagtttc                                        27

<210> SEQ ID NO 281
<211> LENGTH: 59
<212> TYPE: DNA
<213> ORGANISM: Artificial Sequence
<220> FEATURE:
<223> OTHER INFORMATION: synthetic_EMX1_12 1st PCR reverse(5' to 3')

<400> SEQUENCE: 281
gtgactggag ttcagacgtg tgctcttccg atctaaaaag ataggcaaac ataggaaaa     59

<210> SEQ ID NO 282
<211> LENGTH: 54
<212> TYPE: DNA
<213> ORGANISM: Artificial Sequence
<220> FEATURE:
<223> OTHER INFORMATION: synthetic_EMX1_12 2nd PCR forward(5' to 3')

<400> SEQUENCE: 282
acactctttc cctacacgac gctcttccga tcttggacta aaacactgcc caag          54

<210> SEQ ID NO 283
<211> LENGTH: 59
<212> TYPE: DNA
<213> ORGANISM: Artificial Sequence
<220> FEATURE:
<223> OTHER INFORMATION: synthetic_EMX1_12 2nd PCR reverse(5' to 3')

<400> SEQUENCE: 283
gtgactggag ttcagacgtg tgctcttccg atctaaaaag ataggcaaac ataggaaaa     59

<210> SEQ ID NO 284
<211> LENGTH: 20
<212> TYPE: DNA
<213> ORGANISM: Artificial Sequence
<220> FEATURE:
<223> OTHER INFORMATION: synthetic_EMX1_13 1st PCR forward(5' to 3')

<400> SEQUENCE: 284
gcttttctgg ggacatagca                                                20
```

<210> SEQ ID NO 285
<211> LENGTH: 56
<212> TYPE: DNA
<213> ORGANISM: Artificial Sequence
<220> FEATURE:
<223> OTHER INFORMATION: synthetic_EMX1_13 1st PCR reverse(5' to 3')

<400> SEQUENCE: 285
gtgactggag ttcagacgtg tgctcttccg atctaagaat tccaggcagt taacca      56

<210> SEQ ID NO 286
<211> LENGTH: 53
<212> TYPE: DNA
<213> ORGANISM: Artificial Sequence
<220> FEATURE:
<223> OTHER INFORMATION: synthetic_EMX1_13 2nd PCR forward(5' to 3')

<400> SEQUENCE: 286
acactctttc cctacacgac gctcttccga tctacttccc ttgtcatccc aca         53

<210> SEQ ID NO 287
<211> LENGTH: 56
<212> TYPE: DNA
<213> ORGANISM: Artificial Sequence
<220> FEATURE:
<223> OTHER INFORMATION: synthetic_EMX1_13 2nd PCR reverse(5' to 3')

<400> SEQUENCE: 287
gtgactggag ttcagacgtg tgctcttccg atctaagaat tccaggcagt taacca      56

<210> SEQ ID NO 288
<211> LENGTH: 20
<212> TYPE: DNA
<213> ORGANISM: Artificial Sequence
<220> FEATURE:
<223> OTHER INFORMATION: synthetic_EMX1_14 1st PCR forward(5' to 3')

<400> SEQUENCE: 288
cacaggaatg tcttgggtca                                              20

<210> SEQ ID NO 289
<211> LENGTH: 54
<212> TYPE: DNA
<213> ORGANISM: Artificial Sequence
<220> FEATURE:
<223> OTHER INFORMATION: synthetic_EMX1_14 1st PCR reverse(5' to 3')

<400> SEQUENCE: 289
gtgactggag ttcagacgtg tgctcttccg atctctcttc aatccatcgc cagt        54

<210> SEQ ID NO 290
<211> LENGTH: 53
<212> TYPE: DNA
<213> ORGANISM: Artificial Sequence
<220> FEATURE:
<223> OTHER INFORMATION: synthetic_EMX1_14 2nd PCR forward(5' to 3')

<400> SEQUENCE: 290
acactctttc cctacacgac gctcttccga tctcttagcc tgggtcatgc act         53

<210> SEQ ID NO 291
<211> LENGTH: 54
<212> TYPE: DNA
<213> ORGANISM: Artificial Sequence
<220> FEATURE:
<223> OTHER INFORMATION: synthetic_EMX1_14 2nd PCR reverse(5' to 3')

<400> SEQUENCE: 291
gtgactggag ttcagacgtg tgctcttccg atctctcttc aatccatcgc cagt    54

<210> SEQ ID NO 292
<211> LENGTH: 53
<212> TYPE: DNA
<213> ORGANISM: Artificial Sequence
<220> FEATURE:
<223> OTHER INFORMATION: synthetic_EMX1_15 1st PCR forward(5' to 3')

<400> SEQUENCE: 292
acactctttc cctacacgac gctcttccga tcttgaggag gcaaaaggga ata    53

<210> SEQ ID NO 293
<211> LENGTH: 20
<212> TYPE: DNA
<213> ORGANISM: Artificial Sequence
<220> FEATURE:
<223> OTHER INFORMATION: synthetic_EMX1_15 1st PCR reverse(5' to 3')

<400> SEQUENCE: 293
gcacttgttg gccatttgta    20

<210> SEQ ID NO 294
<211> LENGTH: 53
<212> TYPE: DNA
<213> ORGANISM: Artificial Sequence
<220> FEATURE:
<223> OTHER INFORMATION: synthetic_EMX1_15 2nd PCR forward(5' to 3')

<400> SEQUENCE: 294
acactctttc cctacacgac gctcttccga tcttgaggag gcaaaaggga ata    53

<210> SEQ ID NO 295
<211> LENGTH: 61
<212> TYPE: DNA
<213> ORGANISM: Artificial Sequence
<220> FEATURE:
<223> OTHER INFORMATION: synthetic_EMX1_15 2nd PCR reverse(5' to 3')

<400> SEQUENCE: 295
gtgactggag ttcagacgtg tgctcttccg atcttttttga atatgtttta aattctccac    60
a    61

<210> SEQ ID NO 296
<211> LENGTH: 53
<212> TYPE: DNA
<213> ORGANISM: Artificial Sequence
<220> FEATURE:
<223> OTHER INFORMATION: synthetic_EMX1_16 1st PCR forward(5' to 3')

<400> SEQUENCE: 296
acactctttc cctacacgac gctcttccga tctaaggcta gcccagagtc tcc    53

<210> SEQ ID NO 297
<211> LENGTH: 20
<212> TYPE: DNA
<213> ORGANISM: Artificial Sequence
<220> FEATURE:
<223> OTHER INFORMATION: synthetic_EMX1_16 1st PCR reverse(5' to 3')

<400> SEQUENCE: 297
gcacagaggg ttgtttgctt    20

<210> SEQ ID NO 298
<211> LENGTH: 53
<212> TYPE: DNA
<213> ORGANISM: Artificial Sequence
<220> FEATURE:
<223> OTHER INFORMATION: synthetic_EMX1_16 2nd PCR forward(5' to 3')

<400> SEQUENCE: 298
acactctttc cctacacgac gctcttccga tctaaggcta gcccagagtc tcc                53

<210> SEQ ID NO 299
<211> LENGTH: 54
<212> TYPE: DNA
<213> ORGANISM: Artificial Sequence
<220> FEATURE:
<223> OTHER INFORMATION: synthetic_EMX1_16 2nd PCR reverse(5' to 3')

<400> SEQUENCE: 299
gtgactggag ttcagacgtg tgctcttccg atctttcatc cttttgtggg gttc               54

<210> SEQ ID NO 300
<211> LENGTH: 24
<212> TYPE: DNA
<213> ORGANISM: Artificial Sequence
<220> FEATURE:
<223> OTHER INFORMATION: synthetic_EMX1_17 1st PCR forward(5' to 3')

<400> SEQUENCE: 300
ggaatcaatc aatgaagttg aaga                                                24

<210> SEQ ID NO 301
<211> LENGTH: 58
<212> TYPE: DNA
<213> ORGANISM: Artificial Sequence
<220> FEATURE:
<223> OTHER INFORMATION: synthetic_EMX1_17 1st PCR reverse(5' to 3')

<400> SEQUENCE: 301
gtgactggag ttcagacgtg tgctcttccg atcttttgca atttgcttag ttattgaa           58

<210> SEQ ID NO 302
<211> LENGTH: 55
<212> TYPE: DNA
<213> ORGANISM: Artificial Sequence
<220> FEATURE:
<223> OTHER INFORMATION: synthetic_EMX1_17 2nd PCR forward(5' to 3')

<400> SEQUENCE: 302
acactctttc cctacacgac gctcttccga tctgcaatct gaagaacaaa gagca              55

<210> SEQ ID NO 303
<211> LENGTH: 58
<212> TYPE: DNA
<213> ORGANISM: Artificial Sequence
<220> FEATURE:
<223> OTHER INFORMATION: synthetic_EMX1_17 2nd PCR reverse(5' to 3')

<400> SEQUENCE: 303
gtgactggag ttcagacgtg tgctcttccg atcttttgca atttgcttag ttattgaa           58

<210> SEQ ID NO 304
<211> LENGTH: 58
<212> TYPE: DNA
<213> ORGANISM: Artificial Sequence
<220> FEATURE:
<223> OTHER INFORMATION: synthetic_EMX1_18 1st PCR forward(5' to 3')

```
<400> SEQUENCE: 304
acactctttc cctacacgac gctcttccga tcttgacatt tgatagaaca gatgggta        58

<210> SEQ ID NO 305
<211> LENGTH: 26
<212> TYPE: DNA
<213> ORGANISM: Artificial Sequence
<220> FEATURE:
<223> OTHER INFORMATION: synthetic_EMX1_18 1st PCR reverse(5' to 3')

<400> SEQUENCE: 305
tcaagagact gttgttttag attgtc                                          26

<210> SEQ ID NO 306
<211> LENGTH: 58
<212> TYPE: DNA
<213> ORGANISM: Artificial Sequence
<220> FEATURE:
<223> OTHER INFORMATION: synthetic_EMX1_18 2nd PCR forward(5' to 3')

<400> SEQUENCE: 306
acactctttc cctacacgac gctcttccga tcttgacatt tgatagaaca gatgggta        58

<210> SEQ ID NO 307
<211> LENGTH: 54
<212> TYPE: DNA
<213> ORGANISM: Artificial Sequence
<220> FEATURE:
<223> OTHER INFORMATION: synthetic_EMX1_18 2nd PCR reverse(5' to 3')

<400> SEQUENCE: 307
gtgactggag ttcagacgtg tgctcttccg atctcccagt ccaatggctg tagt            54

<210> SEQ ID NO 308
<211> LENGTH: 20
<212> TYPE: DNA
<213> ORGANISM: Artificial Sequence
<220> FEATURE:
<223> OTHER INFORMATION: synthetic_EMX1_19 1st PCR forward(5' to 3')

<400> SEQUENCE: 308
ccctgcaaat tgagtacgtg                                                 20

<210> SEQ ID NO 309
<211> LENGTH: 54
<212> TYPE: DNA
<213> ORGANISM: Artificial Sequence
<220> FEATURE:
<223> OTHER INFORMATION: synthetic_EMX1_19 1st PCR reverse(5' to 3')

<400> SEQUENCE: 309
gtgactggag ttcagacgtg tgctcttccg atctgtcccg aagtgctgga atta            54

<210> SEQ ID NO 310
<211> LENGTH: 54
<212> TYPE: DNA
<213> ORGANISM: Artificial Sequence
<220> FEATURE:
<223> OTHER INFORMATION: synthetic_EMX1_19 2nd PCR forward(5' to 3')

<400> SEQUENCE: 310
acactctttc cctacacgac gctcttccga tcttgggggc cattctttat agtt            54

<210> SEQ ID NO 311
```

```
<211> LENGTH: 54
<212> TYPE: DNA
<213> ORGANISM: Artificial Sequence
<220> FEATURE:
<223> OTHER INFORMATION: synthetic_EMX1_19 2nd PCR reverse(5' to 3')

<400> SEQUENCE: 311
gtgactggag ttcagacgtg tgctcttccg atctgtcccg aagtgctgga atta            54

<210> SEQ ID NO 312
<211> LENGTH: 20
<212> TYPE: DNA
<213> ORGANISM: Artificial Sequence
<220> FEATURE:
<223> OTHER INFORMATION: synthetic_EMX1_20 1st PCR forward(5' to 3')

<400> SEQUENCE: 312
gacagtcctg ggctaggtga                                                  20

<210> SEQ ID NO 313
<211> LENGTH: 54
<212> TYPE: DNA
<213> ORGANISM: Artificial Sequence
<220> FEATURE:
<223> OTHER INFORMATION: synthetic_EMX1_20 1st PCR reverse(5' to 3')

<400> SEQUENCE: 313
gtgactggag ttcagacgtg tgctcttccg atctctctgg actcagctcc catc            54

<210> SEQ ID NO 314
<211> LENGTH: 53
<212> TYPE: DNA
<213> ORGANISM: Artificial Sequence
<220> FEATURE:
<223> OTHER INFORMATION: synthetic_EMX1_20 2nd PCR forward(5' to 3')

<400> SEQUENCE: 314
acactctttc cctacacgac gctcttccga tctgagagtc aggagtgccc agt             53

<210> SEQ ID NO 315
<211> LENGTH: 54
<212> TYPE: DNA
<213> ORGANISM: Artificial Sequence
<220> FEATURE:
<223> OTHER INFORMATION: synthetic_EMX1_20 2nd PCR reverse(5' to 3')

<400> SEQUENCE: 315
gtgactggag ttcagacgtg tgctcttccg atctctctgg actcagctcc catc            54

<210> SEQ ID NO 316
<211> LENGTH: 55
<212> TYPE: DNA
<213> ORGANISM: Artificial Sequence
<220> FEATURE:
<223> OTHER INFORMATION: synthetic_EMX1_21 1st PCR forward(5' to 3')

<400> SEQUENCE: 316
acactctttc cctacacgac gctcttccga tctcctctca tttctaccac cattg           55

<210> SEQ ID NO 317
<211> LENGTH: 20
<212> TYPE: DNA
<213> ORGANISM: Artificial Sequence
<220> FEATURE:
<223> OTHER INFORMATION: synthetic_EMX1_21 1st PCR reverse(5' to 3')

<400> SEQUENCE: 317
```

```
agatgaatgc agggagctgt                                           20

<210> SEQ ID NO 318
<211> LENGTH: 55
<212> TYPE: DNA
<213> ORGANISM: Artificial Sequence
<220> FEATURE:
<223> OTHER INFORMATION: synthetic_EMX1_21 2nd PCR forward(5' to 3')

<400> SEQUENCE: 318
acactctttc cctacacgac gctcttccga tctcctctca tttctaccac cattg    55

<210> SEQ ID NO 319
<211> LENGTH: 60
<212> TYPE: DNA
<213> ORGANISM: Artificial Sequence
<220> FEATURE:
<223> OTHER INFORMATION: synthetic_EMX1_21 2nd PCR reverse(5' to 3')

<400> SEQUENCE: 319
gtgactggag ttcagacgtg tgctcttccg atctttctga attaaaaatg gaaagaactg  60

<210> SEQ ID NO 320
<211> LENGTH: 27
<212> TYPE: DNA
<213> ORGANISM: Artificial Sequence
<220> FEATURE:
<223> OTHER INFORMATION: synthetic_EMX1_22 1st PCR forward(5' to 3')

<400> SEQUENCE: 320
acaatttcag tagtagcatt aaggaat                                   27

<210> SEQ ID NO 321
<211> LENGTH: 54
<212> TYPE: DNA
<213> ORGANISM: Artificial Sequence
<220> FEATURE:
<223> OTHER INFORMATION: synthetic_EMX1_22 1st PCR reverse(5' to 3')

<400> SEQUENCE: 321
gtgactggag ttcagacgtg tgctcttccg atctttgtga caaactgccc tctg     54

<210> SEQ ID NO 322
<211> LENGTH: 53
<212> TYPE: DNA
<213> ORGANISM: Artificial Sequence
<220> FEATURE:
<223> OTHER INFORMATION: synthetic_EMX1_22 2nd PCR forward(5' to 3')

<400> SEQUENCE: 322
acactctttc cctacacgac gctcttccga tctgaatgcc agttctgggt tgt      53

<210> SEQ ID NO 323
<211> LENGTH: 54
<212> TYPE: DNA
<213> ORGANISM: Artificial Sequence
<220> FEATURE:
<223> OTHER INFORMATION: synthetic_EMX1_22 2nd PCR reverse(5' to 3')

<400> SEQUENCE: 323
gtgactggag ttcagacgtg tgctcttccg atctttgtga caaactgccc tctg     54

<210> SEQ ID NO 324
<211> LENGTH: 55
<212> TYPE: DNA
```

```
<213> ORGANISM: Artificial Sequence
<220> FEATURE:
<223> OTHER INFORMATION: synthetic_EMX1_23 1st PCR forward(5' to 3')

<400> SEQUENCE: 324
acactctttc cctacacgac gctcttccga tctaatttct gaacccaaag acagg      55

<210> SEQ ID NO 325
<211> LENGTH: 26
<212> TYPE: DNA
<213> ORGANISM: Artificial Sequence
<220> FEATURE:
<223> OTHER INFORMATION: synthetic_EMX1_23 1st PCR reverse(5' to 3')

<400> SEQUENCE: 325
caaaaatcaa ctcaagatgg attaaa                                       26

<210> SEQ ID NO 326
<211> LENGTH: 55
<212> TYPE: DNA
<213> ORGANISM: Artificial Sequence
<220> FEATURE:
<223> OTHER INFORMATION: synthetic_EMX1_23 2nd PCR forward(5' to 3')

<400> SEQUENCE: 326
acactctttc cctacacgac gctcttccga tctaatttct gaacccaaag acagg      55

<210> SEQ ID NO 327
<211> LENGTH: 58
<212> TYPE: DNA
<213> ORGANISM: Artificial Sequence
<220> FEATURE:
<223> OTHER INFORMATION: synthetic_EMX1_23 2nd PCR reverse(5' to 3')

<400> SEQUENCE: 327
gtgactggag ttcagacgtg tgctcttccg atctgagaac ctagggaaaa ctcttctg   58

<210> SEQ ID NO 328
<211> LENGTH: 57
<212> TYPE: DNA
<213> ORGANISM: Artificial Sequence
<220> FEATURE:
<223> OTHER INFORMATION: synthetic_EMX1_24 1st PCR forward(5' to 3')

<400> SEQUENCE: 328
acactctttc cctacacgac gctcttccga tctccaagct atttaactgg tatgcac    57

<210> SEQ ID NO 329
<211> LENGTH: 22
<212> TYPE: DNA
<213> ORGANISM: Artificial Sequence
<220> FEATURE:
<223> OTHER INFORMATION: synthetic_EMX1_24 1st PCR reverse(5' to 3')

<400> SEQUENCE: 329
cttgtggatc atgggtactg ag                                           22

<210> SEQ ID NO 330
<211> LENGTH: 57
<212> TYPE: DNA
<213> ORGANISM: Artificial Sequence
<220> FEATURE:
<223> OTHER INFORMATION: synthetic_EMX1_24 2nd PCR forward(5' to 3')

<400> SEQUENCE: 330
acactctttc cctacacgac gctcttccga tctccaagct atttaactgg tatgcac    57
```

<210> SEQ ID NO 331
<211> LENGTH: 54
<212> TYPE: DNA
<213> ORGANISM: Artificial Sequence
<220> FEATURE:
<223> OTHER INFORMATION: synthetic_EMX1_24 2nd PCR reverse(5' to 3')

<400> SEQUENCE: 331
gtgactggag ttcagacgtg tgctcttccg atcttgggcc ttggtattag agca        54

<210> SEQ ID NO 332
<211> LENGTH: 57
<212> TYPE: DNA
<213> ORGANISM: Artificial Sequence
<220> FEATURE:
<223> OTHER INFORMATION: synthetic_EMX1_25 1st PCR forward(5' to 3')

<400> SEQUENCE: 332
acactctttc cctacacgac gctcttccga tcttcaaggg ggtatataaa aggaaga     57

<210> SEQ ID NO 333
<211> LENGTH: 26
<212> TYPE: DNA
<213> ORGANISM: Artificial Sequence
<220> FEATURE:
<223> OTHER INFORMATION: synthetic_EMX1_25 1st PCR reverse(5' to 3')

<400> SEQUENCE: 333 tgcttttttca cttgtctagt tttctt                                      26

<210> SEQ ID NO 334
<211> LENGTH: 57
<212> TYPE: DNA
<213> ORGANISM: Artificial Sequence
<220> FEATURE:
<223> OTHER INFORMATION: synthetic_EMX1_25 2nd PCR forward(5' to 3')

<400> SEQUENCE: 334
acactctttc cctacacgac gctcttccga tcttcaaggg ggtatataaa aggaaga     57

<210> SEQ ID NO 335
<211> LENGTH: 55
<212> TYPE: DNA
<213> ORGANISM: Artificial Sequence
<220> FEATURE:
<223> OTHER INFORMATION: synthetic_EMX1_25 2nd PCR reverse(5' to 3')

<400> SEQUENCE: 335
gtgactggag ttcagacgtg tgctcttccg atctaacaat ttcccacaaa gtcca       55

<210> SEQ ID NO 336
<211> LENGTH: 20
<212> TYPE: DNA
<213> ORGANISM: Artificial Sequence
<220> FEATURE:
<223> OTHER INFORMATION: synthetic_FANCF_1 1st PCR forward(5' to 3')

<400> SEQUENCE: 336
ctgaaggtgc tggtttaggg                                              20

<210> SEQ ID NO 337
<211> LENGTH: 54
<212> TYPE: DNA
<213> ORGANISM: Artificial Sequence
<220> FEATURE:

<223> OTHER INFORMATION: synthetic_FANCF_1 1st PCR reverse(5' to 3')

<400> SEQUENCE: 337
gtgactggag ttcagacgtg tgctcttccg atcttgtctg attgagtccc caca 54

<210> SEQ ID NO 338
<211> LENGTH: 54
<212> TYPE: DNA
<213> ORGANISM: Artificial Sequence
<220> FEATURE:
<223> OTHER INFORMATION: synthetic_FANCF_1 2nd PCR forward(5' to 3')

<400> SEQUENCE: 338
acactctttc cctacacgac gctcttccga tcttgacatc cagggtttca agtc 54

<210> SEQ ID NO 339
<211> LENGTH: 54
<212> TYPE: DNA
<213> ORGANISM: Artificial Sequence
<220> FEATURE:
<223> OTHER INFORMATION: synthetic_FANCF_1 2nd PCR reverse(5' to 3')

<400> SEQUENCE: 339
gtgactggag ttcagacgtg tgctcttccg atcttgtctg attgagtccc caca 54

<210> SEQ ID NO 340
<211> LENGTH: 52
<212> TYPE: DNA
<213> ORGANISM: Artificial Sequence
<220> FEATURE:
<223> OTHER INFORMATION: synthetic_FANCF_2 (on target) 1st PCR
      forward(5' to 3')

<400> SEQUENCE: 340
acactctttc cctacacgac gctcttccga tctatggatg tggcgcaggt ag 52

<210> SEQ ID NO 341
<211> LENGTH: 20
<212> TYPE: DNA
<213> ORGANISM: Artificial Sequence
<220> FEATURE:
<223> OTHER INFORMATION: synthetic_FANCF_2 (on target) 1st PCR
      reverse(5' to 3')

<400> SEQUENCE: 341
tgacatgcat ttcgaccaat 20

<210> SEQ ID NO 342
<211> LENGTH: 52
<212> TYPE: DNA
<213> ORGANISM: Artificial Sequence
<220> FEATURE:
<223> OTHER INFORMATION: synthetic_FANCF_2 (on target) 2nd PCR
      forward(5' to 3')

<400> SEQUENCE: 342
acactctttc cctacacgac gctcttccga tctatggatg tggcgcaggt ag 52

<210> SEQ ID NO 343
<211> LENGTH: 54
<212> TYPE: DNA
<213> ORGANISM: Artificial Sequence
<220> FEATURE:
<223> OTHER INFORMATION: synthetic_FANCF_2 (on target) 2nd PCR
      reverse(5' to 3')

<400> SEQUENCE: 343
gtgactggag ttcagacgtg tgctcttccg atctagcatt gcagagaggc gtat            54

<210> SEQ ID NO 344
<211> LENGTH: 20
<212> TYPE: DNA
<213> ORGANISM: Artificial Sequence
<220> FEATURE:
<223> OTHER INFORMATION: synthetic_FANCF_3 1st PCR forward(5' to 3')

<400> SEQUENCE: 344
cctcagggat ggatgaagtg            20

<210> SEQ ID NO 345
<211> LENGTH: 54
<212> TYPE: DNA
<213> ORGANISM: Artificial Sequence
<220> FEATURE:
<223> OTHER INFORMATION: synthetic_FANCF_3 1st PCR reverse(5' to 3')

<400> SEQUENCE: 345
gtgactggag ttcagacgtg tgctcttccg atcttcccag tgagaccagt ttga            54

<210> SEQ ID NO 346
<211> LENGTH: 53
<212> TYPE: DNA
<213> ORGANISM: Artificial Sequence
<220> FEATURE:
<223> OTHER INFORMATION: synthetic_FANCF_3 2nd PCR forward(5' to 3')

<400> SEQUENCE: 346
acactctttc cctacacgac gctcttccga tctcccttac cagatggagg aca            53

<210> SEQ ID NO 347
<211> LENGTH: 54
<212> TYPE: DNA
<213> ORGANISM: Artificial Sequence
<220> FEATURE:
<223> OTHER INFORMATION: synthetic_FANCF_3 2nd PCR reverse(5' to 3')

<400> SEQUENCE: 347
gtgactggag ttcagacgtg tgctcttccg atcttcccag tgagaccagt ttga            54

<210> SEQ ID NO 348
<211> LENGTH: 20
<212> TYPE: DNA
<213> ORGANISM: Artificial Sequence
<220> FEATURE:
<223> OTHER INFORMATION: synthetic_FANCF_4 1st PCR forward(5' to 3')

<400> SEQUENCE: 348
cccttaccag atggaggaca            20

<210> SEQ ID NO 349
<211> LENGTH: 54
<212> TYPE: DNA
<213> ORGANISM: Artificial Sequence
<220> FEATURE:
<223> OTHER INFORMATION: synthetic_FANCF_4 1st PCR reverse(5' to 3')

<400> SEQUENCE: 349
gtgactggag ttcagacgtg tgctcttccg atctaccttg agttttgccc agtg            54

<210> SEQ ID NO 350
<211> LENGTH: 53
<212> TYPE: DNA

```
<213> ORGANISM: Artificial Sequence
<220> FEATURE:
<223> OTHER INFORMATION: synthetic_FANCF_4 2nd PCR forward(5' to 3')

<400> SEQUENCE: 350
acactctttc cctacacgac gctcttccga tctgtgaccc aggtccagtg ttt          53

<210> SEQ ID NO 351
<211> LENGTH: 54
<212> TYPE: DNA
<213> ORGANISM: Artificial Sequence
<220> FEATURE:
<223> OTHER INFORMATION: synthetic_FANCF_4 2nd PCR reverse(5' to 3')

<400> SEQUENCE: 351
gtgactggag ttcagacgtg tgctcttccg atctaccttg agttttgccc agtg         54

<210> SEQ ID NO 352
<211> LENGTH: 21
<212> TYPE: DNA
<213> ORGANISM: Artificial Sequence
<220> FEATURE:
<223> OTHER INFORMATION: synthetic_FANCF_5 1st PCR forward(5' to 3')

<400> SEQUENCE: 352
agctttaaaa tggggaatcc a                                             21

<210> SEQ ID NO 353
<211> LENGTH: 54
<212> TYPE: DNA
<213> ORGANISM: Artificial Sequence
<220> FEATURE:
<223> OTHER INFORMATION: synthetic_FANCF_5 1st PCR reverse(5' to 3')

<400> SEQUENCE: 353
gtgactggag ttcagacgtg tgctcttccg atctttccca gcactgttct gttg         54

<210> SEQ ID NO 354
<211> LENGTH: 53
<212> TYPE: DNA
<213> ORGANISM: Artificial Sequence
<220> FEATURE:
<223> OTHER INFORMATION: synthetic_FANCF_5 2nd PCR forward(5' to 3')

<400> SEQUENCE: 354
acactctttc cctacacgac gctcttccga tctctccagt acaggggctt ttg          53

<210> SEQ ID NO 355
<211> LENGTH: 54
<212> TYPE: DNA
<213> ORGANISM: Artificial Sequence
<220> FEATURE:
<223> OTHER INFORMATION: synthetic_FANCF_5 2nd PCR reverse(5' to 3')

<400> SEQUENCE: 355
gtgactggag ttcagacgtg tgctcttccg atctttccca gcactgttct gttg         54

<210> SEQ ID NO 356
<211> LENGTH: 20
<212> TYPE: DNA
<213> ORGANISM: Artificial Sequence
<220> FEATURE:
<223> OTHER INFORMATION: synthetic_FANCF_6 1st PCR forward(5' to 3')

<400> SEQUENCE: 356
acacagggtg cagtggtaca                                               20
```

<210> SEQ ID NO 357
<211> LENGTH: 54
<212> TYPE: DNA
<213> ORGANISM: Artificial Sequence
<220> FEATURE:
<223> OTHER INFORMATION: synthetic_FANCF_6 1st PCR reverse(5' to 3')

<400> SEQUENCE: 357
gtgactggag ttcagacgtg tgctcttccg atcttgggga gtatccttgc aatc    54

<210> SEQ ID NO 358
<211> LENGTH: 53
<212> TYPE: DNA
<213> ORGANISM: Artificial Sequence
<220> FEATURE:
<223> OTHER INFORMATION: synthetic_FANCF_6 2nd PCR forward(5' to 3')

<400> SEQUENCE: 358
acactctttc cctacacgac gctcttccga tctaggtgct tctgcaggtc atc    53

<210> SEQ ID NO 359
<211> LENGTH: 54
<212> TYPE: DNA
<213> ORGANISM: Artificial Sequence
<220> FEATURE:
<223> OTHER INFORMATION: synthetic_FANCF_6 2nd PCR reverse(5' to 3')

<400> SEQUENCE: 359
gtgactggag ttcagacgtg tgctcttccg atcttgggga gtatccttgc aatc    54

<210> SEQ ID NO 360
<211> LENGTH: 20
<212> TYPE: DNA
<213> ORGANISM: Artificial Sequence
<220> FEATURE:
<223> OTHER INFORMATION: synthetic_FANCF_7 1st PCR forward(5' to 3')

<400> SEQUENCE: 360
acgccagcac tttctaagga    20

<210> SEQ ID NO 361
<211> LENGTH: 54
<212> TYPE: DNA
<213> ORGANISM: Artificial Sequence
<220> FEATURE:
<223> OTHER INFORMATION: synthetic_FANCF_7 1st PCR reverse(5' to 3')

<400> SEQUENCE: 361
gtgactggag ttcagacgtg tgctcttccg atctcacaga ttgatgccac tgga    54

<210> SEQ ID NO 362
<211> LENGTH: 54
<212> TYPE: DNA
<213> ORGANISM: Artificial Sequence
<220> FEATURE:
<223> OTHER INFORMATION: synthetic_FANCF_7 2nd PCR forward(5' to 3')

<400> SEQUENCE: 362
acactctttc cctacacgac gctcttccga tctgcctgct gcactctctg agta    54

<210> SEQ ID NO 363
<211> LENGTH: 54
<212> TYPE: DNA
<213> ORGANISM: Artificial Sequence
<220> FEATURE:

<223> OTHER INFORMATION: synthetic_FANCF_7 2nd PCR reverse(5' to 3')

<400> SEQUENCE: 363
gtgactggag ttcagacgtg tgctcttccg atctcacaga ttgatgccac tgga     54

<210> SEQ ID NO 364
<211> LENGTH: 54
<212> TYPE: DNA
<213> ORGANISM: Artificial Sequence
<220> FEATURE:
<223> OTHER INFORMATION: synthetic_FANCF_8 1st PCR forward(5' to 3')

<400> SEQUENCE: 364
acactctttc cctacacgac gctcttccga tcttttcctc aacctttcct gctg     54

<210> SEQ ID NO 365
<211> LENGTH: 18
<212> TYPE: DNA
<213> ORGANISM: Artificial Sequence
<220> FEATURE:
<223> OTHER INFORMATION: synthetic_FANCF_8 1st PCR reverse(5' to 3')

<400> SEQUENCE: 365
acacctccga ggccttct     18

<210> SEQ ID NO 366
<211> LENGTH: 54
<212> TYPE: DNA
<213> ORGANISM: Artificial Sequence
<220> FEATURE:
<223> OTHER INFORMATION: synthetic_FANCF_8 2nd PCR forward(5' to 3')

<400> SEQUENCE: 366
acactctttc cctacacgac gctcttccga tcttttcctc aacctttcct gctg     54

<210> SEQ ID NO 367
<211> LENGTH: 54
<212> TYPE: DNA
<213> ORGANISM: Artificial Sequence
<220> FEATURE:
<223> OTHER INFORMATION: synthetic_FANCF_8 2nd PCR reverse(5' to 3')

<400> SEQUENCE: 367
gtgactggag ttcagacgtg tgctcttccg atctcaggtc ctcctctccc agtt     54

<210> SEQ ID NO 368
<211> LENGTH: 58
<212> TYPE: DNA
<213> ORGANISM: Artificial Sequence
<220> FEATURE:
<223> OTHER INFORMATION: synthetic_FANCF_9 1st PCR forward(5' to 3')

<400> SEQUENCE: 368
acactctttc cctacacgac gctcttccga tctcctgaat aactaaatga caacatgg     58

<210> SEQ ID NO 369
<211> LENGTH: 20
<212> TYPE: DNA
<213> ORGANISM: Artificial Sequence
<220> FEATURE:
<223> OTHER INFORMATION: synthetic_FANCF_9 1st PCR reverse(5' to 3')

<400> SEQUENCE: 369
gccaggattt cctcaaacaa     20

```
<210> SEQ ID NO 370
<211> LENGTH: 58
<212> TYPE: DNA
<213> ORGANISM: Artificial Sequence
<220> FEATURE:
<223> OTHER INFORMATION: synthetic_FANCF_9 2nd PCR forward(5' to 3')

<400> SEQUENCE: 370
acactctttc cctacacgac gctcttccga tctcctgaat aactaaatga caacatgg        58

<210> SEQ ID NO 371
<211> LENGTH: 54
<212> TYPE: DNA
<213> ORGANISM: Artificial Sequence
<220> FEATURE:
<223> OTHER INFORMATION: synthetic_FANCF_9 2nd PCR reverse(5' to 3')

<400> SEQUENCE: 371
gtgactggag ttcagacgtg tgctcttccg atctgccaag ttcccataag caaa           54

<210> SEQ ID NO 372
<211> LENGTH: 20
<212> TYPE: DNA
<213> ORGANISM: Artificial Sequence
<220> FEATURE:
<223> OTHER INFORMATION: synthetic_FANCF_10 1st PCR forward(5' to 3')

<400> SEQUENCE: 372
gctctcaaat ggctccaaac                                                 20

<210> SEQ ID NO 373
<211> LENGTH: 55
<212> TYPE: DNA
<213> ORGANISM: Artificial Sequence
<220> FEATURE:
<223> OTHER INFORMATION: synthetic_FANCF_10 1st PCR reverse(5' to 3')

<400> SEQUENCE: 373
gtgactggag ttcagacgtg tgctcttccg atctcagagt ggcctgctta caatc          55

<210> SEQ ID NO 374
<211> LENGTH: 53
<212> TYPE: DNA
<213> ORGANISM: Artificial Sequence
<220> FEATURE:
<223> OTHER INFORMATION: synthetic_FANCF_10 2nd PCR forward(5' to 3')

<400> SEQUENCE: 374
acactctttc cctacacgac gctcttccga tcttcctcca tctcattccc atc            53

<210> SEQ ID NO 375
<211> LENGTH: 55
<212> TYPE: DNA
<213> ORGANISM: Artificial Sequence
<220> FEATURE:
<223> OTHER INFORMATION: synthetic_FANCF_10 2nd PCR reverse(5' to 3')

<400> SEQUENCE: 375
gtgactggag ttcagacgtg tgctcttccg atctcagagt ggcctgctta caatc          55

<210> SEQ ID NO 376
<211> LENGTH: 20
<212> TYPE: DNA
<213> ORGANISM: Artificial Sequence
<220> FEATURE:
<223> OTHER INFORMATION: synthetic_FANCF_11 1st PCR forward(5' to 3')
```

<400> SEQUENCE: 376
gccgagaatt accacgacat                                              20

<210> SEQ ID NO 377
<211> LENGTH: 54
<212> TYPE: DNA
<213> ORGANISM: Artificial Sequence
<220> FEATURE:
<223> OTHER INFORMATION: synthetic_FANCF_11 1st PCR reverse(5' to 3')

<400> SEQUENCE: 377
gtgactggag ttcagacgtg tgctcttccg atctggcaca cagctgtacg tagg         54

<210> SEQ ID NO 378
<211> LENGTH: 53
<212> TYPE: DNA
<213> ORGANISM: Artificial Sequence
<220> FEATURE:
<223> OTHER INFORMATION: synthetic_FANCF_11 2nd PCR forward(5' to 3')

<400> SEQUENCE: 378
acactctttc cctacacgac gctcttccga tcttcacagc gaggaaggac aat          53

<210> SEQ ID NO 379
<211> LENGTH: 54
<212> TYPE: DNA
<213> ORGANISM: Artificial Sequence
<220> FEATURE:
<223> OTHER INFORMATION: synthetic_FANCF_11 2nd PCR reverse(5' to 3')

<400> SEQUENCE: 379
gtgactggag ttcagacgtg tgctcttccg atctggcaca cagctgtacg tagg         54

<210> SEQ ID NO 380
<211> LENGTH: 53
<212> TYPE: DNA
<213> ORGANISM: Artificial Sequence
<220> FEATURE:
<223> OTHER INFORMATION: synthetic_FANCF_12 1st PCR forward(5' to 3')

<400> SEQUENCE: 380
acactctttc cctacacgac gctcttccga tctggagctc tcagttggac tgg          53

<210> SEQ ID NO 381
<211> LENGTH: 20
<212> TYPE: DNA
<213> ORGANISM: Artificial Sequence
<220> FEATURE:
<223> OTHER INFORMATION: synthetic_FANCF_12 1st PCR reverse(5' to 3')

<400> SEQUENCE: 381
ctcctcagtg ggtgaagtcc                                              20

<210> SEQ ID NO 382
<211> LENGTH: 53
<212> TYPE: DNA
<213> ORGANISM: Artificial Sequence
<220> FEATURE:
<223> OTHER INFORMATION: synthetic_FANCF_12 2nd PCR forward(5' to 3')

<400> SEQUENCE: 382
acactctttc cctacacgac gctcttccga tctggagctc tcagttggac tgg          53

<210> SEQ ID NO 383
<211> LENGTH: 54

<212> TYPE: DNA
<213> ORGANISM: Artificial Sequence
<220> FEATURE:
<223> OTHER INFORMATION: synthetic_FANCF_12 2nd PCR reverse(5' to 3')

<400> SEQUENCE: 383
gtgactggag ttcagacgtg tgctcttccg atctacggag aggtcacatg aagg        54

<210> SEQ ID NO 384
<211> LENGTH: 23
<212> TYPE: DNA
<213> ORGANISM: Artificial Sequence
<220> FEATURE:
<223> OTHER INFORMATION: synthetic_FANCF_13 1st PCR forward(5' to 3')

<400> SEQUENCE: 384
tgaaaagcag tctaggacac aaa        23

<210> SEQ ID NO 385
<211> LENGTH: 54
<212> TYPE: DNA
<213> ORGANISM: Artificial Sequence
<220> FEATURE:
<223> OTHER INFORMATION: synthetic_FANCF_13 1st PCR reverse(5' to 3')

<400> SEQUENCE: 385
gtgactggag ttcagacgtg tgctcttccg atctcaactc tgccatgtgc ctta        54

<210> SEQ ID NO 386
<211> LENGTH: 53
<212> TYPE: DNA
<213> ORGANISM: Artificial Sequence
<220> FEATURE:
<223> OTHER INFORMATION: synthetic_FANCF_13 2nd PCR forward(5' to 3')

<400> SEQUENCE: 386
acactctttc cctacacgac gctcttccga tcttggcagg ctaggtttag agc        53

<210> SEQ ID NO 387
<211> LENGTH: 54
<212> TYPE: DNA
<213> ORGANISM: Artificial Sequence
<220> FEATURE:
<223> OTHER INFORMATION: synthetic_FANCF_13 2nd PCR reverse(5' to 3')

<400> SEQUENCE: 387
gtgactggag ttcagacgtg tgctcttccg atctcaactc tgccatgtgc ctta        54

<210> SEQ ID NO 388
<211> LENGTH: 27
<212> TYPE: DNA
<213> ORGANISM: Artificial Sequence
<220> FEATURE:
<223> OTHER INFORMATION: synthetic_FANCF_14 1st PCR forward(5' to 3')

<400> SEQUENCE: 388
cacatatgaa atattaaatt tgaacca        27

<210> SEQ ID NO 389
<211> LENGTH: 60
<212> TYPE: DNA
<213> ORGANISM: Artificial Sequence
<220> FEATURE:
<223> OTHER INFORMATION: synthetic_FANCF_14 1st PCR reverse(5' to 3')

<400> SEQUENCE: 389
gtgactggag ttcagacgtg tgctcttccg atctgggaat atagaaaaat caagagatgg    60

<210> SEQ ID NO 390
<211> LENGTH: 55
<212> TYPE: DNA
<213> ORGANISM: Artificial Sequence
<220> FEATURE:
<223> OTHER INFORMATION: synthetic_FANCF_14 2nd PCR forward(5' to 3')

<400> SEQUENCE: 390
acactctttc cctacacgac gctcttccga tcttgaacca tgttaccttt tgacc    55

<210> SEQ ID NO 391
<211> LENGTH: 60
<212> TYPE: DNA
<213> ORGANISM: Artificial Sequence
<220> FEATURE:
<223> OTHER INFORMATION: synthetic_FANCF_14 2nd PCR reverse(5' to 3')

<400> SEQUENCE: 391
gtgactggag ttcagacgtg tgctcttccg atctgggaat atagaaaaat caagagatgg    60

<210> SEQ ID NO 392
<211> LENGTH: 20
<212> TYPE: DNA
<213> ORGANISM: Artificial Sequence
<220> FEATURE:
<223> OTHER INFORMATION: synthetic_FANCF_15 1st PCR forward(5' to 3')

<400> SEQUENCE: 392
cgtcttcgct ctttggtttt    20

<210> SEQ ID NO 393
<211> LENGTH: 56
<212> TYPE: DNA
<213> ORGANISM: Artificial Sequence
<220> FEATURE:
<223> OTHER INFORMATION: synthetic_FANCF_15 1st PCR reverse(5' to 3')

<400> SEQUENCE: 393
gtgactggag ttcagacgtg tgctcttccg atctcaccct gtagatctct ctcacg    56

<210> SEQ ID NO 394
<211> LENGTH: 55
<212> TYPE: DNA
<213> ORGANISM: Artificial Sequence
<220> FEATURE:
<223> OTHER INFORMATION: synthetic_FANCF_15 2nd PCR forward(5' to 3')

<400> SEQUENCE: 394
acactctttc cctacacgac gctcttccga tcttgtggca catagtcgta acctc    55

<210> SEQ ID NO 395
<211> LENGTH: 56
<212> TYPE: DNA
<213> ORGANISM: Artificial Sequence
<220> FEATURE:
<223> OTHER INFORMATION: synthetic_FANCF_15 2nd PCR reverse(5' to 3')

<400> SEQUENCE: 395
gtgactggag ttcagacgtg tgctcttccg atctcaccct gtagatctct ctcacg    56

<210> SEQ ID NO 396
<211> LENGTH: 20
<212> TYPE: DNA
<213> ORGANISM: Artificial Sequence
<220> FEATURE:
<223> OTHER INFORMATION: synthetic_RNF2_1 (on target) 1st PCR forward(5'
      to 3')

<400> SEQUENCE: 396
ccatagcact tcccttccaa                                                   20

<210> SEQ ID NO 397
<211> LENGTH: 56
<212> TYPE: DNA
<213> ORGANISM: Artificial Sequence
<220> FEATURE:
<223> OTHER INFORMATION: synthetic_RNF2_1 (on target) 1st PCR reverse(5'
      to 3')

<400> SEQUENCE: 397
gtgactggag ttcagacgtg tgctcttccg atctgccaac atacagaagt caggaa          56

<210> SEQ ID NO 398
<211> LENGTH: 53
<212> TYPE: DNA
<213> ORGANISM: Artificial Sequence
<220> FEATURE:
<223> OTHER INFORMATION: synthetic_RNF2_1 (on target) 2nd PCR forward(5'
      to 3')

<400> SEQUENCE: 398
acactctttc cctacacgac gctcttccga tctatttcca gcaatgtctc agg             53

<210> SEQ ID NO 399
<211> LENGTH: 56
<212> TYPE: DNA
<213> ORGANISM: Artificial Sequence
<220> FEATURE:
<223> OTHER INFORMATION: synthetic_RNF2_1 (on target) 2nd PCR reverse(5'
      to 3')

<400> SEQUENCE: 399
gtgactggag ttcagacgtg tgctcttccg atctgccaac atacagaagt caggaa          56

<210> SEQ ID NO 400
<211> LENGTH: 21
<212> TYPE: DNA
<213> ORGANISM: Artificial Sequence
<220> FEATURE:
<223> OTHER INFORMATION: synthetic_HBB_1 (on target) 1st PCR forward(5'
      to 3')

<400> SEQUENCE: 400
ggcagagaga gtcagtgcct a                                                 21

<210> SEQ ID NO 401
<211> LENGTH: 53
<212> TYPE: DNA
<213> ORGANISM: Artificial Sequence
<220> FEATURE:
<223> OTHER INFORMATION: synthetic_HBB_1 (on target) 1st PCR reverse(5'
      to 3')

<400> SEQUENCE: 401
gtgactggag ttcagacgtg tgctcttccg atctcagggc tgggcataaa agt             53

<210> SEQ ID NO 402
<211> LENGTH: 53
<212> TYPE: DNA
<213> ORGANISM: Artificial Sequence
<220> FEATURE:

```
<223> OTHER INFORMATION: synthetic_HBB_1 (on target) 2nd PCR forward(5'
      to 3')

<400> SEQUENCE: 402
acactctttc cctacacgac gctcttccga tctgtctcca catgcccagt ttc      53

<210> SEQ ID NO 403
<211> LENGTH: 53
<212> TYPE: DNA
<213> ORGANISM: Artificial Sequence
<220> FEATURE:
<223> OTHER INFORMATION: synthetic_HBB_1 (on target) 2nd PCR reverse(5'
      to 3')

<400> SEQUENCE: 403
gtgactggag ttcagacgtg tgctcttccg atctcagggc tgggcataaa agt      53

<210> SEQ ID NO 404
<211> LENGTH: 53
<212> TYPE: DNA
<213> ORGANISM: Artificial Sequence
<220> FEATURE:
<223> OTHER INFORMATION: synthetic_HBB_2 1st PCR forward(5' to 3')

<400> SEQUENCE: 404
acactctttc cctacacgac gctcttccga tctcctacag cctgcgagga ata      53

<210> SEQ ID NO 405
<211> LENGTH: 19
<212> TYPE: DNA
<213> ORGANISM: Artificial Sequence
<220> FEATURE:
<223> OTHER INFORMATION: synthetic_HBB_2 1st PCR reverse(5' to 3')

<400> SEQUENCE: 405
gtgggtgtcc tgggttgtt                                             19

<210> SEQ ID NO 406
<211> LENGTH: 53
<212> TYPE: DNA
<213> ORGANISM: Artificial Sequence
<220> FEATURE:
<223> OTHER INFORMATION: synthetic_HBB_2 2nd PCR forward(5' to 3')

<400> SEQUENCE: 406
acactctttc cctacacgac gctcttccga tctcctacag cctgcgagga ata      53

<210> SEQ ID NO 407
<211> LENGTH: 53
<212> TYPE: DNA
<213> ORGANISM: Artificial Sequence
<220> FEATURE:
<223> OTHER INFORMATION: synthetic_HBB_2 2nd PCR reverse(5' to 3')

<400> SEQUENCE: 407
gtgactggag ttcagacgtg tgctcttccg atctcacctg gaggctaggc act      53

<210> SEQ ID NO 408
<211> LENGTH: 20
<212> TYPE: DNA
<213> ORGANISM: Artificial Sequence
<220> FEATURE:
<223> OTHER INFORMATION: synthetic_HBB_3 1st PCR forward(5' to 3')

<400> SEQUENCE: 408
cccacacagg ttttctcctc                                            20
```

-continued

<210> SEQ ID NO 409
<211> LENGTH: 54
<212> TYPE: DNA
<213> ORGANISM: Artificial Sequence
<220> FEATURE:
<223> OTHER INFORMATION: synthetic_HBB_3 1st PCR reverse(5' to 3')

<400> SEQUENCE: 409
gtgactggag ttcagacgtg tgctcttccg atctctaggc cttcacctgg aacc        54

<210> SEQ ID NO 410
<211> LENGTH: 53
<212> TYPE: DNA
<213> ORGANISM: Artificial Sequence
<220> FEATURE:
<223> OTHER INFORMATION: synthetic_HBB_3 2nd PCR forward(5' to 3')

<400> SEQUENCE: 410
acactctttc cctacacgac gctcttccga tctcttccct agacctgcct cct         53

<210> SEQ ID NO 411
<211> LENGTH: 54
<212> TYPE: DNA
<213> ORGANISM: Artificial Sequence
<220> FEATURE:
<223> OTHER INFORMATION: synthetic_HBB_3 2nd PCR reverse(5' to 3')

<400> SEQUENCE: 411
gtgactggag ttcagacgtg tgctcttccg atctctaggc cttcacctgg aacc        54

<210> SEQ ID NO 412
<211> LENGTH: 54
<212> TYPE: DNA
<213> ORGANISM: Artificial Sequence
<220> FEATURE:
<223> OTHER INFORMATION: synthetic_HBB_4 1st PCR forward(5' to 3')

<400> SEQUENCE: 412
acactctttc cctacacgac gctcttccga tctttgtgta acagccactc acca        54

<210> SEQ ID NO 413
<211> LENGTH: 24
<212> TYPE: DNA
<213> ORGANISM: Artificial Sequence
<220> FEATURE:
<223> OTHER INFORMATION: synthetic_HBB_4 1st PCR reverse(5' to 3')

<400> SEQUENCE: 413
cagaaaataa agcagctgac tcac                                        24

<210> SEQ ID NO 414
<211> LENGTH: 54
<212> TYPE: DNA
<213> ORGANISM: Artificial Sequence
<220> FEATURE:
<223> OTHER INFORMATION: synthetic_HBB_4 2nd PCR forward(5' to 3')

<400> SEQUENCE: 414
acactctttc cctacacgac gctcttccga tctttgtgta acagccactc acca        54

<210> SEQ ID NO 415
<211> LENGTH: 54
<212> TYPE: DNA
<213> ORGANISM: Artificial Sequence
<220> FEATURE:

```
<223> OTHER INFORMATION: synthetic_HBB_4 2nd PCR reverse(5' to 3')

<400> SEQUENCE: 415
gtgactggag ttcagacgtg tgctcttccg atctcctggc aaaagtgttt ggat        54

<210> SEQ ID NO 416
<211> LENGTH: 24
<212> TYPE: DNA
<213> ORGANISM: Artificial Sequence
<220> FEATURE:
<223> OTHER INFORMATION: synthetic_HBB_5 1st PCR forward(5' to 3')

<400> SEQUENCE: 416
tttgcattcc ttttagcttc tttt                                         24

<210> SEQ ID NO 417
<211> LENGTH: 56
<212> TYPE: DNA
<213> ORGANISM: Artificial Sequence
<220> FEATURE:
<223> OTHER INFORMATION: synthetic_HBB_5 1st PCR reverse(5' to 3')

<400> SEQUENCE: 417
gtgactggag ttcagacgtg tgctcttccg atctagctac cacggtgaca gtaaca      56

<210> SEQ ID NO 418
<211> LENGTH: 53
<212> TYPE: DNA
<213> ORGANISM: Artificial Sequence
<220> FEATURE:
<223> OTHER INFORMATION: synthetic_HBB_5 2nd PCR forward(5' to 3')

<400> SEQUENCE: 418
acactctttc cctacacgac gctcttccga tctatggctg ttattcaggg aaa         53

<210> SEQ ID NO 419
<211> LENGTH: 56
<212> TYPE: DNA
<213> ORGANISM: Artificial Sequence
<220> FEATURE:
<223> OTHER INFORMATION: synthetic_HBB_5 2nd PCR reverse(5' to 3')

<400> SEQUENCE: 419
gtgactggag ttcagacgtg tgctcttccg atctagctac cacggtgaca gtaaca      56

<210> SEQ ID NO 420
<211> LENGTH: 57
<212> TYPE: DNA
<213> ORGANISM: Artificial Sequence
<220> FEATURE:
<223> OTHER INFORMATION: synthetic_HBB_6 1st PCR forward(5' to 3')

<400> SEQUENCE: 420
acactctttc cctacacgac gctcttccga tcttccactt tgttagtcag gagattc     57

<210> SEQ ID NO 421
<211> LENGTH: 25
<212> TYPE: DNA
<213> ORGANISM: Artificial Sequence
<220> FEATURE:
<223> OTHER INFORMATION: synthetic_HBB_6 1st PCR reverse(5' to 3')

<400> SEQUENCE: 421
aaatggtaaa aagaaactca aatgc                                        25
```

```
<210> SEQ ID NO 422
<211> LENGTH: 57
<212> TYPE: DNA
<213> ORGANISM: Artificial Sequence
<220> FEATURE:
<223> OTHER INFORMATION: synthetic_HBB_6 2nd PCR forward(5' to 3')

<400> SEQUENCE: 422
acactctttc cctacacgac gctcttccga tcttccactt tgttagtcag gagattc        57

<210> SEQ ID NO 423
<211> LENGTH: 54
<212> TYPE: DNA
<213> ORGANISM: Artificial Sequence
<220> FEATURE:
<223> OTHER INFORMATION: synthetic_HBB_6 2nd PCR reverse(5' to 3')

<400> SEQUENCE: 423
gtgactggag ttcagacgtg tgctcttccg atctggatac cactgggctt ctga           54

<210> SEQ ID NO 424
<211> LENGTH: 27
<212> TYPE: DNA
<213> ORGANISM: Artificial Sequence
<220> FEATURE:
<223> OTHER INFORMATION: synthetic_HBB_7 1st PCR forward(5' to 3')

<400> SEQUENCE: 424
ttcaaatctg gaaataatc tatcacc                                          27

<210> SEQ ID NO 425
<211> LENGTH: 54
<212> TYPE: DNA
<213> ORGANISM: Artificial Sequence
<220> FEATURE:
<223> OTHER INFORMATION: synthetic_HBB_7 1st PCR reverse(5' to 3')

<400> SEQUENCE: 425
gtgactggag ttcagacgtg tgctcttccg atctatttcc aggctatgct tcca           54

<210> SEQ ID NO 426
<211> LENGTH: 53
<212> TYPE: DNA
<213> ORGANISM: Artificial Sequence
<220> FEATURE:
<223> OTHER INFORMATION: synthetic_HBB_7 2nd PCR forward(5' to 3')

<400> SEQUENCE: 426
acactctttc cctacacgac gctcttccga tcttttcata ccctttcccg ttc            53

<210> SEQ ID NO 427
<211> LENGTH: 54
<212> TYPE: DNA
<213> ORGANISM: Artificial Sequence
<220> FEATURE:
<223> OTHER INFORMATION: synthetic_HBB_7 2nd PCR reverse(5' to 3')

<400> SEQUENCE: 427
gtgactggag ttcagacgtg tgctcttccg atctatttcc aggctatgct tcca           54

<210> SEQ ID NO 428
<211> LENGTH: 54
<212> TYPE: DNA
<213> ORGANISM: Artificial Sequence
<220> FEATURE:
<223> OTHER INFORMATION: synthetic_HEK2_1 1st PCR forward(5' to 3')
```

<400> SEQUENCE: 428
acactctttc cctacacgac gctcttccga tctcgtacta tgcaagccac attg    54

<210> SEQ ID NO 429
<211> LENGTH: 24
<212> TYPE: DNA
<213> ORGANISM: Artificial Sequence
<220> FEATURE:
<223> OTHER INFORMATION: synthetic_HEK2_1 1st PCR reverse(5' to 3')

<400> SEQUENCE: 429
ttttcttgtg aaacagaaat gtca    24

<210> SEQ ID NO 430
<211> LENGTH: 54
<212> TYPE: DNA
<213> ORGANISM: Artificial Sequence
<220> FEATURE:
<223> OTHER INFORMATION: synthetic_HEK2_1 2nd PCR forward(5' to 3')

<400> SEQUENCE: 430
acactctttc cctacacgac gctcttccga tctcgtacta tgcaagccac attg    54

<210> SEQ ID NO 431
<211> LENGTH: 54
<212> TYPE: DNA
<213> ORGANISM: Artificial Sequence
<220> FEATURE:
<223> OTHER INFORMATION: synthetic_HEK2_1 2nd PCR reverse(5' to 3')

<400> SEQUENCE: 431
gtgactggag ttcagacgtg tgctcttccg atctaatgct cccacaccat tttt    54

<210> SEQ ID NO 432
<211> LENGTH: 53
<212> TYPE: DNA
<213> ORGANISM: Artificial Sequence
<220> FEATURE:
<223> OTHER INFORMATION: synthetic_HEK2_2 (on target) 1st PCR forward(5'
      to 3')

<400> SEQUENCE: 432
acactctttc cctacacgac gctcttccga tctaggacgt ctgcccaata tgt    53

<210> SEQ ID NO 433
<211> LENGTH: 20
<212> TYPE: DNA
<213> ORGANISM: Artificial Sequence
<220> FEATURE:
<223> OTHER INFORMATION: synthetic_HEK2_2 (on target) 1st PCR reverse(5'
      to 3')

<400> SEQUENCE: 433
ttcccaagtg agaagccagt    20

<210> SEQ ID NO 434
<211> LENGTH: 53
<212> TYPE: DNA
<213> ORGANISM: Artificial Sequence
<220> FEATURE:
<223> OTHER INFORMATION: synthetic_HEK2_2 (on target) 2nd PCR forward(5'
      to 3')

<400> SEQUENCE: 434
acactctttc cctacacgac gctcttccga tctaggacgt ctgcccaata tgt    53

<210> SEQ ID NO 435
<211> LENGTH: 54
<212> TYPE: DNA
<213> ORGANISM: Artificial Sequence
<220> FEATURE:
<223> OTHER INFORMATION: synthetic_HEK2_2 (on target) 2nd PCR reverse(5'
      to 3')

<400> SEQUENCE: 435
gtgactggag ttcagacgtg tgctcttccg atctaaaatt gtccagcccc atct            54

<210> SEQ ID NO 436
<211> LENGTH: 27
<212> TYPE: DNA
<213> ORGANISM: Artificial Sequence
<220> FEATURE:
<223> OTHER INFORMATION: synthetic_HEK2_3 1st PCR forward(5' to 3')

<400> SEQUENCE: 436
atttacaaaa cttaggagaa tcaaagg                                         27

<210> SEQ ID NO 437
<211> LENGTH: 55
<212> TYPE: DNA
<213> ORGANISM: Artificial Sequence
<220> FEATURE:
<223> OTHER INFORMATION: synthetic_HEK2_3 1st PCR reverse(5' to 3')

<400> SEQUENCE: 437
gtgactggag ttcagacgtg tgctcttccg atctcagctg ctgttatcct tcctc          55

<210> SEQ ID NO 438
<211> LENGTH: 53
<212> TYPE: DNA
<213> ORGANISM: Artificial Sequence
<220> FEATURE:
<223> OTHER INFORMATION: synthetic_HEK2_3 2nd PCR forward(5' to 3')

<400> SEQUENCE: 438
acactctttc cctacacgac gctcttccga tcttcaaagg aaaagcaacg tga            53

<210> SEQ ID NO 439
<211> LENGTH: 55
<212> TYPE: DNA
<213> ORGANISM: Artificial Sequence
<220> FEATURE:
<223> OTHER INFORMATION: synthetic_HEK2_3 2nd PCR reverse(5' to 3')

<400> SEQUENCE: 439
gtgactggag ttcagacgtg tgctcttccg atctcagctg ctgttatcct tcctc          55

<210> SEQ ID NO 440
<211> LENGTH: 23
<212> TYPE: DNA
<213> ORGANISM: Artificial Sequence
<220> FEATURE:
<223> OTHER INFORMATION: synthetic_HEK3_1 1st PCR forward(5' to 3')

<400> SEQUENCE: 440
gcagttgctt gactagaggt agc                                             23

<210> SEQ ID NO 441
<211> LENGTH: 54
<212> TYPE: DNA
<213> ORGANISM: Artificial Sequence
<220> FEATURE:

<223> OTHER INFORMATION: synthetic_HEK3_1 1st PCR reverse(5' to 3')

<400> SEQUENCE: 441
gtgactggag ttcagacgtg tgctcttccg atctagtgat gtgggaggtt cctg      54

<210> SEQ ID NO 442
<211> LENGTH: 53
<212> TYPE: DNA
<213> ORGANISM: Artificial Sequence
<220> FEATURE:
<223> OTHER INFORMATION: synthetic_HEK3_1 2nd PCR forward(5' to 3')

<400> SEQUENCE: 442
acactctttc cctacacgac gctcttccga tcttccagat tcctggtcca aag       53

<210> SEQ ID NO 443
<211> LENGTH: 54
<212> TYPE: DNA
<213> ORGANISM: Artificial Sequence
<220> FEATURE:
<223> OTHER INFORMATION: synthetic_HEK3_1 2nd PCR reverse(5' to 3')

<400> SEQUENCE: 443
gtgactggag ttcagacgtg tgctcttccg atctagtgat gtgggaggtt cctg      54

<210> SEQ ID NO 444
<211> LENGTH: 20
<212> TYPE: DNA
<213> ORGANISM: Artificial Sequence
<220> FEATURE:
<223> OTHER INFORMATION: synthetic_HEK3_2 (on target) 1st PCR forward(5'
      to 3')

<400> SEQUENCE: 444
aaggcatgga tgagagaagc                                             20

<210> SEQ ID NO 445
<211> LENGTH: 53
<212> TYPE: DNA
<213> ORGANISM: Artificial Sequence
<220> FEATURE:
<223> OTHER INFORMATION: synthetic_HEK3_2 (on target) 1st PCR reverse(5'
      to 3')

<400> SEQUENCE: 445
gtgactggag ttcagacgtg tgctcttccg atctctccct aggtgctggc ttc        53

<210> SEQ ID NO 446
<211> LENGTH: 53
<212> TYPE: DNA
<213> ORGANISM: Artificial Sequence
<220> FEATURE:
<223> OTHER INFORMATION: synthetic_HEK3_2 (on target) 2nd PCR forward(5'
      to 3')

<400> SEQUENCE: 446
acactctttc cctacacgac gctcttccga tctaaacgcc catgcaatta gtc        53

<210> SEQ ID NO 447
<211> LENGTH: 53
<212> TYPE: DNA
<213> ORGANISM: Artificial Sequence
<220> FEATURE:
<223> OTHER INFORMATION: synthetic_HEK3_2 (on target) 2nd PCR reverse(5'
      to 3')

<400> SEQUENCE: 447

```
gtgactggag ttcagacgtg tgctcttccg atctctccct aggtgctggc ttc            53
```

<210> SEQ ID NO 448
<211> LENGTH: 20
<212> TYPE: DNA
<213> ORGANISM: Artificial Sequence
<220> FEATURE:
<223> OTHER INFORMATION: synthetic_HEK3_3 1st PCR forward(5' to 3')

<400> SEQUENCE: 448

```
ctcaggaggc tgaggtagga                                                 20
```

<210> SEQ ID NO 449
<211> LENGTH: 53
<212> TYPE: DNA
<213> ORGANISM: Artificial Sequence
<220> FEATURE:
<223> OTHER INFORMATION: synthetic_HEK3_3 1st PCR reverse(5' to 3')

<400> SEQUENCE: 449

```
gtgactggag ttcagacgtg tgctcttccg atctacgtgt ctgcggttag cag            53
```

<210> SEQ ID NO 450
<211> LENGTH: 53
<212> TYPE: DNA
<213> ORGANISM: Artificial Sequence
<220> FEATURE:
<223> OTHER INFORMATION: synthetic_HEK3_3 2nd PCR forward(5' to 3')

<400> SEQUENCE: 450

```
acactctttc cctacacgac gctcttccga tctaggaaga tgaggctgca gtg            53
```

<210> SEQ ID NO 451
<211> LENGTH: 53
<212> TYPE: DNA
<213> ORGANISM: Artificial Sequence
<220> FEATURE:
<223> OTHER INFORMATION: synthetic_HEK3_3 2nd PCR reverse(5' to 3')

<400> SEQUENCE: 451

```
gtgactggag ttcagacgtg tgctcttccg atctacgtgt ctgcggttag cag            53
```

<210> SEQ ID NO 452
<211> LENGTH: 20
<212> TYPE: DNA
<213> ORGANISM: Artificial Sequence
<220> FEATURE:
<223> OTHER INFORMATION: synthetic_HEK3_4 1st PCR forward(5' to 3')

<400> SEQUENCE: 452

```
ttatgcggca aaacaaaatg                                                 20
```

<210> SEQ ID NO 453
<211> LENGTH: 54
<212> TYPE: DNA
<213> ORGANISM: Artificial Sequence
<220> FEATURE:
<223> OTHER INFORMATION: synthetic_HEK3_4 1st PCR reverse(5' to 3')

<400> SEQUENCE: 453

```
gtgactggag ttcagacgtg tgctcttccg atcttcgtcg ctgacaattt ctga           54
```

<210> SEQ ID NO 454
<211> LENGTH: 53
<212> TYPE: DNA

```
<213> ORGANISM: Artificial Sequence
<220> FEATURE:
<223> OTHER INFORMATION: synthetic_HEK3_4 2nd PCR forward(5' to 3')

<400> SEQUENCE: 454
acactctttc cctacacgac gctcttccga tctgatctca tccctgttg acc         53

<210> SEQ ID NO 455
<211> LENGTH: 54
<212> TYPE: DNA
<213> ORGANISM: Artificial Sequence
<220> FEATURE:
<223> OTHER INFORMATION: synthetic_HEK3_4 2nd PCR reverse(5' to 3')

<400> SEQUENCE: 455
gtgactggag ttcagacgtg tgctcttccg atcttcgtcg ctgacaattt ctga        54

<210> SEQ ID NO 456
<211> LENGTH: 20
<212> TYPE: DNA
<213> ORGANISM: Artificial Sequence
<220> FEATURE:
<223> OTHER INFORMATION: synthetic_HEK3_5 1st PCR forward(5' to 3')

<400> SEQUENCE: 456
tgttatcaac tggggggttgc                                              20

<210> SEQ ID NO 457
<211> LENGTH: 54
<212> TYPE: DNA
<213> ORGANISM: Artificial Sequence
<220> FEATURE:
<223> OTHER INFORMATION: synthetic_HEK3_5 1st PCR reverse(5' to 3')

<400> SEQUENCE: 457
gtgactggag ttcagacgtg tgctcttccg atcttccttc atggactggt aggc        54

<210> SEQ ID NO 458
<211> LENGTH: 53
<212> TYPE: DNA
<213> ORGANISM: Artificial Sequence
<220> FEATURE:
<223> OTHER INFORMATION: synthetic_HEK3_5 2nd PCR forward(5' to 3')

<400> SEQUENCE: 458
acactctttc cctacacgac gctcttccga tctagagggg catctcgtgt aga         53

<210> SEQ ID NO 459
<211> LENGTH: 54
<212> TYPE: DNA
<213> ORGANISM: Artificial Sequence
<220> FEATURE:
<223> OTHER INFORMATION: synthetic_HEK3_5 2nd PCR reverse(5' to 3')

<400> SEQUENCE: 459
gtgactggag ttcagacgtg tgctcttccg atcttccttc atggactggt aggc        54

<210> SEQ ID NO 460
<211> LENGTH: 53
<212> TYPE: DNA
<213> ORGANISM: Artificial Sequence
<220> FEATURE:
<223> OTHER INFORMATION: synthetic_HEK3_6 1st PCR forward(5' to 3')

<400> SEQUENCE: 460
acactctttc cctacacgac gctcttccga tcttgtgtgc atggttcatc tcc         53
```

<210> SEQ ID NO 461
<211> LENGTH: 23
<212> TYPE: DNA
<213> ORGANISM: Artificial Sequence
<220> FEATURE:
<223> OTHER INFORMATION: synthetic_HEK3_6 1st PCR reverse(5' to 3')

<400> SEQUENCE: 461
aagctatgat gtgatgtgac tgg                                              23

<210> SEQ ID NO 462
<211> LENGTH: 53
<212> TYPE: DNA
<213> ORGANISM: Artificial Sequence
<220> FEATURE:
<223> OTHER INFORMATION: synthetic_HEK3_6 2nd PCR forward(5' to 3')

<400> SEQUENCE: 462
acactctttc cctacacgac gctcttccga tcttgtgtgc atggttcatc tcc             53

<210> SEQ ID NO 463
<211> LENGTH: 54
<212> TYPE: DNA
<213> ORGANISM: Artificial Sequence
<220> FEATURE:
<223> OTHER INFORMATION: synthetic_HEK3_6 2nd PCR reverse(5' to 3')

<400> SEQUENCE: 463
gtgactggag ttcagacgtg tgctcttccg atctcatggt gtctcacccc tgta            54

<210> SEQ ID NO 464
<211> LENGTH: 20
<212> TYPE: DNA
<213> ORGANISM: Artificial Sequence
<220> FEATURE:
<223> OTHER INFORMATION: synthetic_HEK3_7 1st PCR forward(5' to 3')

<400> SEQUENCE: 464
gccatgatcc tcgtgatttt                                                  20

<210> SEQ ID NO 465
<211> LENGTH: 54
<212> TYPE: DNA
<213> ORGANISM: Artificial Sequence
<220> FEATURE:
<223> OTHER INFORMATION: synthetic_HEK3_7 1st PCR reverse(5' to 3')

<400> SEQUENCE: 465
gtgactggag ttcagacgtg tgctcttccg atctacttac cgaaggcagg gact            54

<210> SEQ ID NO 466
<211> LENGTH: 56
<212> TYPE: DNA
<213> ORGANISM: Artificial Sequence
<220> FEATURE:
<223> OTHER INFORMATION: synthetic_HEK3_7 2nd PCR forward(5' to 3')

<400> SEQUENCE: 466
acactctttc cctacacgac gctcttccga tcttctcatg ctgtcttgga taaaca          56

<210> SEQ ID NO 467
<211> LENGTH: 54
<212> TYPE: DNA
<213> ORGANISM: Artificial Sequence
<220> FEATURE:

<223> OTHER INFORMATION: synthetic_HEK3_7 2nd PCR reverse(5' to 3')

<400> SEQUENCE: 467
gtgactggag ttcagacgtg tgctcttccg atctacttac cgaaggcagg gact        54

<210> SEQ ID NO 468
<211> LENGTH: 53
<212> TYPE: DNA
<213> ORGANISM: Artificial Sequence
<220> FEATURE:
<223> OTHER INFORMATION: synthetic_HEK4_1 (on target) 1st PCR forward(5' to 3')

<400> SEQUENCE: 468
acactctttc cctacacgac gctcttccga tctctccctt caagatggct gac         53

<210> SEQ ID NO 469
<211> LENGTH: 20
<212> TYPE: DNA
<213> ORGANISM: Artificial Sequence
<220> FEATURE:
<223> OTHER INFORMATION: synthetic_HEK4_1 (on target) 1st PCR reverse(5' to 3')

<400> SEQUENCE: 469
gacgtccaaa accagactcc        20

<210> SEQ ID NO 470
<211> LENGTH: 53
<212> TYPE: DNA
<213> ORGANISM: Artificial Sequence
<220> FEATURE:
<223> OTHER INFORMATION: synthetic_HEK4_1 (on target) 2nd PCR forward(5' to 3')

<400> SEQUENCE: 470
acactctttc cctacacgac gctcttccga tctctccctt caagatggct gac         53

<210> SEQ ID NO 471
<211> LENGTH: 53
<212> TYPE: DNA
<213> ORGANISM: Artificial Sequence
<220> FEATURE:
<223> OTHER INFORMATION: synthetic_HEK4_1 (on target) 2nd PCR reverse(5' to 3')

<400> SEQUENCE: 471
gtgactggag ttcagacgtg tgctcttccg atctactcct tctggggcct ttt         53

<210> SEQ ID NO 472
<211> LENGTH: 20
<212> TYPE: DNA
<213> ORGANISM: Artificial Sequence
<220> FEATURE:
<223> OTHER INFORMATION: synthetic_HEK4_2 1st PCR forward(5' to 3')

<400> SEQUENCE: 472
tccccaatgt tttcttgtga        20

<210> SEQ ID NO 473
<211> LENGTH: 55
<212> TYPE: DNA
<213> ORGANISM: Artificial Sequence
<220> FEATURE:
<223> OTHER INFORMATION: synthetic_HEK4_2 1st PCR reverse(5' to 3')

<400> SEQUENCE: 473
gtgactggag ttcagacgtg tgctcttccg atctgattac acagaggagg cacca    55

<210> SEQ ID NO 474
<211> LENGTH: 53
<212> TYPE: DNA
<213> ORGANISM: Artificial Sequence
<220> FEATURE:
<223> OTHER INFORMATION: synthetic_HEK4_2 2nd PCR forward(5' to 3')

<400> SEQUENCE: 474
acactctttc cctacacgac gctcttccga tcttagaagc ggaccccaca tag    53

<210> SEQ ID NO 475
<211> LENGTH: 55
<212> TYPE: DNA
<213> ORGANISM: Artificial Sequence
<220> FEATURE:
<223> OTHER INFORMATION: synthetic_HEK4_2 2nd PCR reverse(5' to 3')

<400> SEQUENCE: 475
gtgactggag ttcagacgtg tgctcttccg atctgattac acagaggagg cacca    55

<210> SEQ ID NO 476
<211> LENGTH: 20
<212> TYPE: DNA
<213> ORGANISM: Artificial Sequence
<220> FEATURE:
<223> OTHER INFORMATION: synthetic_HEK4_3 1st PCR forward(5' to 3')

<400> SEQUENCE: 476
tgagagaaca tggtgctttg    20

<210> SEQ ID NO 477
<211> LENGTH: 54
<212> TYPE: DNA
<213> ORGANISM: Artificial Sequence
<220> FEATURE:
<223> OTHER INFORMATION: synthetic_HEK4_3 1st PCR reverse(5' to 3')

<400> SEQUENCE: 477
gtgactggag ttcagacgtg tgctcttccg atctaggctg tggtagggac tcac    54

<210> SEQ ID NO 478
<211> LENGTH: 53
<212> TYPE: DNA
<213> ORGANISM: Artificial Sequence
<220> FEATURE:
<223> OTHER INFORMATION: synthetic_HEK4_3 2nd PCR forward(5' to 3')

<400> SEQUENCE: 478
acactctttc cctacacgac gctcttccga tctgaatgtg dacagcattg cat    53

<210> SEQ ID NO 479
<211> LENGTH: 54
<212> TYPE: DNA
<213> ORGANISM: Artificial Sequence
<220> FEATURE:
<223> OTHER INFORMATION: synthetic_HEK4_3 2nd PCR reverse(5' to 3')

<400> SEQUENCE: 479
gtgactggag ttcagacgtg tgctcttccg atctaggctg tggtagggac tcac    54

<210> SEQ ID NO 480
<211> LENGTH: 53
<212> TYPE: DNA

```
<213> ORGANISM: Artificial Sequence
<220> FEATURE:
<223> OTHER INFORMATION: synthetic_HEK4_4 1st PCR forward(5' to 3')

<400> SEQUENCE: 480
acactctttc cctacacgac gctcttccga tctccagaag agtgtggtgc agt         53

<210> SEQ ID NO 481
<211> LENGTH: 20
<212> TYPE: DNA
<213> ORGANISM: Artificial Sequence
<220> FEATURE:
<223> OTHER INFORMATION: synthetic_HEK4_4 1st PCR reverse(5' to 3')

<400> SEQUENCE: 481
aaccaacatg gtgggacact                                              20

<210> SEQ ID NO 482
<211> LENGTH: 53
<212> TYPE: DNA
<213> ORGANISM: Artificial Sequence
<220> FEATURE:
<223> OTHER INFORMATION: synthetic_HEK4_4 2nd PCR forward(5' to 3')

<400> SEQUENCE: 482
acactctttc cctacacgac gctcttccga tctccagaag agtgtggtgc agt         53

<210> SEQ ID NO 483
<211> LENGTH: 54
<212> TYPE: DNA
<213> ORGANISM: Artificial Sequence
<220> FEATURE:
<223> OTHER INFORMATION: synthetic_HEK4_4 2nd PCR reverse(5' to 3')

<400> SEQUENCE: 483
gtgactggag ttcagacgtg tgctcttccg atctaggctg tggtgaagag gatg        54

<210> SEQ ID NO 484
<211> LENGTH: 21
<212> TYPE: DNA
<213> ORGANISM: Artificial Sequence
<220> FEATURE:
<223> OTHER INFORMATION: synthetic_HEK4_5 1st PCR forward(5' to 3')

<400> SEQUENCE: 484
ggagttaggc gtagcttcag g                                            21

<210> SEQ ID NO 485
<211> LENGTH: 54
<212> TYPE: DNA
<213> ORGANISM: Artificial Sequence
<220> FEATURE:
<223> OTHER INFORMATION: synthetic_HEK4_5 1st PCR reverse(5' to 3')

<400> SEQUENCE: 485
gtgactggag ttcagacgtg tgctcttccg atctcctggc acagaccttc ctaa        54

<210> SEQ ID NO 486
<211> LENGTH: 53
<212> TYPE: DNA
<213> ORGANISM: Artificial Sequence
<220> FEATURE:
<223> OTHER INFORMATION: synthetic_HEK4_5 2nd PCR forward(5' to 3')

<400> SEQUENCE: 486
acactctttc cctacacgac gctcttccga tctaatccaa tcaatgggag cat         53
```

<210> SEQ ID NO 487
<211> LENGTH: 54
<212> TYPE: DNA
<213> ORGANISM: Artificial Sequence
<220> FEATURE:
<223> OTHER INFORMATION: synthetic_HEK4_5 2nd PCR reverse(5' to 3')

<400> SEQUENCE: 487
gtgactggag ttcagacgtg tgctcttccg atctcctggc acagaccttc ctaa            54

<210> SEQ ID NO 488
<211> LENGTH: 53
<212> TYPE: DNA
<213> ORGANISM: Artificial Sequence
<220> FEATURE:
<223> OTHER INFORMATION: synthetic_HEK4_6 1st PCR forward(5' to 3')

<400> SEQUENCE: 488
acactctttc cctacacgac gctcttccga tctaaagccc agctctgctg ata             53

<210> SEQ ID NO 489
<211> LENGTH: 20
<212> TYPE: DNA
<213> ORGANISM: Artificial Sequence
<220> FEATURE:
<223> OTHER INFORMATION: synthetic_HEK4_6 1st PCR reverse(5' to 3')

<400> SEQUENCE: 489
gctggtcatg cagtgtctgt                                                  20

<210> SEQ ID NO 490
<211> LENGTH: 53
<212> TYPE: DNA
<213> ORGANISM: Artificial Sequence
<220> FEATURE:
<223> OTHER INFORMATION: synthetic_HEK4_6 2nd PCR forward(5' to 3')

<400> SEQUENCE: 490
acactctttc cctacacgac gctcttccga tctaaagccc agctctgctg ata             53

<210> SEQ ID NO 491
<211> LENGTH: 53
<212> TYPE: DNA
<213> ORGANISM: Artificial Sequence
<220> FEATURE:
<223> OTHER INFORMATION: synthetic_HEK4_6 2nd PCR reverse(5' to 3')

<400> SEQUENCE: 491
gtgactggag ttcagacgtg tgctcttccg atctccccat ttctgcctga ttt             53

<210> SEQ ID NO 492
<211> LENGTH: 52
<212> TYPE: DNA
<213> ORGANISM: Artificial Sequence
<220> FEATURE:
<223> OTHER INFORMATION: synthetic_HEK4_7 1st PCR forward(5' to 3')

<400> SEQUENCE: 492
acactctttc cctacacgac gctcttccga tctgggcatg gcttctgaga ct              52

<210> SEQ ID NO 493
<211> LENGTH: 18
<212> TYPE: DNA
<213> ORGANISM: Artificial Sequence
<220> FEATURE:

-continued

<223> OTHER INFORMATION: synthetic_HEK4_7 1st PCR reverse(5' to 3')

<400> SEQUENCE: 493
tgggctcaac ccaggtgt                                                         18

<210> SEQ ID NO 494
<211> LENGTH: 52
<212> TYPE: DNA
<213> ORGANISM: Artificial Sequence
<220> FEATURE:
<223> OTHER INFORMATION: synthetic_HEK4_7 2nd PCR forward(5' to 3')

<400> SEQUENCE: 494
acactctttc cctacacgac gctcttccga tctgggcatg gcttctgaga ct                   52

<210> SEQ ID NO 495
<211> LENGTH: 55
<212> TYPE: DNA
<213> ORGANISM: Artificial Sequence
<220> FEATURE:
<223> OTHER INFORMATION: synthetic_HEK4_7 2nd PCR reverse(5' to 3')

<400> SEQUENCE: 495
gtgactggag ttcagacgtg tgctcttccg atctccggat gattctccta cttcc               55

<210> SEQ ID NO 496
<211> LENGTH: 53
<212> TYPE: DNA
<213> ORGANISM: Artificial Sequence
<220> FEATURE:
<223> OTHER INFORMATION: synthetic_HEK4_8 1st PCR forward(5' to 3')

<400> SEQUENCE: 496
acactctttc cctacacgac gctcttccga tctgccaact agaggcagac agg                 53

<210> SEQ ID NO 497
<211> LENGTH: 20
<212> TYPE: DNA
<213> ORGANISM: Artificial Sequence
<220> FEATURE:
<223> OTHER INFORMATION: synthetic_HEK4_8 1st PCR reverse(5' to 3')

<400> SEQUENCE: 497
agttgtgggg ttttctgctg                                                      20

<210> SEQ ID NO 498
<211> LENGTH: 53
<212> TYPE: DNA
<213> ORGANISM: Artificial Sequence
<220> FEATURE:
<223> OTHER INFORMATION: synthetic_HEK4_8 2nd PCR forward(5' to 3')

<400> SEQUENCE: 498
acactctttc cctacacgac gctcttccga tctgccaact agaggcagac agg                 53

<210> SEQ ID NO 499
<211> LENGTH: 54
<212> TYPE: DNA
<213> ORGANISM: Artificial Sequence
<220> FEATURE:
<223> OTHER INFORMATION: synthetic_HEK4_8 2nd PCR reverse(5' to 3')

<400> SEQUENCE: 499
gtgactggag ttcagacgtg tgctcttccg atctattctg gaggcaactc ctca                54

```
<210> SEQ ID NO 500
<211> LENGTH: 20
<212> TYPE: DNA
<213> ORGANISM: Artificial Sequence
<220> FEATURE:
<223> OTHER INFORMATION: synthetic_HEK4_9 1st PCR forward(5' to 3')

<400> SEQUENCE: 500
ggcaaaaccc attccagaag                                               20

<210> SEQ ID NO 501
<211> LENGTH: 54
<212> TYPE: DNA
<213> ORGANISM: Artificial Sequence
<220> FEATURE:
<223> OTHER INFORMATION: synthetic_HEK4_9 1st PCR reverse(5' to 3')

<400> SEQUENCE: 501
gtgactggag ttcagacgtg tgctcttccg atcttgttag gagctcccca tcac         54

<210> SEQ ID NO 502
<211> LENGTH: 53
<212> TYPE: DNA
<213> ORGANISM: Artificial Sequence
<220> FEATURE:
<223> OTHER INFORMATION: synthetic_HEK4_9 2nd PCR forward(5' to 3')

<400> SEQUENCE: 502
acactctttc cctacacgac gctcttccga tctaccacgt caggacttgt gtg          53

<210> SEQ ID NO 503
<211> LENGTH: 54
<212> TYPE: DNA
<213> ORGANISM: Artificial Sequence
<220> FEATURE:
<223> OTHER INFORMATION: synthetic_HEK4_9 2nd PCR reverse(5' to 3')

<400> SEQUENCE: 503
gtgactggag ttcagacgtg tgctcttccg atcttgttag gagctcccca tcac         54

<210> SEQ ID NO 504
<211> LENGTH: 20
<212> TYPE: DNA
<213> ORGANISM: Artificial Sequence
<220> FEATURE:
<223> OTHER INFORMATION: synthetic_HEK4_10 1st PCR forward(5' to 3')

<400> SEQUENCE: 504
atgttagccg ggatggtcta                                               20

<210> SEQ ID NO 505
<211> LENGTH: 55
<212> TYPE: DNA
<213> ORGANISM: Artificial Sequence
<220> FEATURE:
<223> OTHER INFORMATION: synthetic_HEK4_10 1st PCR reverse(5' to 3')

<400> SEQUENCE: 505
gtgactggag ttcagacgtg tgctcttccg atcttccagg gtatcaggaa aggtt        55

<210> SEQ ID NO 506
<211> LENGTH: 55
<212> TYPE: DNA
<213> ORGANISM: Artificial Sequence
<220> FEATURE:
<223> OTHER INFORMATION: synthetic_HEK4_10 2nd PCR forward(5' to 3')
```

<400> SEQUENCE: 506
acactctttc cctacacgac gctcttccga tctgatctct tgacttggtg atcca    55

<210> SEQ ID NO 507
<211> LENGTH: 55
<212> TYPE: DNA
<213> ORGANISM: Artificial Sequence
<220> FEATURE:
<223> OTHER INFORMATION: synthetic_HEK4_10 2nd PCR reverse(5' to 3')

<400> SEQUENCE: 507
gtgactggag ttcagacgtg tgctcttccg atcttccagg gtatcaggaa aggtt    55

<210> SEQ ID NO 508
<211> LENGTH: 53
<212> TYPE: DNA
<213> ORGANISM: Artificial Sequence
<220> FEATURE:
<223> OTHER INFORMATION: synthetic_HEK4_11 1st PCR forward(5' to 3')

<400> SEQUENCE: 508
acactctttc cctacacgac gctcttccga tctaaatcct cagcacacga caa    53

<210> SEQ ID NO 509
<211> LENGTH: 20
<212> TYPE: DNA
<213> ORGANISM: Artificial Sequence
<220> FEATURE:
<223> OTHER INFORMATION: synthetic_HEK4_11 1st PCR reverse(5' to 3')

<400> SEQUENCE: 509
cacagcccat ctctccactc    20

<210> SEQ ID NO 510
<211> LENGTH: 53
<212> TYPE: DNA
<213> ORGANISM: Artificial Sequence
<220> FEATURE:
<223> OTHER INFORMATION: synthetic_HEK4_11 2nd PCR forward(5' to 3')

<400> SEQUENCE: 510
acactctttc cctacacgac gctcttccga tctaaatcct cagcacacga caa    53

<210> SEQ ID NO 511
<211> LENGTH: 54
<212> TYPE: DNA
<213> ORGANISM: Artificial Sequence
<220> FEATURE:
<223> OTHER INFORMATION: synthetic_HEK4_11 2nd PCR reverse(5' to 3')

<400> SEQUENCE: 511
gtgactggag ttcagacgtg tgctcttccg atcttgggct ccaacctctt ctaa    54

<210> SEQ ID NO 512
<211> LENGTH: 19
<212> TYPE: DNA
<213> ORGANISM: Artificial Sequence
<220> FEATURE:
<223> OTHER INFORMATION: synthetic_HEK4_12 1st PCR forward(5' to 3')

<400> SEQUENCE: 512
ccctggtgag caaacacac    19

<210> SEQ ID NO 513
<211> LENGTH: 52

```
<212> TYPE: DNA
<213> ORGANISM: Artificial Sequence
<220> FEATURE:
<223> OTHER INFORMATION: synthetic_HEK4_12 1st PCR reverse(5' to 3')

<400> SEQUENCE: 513
gtgactggag ttcagacgtg tgctcttccg atctcaggtc ctgtgccacc tc          52

<210> SEQ ID NO 514
<211> LENGTH: 53
<212> TYPE: DNA
<213> ORGANISM: Artificial Sequence
<220> FEATURE:
<223> OTHER INFORMATION: synthetic_HEK4_12 2nd PCR forward(5' to 3')

<400> SEQUENCE: 514
acactctttc cctacacgac gctcttccga tctcccacgt ggtattcacc tct         53

<210> SEQ ID NO 515
<211> LENGTH: 52
<212> TYPE: DNA
<213> ORGANISM: Artificial Sequence
<220> FEATURE:
<223> OTHER INFORMATION: synthetic_HEK4_12 2nd PCR reverse(5' to 3')

<400> SEQUENCE: 515
gtgactggag ttcagacgtg tgctcttccg atctcaggtc ctgtgccacc tc          52

<210> SEQ ID NO 516
<211> LENGTH: 20
<212> TYPE: DNA
<213> ORGANISM: Artificial Sequence
<220> FEATURE:
<223> OTHER INFORMATION: synthetic_HEK4_13 1st PCR forward(5' to 3')

<400> SEQUENCE: 516
gccatctaat cacagccaca                                              20

<210> SEQ ID NO 517
<211> LENGTH: 54
<212> TYPE: DNA
<213> ORGANISM: Artificial Sequence
<220> FEATURE:
<223> OTHER INFORMATION: synthetic_HEK4_13 1st PCR reverse(5' to 3')

<400> SEQUENCE: 517
gtgactggag ttcagacgtg tgctcttccg atctgcatct tgtcccttct cagc        54

<210> SEQ ID NO 518
<211> LENGTH: 53
<212> TYPE: DNA
<213> ORGANISM: Artificial Sequence
<220> FEATURE:
<223> OTHER INFORMATION: synthetic_HEK4_13 2nd PCR forward(5' to 3')

<400> SEQUENCE: 518
acactctttc cctacacgac gctcttccga tctctcctgg gtgctcagac ttc         53

<210> SEQ ID NO 519
<211> LENGTH: 54
<212> TYPE: DNA
<213> ORGANISM: Artificial Sequence
<220> FEATURE:
<223> OTHER INFORMATION: synthetic_HEK4_13 2nd PCR reverse(5' to 3')

<400> SEQUENCE: 519
```
gtgactggag ttcagacgtg tgctcttccg atctgcatct tgtcccttct cagc        54

<210> SEQ ID NO 520
<211> LENGTH: 53
<212> TYPE: DNA
<213> ORGANISM: Artificial Sequence
<220> FEATURE:
<223> OTHER INFORMATION: synthetic_HEK4_14 1st PCR forward(5' to 3')

<400> SEQUENCE: 520
acactctttc cctacacgac gctcttccga tctgttgaga agcagcaagg tga         53

<210> SEQ ID NO 521
<211> LENGTH: 20
<212> TYPE: DNA
<213> ORGANISM: Artificial Sequence
<220> FEATURE:
<223> OTHER INFORMATION: synthetic_HEK4_14 1st PCR reverse(5' to 3')

<400> SEQUENCE: 521
caccatgcct ggctaatttt                                              20

<210> SEQ ID NO 522
<211> LENGTH: 53
<212> TYPE: DNA
<213> ORGANISM: Artificial Sequence
<220> FEATURE:
<223> OTHER INFORMATION: synthetic_HEK4_14 2nd PCR forward(5' to 3')

<400> SEQUENCE: 522
acactctttc cctacacgac gctcttccga tctgttgaga agcagcaagg tga         53

<210> SEQ ID NO 523
<211> LENGTH: 54
<212> TYPE: DNA
<213> ORGANISM: Artificial Sequence
<220> FEATURE:
<223> OTHER INFORMATION: synthetic_HEK4_14 2nd PCR reverse(5' to 3')

<400> SEQUENCE: 523
gtgactggag ttcagacgtg tgctcttccg atctttagta gggacggggt tca         54

<210> SEQ ID NO 524
<211> LENGTH: 20
<212> TYPE: DNA
<213> ORGANISM: Artificial Sequence
<220> FEATURE:
<223> OTHER INFORMATION: synthetic_HEK4_15 1st PCR forward(5' to 3')

<400> SEQUENCE: 524
cagaacccaa ggctcttgac                                              20

<210> SEQ ID NO 525
<211> LENGTH: 54
<212> TYPE: DNA
<213> ORGANISM: Artificial Sequence
<220> FEATURE:
<223> OTHER INFORMATION: synthetic_HEK4_15 1st PCR reverse(5' to 3')

<400> SEQUENCE: 525
gtgactggag ttcagacgtg tgctcttccg atctattttg ctcagaccca gcat        54

<210> SEQ ID NO 526
<211> LENGTH: 53
<212> TYPE: DNA
<213> ORGANISM: Artificial Sequence

```
<220> FEATURE:
<223> OTHER INFORMATION: synthetic_HEK4_15 2nd PCR forward(5' to 3')

<400> SEQUENCE: 526
acactctttc cctacacgac gctcttccga tcttccaaga tgccttctgc tct          53

<210> SEQ ID NO 527
<211> LENGTH: 54
<212> TYPE: DNA
<213> ORGANISM: Artificial Sequence
<220> FEATURE:
<223> OTHER INFORMATION: synthetic_HEK4_15 2nd PCR reverse(5' to 3')

<400> SEQUENCE: 527
gtgactggag ttcagacgtg tgctcttccg atctattttg ctcagaccca gcat         54

<210> SEQ ID NO 528
<211> LENGTH: 53
<212> TYPE: DNA
<213> ORGANISM: Artificial Sequence
<220> FEATURE:
<223> OTHER INFORMATION: synthetic_HEK4_16 1st PCR forward(5' to 3')

<400> SEQUENCE: 528
acactctttc cctacacgac gctcttccga tctaacagag ccctgcagaa cat          53

<210> SEQ ID NO 529
<211> LENGTH: 21
<212> TYPE: DNA
<213> ORGANISM: Artificial Sequence
<220> FEATURE:
<223> OTHER INFORMATION: synthetic_HEK4_16 1st PCR reverse(5' to 3')

<400> SEQUENCE: 529
tttctcacga tgacattttg g                                             21

<210> SEQ ID NO 530
<211> LENGTH: 53
<212> TYPE: DNA
<213> ORGANISM: Artificial Sequence
<220> FEATURE:
<223> OTHER INFORMATION: synthetic_HEK4_16 2nd PCR forward(5' to 3')

<400> SEQUENCE: 530
acactctttc cctacacgac gctcttccga tctaacagag ccctgcagaa cat          53

<210> SEQ ID NO 531
<211> LENGTH: 54
<212> TYPE: DNA
<213> ORGANISM: Artificial Sequence
<220> FEATURE:
<223> OTHER INFORMATION: synthetic_HEK4_16 2nd PCR reverse(5' to 3')

<400> SEQUENCE: 531
gtgactggag ttcagacgtg tgctcttccg atctcggagg aggtagattg gaga         54

<210> SEQ ID NO 532
<211> LENGTH: 54
<212> TYPE: DNA
<213> ORGANISM: Artificial Sequence
<220> FEATURE:
<223> OTHER INFORMATION: synthetic_HEK4_17 1st PCR forward(5' to 3')

<400> SEQUENCE: 532
acactctttc cctacacgac gctcttccga tctcatgtat gcagctgctt ttga         54
```

<210> SEQ ID NO 533
<211> LENGTH: 22
<212> TYPE: DNA
<213> ORGANISM: Artificial Sequence
<220> FEATURE:
<223> OTHER INFORMATION: synthetic_HEK4_17 1st PCR reverse(5' to 3')

<400> SEQUENCE: 533
tgttcctaga gcaaccttca ca                                              22

<210> SEQ ID NO 534
<211> LENGTH: 54
<212> TYPE: DNA
<213> ORGANISM: Artificial Sequence
<220> FEATURE:
<223> OTHER INFORMATION: synthetic_HEK4_17 2nd PCR forward(5' to 3')

<400> SEQUENCE: 534
acactctttc cctacacgac gctcttccga tctcatgtat gcagctgctt ttga            54

<210> SEQ ID NO 535
<211> LENGTH: 54
<212> TYPE: DNA
<213> ORGANISM: Artificial Sequence
<220> FEATURE:
<223> OTHER INFORMATION: synthetic_HEK4_17 2nd PCR reverse(5' to 3')

<400> SEQUENCE: 535
gtgactggag ttcagacgtg tgctcttccg atctggagag ccagagtggc taaa            54

<210> SEQ ID NO 536
<211> LENGTH: 20
<212> TYPE: DNA
<213> ORGANISM: Artificial Sequence
<220> FEATURE:
<223> OTHER INFORMATION: synthetic_HEK4_18 1st PCR forward(5' to 3')

<400> SEQUENCE: 536
ctgaaagagg gaggggagac                                                 20

<210> SEQ ID NO 537
<211> LENGTH: 54
<212> TYPE: DNA
<213> ORGANISM: Artificial Sequence
<220> FEATURE:
<223> OTHER INFORMATION: synthetic_HEK4_18 1st PCR reverse(5' to 3')

<400> SEQUENCE: 537
gtgactggag ttcagacgtg tgctcttccg atctcttcgc caggtcttct gttc            54

<210> SEQ ID NO 538
<211> LENGTH: 53
<212> TYPE: DNA
<213> ORGANISM: Artificial Sequence
<220> FEATURE:
<223> OTHER INFORMATION: synthetic_HEK4_18 2nd PCR forward(5' to 3')

<400> SEQUENCE: 538
acactctttc cctacacgac gctcttccga tctctcggga gagaggaaag gac             53

<210> SEQ ID NO 539
<211> LENGTH: 54
<212> TYPE: DNA
<213> ORGANISM: Artificial Sequence
<220> FEATURE:
<223> OTHER INFORMATION: synthetic_HEK4_18 2nd PCR reverse(5' to 3')

<400> SEQUENCE: 539
gtgactggag ttcagacgtg tgctcttccg atctcttcgc caggtcttct gttc    54

<210> SEQ ID NO 540
<211> LENGTH: 53
<212> TYPE: DNA
<213> ORGANISM: Artificial Sequence
<220> FEATURE:
<223> OTHER INFORMATION: synthetic_HEK4_19 1st PCR forward(5' to 3')

<400> SEQUENCE: 540
acactctttc cctacacgac gctcttccga tctcccggcc gatttaactt tta    53

<210> SEQ ID NO 541
<211> LENGTH: 18
<212> TYPE: DNA
<213> ORGANISM: Artificial Sequence
<220> FEATURE:
<223> OTHER INFORMATION: synthetic_HEK4_19 1st PCR reverse(5' to 3')

<400> SEQUENCE: 541
gacgcatccc acctcctc    18

<210> SEQ ID NO 542
<211> LENGTH: 53
<212> TYPE: DNA
<213> ORGANISM: Artificial Sequence
<220> FEATURE:
<223> OTHER INFORMATION: synthetic_HEK4_19 2nd PCR forward(5' to 3')

<400> SEQUENCE: 542
acactctttc cctacacgac gctcttccga tctcccggcc gatttaactt tta    53

<210> SEQ ID NO 543
<211> LENGTH: 52
<212> TYPE: DNA
<213> ORGANISM: Artificial Sequence
<220> FEATURE:
<223> OTHER INFORMATION: synthetic_HEK4_19 2nd PCR reverse(5' to 3')

<400> SEQUENCE: 543
gtgactggag ttcagacgtg tgctcttccg atctctgggg cacgaaatgt cc    52

<210> SEQ ID NO 544
<211> LENGTH: 19
<212> TYPE: DNA
<213> ORGANISM: Artificial Sequence
<220> FEATURE:
<223> OTHER INFORMATION: synthetic_HEK4_20 1st PCR forward(5' to 3')

<400> SEQUENCE: 544
ccaggaacag agggaccat    19

<210> SEQ ID NO 545
<211> LENGTH: 54
<212> TYPE: DNA
<213> ORGANISM: Artificial Sequence
<220> FEATURE:
<223> OTHER INFORMATION: synthetic_HEK4_20 1st PCR reverse(5' to 3')

<400> SEQUENCE: 545
gtgactggag ttcagacgtg tgctcttccg atctcctggt tccagtcacc tctc    54

<210> SEQ ID NO 546

```
<211> LENGTH: 53
<212> TYPE: DNA
<213> ORGANISM: Artificial Sequence
<220> FEATURE:
<223> OTHER INFORMATION: synthetic_HEK4_20 2nd PCR forward(5' to 3')

<400> SEQUENCE: 546
acactctttc cctacacgac gctcttccga tctccaggtc cagagacaag acg            53

<210> SEQ ID NO 547
<211> LENGTH: 54
<212> TYPE: DNA
<213> ORGANISM: Artificial Sequence
<220> FEATURE:
<223> OTHER INFORMATION: synthetic_HEK4_20 2nd PCR reverse(5' to 3')

<400> SEQUENCE: 547
gtgactggag ttcagacgtg tgctcttccg atctcctggt tccagtcacc tctc           54

<210> SEQ ID NO 548
<211> LENGTH: 23
<212> TYPE: DNA
<213> ORGANISM: Artificial Sequence
<220> FEATURE:
<223> OTHER INFORMATION: synthetic_Fig. 4a_Sequences

<400> SEQUENCE: 548
gagtccgagc agaagaagaa ggg                                             23

<210> SEQ ID NO 549
<211> LENGTH: 23
<212> TYPE: DNA
<213> ORGANISM: Artificial Sequence
<220> FEATURE:
<223> OTHER INFORMATION: synthetic_Fig. 4a_Sequences

<400> SEQUENCE: 549
cccttcttct tctgctcgga ctc                                             23

<210> SEQ ID NO 550
<211> LENGTH: 23
<212> TYPE: DNA
<213> ORGANISM: Artificial Sequence
<220> FEATURE:
<223> OTHER INFORMATION: synthetic_Fig. 4a_Sequences
<220> FEATURE:
<221> NAME/KEY: misc_feature
<222> LOCATION: (5)..(6)
<223> OTHER INFORMATION: n is uracil

<400> SEQUENCE: 550
gagtnngagc agaagaagaa ggg                                             23

<210> SEQ ID NO 551
<211> LENGTH: 23
<212> TYPE: DNA
<213> ORGANISM: Artificial Sequence
<220> FEATURE:
<223> OTHER INFORMATION: synthetic_Fig. 4a_Sequences

<400> SEQUENCE: 551
cccttcttct tctgctcgga ctc                                             23

<210> SEQ ID NO 552
<211> LENGTH: 23
<212> TYPE: DNA
<213> ORGANISM: Artificial Sequence
```

<220> FEATURE:
<223> OTHER INFORMATION: synthetic_Fig. 4a_Sequences
<220> FEATURE:
<221> NAME/KEY: misc_feature
<222> LOCATION: (5)..(6)
<223> OTHER INFORMATION: n is absent

<400> SEQUENCE: 552
gagtnngagc agaagaagaa ggg        23

<210> SEQ ID NO 553
<211> LENGTH: 23
<212> TYPE: DNA
<213> ORGANISM: Artificial Sequence
<220> FEATURE:
<223> OTHER INFORMATION: synthetic_Fig. 4a_Sequences

<400> SEQUENCE: 553
cccttcttct tctgctcgga ctc        23

<210> SEQ ID NO 554
<211> LENGTH: 21
<212> TYPE: DNA
<213> ORGANISM: Artificial Sequence
<220> FEATURE:
<223> OTHER INFORMATION: synthetic_Fig. 4a_Sequences

<400> SEQUENCE: 554
gagtgagcag aagaagaagg g        21

<210> SEQ ID NO 555
<211> LENGTH: 23
<212> TYPE: DNA
<213> ORGANISM: Artificial Sequence
<220> FEATURE:
<223> OTHER INFORMATION: synthetic_Fig. 4a_Sequences

<400> SEQUENCE: 555
cccttcttct tctgctcgga ctc        23

<210> SEQ ID NO 556
<211> LENGTH: 17
<212> TYPE: DNA
<213> ORGANISM: Artificial Sequence
<220> FEATURE:
<223> OTHER INFORMATION: synthetic_Fig. 4a_Sequences

<400> SEQUENCE: 556
gagtccgagc agaagaa        17

<210> SEQ ID NO 557
<211> LENGTH: 17
<212> TYPE: DNA
<213> ORGANISM: Artificial Sequence
<220> FEATURE:
<223> OTHER INFORMATION: synthetic_Fig. 4a_Sequences

<400> SEQUENCE: 557
ttcttctgct cggactc        17

<210> SEQ ID NO 558
<211> LENGTH: 17
<212> TYPE: DNA
<213> ORGANISM: Artificial Sequence
<220> FEATURE:
<223> OTHER INFORMATION: synthetic_Fig. 4a_Sequences -continued

<400> SEQUENCE: 558
gagcagaaga agaaggg                                                  17

<210> SEQ ID NO 559
<211> LENGTH: 17
<212> TYPE: DNA
<213> ORGANISM: Artificial Sequence
<220> FEATURE:
<223> OTHER INFORMATION: synthetic_Fig. 4a_Sequences

<400> SEQUENCE: 559
cccttcttct tctgctc                                                  17

<210> SEQ ID NO 560
<211> LENGTH: 23
<212> TYPE: DNA
<213> ORGANISM: Artificial Sequence
<220> FEATURE:
<223> OTHER INFORMATION: synthetic_Fig. 4c_Sequences

<400> SEQUENCE: 560
gagtccgagc agaagaagaa ggg                                           23

<210> SEQ ID NO 561
<211> LENGTH: 23
<212> TYPE: DNA
<213> ORGANISM: Artificial Sequence
<220> FEATURE:
<223> OTHER INFORMATION: synthetic_Fig. 4c_Sequences

<400> SEQUENCE: 561
gagttcgagc agaagaagaa ggg                                           23

<210> SEQ ID NO 562
<211> LENGTH: 23
<212> TYPE: DNA
<213> ORGANISM: Artificial Sequence
<220> FEATURE:
<223> OTHER INFORMATION: synthetic_Fig. 4c_Sequences

<400> SEQUENCE: 562
gagtccgagc agaagaagaa ggg                                           23

<210> SEQ ID NO 563
<211> LENGTH: 23
<212> TYPE: DNA
<213> ORGANISM: Artificial Sequence
<220> FEATURE:
<223> OTHER INFORMATION: synthetic_Fig. 4d_Sequences

<400> SEQUENCE: 563
gagtccgagc agaagaagaa ggg                                           23

<210> SEQ ID NO 564
<211> LENGTH: 23
<212> TYPE: DNA
<213> ORGANISM: Artificial Sequence
<220> FEATURE:
<223> OTHER INFORMATION: synthetic_Fig. 5_Sequences

<400> SEQUENCE: 564
ccaggtgctg cagaagggat tcc                                           23

<210> SEQ ID NO 565
<211> LENGTH: 23

```
<212> TYPE: DNA
<213> ORGANISM: Artificial Sequence
<220> FEATURE:
<223> OTHER INFORMATION: synthetic_Fig. 5_Sequences

<400> SEQUENCE: 565
cctcaggtaa tgactaagat gac                                              23

<210> SEQ ID NO 566
<211> LENGTH: 23
<212> TYPE: DNA
<213> ORGANISM: Artificial Sequence
<220> FEATURE:
<223> OTHER INFORMATION: synthetic_Fig. 5_Sequences

<400> SEQUENCE: 566
cttgccccac agggcagtaa cgg                                              23

<210> SEQ ID NO 567
<211> LENGTH: 23
<212> TYPE: DNA
<213> ORGANISM: Artificial Sequence
<220> FEATURE:
<223> OTHER INFORMATION: synthetic_Fig. 5_Sequences

<400> SEQUENCE: 567
gaacacaaag catagactgc ggg                                              23

<210> SEQ ID NO 568
<211> LENGTH: 23
<212> TYPE: DNA
<213> ORGANISM: Artificial Sequence
<220> FEATURE:
<223> OTHER INFORMATION: synthetic_Fig. 5_Sequences

<400> SEQUENCE: 568
ggcccagact gagcacgtga tgg                                              23

<210> SEQ ID NO 569
<211> LENGTH: 23
<212> TYPE: DNA
<213> ORGANISM: Artificial Sequence
<220> FEATURE:
<223> OTHER INFORMATION: synthetic_Fig. 5_Sequences

<400> SEQUENCE: 569
ggcactgcgg ctggaggtgg ggg                                              23

<210> SEQ ID NO 570
<211> LENGTH: 23
<212> TYPE: DNA
<213> ORGANISM: Artificial Sequence
<220> FEATURE:
<223> OTHER INFORMATION: synthetic_Fig. 6c_Sequences
<220> FEATURE:
<221> NAME/KEY: misc_feature
<222> LOCATION: (21)
<223> OTHER INFORMATION: n is A, T, G, or C

<400> SEQUENCE: 570
gagtccgagc agaagaagaa ngg                                              23

<210> SEQ ID NO 571
<211> LENGTH: 23
<212> TYPE: DNA
<213> ORGANISM: Artificial Sequence
<220> FEATURE:
```

```
<223> OTHER INFORMATION: synthetic_Fig. 6c_Sequences
<220> FEATURE:
<221> NAME/KEY: misc_feature
<222> LOCATION: (21)
<223> OTHER INFORMATION: n is A, T, G, or C

<400> SEQUENCE: 571
gagtccgagc agaagaagaa ngg                                              23

<210> SEQ ID NO 572
<211> LENGTH: 23
<212> TYPE: DNA
<213> ORGANISM: Artificial Sequence
<220> FEATURE:
<223> OTHER INFORMATION: synthetic_Fig. 6d_Sequences
<220> FEATURE:
<221> NAME/KEY: misc_feature
<222> LOCATION: (21)
<223> OTHER INFORMATION: n is A, T, G, or C

<400> SEQUENCE: 572
cttgccccac agggcagtaa ngg                                              23

<210> SEQ ID NO 573
<211> LENGTH: 23
<212> TYPE: DNA
<213> ORGANISM: Artificial Sequence
<220> FEATURE:
<223> OTHER INFORMATION: synthetic_Fig. 6d_Sequences
<220> FEATURE:
<221> NAME/KEY: misc_feature
<222> LOCATION: (21)
<223> OTHER INFORMATION: n is A, T, G, or C

<400> SEQUENCE: 573
cttgccccac agggcagtaa ngg                                              23

<210> SEQ ID NO 574
<211> LENGTH: 23
<212> TYPE: DNA
<213> ORGANISM: Artificial Sequence
<220> FEATURE:
<223> OTHER INFORMATION: synthetic_Fig. 13_Sequences

<400> SEQUENCE: 574
gagttagagc agaagaagaa agg                                              23

<210> SEQ ID NO 575
<211> LENGTH: 23
<212> TYPE: DNA
<213> ORGANISM: Artificial Sequence
<220> FEATURE:
<223> OTHER INFORMATION: synthetic_Fig. 13_Sequences

<400> SEQUENCE: 575
attaagatag catagactgc agg                                              23

<210> SEQ ID NO 576
<211> LENGTH: 23
<212> TYPE: DNA
<213> ORGANISM: Artificial Sequence
<220> FEATURE:
<223> OTHER INFORMATION: synthetic_Fig. 13_Sequences

<400> SEQUENCE: 576
ggcaatgtgg ctgaaggtgg ggg                                              23
```

-continued

```
<210> SEQ ID NO 577
<211> LENGTH: 23
<212> TYPE: DNA
<213> ORGANISM: Artificial Sequence
<220> FEATURE:
<223> OTHER INFORMATION: synthetic_Fig. 13_Sequences

<400> SEQUENCE: 577
attattttag tcattaccttt tgg                                              23

<210> SEQ ID NO 578
<211> LENGTH: 23
<212> TYPE: DNA
<213> ORGANISM: Artificial Sequence
<220> FEATURE:
<223> OTHER INFORMATION: synthetic_Fig. 13_Sequences

<400> SEQUENCE: 578
aaataagact gagcacgtgg tgg                                               23

<210> SEQ ID NO 579
<211> LENGTH: 23
<212> TYPE: DNA
<213> ORGANISM: Artificial Sequence
<220> FEATURE:
<223> OTHER INFORMATION: synthetic_Fig. 14a_Sequences

<400> SEQUENCE: 579
gagtccgagc agaagaagaa ggg                                               23

<210> SEQ ID NO 580
<211> LENGTH: 23
<212> TYPE: DNA
<213> ORGANISM: Artificial Sequence
<220> FEATURE:
<223> OTHER INFORMATION: synthetic_Fig. 14a_Sequences

<400> SEQUENCE: 580
gagccggagc agaagaagga ggg                                               23

<210> SEQ ID NO 581
<211> LENGTH: 23
<212> TYPE: DNA
<213> ORGANISM: Artificial Sequence
<220> FEATURE:
<223> OTHER INFORMATION: synthetic_Fig. 14a_Sequences

<400> SEQUENCE: 581
aagtcccggc agaggaagaa ggg                                               23

<210> SEQ ID NO 582
<211> LENGTH: 23
<212> TYPE: DNA
<213> ORGANISM: Artificial Sequence
<220> FEATURE:
<223> OTHER INFORMATION: synthetic_Fig. 14a_Sequences

<400> SEQUENCE: 582
gagcacgagc aagagaagaa ggg                                               23

<210> SEQ ID NO 583
<211> LENGTH: 23
<212> TYPE: DNA
<213> ORGANISM: Artificial Sequence
<220> FEATURE:
<223> OTHER INFORMATION: synthetic_Fig. 14a_Sequences
```

```
<400> SEQUENCE: 583
gagtctaagc aggagaataa agg                                              23

<210> SEQ ID NO 584
<211> LENGTH: 23
<212> TYPE: DNA
<213> ORGANISM: Artificial Sequence
<220> FEATURE:
<223> OTHER INFORMATION: synthetic_Fig. 14a_Sequences

<400> SEQUENCE: 584
gagtcagagc aaaagaagta gtg                                              23

<210> SEQ ID NO 585
<211> LENGTH: 23
<212> TYPE: DNA
<213> ORGANISM: Artificial Sequence
<220> FEATURE:
<223> OTHER INFORMATION: synthetic_Fig. 14a_Sequences

<400> SEQUENCE: 585
gaggcagaga gaaagaagaa agg                                              23

<210> SEQ ID NO 586
<211> LENGTH: 23
<212> TYPE: DNA
<213> ORGANISM: Artificial Sequence
<220> FEATURE:
<223> OTHER INFORMATION: synthetic_Fig. 14a_Sequences

<400> SEQUENCE: 586
gagcctgagc agaaggagaa ggg                                              23

<210> SEQ ID NO 587
<211> LENGTH: 23
<212> TYPE: DNA
<213> ORGANISM: Artificial Sequence
<220> FEATURE:
<223> OTHER INFORMATION: synthetic_Fig. 14a_Sequences

<400> SEQUENCE: 587
aagtctgaga agaagaagaa aga                                              23

<210> SEQ ID NO 588
<211> LENGTH: 23
<212> TYPE: DNA
<213> ORGANISM: Artificial Sequence
<220> FEATURE:
<223> OTHER INFORMATION: synthetic_Fig. 14a_Sequences

<400> SEQUENCE: 588
aagtcagaga agaagaagaa ggg                                              23

<210> SEQ ID NO 589
<211> LENGTH: 23
<212> TYPE: DNA
<213> ORGANISM: Artificial Sequence
<220> FEATURE:
<223> OTHER INFORMATION: synthetic_Fig. 14a_Sequences

<400> SEQUENCE: 589
gagtcccaga agaagaagag agg                                              23

<210> SEQ ID NO 590
<211> LENGTH: 23
```

-continued

```
<212> TYPE: DNA
<213> ORGANISM: Artificial Sequence
<220> FEATURE:
<223> OTHER INFORMATION: synthetic_Fig. 14a_Sequences

<400> SEQUENCE: 590
aagtccagac agaagaagaa gga                                              23

<210> SEQ ID NO 591
<211> LENGTH: 23
<212> TYPE: DNA
<213> ORGANISM: Artificial Sequence
<220> FEATURE:
<223> OTHER INFORMATION: synthetic_Fig. 14b_Sequences

<400> SEQUENCE: 591
cttgccccac agggcagtaa cgg                                              23

<210> SEQ ID NO 592
<211> LENGTH: 23
<212> TYPE: DNA
<213> ORGANISM: Artificial Sequence
<220> FEATURE:
<223> OTHER INFORMATION: synthetic_Fig. 14b_Sequences

<400> SEQUENCE: 592
aaagccccac agggtagtag agg                                              23

<210> SEQ ID NO 593
<211> LENGTH: 23
<212> TYPE: DNA
<213> ORGANISM: Artificial Sequence
<220> FEATURE:
<223> OTHER INFORMATION: synthetic_Fig. 14b_Sequences

<400> SEQUENCE: 593
gctaccccac agggcattag ggg                                              23

<210> SEQ ID NO 594
<211> LENGTH: 23
<212> TYPE: DNA
<213> ORGANISM: Artificial Sequence
<220> FEATURE:
<223> OTHER INFORMATION: synthetic_Fig. 14b_Sequences

<400> SEQUENCE: 594
cataccccac aggtcagtaa gga                                              23

<210> SEQ ID NO 595
<211> LENGTH: 23
<212> TYPE: DNA
<213> ORGANISM: Artificial Sequence
<220> FEATURE:
<223> OTHER INFORMATION: synthetic_Fig. 14b_Sequences

<400> SEQUENCE: 595
tctgccccac atggcagtaa tga                                              23

<210> SEQ ID NO 596
<211> LENGTH: 23
<212> TYPE: DNA
<213> ORGANISM: Artificial Sequence
<220> FEATURE:
<223> OTHER INFORMATION: synthetic_Fig. 14b_Sequences

<400> SEQUENCE: 596
```
tttgccccct caggcagcta agg                                    23

<210> SEQ ID NO 597
<211> LENGTH: 23
<212> TYPE: DNA
<213> ORGANISM: Artificial Sequence
<220> FEATURE:
<223> OTHER INFORMATION: synthetic_Fig. 14b_Sequences

<400> SEQUENCE: 597
cctgccccac agggcaatta tgg                                    23

<210> SEQ ID NO 598
<211> LENGTH: 23
<212> TYPE: DNA
<213> ORGANISM: Artificial Sequence
<220> FEATURE:
<223> OTHER INFORMATION: synthetic_Fig. 14b_Sequences

<400> SEQUENCE: 598
gctgccccct cagggacagta tgg                                   23

<210> SEQ ID NO 599
<211> LENGTH: 23
<212> TYPE: DNA
<213> ORGANISM: Artificial Sequence
<220> FEATURE:
<223> OTHER INFORMATION: synthetic_Fig. 14b_Sequences

<400> SEQUENCE: 599
gttgtcccac aggacagtga ggg                                    23

<210> SEQ ID NO 600
<211> LENGTH: 23
<212> TYPE: DNA
<213> ORGANISM: Artificial Sequence
<220> FEATURE:
<223> OTHER INFORMATION: synthetic_Fig. 14b_Sequences

<400> SEQUENCE: 600
atggccccac aaggcagaaa tgg                                    23

<210> SEQ ID NO 601
<211> LENGTH: 23
<212> TYPE: DNA
<213> ORGANISM: Artificial Sequence
<220> FEATURE:
<223> OTHER INFORMATION: synthetic_Fig. 14b_Sequences

<400> SEQUENCE: 601
gttgcccctc aggacagtac agg                                    23

<210> SEQ ID NO 602
<211> LENGTH: 23
<212> TYPE: DNA
<213> ORGANISM: Artificial Sequence
<220> FEATURE:
<223> OTHER INFORMATION: synthetic_Fig. 14b_Sequences

<400> SEQUENCE: 602
gcagccccac aggtcagtga ggg                                    23

<210> SEQ ID NO 603
<211> LENGTH: 23
<212> TYPE: DNA
<213> ORGANISM: Artificial Sequence

```
<220> FEATURE:
<223> OTHER INFORMATION: synthetic_Fig. 14c_Sequences

<400> SEQUENCE: 603
gtcatcttag tcattacctg agg                                              23

<210> SEQ ID NO 604
<211> LENGTH: 23
<212> TYPE: DNA
<213> ORGANISM: Artificial Sequence
<220> FEATURE:
<223> OTHER INFORMATION: synthetic_Fig. 14c_Sequences

<400> SEQUENCE: 604
ggtatctaag tcattacctg tgg                                              23

<210> SEQ ID NO 605
<211> LENGTH: 23
<212> TYPE: DNA
<213> ORGANISM: Artificial Sequence
<220> FEATURE:
<223> OTHER INFORMATION: synthetic_Fig. 14c_Sequences

<400> SEQUENCE: 605
aatatgttag tcattacctg agg                                              23

<210> SEQ ID NO 606
<211> LENGTH: 23
<212> TYPE: DNA
<213> ORGANISM: Artificial Sequence
<220> FEATURE:
<223> OTHER INFORMATION: synthetic_Fig. 15a_Sequences

<400> SEQUENCE: 606
gagtccgagc agaagaagaa ggg                                              23

<210> SEQ ID NO 607
<211> LENGTH: 23
<212> TYPE: DNA
<213> ORGANISM: Artificial Sequence
<220> FEATURE:
<223> OTHER INFORMATION: synthetic_Fig. 15a_Sequences

<400> SEQUENCE: 607
gagactgaga agaagaagaa agg                                              23

<210> SEQ ID NO 608
<211> LENGTH: 23
<212> TYPE: DNA
<213> ORGANISM: Artificial Sequence
<220> FEATURE:
<223> OTHER INFORMATION: synthetic_Fig. 15a_Sequences

<400> SEQUENCE: 608
gcgacagagc agaagaagaa ggg                                              23

<210> SEQ ID NO 609
<211> LENGTH: 23
<212> TYPE: DNA
<213> ORGANISM: Artificial Sequence
<220> FEATURE:
<223> OTHER INFORMATION: synthetic_Fig. 15a_Sequences

<400> SEQUENCE: 609
gagcctgagc agaaggagaa ggg                                              23
```

-continued

```
<210> SEQ ID NO 610
<211> LENGTH: 23
<212> TYPE: DNA
<213> ORGANISM: Artificial Sequence
<220> FEATURE:
<223> OTHER INFORMATION: synthetic_Fig. 15a_Sequences

<400> SEQUENCE: 610
gagtccggga aggagaagaa agg                                              23

<210> SEQ ID NO 611
<211> LENGTH: 23
<212> TYPE: DNA
<213> ORGANISM: Artificial Sequence
<220> FEATURE:
<223> OTHER INFORMATION: synthetic_Fig. 15a_Sequences

<400> SEQUENCE: 611
gagtcccagg agaagaagag agg                                              23

<210> SEQ ID NO 612
<211> LENGTH: 23
<212> TYPE: DNA
<213> ORGANISM: Artificial Sequence
<220> FEATURE:
<223> OTHER INFORMATION: synthetic_Fig. 15a_Sequences

<400> SEQUENCE: 612
aagtcagagg agaagaagaa ggg                                              23

<210> SEQ ID NO 613
<211> LENGTH: 23
<212> TYPE: DNA
<213> ORGANISM: Artificial Sequence
<220> FEATURE:
<223> OTHER INFORMATION: synthetic_Fig. 15a_Sequences

<400> SEQUENCE: 613
gactccgagc agcagaagga tgg                                              23

<210> SEQ ID NO 614
<211> LENGTH: 23
<212> TYPE: DNA
<213> ORGANISM: Artificial Sequence
<220> FEATURE:
<223> OTHER INFORMATION: synthetic_Fig. 15a_Sequences

<400> SEQUENCE: 614
gactcctagc aaaagaagaa tgg                                              23

<210> SEQ ID NO 615
<211> LENGTH: 23
<212> TYPE: DNA
<213> ORGANISM: Artificial Sequence
<220> FEATURE:
<223> OTHER INFORMATION: synthetic_Fig. 15a_Sequences

<400> SEQUENCE: 615
gagccggagc agaagaagga ggg                                              23

<210> SEQ ID NO 616
<211> LENGTH: 23
<212> TYPE: DNA
<213> ORGANISM: Artificial Sequence
<220> FEATURE:
<223> OTHER INFORMATION: synthetic_Fig. 15a_Sequences
```

-continued

<400> SEQUENCE: 616
gagtcagagc agaactagaa ggg                                              23

<210> SEQ ID NO 617
<211> LENGTH: 23
<212> TYPE: DNA
<213> ORGANISM: Artificial Sequence
<220> FEATURE:
<223> OTHER INFORMATION: synthetic_Fig. 15a_Sequences

<400> SEQUENCE: 617
gattcctacc agaagaagaa tgg                                              23

<210> SEQ ID NO 618
<211> LENGTH: 23
<212> TYPE: DNA
<213> ORGANISM: Artificial Sequence
<220> FEATURE:
<223> OTHER INFORMATION: synthetic_Fig. 15b_Sequences

<400> SEQUENCE: 618
cttgccccac agggcagtaa cgg                                              23

<210> SEQ ID NO 619
<211> LENGTH: 23
<212> TYPE: DNA
<213> ORGANISM: Artificial Sequence
<220> FEATURE:
<223> OTHER INFORMATION: synthetic_Fig. 15b_Sequences

<400> SEQUENCE: 619
ctcgcccctc agggcagtag tgg                                              23

<210> SEQ ID NO 620
<211> LENGTH: 23
<212> TYPE: DNA
<213> ORGANISM: Artificial Sequence
<220> FEATURE:
<223> OTHER INFORMATION: synthetic_Fig. 15b_Sequences

<400> SEQUENCE: 620
cctgtcccac agggcaggaa ggg                                              23

<210> SEQ ID NO 621
<211> LENGTH: 23
<212> TYPE: DNA
<213> ORGANISM: Artificial Sequence
<220> FEATURE:
<223> OTHER INFORMATION: synthetic_Fig. 15b_Sequences

<400> SEQUENCE: 621
cttgcaccac agagcactaa ggg                                              23

<210> SEQ ID NO 622
<211> LENGTH: 23
<212> TYPE: DNA
<213> ORGANISM: Artificial Sequence
<220> FEATURE:
<223> OTHER INFORMATION: synthetic_Fig. 15b_Sequences

<400> SEQUENCE: 622
cttggcccac agggcactga ggg                                              23

<210> SEQ ID NO 623

```
<211> LENGTH: 23
<212> TYPE: DNA
<213> ORGANISM: Artificial Sequence
<220> FEATURE:
<223> OTHER INFORMATION: synthetic_Fig. 15b_Sequences

<400> SEQUENCE: 623
cctctcccac agggcagtaa agg                                              23

<210> SEQ ID NO 624
<211> LENGTH: 23
<212> TYPE: DNA
<213> ORGANISM: Artificial Sequence
<220> FEATURE:
<223> OTHER INFORMATION: synthetic_Fig. 15b_Sequences

<400> SEQUENCE: 624
cttgccccag agggctgtta agg                                              23

<210> SEQ ID NO 625
<211> LENGTH: 23
<212> TYPE: DNA
<213> ORGANISM: Artificial Sequence
<220> FEATURE:
<223> OTHER INFORMATION: synthetic_Fig. 15b_Sequences

<400> SEQUENCE: 625
cctgccccac agggcagcca agg                                              23

<210> SEQ ID NO 626
<211> LENGTH: 23
<212> TYPE: DNA
<213> ORGANISM: Artificial Sequence
<220> FEATURE:
<223> OTHER INFORMATION: synthetic_Fig. 15b_Sequences

<400> SEQUENCE: 626
ctagccccac agggtaggaa agg                                              23

<210> SEQ ID NO 627
<211> LENGTH: 23
<212> TYPE: DNA
<213> ORGANISM: Artificial Sequence
<220> FEATURE:
<223> OTHER INFORMATION: synthetic_Fig. 15b_Sequences

<400> SEQUENCE: 627
cttgccccac agggttgtta tgg                                              23

<210> SEQ ID NO 628
<211> LENGTH: 23
<212> TYPE: DNA
<213> ORGANISM: Artificial Sequence
<220> FEATURE:
<223> OTHER INFORMATION: synthetic_Fig. 15b_Sequences

<400> SEQUENCE: 628
cctgccccac agggcaatta tgg                                              23

<210> SEQ ID NO 629
<211> LENGTH: 23
<212> TYPE: DNA
<213> ORGANISM: Artificial Sequence
<220> FEATURE:
<223> OTHER INFORMATION: synthetic_Fig. 15b_Sequences

<400> SEQUENCE: 629
```
cttcacccac agggcagtca tgg 23

<210> SEQ ID NO 630
<211> LENGTH: 23
<212> TYPE: DNA
<213> ORGANISM: Artificial Sequence
<220> FEATURE:
<223> OTHER INFORMATION: synthetic_Fig. 15c_Sequences

<400> SEQUENCE: 630
gtcatcttag tcattacctg agg 23

<210> SEQ ID NO 631
<211> LENGTH: 23
<212> TYPE: DNA
<213> ORGANISM: Artificial Sequence
<220> FEATURE:
<223> OTHER INFORMATION: synthetic_Fig. 15c_Sequences

<400> SEQUENCE: 631
gtcatcctag tgcttacctg agg 23

<210> SEQ ID NO 632
<211> LENGTH: 23
<212> TYPE: DNA
<213> ORGANISM: Artificial Sequence
<220> FEATURE:
<223> OTHER INFORMATION: synthetic_Fig. 15c_Sequences

<400> SEQUENCE: 632
ggtatctaag tcattacctg tgg 23

<210> SEQ ID NO 633
<211> LENGTH: 23
<212> TYPE: DNA
<213> ORGANISM: Artificial Sequence
<220> FEATURE:
<223> OTHER INFORMATION: synthetic_Fig. 15c_Sequences

<400> SEQUENCE: 633
gtcatcctag tcatttactg ggg 23

<210> SEQ ID NO 634
<211> LENGTH: 23
<212> TYPE: DNA
<213> ORGANISM: Artificial Sequence
<220> FEATURE:
<223> OTHER INFORMATION: synthetic_Fig. 15c_Sequences

<400> SEQUENCE: 634
gtaatctgag tcatttcctg ggg 23

<210> SEQ ID NO 635
<211> LENGTH: 23
<212> TYPE: DNA
<213> ORGANISM: Artificial Sequence
<220> FEATURE:
<223> OTHER INFORMATION: synthetic_Fig. 15c_Sequences

<400> SEQUENCE: 635
gtaatattag tcattaccgg tgg 23

<210> SEQ ID NO 636
<211> LENGTH: 23
<212> TYPE: DNA

```
-continued

<213> ORGANISM: Artificial Sequence
<220> FEATURE:
<223> OTHER INFORMATION: synthetic_Fig. 15c_Sequences

<400> SEQUENCE: 636
gtcatctgag gcattaactg ggg                                              23

<210> SEQ ID NO 637
<211> LENGTH: 23
<212> TYPE: DNA
<213> ORGANISM: Artificial Sequence
<220> FEATURE:
<223> OTHER INFORMATION: HBB target sequence
<220> FEATURE:
<221> NAME/KEY: misc_feature
<222> LOCATION: (21)
<223> OTHER INFORMATION: n is A, T, G, or C

<400> SEQUENCE: 637
cttgccccac agggcagtaa ngg                                              23

<210> SEQ ID NO 638
<211> LENGTH: 18
<212> TYPE: RNA
<213> ORGANISM: Artificial Sequence
<220> FEATURE:
<223> OTHER INFORMATION: synthetic_Fig. 16a_Sequences

<400> SEQUENCE: 638
ggccccacag ggcaguaa                                                    18

<210> SEQ ID NO 639
<211> LENGTH: 19
<212> TYPE: RNA
<213> ORGANISM: Artificial Sequence
<220> FEATURE:
<223> OTHER INFORMATION: synthetic_Fig. 16a_Sequences

<400> SEQUENCE: 639
gugccccaca gggcaguaa                                                   19

<210> SEQ ID NO 640
<211> LENGTH: 19
<212> TYPE: RNA
<213> ORGANISM: Artificial Sequence
<220> FEATURE:
<223> OTHER INFORMATION: synthetic_Fig. 16a_Sequences

<400> SEQUENCE: 640
guugcccaca gggcaguaa                                                   19

<210> SEQ ID NO 641
<211> LENGTH: 21
<212> TYPE: RNA
<213> ORGANISM: Artificial Sequence
<220> FEATURE:
<223> OTHER INFORMATION: synthetic_Fig. 16a_Sequences

<400> SEQUENCE: 641
gcuugcccca cagggcagua a                                                21

<210> SEQ ID NO 642
<211> LENGTH: 22
<212> TYPE: RNA
<213> ORGANISM: Artificial Sequence
<220> FEATURE:
<223> OTHER INFORMATION: synthetic_Fig. 16a_Sequences
```

-continued

<400> SEQUENCE: 642
ggcuugcccc acagggcagu aa                                          22

<210> SEQ ID NO 643
<211> LENGTH: 23
<212> TYPE: DNA
<213> ORGANISM: Artificial Sequence
<220> FEATURE:
<223> OTHER INFORMATION: synthetic_Fig. 16b_Sequences

<400> SEQUENCE: 643
tcagccccac agggcagtaa ggg                                         23

<210> SEQ ID NO 644
<211> LENGTH: 23
<212> TYPE: DNA
<213> ORGANISM: Artificial Sequence
<220> FEATURE:
<223> OTHER INFORMATION: synthetic_Fig. 16b_Sequences

<400> SEQUENCE: 644
attgccccac ggggcagtga cgg                                         23

<210> SEQ ID NO 645
<211> LENGTH: 23
<212> TYPE: DNA
<213> ORGANISM: Artificial Sequence
<220> FEATURE:
<223> OTHER INFORMATION: synthetic_Fig. 16b_Sequences

<400> SEQUENCE: 645
gtggccccac agggcaggaa tgg                                         23

<210> SEQ ID NO 646
<211> LENGTH: 23
<212> TYPE: DNA
<213> ORGANISM: Artificial Sequence
<220> FEATURE:
<223> OTHER INFORMATION: synthetic_Fig. 16b_Sequences

<400> SEQUENCE: 646
gctgccccac agggcagcaa agg                                         23

<210> SEQ ID NO 647
<211> LENGTH: 23
<212> TYPE: DNA
<213> ORGANISM: Artificial Sequence
<220> FEATURE:
<223> OTHER INFORMATION: synthetic_Fig. 16b_Sequences

<400> SEQUENCE: 647
ttgctcccac agggcagtaa acg                                         23

<210> SEQ ID NO 648
<211> LENGTH: 23
<212> TYPE: DNA
<213> ORGANISM: Artificial Sequence
<220> FEATURE:
<223> OTHER INFORMATION: synthetic_Fig. 16b_Sequences

<400> SEQUENCE: 648
cttgccccac agggcagtaa cgg                                         23

<210> SEQ ID NO 649

```
<211> LENGTH: 23
<212> TYPE: DNA
<213> ORGANISM: Artificial Sequence
<220> FEATURE:
<223> OTHER INFORMATION: EMX1 target sequence
<220> FEATURE:
<221> NAME/KEY: misc_feature
<222> LOCATION: (21)
<223> OTHER INFORMATION: n is A, T, G, or C

<400> SEQUENCE: 649
gagtccgagc agaagaagaa ngg                                           23

<210> SEQ ID NO 650
<211> LENGTH: 18
<212> TYPE: RNA
<213> ORGANISM: Artificial Sequence
<220> FEATURE:
<223> OTHER INFORMATION: synthetic_Fig. 17a_Sequences

<400> SEQUENCE: 650
guccgagcag aagaagaa                                                 18

<210> SEQ ID NO 651
<211> LENGTH: 19
<212> TYPE: RNA
<213> ORGANISM: Artificial Sequence
<220> FEATURE:
<223> OTHER INFORMATION: synthetic_Fig. 17a_Sequences

<400> SEQUENCE: 651
gguccgagca gaagaagaa                                                19

<210> SEQ ID NO 652
<211> LENGTH: 20
<212> TYPE: RNA
<213> ORGANISM: Artificial Sequence
<220> FEATURE:
<223> OTHER INFORMATION: synthetic_Fig. 17a_Sequences

<400> SEQUENCE: 652
gaguccgagc agaagaagaa                                               20

<210> SEQ ID NO 653
<211> LENGTH: 21
<212> TYPE: RNA
<213> ORGANISM: Artificial Sequence
<220> FEATURE:
<223> OTHER INFORMATION: synthetic_Fig. 17a_Sequences

<400> SEQUENCE: 653
ggaguccgag cagaagaaga a                                             21

<210> SEQ ID NO 654
<211> LENGTH: 22
<212> TYPE: RNA
<213> ORGANISM: Artificial Sequence
<220> FEATURE:
<223> OTHER INFORMATION: synthetic_Fig. 17a_Sequences

<400> SEQUENCE: 654
gggaguccga gcagaagaag aa                                            22

<210> SEQ ID NO 655
<211> LENGTH: 23
<212> TYPE: DNA
<213> ORGANISM: Artificial Sequence
```

<220> FEATURE:
<223> OTHER INFORMATION: synthetic_Fig. 17b_Sequences

<400> SEQUENCE: 655
acgtctgagc agaagaagaa tgg    23

<210> SEQ ID NO 656
<211> LENGTH: 22
<212> TYPE: DNA
<213> ORGANISM: Artificial Sequence
<220> FEATURE:
<223> OTHER INFORMATION: synthetic_Fig. 17b_Sequences

<400> SEQUENCE: 656
gagtcctaga gaagaaaaag gg    22

<210> SEQ ID NO 657
<211> LENGTH: 23
<212> TYPE: DNA
<213> ORGANISM: Artificial Sequence
<220> FEATURE:
<223> OTHER INFORMATION: synthetic_Fig. 17b_Sequences

<400> SEQUENCE: 657
aagtccatgc agaagaggaa ggg    23

<210> SEQ ID NO 658
<211> LENGTH: 23
<212> TYPE: DNA
<213> ORGANISM: Artificial Sequence
<220> FEATURE:
<223> OTHER INFORMATION: synthetic_Fig. 17b_Sequences

<400> SEQUENCE: 658
gaatccaagc aggagaagaa gga    23

<210> SEQ ID NO 659
<211> LENGTH: 23
<212> TYPE: DNA
<213> ORGANISM: Artificial Sequence
<220> FEATURE:
<223> OTHER INFORMATION: synthetic_Fig. 17b_Sequences

<400> SEQUENCE: 659
agttccaagc agaagaagca tgg    23

<210> SEQ ID NO 660
<211> LENGTH: 23
<212> TYPE: DNA
<213> ORGANISM: Artificial Sequence
<220> FEATURE:
<223> OTHER INFORMATION: synthetic_Fig. 17b_Sequences

<400> SEQUENCE: 660
gaggccgagc agaagaaaga cgg    23

<210> SEQ ID NO 661
<211> LENGTH: 22
<212> TYPE: DNA
<213> ORGANISM: Artificial Sequence
<220> FEATURE:
<223> OTHER INFORMATION: synthetic_Fig. 17b_Sequences

<400> SEQUENCE: 661
gtgtcctaga gaagaagaag gg    22

<210> SEQ ID NO 662
<211> LENGTH: 23
<212> TYPE: DNA
<213> ORGANISM: Artificial Sequence
<220> FEATURE:
<223> OTHER INFORMATION: synthetic_Fig. 17b_Sequences

<400> SEQUENCE: 662
gagtccaagc agtagaggaa ggg                                      23

<210> SEQ ID NO 663
<211> LENGTH: 23
<212> TYPE: DNA
<213> ORGANISM: Artificial Sequence
<220> FEATURE:
<223> OTHER INFORMATION: synthetic_Fig. 17b_Sequences

<400> SEQUENCE: 663
gagtcctagc aggagaagaa gag                                      23

<210> SEQ ID NO 664
<211> LENGTH: 22
<212> TYPE: DNA
<213> ORGANISM: Artificial Sequence
<220> FEATURE:
<223> OTHER INFORMATION: synthetic_Fig. 17b_Sequences

<400> SEQUENCE: 664
gaatccaaga gaagaagaat gg                                       22

<210> SEQ ID NO 665
<211> LENGTH: 23
<212> TYPE: DNA
<213> ORGANISM: Artificial Sequence
<220> FEATURE:
<223> OTHER INFORMATION: synthetic_Fig. 17b_Sequences

<400> SEQUENCE: 665
aagtctgagc acaagaagaa tgg                                      23

<210> SEQ ID NO 666
<211> LENGTH: 23
<212> TYPE: DNA
<213> ORGANISM: Artificial Sequence
<220> FEATURE:
<223> OTHER INFORMATION: synthetic_Fig. 17b_Sequences

<400> SEQUENCE: 666
gaatccaagc agaagaagag aag                                      23

<210> SEQ ID NO 667
<211> LENGTH: 23
<212> TYPE: DNA
<213> ORGANISM: Artificial Sequence
<220> FEATURE:
<223> OTHER INFORMATION: synthetic_Fig. 17b_Sequences

<400> SEQUENCE: 667
gagtctaagc agaagaagaa gag                                      23

<210> SEQ ID NO 668
<211> LENGTH: 23
<212> TYPE: DNA
<213> ORGANISM: Artificial Sequence
<220> FEATURE:
<223> OTHER INFORMATION: synthetic_Fig. 17b_Sequences -continued

<400> SEQUENCE: 668
gagtccgagc agaagaagaa ggg					23

<210> SEQ ID NO 669
<211> LENGTH: 23
<212> TYPE: DNA
<213> ORGANISM: Artificial Sequence
<220> FEATURE:
<223> OTHER INFORMATION: synthetic_Fig. 22_Sequences

<400> SEQUENCE: 669
gagtccgagc agaagaagaa ggg					23

<210> SEQ ID NO 670
<211> LENGTH: 23
<212> TYPE: DNA
<213> ORGANISM: Artificial Sequence
<220> FEATURE:
<223> OTHER INFORMATION: synthetic_Fig. 22_Sequences

<400> SEQUENCE: 670
cccttcttct tctgctcgga ctc					23

<210> SEQ ID NO 671
<211> LENGTH: 23
<212> TYPE: DNA
<213> ORGANISM: Artificial Sequence
<220> FEATURE:
<223> OTHER INFORMATION: synthetic_Fig. 22_Sequences
<220> FEATURE:
<221> NAME/KEY: misc_feature
<222> LOCATION: (5)..(6)
<223> OTHER INFORMATION: n is uracil

<400> SEQUENCE: 671
gagtnngagc agaagaagaa ggg					23

<210> SEQ ID NO 672
<211> LENGTH: 23
<212> TYPE: DNA
<213> ORGANISM: Artificial Sequence
<220> FEATURE:
<223> OTHER INFORMATION: synthetic_Fig. 22_Sequences

<400> SEQUENCE: 672
cccttcttct tctgctcgga ctc					23

<210> SEQ ID NO 673
<211> LENGTH: 23
<212> TYPE: DNA
<213> ORGANISM: Artificial Sequence
<220> FEATURE:
<223> OTHER INFORMATION: synthetic_Fig. 22_Sequences
<220> FEATURE:
<221> NAME/KEY: misc_feature
<222> LOCATION: (5)..(6)
<223> OTHER INFORMATION: n is absent

<400> SEQUENCE: 673
gagtnngagc agaagaagaa ggg					23

<210> SEQ ID NO 674
<211> LENGTH: 23
<212> TYPE: DNA
<213> ORGANISM: Artificial Sequence
<220> FEATURE:

```
<223> OTHER INFORMATION: synthetic_Fig. 22_Sequences

<400> SEQUENCE: 674
cccttcttct tctgctcgga ctc                                              23

<210> SEQ ID NO 675
<211> LENGTH: 21
<212> TYPE: DNA
<213> ORGANISM: Artificial Sequence
<220> FEATURE:
<223> OTHER INFORMATION: synthetic_Fig. 22_Sequences

<400> SEQUENCE: 675
gagtgagcag aagaagaagg g                                                21

<210> SEQ ID NO 676
<211> LENGTH: 23
<212> TYPE: DNA
<213> ORGANISM: Artificial Sequence
<220> FEATURE:
<223> OTHER INFORMATION: synthetic_Fig. 22_Sequences
<220> FEATURE:
<221> NAME/KEY: misc_feature
<222> LOCATION: (18)..(19)
<223> OTHER INFORMATION: n is absent

<400> SEQUENCE: 676
cccttcttct tctgctcnna ctc                                              23
```